United States Patent
Roquet et al.

(10) Patent No.: US 11,227,219 B2
(45) Date of Patent: Jan. 18, 2022

(54) COMPOSITIONS AND METHODS FOR NUCLEIC ACID-BASED DATA STORAGE

(71) Applicant: Catalog Technologies, Inc., Charlestown, MA (US)

(72) Inventors: Nathaniel Roquet, Charlestown, MA (US); Hyunjun Park, Charlestown, MA (US); Swapnil P. Bhatia, Charlestown, MA (US); Devin Leake, Charlestown, MA (US)

(73) Assignee: CATALOG TECHNOLOGIES, INC., Charlestown, MA (US)

( * ) Notice: Subject to any disclaimer, the term of this patent is extended or adjusted under 35 U.S.C. 154(b) by 0 days.

(21) Appl. No.: 17/206,803

(22) Filed: Mar. 19, 2021

(65) Prior Publication Data

US 2021/0209479 A1 Jul. 8, 2021

Related U.S. Application Data

(63) Continuation of application No. 16/414,758, filed on May 16, 2019.
(Continued)

(51) Int. Cl.
*G01N 33/48* (2006.01)
*G01N 33/50* (2006.01)
(Continued)

(52) U.S. Cl.
CPC ............. *G06N 3/123* (2013.01); *G16B 25/00* (2019.02); *G16B 25/20* (2019.02); *G16B 30/00* (2019.02);
(Continued)

(58) Field of Classification Search
CPC ........ G06N 3/123; G16B 25/20; G16B 99/00; G16B 25/00; G16B 30/00; G16B 50/30; B82Y 10/00
See application file for complete search history.

(56) References Cited

U.S. PATENT DOCUMENTS 6,030,657 A 2/2000 Butland et al.
6,187,537 B1 2/2001 Zinn, Jr. et al.
(Continued)

FOREIGN PATENT DOCUMENTS

EP 1512749 3/2005
EP 2329425 6/2011
(Continued)

OTHER PUBLICATIONS

Craig et al. Ordering of cosmid clones covering the Herpes simplex virus type I (HSV-I) genome: a test case for fingerprinting by hybridization. Nucleic Acids Research, vol. 18, pp. 2653-2660. (Year: 1990).*

(Continued)

*Primary Examiner* — Russell S Negin
(74) *Attorney, Agent, or Firm* — White & Case LLP

(57) ABSTRACT

The present disclosure provides systems and methods for storing digital information into nucleic acid molecules in various ways. Digital information may be received as a sting of symbols, wherein each symbol in the string of symbols has a symbol value and a symbol position within the string of symbols. A first identifier nucleic acid molecule may be formed by depositing M selected component nucleic acid molecules into a compartment, the M selected component nucleic acid molecules being selected from a set of distinct component nucleic acid molecules that are separated into M different layers, and physically assembling the M selected component nucleic acid molecules. A plurality of identifier nucleic acid molecules may be formed, each corresponding to a respective symbol position. The identifier nucleic acid molecules may be formed in a pool having powder, liquid, or solid form.

29 Claims, 51 Drawing Sheets

Related U.S. Application Data

(60) Provisional application No. 62/672,495, filed on May 16, 2018.

(51) Int. Cl.

| | | |
|---|---|---|
| *G06N 3/12* | (2006.01) | |
| *G16B 50/30* | (2019.01) | |
| *G16B 30/00* | (2019.01) | |
| *G16B 99/00* | (2019.01) | |
| *G16B 25/20* | (2019.01) | |
| *G16B 25/00* | (2019.01) | |
| *B82Y 10/00* | (2011.01) | |

(52) U.S. Cl.
CPC ............ *G16B 50/30* (2019.02); *G16B 99/00* (2019.02); *B82Y 10/00* (2013.01)

(56) References Cited

U.S. PATENT DOCUMENTS

| | | |
|---|---|---|
| 6,221,653 B1 | 4/2001 | Caren et al. |
| 6,309,828 B1 | 10/2001 | Schleifer et al. |
| 6,384,210 B1 | 5/2002 | Blanchard |
| 6,419,883 B1 | 7/2002 | Blanchard |
| 6,446,642 B1 | 9/2002 | Caren et al. |
| 6,458,583 B1 | 10/2002 | Bruhn et al. |
| 6,537,747 B1 | 3/2003 | Mills, Jr. et al. |
| 6,796,634 B2 | 9/2004 | Caren et al. |
| 7,176,297 B2 | 2/2007 | Li et al. |
| 7,306,316 B2 | 12/2007 | Doak |
| 7,491,422 B2 | 2/2009 | Zhang et al. |
| 7,600,840 B2 | 10/2009 | Kim et al. |
| 7,802,517 B2 | 9/2010 | Wessels et al. |
| 7,833,701 B2 | 11/2010 | Oshima |
| 7,909,427 B2 | 3/2011 | Kim et al. |
| 7,951,334 B2 | 5/2011 | Mirkin et al. |
| 8,071,168 B2 | 12/2011 | Cruchon-Dupeyrat et al. |
| 8,114,207 B2 | 2/2012 | Josten |
| 8,136,936 B2 | 3/2012 | Hook et al. |
| 8,496,326 B2 | 7/2013 | Hook et al. |
| 8,735,327 B2 | 5/2014 | Macula |
| 8,769,689 B2 | 7/2014 | Hoglund |
| 8,806,127 B2 | 8/2014 | Brownell et al. |
| 8,856,940 B2 | 10/2014 | Kencl et al. |
| 8,937,564 B2 | 1/2015 | Aloni et al. |
| 9,061,494 B2 | 6/2015 | Rogers et al. |
| 9,062,218 B2 | 6/2015 | Oshima et al. |
| 9,187,777 B2 | 11/2015 | Jacobson et al. |
| 9,266,370 B2 | 2/2016 | Jung et al. |
| 9,317,664 B2 | 4/2016 | Ahuja et al. |
| 9,384,320 B2 | 7/2016 | Church |
| 9,403,180 B2 | 8/2016 | Ha et al. |
| 9,487,002 B2 | 11/2016 | Rogers et al. |
| 9,616,661 B2 | 4/2017 | Pierik et al. |
| 9,679,030 B2 | 6/2017 | Hatami-Hanza |
| 9,684,678 B2 | 6/2017 | Hatami-Hanza |
| 9,774,351 B2 | 9/2017 | Huetter et al. |
| 9,830,553 B2 | 11/2017 | Chen et al. |
| 9,904,734 B2 | 2/2018 | Murrah et al. |
| 9,928,869 B2 | 3/2018 | Church |
| 9,996,778 B2 | 6/2018 | Church |
| 10,020,826 B2 | 7/2018 | Gladwin et al. |
| 10,027,347 B2 | 7/2018 | Le Scouarnec et al. |
| 10,047,235 B2 | 8/2018 | Wilsher et al. |
| 10,050,959 B2 | 8/2018 | Soon-Shiong et al. |
| 10,287,573 B2 | 5/2019 | Macula |
| 10,289,801 B2 | 5/2019 | Church |
| 10,370,246 B1 | 8/2019 | Milenkovic et al. |
| 10,387,301 B2 | 8/2019 | Goldman et al. |
| 10,417,457 B2 | 9/2019 | Peck |
| 10,423,341 B1 | 9/2019 | Kermani |
| 10,438,662 B2 | 10/2019 | Predki |
| 10,460,220 B2 | 10/2019 | Church |
| 10,566,077 B1 | 2/2020 | Milenkovic et al. |
| 10,640,822 B2 | 5/2020 | Predki et al. |
| 10,650,312 B2 | 5/2020 | Roquet et al. |
| 10,669,558 B2 | 6/2020 | Ganjam |
| 10,742,233 B2 | 8/2020 | Erlich |
| 10,754,994 B2 | 8/2020 | Peck |
| 10,774,379 B2 | 9/2020 | Chen et al. |
| 10,787,699 B2 | 9/2020 | Chen et al. |
| 10,793,897 B2 | 10/2020 | Chen et al. |
| 10,818,378 B2 | 10/2020 | Hutchison, III et al. |
| 10,838,939 B2 | 11/2020 | Walder et al. |
| 10,839,295 B2 | 11/2020 | Shen et al. |
| 10,853,244 B2 | 12/2020 | Petti et al. |
| 10,883,140 B2 | 1/2021 | Church et al. |
| 10,902,939 B2 | 1/2021 | Merriman et al. |
| 10,917,109 B1 | 2/2021 | Dimopoulou et al. |
| 10,920,274 B2 | 2/2021 | Hogan et al. |
| 10,929,039 B2 | 2/2021 | Kwon et al. |
| 10,936,953 B2 | 3/2021 | Peck et al. |
| 10,956,806 B2 | 3/2021 | Masuda et al. |
| 2003/0116630 A1 | 6/2003 | Carey et al. |
| 2004/0244623 A1 | 12/2004 | Hayashizaki |
| 2005/0019760 A1 | 1/2005 | Southern |
| 2005/0166782 A2 | 8/2005 | Hayashizaki |
| 2005/0243618 A1 | 11/2005 | Boland et al. |
| 2006/0263534 A1 | 11/2006 | Laurent et al. |
| 2008/0252679 A1 | 10/2008 | Pierik et al. |
| 2008/0269152 A1 | 10/2008 | Verdine et al. |
| 2008/0303870 A1 | 12/2008 | Verbeek et al. |
| 2008/0309701 A1 | 12/2008 | Pierik et al. |
| 2009/0023607 A1 | 1/2009 | Rozhok et al. |
| 2009/0033690 A1 | 2/2009 | Pierik et al. |
| 2009/0062129 A1 | 3/2009 | McKernan et al. |
| 2009/0253141 A1 | 10/2009 | Quake |
| 2010/0029490 A1 | 2/2010 | Pierik et al. |
| 2010/0056381 A1 | 3/2010 | Kurt et al. |
| 2011/0195850 A1 | 8/2011 | Rozhok et al. |
| 2011/0312779 A1 | 12/2011 | Silverbrook et al. |
| 2011/0312782 A1 | 12/2011 | Azimi et al. |
| 2011/0312847 A1 | 12/2011 | Silverbrook et al. |
| 2011/0312851 A1 | 12/2011 | Silverbrook et al. |
| 2011/0312853 A1 | 12/2011 | Azimi et al. |
| 2011/0312855 A1 | 12/2011 | Silverbrook et al. |
| 2011/0312856 A1 | 12/2011 | Silverbrook et al. |
| 2012/0164396 A1 | 6/2012 | Mirkin et al. |
| 2012/0329561 A1 | 12/2012 | Evans et al. |
| 2013/0231254 A1 | 9/2013 | Kawashima et al. |
| 2013/0233709 A1 | 9/2013 | Dunbar et al. |
| 2014/0065609 A1 | 3/2014 | Hicks et al. |
| 2014/0296087 A1 | 10/2014 | Verdine et al. |
| 2014/0371100 A1 | 12/2014 | Kawashima et al. |
| 2015/0083797 A1 | 3/2015 | Tran et al. |
| 2015/0261664 A1 | 9/2015 | Goldman et al. |
| 2015/0269313 A1 | 9/2015 | Church |
| 2015/0312212 A1 | 10/2015 | Holmes et al. |
| 2016/0007893 A1 | 1/2016 | Roberts |
| 2016/0051985 A1 | 2/2016 | Knight et al. |
| 2016/0168579 A1 | 6/2016 | Hutchison et al. |
| 2016/0258939 A1 | 9/2016 | Morin et al. |
| 2016/0304948 A1 | 10/2016 | Lee et al. |
| 2016/0371434 A1 | 12/2016 | Strauss et al. |
| 2017/0017436 A1 | 1/2017 | Church |
| 2017/0021611 A1 | 1/2017 | Jung et al. |
| 2017/0081716 A1 | 3/2017 | Peck |
| 2017/0093851 A1 | 3/2017 | Allen |
| 2017/0136452 A1 | 5/2017 | Niles et al. |
| 2017/0140095 A1 | 5/2017 | Kim |
| 2017/0218228 A1 | 8/2017 | Jose et al. |
| 2017/0363953 A1 | 12/2017 | Steinhart et al. |
| 2018/0068060 A1 | 3/2018 | Ceze et al. |
| 2018/0086781 A1 | 3/2018 | Liss |
| 2018/0101487 A1 | 4/2018 | Peck |
| 2018/0121478 A1 | 5/2018 | Walder et al. |
| 2018/0137418 A1 | 5/2018 | Roquet et al. |
| 2018/0173710 A1 | 6/2018 | Maftuleac et al. |
| 2018/0173738 A1 | 6/2018 | Lopez-Ortiz et al. |
| 2018/0253563 A1 | 9/2018 | Peck et al. |
| 2019/0020651 A1 | 1/2019 | Soon-Shiong et al. |
| 2019/0136307 A1* | 5/2019 | Predki .................. C12Q 1/6869 |
| 2019/0142882 A1 | 5/2019 | Shepherd et al. |

(56) References Cited

U.S. PATENT DOCUMENTS

| | | | |
|---|---|---|---|
| 2019/0271032 | A1 | 9/2019 | Owen |
| 2019/0355442 | A1 | 11/2019 | Merriman |
| 2021/0010065 | A1 | 1/2021 | Salk et al. |

FOREIGN PATENT DOCUMENTS

| | | | |
|---|---|---|---|
| EP | 2856375 | 7/2018 | |
| EP | 3346404 | 7/2018 | |
| JP | 2009244996 | 10/2009 | |
| WO | WO-03025123 | 3/2003 | |
| WO | WO-2004009844 | 1/2004 | |
| WO | WO-2012058638 A2 * | 5/2012 | ........... C12Q 1/6825 |
| WO | WO-2014014991 | 1/2014 | |
| WO | WO-2015144858 | 10/2015 | |
| WO | WO-2016015701 | 2/2016 | |
| WO | WO-2016032562 A1 | 3/2016 | |
| WO | WO-2016059610 | 4/2016 | |
| WO | WO-2016081834 | 5/2016 | |
| WO | WO-2016164779 | 10/2016 | |
| WO | WO-2016182814 | 11/2016 | |
| WO | WO-2017151195 | 9/2017 | |
| WO | WO-2017189914 | 11/2017 | |
| WO | WO-2017190297 | 11/2017 | |
| WO | WO-2018017131 | 1/2018 | |
| WO | WO-2018049272 | 3/2018 | |
| WO | WO-2018094108 | 5/2018 | |
| WO | WO-2018132457 | 7/2018 | |
| WO | WO-2018148260 | 8/2018 | |
| WO | WO-2018148458 | 8/2018 | |
| WO | WO-2018213856 | 11/2018 | |
| WO | WO-2019081145 A1 | 5/2019 | |
| WO | WO-2019178551 | 9/2019 | |

OTHER PUBLICATIONS

Bonnet et al., "Rewritable digital data storage in live cells via engineered control of recombination directionality," Proceeding of the National Academy of Sciences, vol. 109(23): 8884-8889 (2012).

Bornholt et al., "A DNA-Based Archival Storage System," International Conference on Architectural Support for Programming Languages and Operating Systems (ASPLOS), Apr. 2-6, 2016, Atlanta, GA, 637-649.

Buschmann, et al., "Levenshtein Error-Correcting Barcodes for Multiplexed DNA Sequencing", BMC Bioinformatics, vol. 14, No. 1., pp. 1-10 (2013).

Bystrykh, et al., "Generalized DNA Barcode Design Based on Hamming Codes", PLOS One, vol. 7, No. 5, pp. 1-8, (May 2012).

Casini, A. "Advanced DNA assembly strategies and standards for synthetic biology," Thesis, Department of Life Sciences, Imperial College London: 1-178 (2014).

Clarke, et al., "Continuous base identification for single-molecule nanopore DNA sequencing", Nature Nanotechnology, vol. 4, pp. 265-270, (2009).

De Silva, et al., "New Trends of Digital Data Storage in DNA", BioMed Research International, vol. 2016, Article ID 8072463, 14 pages (Sep. 5, 2016) ps. 14.

Deorowicz et al., "Data compression for sequencing data," Algorithms for Molecular Biology, vol. 8(25): 1-13 (2013).

Engler et al., "A One Pot, One Step, Precision Cloning Method with High Throughput Capability," PLoS ONE, vol. 3(11): E3647 (2008) printed as pp. 1-7.

Engler et al., "Chapter 12: Combinatorial DNA Assembly Using Golden Gate Cloning," Karen M. Polizzi and Cleo Kontoravadi (eds.), Synthetic Biology, Methods in Molecular Biology, vol. 1073 , Springer Science+Business Media, New York: 141-156 (2013).

Extended European Search Report for EP Application No. 17872172.6 dated Oct. 27, 2020.

Fogg et al., "New Applications for Phage Integrases," Journal of Molecular Biology, vol. 426(15): 2703-2716(2014).

Goldman et al., "Towards practical, high-capacity, low-maintenance information storage in synthesized DNA," Nature, vol. 494: 77-80 (2013).

Kivioja et al., "Counting absolute numbers of molecules using unique molecular identifiers," Nature Methods, vol. 9(1): 72-74 (2011), including pp. 1-2 of Online Methods, and pp. 1-14 of Supplementary Information.

Lee, et al., "Enzymatic DNA synthesis for digital information storage", bioRxiv, XP055603868, DOI: 10.1101/348987 Retrieved from the Internet: URL:https://www.biorxiv.org/content/biorxiv/early/2018/06/16/348987.full.pdf [retrieved on Nov. 20, 2019] abstract, pp. 31 pages (2018).

Leier et al., "Cryptography with DNA binary strands," Biosystems, vol. 57: 13-22 (2000).

Navarro, et al., "Compressed Full-Text Indexes", ACM Computing Surveys, ACM, New York, NY, vol. 39, No. 1, Apr. 12, 2007.

Organick, et al., "Random access in large-scale DNA data storage", Nature Biotechnology, 36(3): 242-248, (2018).

Patrick, et al., DNA Assembly in 3D Printed Fluidics, PLOS One, 10(12): e014636 18 pages (2015).

PCT/US2017/062098 International Search Report and Written Opinion dated, Mar. 14, 2018.

PCT/US2017/062106 International Search Report and Written Opinion dated, Feb. 22, 2018.

PCT/US2019/022596 International Search Report and Written Opinion dated, Jun. 28, 2019.

PCT/US2019/032756 International Search Report and Written Opinion dated, Sep. 4, 2019.

PCT/US2019/045160 International Search Report and Written Opinion dated, Jan. 1, 2020.

PCT/US2020/032384 International Search Report and Written Opinion dated, Jul. 30, 2020.

Quetier et al., "The CRISPR-Cas9 technology: Closer to the ultimate toolkit for targeted genome editing," Plant Science, vol. 242: 65-76 (2015).

Roquet et al., "Synthetic recombinase-based state machines in living cells," Science, vol. 353(6297): 363, aad8559-1-aad8559-13 (2016).

Sands, B. and Brent, R., "Overview of Post Cohen-Boyer Methods for Single Segment Cloning and for Multisegment DNA Assembly," Current Protocols in Molecular Biology, vol. 113: 3.26.1-3.26-20 (2016).

Sorek et al., "CRISPR-Mediated Adaptive Immune Systems in Bacteria and Archaea," Annual Review of Biochemistry, vol. 82: 237-266 (2013).

Sun et al., "Recent advances in targeted genome engineering in mammalian systems," Biotechnology Journal, vol. 7: 1074-1087 (2012).

Tulpan, et al., "HyDEn: A Hybrid Steganocryptographic Approach for Data Encryption Using Randomized Error Correcting DNA Codes,", Biomed Research International, vol. 32, No. 4839, pp. 1-11, (2013).

Yang et al., "Permanent genetic memory with >1-byte capacity," Nature Methods, vol. 11(12): 1261-1266 (2014) including pp. 1-3 of Online Methods, and pp. 1-30 of Supplementary Figures and Text.

Yazdi et al., "A Rewritable, Random-Access DNA-Based Storage System," Scientific Reports, vol. 5(14138): 1-10 (2015), including pp. 1-19 of Supplementary Information.

Yazdi et al., "DNA-based storage: Trends and Methods," IEEE Transactions on Molecular, Biological, and Multi-Scale Communications, vol. 1(3): 230-248 (Sep. 1, 2015).

Yazdi, et al., "Portable and Error-Free DNA-Based Data Storage", bioRxiv preprint doi: https://doi.org/10.1101/079442 (2016).

Yim et al., "The essential component in DNA-based information storage system: robust error-tolerating module," Frontiers in Bioengineering and Biotechnology, vol. 2, Article 49: 1-5 (2014).

Zhu et al., "High-throughput DNA sequence data compression," Briefings in Bioinformatics, 16(1): 1-15 (2015).

PCT/US2020/055351 International Search Report and Written Opinion dated, Mar. 31, 2021.

Arppe, R., et al., "Physical Unclonable Functions Generated Through Chemical Methods for Anti-Counterfeiting", Nature Reviews Chemistry, 1, 31 (2017).

(56) References Cited

OTHER PUBLICATIONS

Chandrasekaran, A. R., et al., "Addressable Configurations of DNA Nanostructures for Rewritable Memory", Nucleic Acids Res., 45, 19, pp. 11459-11465. (2017).
Church, G. M., et al., "Next-Generation Digital Information Storage in DNA", Science 2012, 337 (6102), 1628 (2012).
Clelland, C. T., et al., "Hiding Messages in DNA microdots", Nature, 399, 533. (1999).
Erlich, Y., et al., "DNA Fountain Enables a Robust and Efficient Storage Architecture", Science, 355 (6328), 950-954 (2017).
Gehani, A., et al., DNA-based Cryptography. In Aspects of Molecular Computing; Jonoska, N., Păun, G., Rozenberg, G., Eds.; Springer: Berlin, Heidelberg, 2004; pp. 167-188 (2004).
Grass, R. N., et al., "Robust Chemical Preservation of Digital Information on DNA in Silica with Error-Correcting Codes", Angew. Chem., Int. Ed. 2015, 54 (8), 2552-2555 (2015).
Halvorsen, K., et al., "Binary DNA Nanostructures for Data Encryption", PLoS One 2012, 7 (9), No. e44212. (2012).
Holden, et al., "Encrypted Oligonucleotide Arrays for Molecular Authentication", American Chemical Society, 6 pages (Jul. 5, 2019).
Shoshani, S., et al., "A Molecular Cryptosystem for Images by DNA Computing", Angew. Chem., Int. Ed., 51 (12), 2883-2887 (2012).
Lee et al., DNA detection using commercial mobile phones, Biosensors and Bioelectronics, 2011, 26, 4349-4354 (Year: 2011).

\* cited by examiner $C_{xy}$ is the yth component in layer x. For a starting library with M layers, each with N components, the identifiers would have the following architecture:

where a, b, c represent elements in the set {1, 2, ..., N}

$C_{xy}$ is the yth component in layer x. For a starting library with M layers, each with N components, the identifiers would have the following architecture:

where b, e, h are elements in the set {1, 2, ..., N}, and a, d, f are unique elements in the set {1, 2, ..., M}.

The combinatorial space of possible identifiers is $N^M M!$ $C_{xy}$ is the yth component in layer x. For a starting library with M layers, each with N components, Identifiers assemble a fixed number of components, k, and have the following architecture:

where b, e, h are elements in the set {1, 2, ..., N}, and a, d, f among k unique, rank-ordered elements in the set {1, 2, ..., M}.

The combinatorial space of possible identifiers is $N^k M choose k$

*Road Not Taken*
(5856 bits)

encode → write + read →

*The Raven, Ozymandias, Where the Sidewalk Ends*
(62824 bits)

encode → write + read →

Possible sticky-end component structures made from two oligos, X and Y. Arrows represent oligos. The arrows point along the 5' to 3' direction.

COMPOSITIONS AND METHODS FOR NUCLEIC ACID-BASED DATA STORAGE

CROSS-REFERENCE TO RELATED APPLICATIONS

This application is a Continuation of U.S. patent application Ser. No. 16/414,758, filed on May 16, 2019, which claims priority to and the benefit of U.S. Provisional Patent Application No. 62/672,495, filed on May 16, 2018, and entitled "COMPOSITIONS AND METHODS FOR NUCLEIC ACID-BASED DATA STORAGE". The entire contents of the above-referenced applications are incorporated herein by reference.

BACKGROUND

Nucleic acid digital data storage is a stable approach for encoding and storing information for long periods of time, with data stored at higher densities than magnetic tape or hard drive storage systems. Additionally, digital data stored in nucleic acid molecules that are stored in cold and dry conditions can be retrieved as long as 60,000 years later or longer.

To access digital data stored in nucleic acid molecules, the nucleic acid molecules may be sequenced. As such, nucleic acid digital data storage may be an ideal method for storing data that is not frequently accessed but may have a high volume of information to be stored or archived for long periods of time.

Current methods rely on encoding the digital information (e.g., binary code) into base-by-base nucleic acids sequences, such that the base to base relationship in the sequence directly translates into the digital information (e.g., binary code). Sequencing of digital data stored in base-by-base sequences that can be read into bit-streams or bytes of digitally encoded information can be error prone and costly to encode since the cost of de novo base-by-base nucleic acid synthesis can be expensive. Opportunities for new methods of performing nucleic acid digital data storage may provide approaches for encoding and retrieving data that are less costly and easier to commercially implement.

SUMMARY

The present disclosure provides systems and methods for storing digital information into nucleic acid molecules in various ways to improve the efficiency of the retrieval and access of that digital information. For example, component nucleic acid molecules (e.g., components) are selected and concatenated to one another to form identifier nucleic acid molecules (e.g., identifiers), each of which corresponds to a particular symbol (e.g., bit or series of bits), or that symbol's position (e.g., rank or address), in a string of symbols (e.g., a bitstream). Those components may be organized in a structural manner, so as to provide an efficient scheme for representing digital data. For example, the structure of the components may cause the component molecules to self-assemble, or otherwise sort themselves in a predetermined order after the multiple component molecules are deposited or dispensed into the same compartment.

Provided herein are methods for storing digital information into nucleic acid molecules, the method comprising: (a) receiving the digital information as a string of symbols, wherein each symbol in the string of symbols has a symbol value and a symbol position within the string of symbols; (b) forming a first identifier nucleic acid molecule by: (1) selecting, from a set of distinct component nucleic acid molecules that are separated into M different layers, one component nucleic acid molecule from each of the M layers; (2) depositing the M selected component nucleic acid molecules into a compartment; (3) physically assembling the M selected component nucleic acid molecules in (2) to form the first identifier nucleic acid molecule having first and second end molecules and a third molecule positioned between the first and second end molecules, such that the component nucleic acid molecules from first and second layers correspond to the first and second end molecules of the identifier nucleic acid molecule, and the component nucleic acid molecule in a third layer corresponds to the third molecule of the identifier nucleic acid molecule, to define a physical order of the M layers in the first identifier nucleic acid molecule; (c) forming a plurality of additional identifier nucleic acid molecules, each (1) having first and second end molecules and a third molecule positioned between the first and second end molecules, and (2) corresponding to a respective symbol position, wherein at least one of the first end molecule, second end molecule, and third molecule of at least one additional identifier nucleic acid molecule is identical to a target molecule of the first identifier nucleic acid molecule in (b), so as to enable a probe to select at least two identifier nucleic acid molecules corresponding to respective symbols having contiguous symbol positions within the string of symbols, and (d) collecting the identifier nucleic acid molecules in (b) and (c) in a pool having powder, liquid, or solid form.

In some implementations, a population of identifier nucleic acid molecules share the same target molecule, while other identifier nucleic acid molecules in the same pool may have different target molecules. At least one of the first and second end molecules of the at least one additional identifier nucleic acid molecule may be identical to a target molecule of the first identifier nucleic acid molecule in (b). In some implementations, physically assembling the M selected component nucleic acid molecules comprises ligation of the component nucleic acid molecules.

In some implementations, the component nucleic acid molecules from each layer comprise at least one sticky end which is complementary to at least one sticky end of component nucleic acid molecules from another layer, so as to enable sticky end ligation for formation of the identifier nucleic acid molecules in (b) and (c). For example, all components within each layer (e.g., A, B, C) may have the same sticky ends as one another, and one sticky end of all components in layer A are complementary to one sticky end of all components in layer B. Moreover, the other sticky end of all components in layer B may be complementary to one sticky end of all components in layer C, and so on. In some implementations, first molecule of the at least one additional identifier nucleic acid molecule in (c) is identical to the first end molecule of the identifier nucleic acid molecule in (b), and the second end molecule of the at least one additional identifier nucleic acid molecule in (c) is identical to the second end molecule of the identifier nucleic acid molecule in (b).

In some implementations, the method further comprises using the probe to hybridize to the target molecule of at least some identifier nucleic acid molecules in the first identifier nucleic acid molecule and the plurality of additional identifier nucleic acid molecules to select identifier nucleic acid molecules corresponding to respective symbols having contiguous symbol positions. Symbols with contiguous symbol positions are adjacent to one another and may share similar characteristics by virtue of being in a similar neighborhood.

Accordingly, it may be desirable to select identifier nucleic acid molecules that are positioned near one another using the same probe. In some implementations, the method further comprises applying a single PCR reaction to amplify at least two identifier nucleic acid molecules corresponding to respective symbols having contiguous symbol positions. In some implementations, the at least two identifier nucleic acid molecules corresponding to respective symbols having contiguous symbol positions are able to be further amplified by another PCR reaction that targets a specific component nucleic acid molecule in the third molecule of the identifier nucleic acid molecule.

In some implementations, the component nucleic acid molecules in each layer are structured with first and second end regions, and the first end region of each component nucleic acid molecule from one of the M layers is structured to bind to the second end region of any component nucleic acid molecule from another of the M layers. In some implementations, M is greater than or equal to three. In some implementations, each symbol position within the string of symbols has a corresponding different identifier nucleic acid molecule. In some implementations, the identifier nucleic acid molecules in (b) and (c) are representative of a subset of a combinatorial space of possible identifier nucleic acid molecules, each including one component nucleic acid molecule from each of the M layers.

In some implementations, the presence or absence of an identifier nucleic acid molecule in the pool in (d) is representative of the symbol value of the corresponding respective symbol position within the string of symbols. For example, the presence of an identifier may represent the symbol value at the corresponding symbol position is one, while the absence represents the symbol value is zero, or vice versa. In some implementations, the symbols having contiguous symbol position encode similar digital information. In some implementations, the distribution of numbers of component nucleic acid molecules in each of the M layers is non-uniform. For example, one layer may have more component nucleic acid molecules than another layer, so as to adjust the number and/or variety of possible permutations for creating identifier nucleic acid molecules.

In some implementations, wherein when the third layer includes more component nucleic acid molecules than either of the first layer or the second layer, a PCR query used to access the pool in (d) results in a larger pool of accessed identifier nucleic acid molecules than if the third layer included fewer component nucleic acid molecules than either of the first layer or the second layer.

In some implementations, wherein when the third layer includes fewer component nucleic acid molecules than either of the first layer or the second layer, a PCR query used to access the pool in (d) results in a smaller pool of accessed identifier nucleic acid molecules than if the third layer included more component nucleic acid molecules than either of the first layer or the second layer, wherein the smaller pool of accessed identifier nucleic acid molecules corresponds to a higher resolution of access to the symbols in the string of symbols.

In some implementations, the first layer has a highest priority, the second layer has a second highest priority, and the remaining M−2 layers have corresponding component nucleic acid molecules between the first and second end molecules. In some implementations, the pool in (d) is able to be used to access all identifier nucleic acid molecules in the pool that have particular component nucleic acid molecules at the first and second end molecules, in one PCR reaction.

In an aspect, the present disclosure provides a method for storing digital information into nucleic acid molecules, the method comprising: (a) receiving the digital information as a string of symbols, wherein each symbol in the string of symbols has a symbol value and a symbol position within the string of symbols, wherein the digital information includes image data represented by a collection of vectors; (b) forming a first identifier nucleic acid molecule by: (1) selecting, from a set of distinct component nucleic acid molecules that are separated into M different layers, one component nucleic acid molecule from each of the M layers; (2) depositing the M selected component nucleic acid molecules into a compartment; and (3) physically assembling the M selected component nucleic acid molecules in (2) to form the first identifier nucleic acid molecule having first and second end molecules and a third molecule positioned between the first and second end molecules, such that the component nucleic acid molecules from first and second layers correspond to the first and second end molecules of the identifier nucleic acid molecule, and the component nucleic acid molecule in a third layer corresponds to the third molecule of the identifier nucleic acid molecule, to define a physical order of the M layers in the first identifier nucleic acid molecule.

In some implementations, the method comprises step (a) above, (b) forming a first identifier nucleic acid molecule by depositing M selected component nucleic acid molecules into a compartment, the M selected component nucleic acid molecules being selected from a set of distinct component nucleic acid molecules that are separated into M different layers, and physically assembling the M selected component nucleic acid molecules; (c) forming a plurality of identifier nucleic acid molecules, each corresponding to a respective symbol position; and (d) collecting the identifier nucleic acid molecules in (b) and (c) in a pool having powder, liquid, or solid form.

In some implementations, at least some of the M layers correspond to different features of the image data. In some implementations, the different features include an x-coordinate, a y-coordinate, and an intensity value or a range of intensity values. Storing the image data into nucleic acid molecules may allow for any neighborhood of pixels to be queried for color values using a random access scheme, such as any of the access schemes described herein. In some implementations, storing the image data into nucleic acid molecules allows for the image data to be decoded at a fraction of an original resolution of the image data.

In an aspect, the present disclosure provides a method for storing digital information into nucleic acid molecules, the method comprising: (a) receiving the digital information as a string of symbols, wherein each symbol in the string of symbols has a symbol value and a symbol position within the string of symbols, wherein the digital information includes image data represented by a collection of vectors; (b) forming a first identifier nucleic acid molecule by depositing M selected component nucleic acid molecules into a compartment, the M selected component nucleic acid molecules being selected from a set of distinct component nucleic acid molecules that are separated into M different layers; (c) forming a plurality of identifier nucleic acid molecules, each having first and second end molecules and a third molecule positioned between the first and second end molecules and corresponding to a respective symbol position, wherein at least one of the first end molecule, second end molecule, and third molecule of at least one additional identifier nucleic acid molecule is identical to a target molecule of the first identifier nucleic acid molecule in (b), so as to enable a single probe to select at least two identifier nucleic acid molecules corresponding to respective symbols having related symbol positions within the string of symbols, and (d) collecting the identifier nucleic acid molecules in (b) and (c) in a pool having powder, liquid, or solid form. Storing the image data into nucleic acid molecules may allow for any neighborhood of pixels to be queried for color values using a random access scheme.

In some implementations, storing the image data into nucleic acid molecules allows for the image data to be decoded at a fraction of an original resolution of the image data, and decoding the image data at the fraction is used to search for a specific visual feature in an archive of surveillance images or in a video archive to identify frames of interest.

In an aspect, the present disclosure provides a method for storing digital information into nucleic acid molecules, the method comprising: (a) receiving the digital information as a string of symbols, wherein each symbol in the string of symbols has a symbol value and a symbol position within the string of symbols; (b) forming a first identifier nucleic acid molecule by depositing M selected component nucleic acid molecules into a compartment, the M selected component nucleic acid molecules being selected from a set of distinct component nucleic acid molecules that are separated into M different layers, and physically assembling the M selected component nucleic acid molecules; (c) forming a plurality of identifier nucleic acid molecules, each having first and second end molecules and a third molecule positioned between the first and second end molecules and corresponding to a respective symbol position, wherein at least one of the first end molecule, second end molecule, and third molecule of at least one additional identifier nucleic acid molecule is identical to a target molecule of the first identifier nucleic acid molecule in (b), so as to enable a single probe to select at least two identifier nucleic acid molecules corresponding to respective symbols having related symbol positions within the string of symbols, wherein physically assembling the M selected component nucleic acid molecules to form the identifier nucleic acid molecule in (b) comprises using click chemistry, and (d) collecting the identifier nucleic acid molecules in (b) and (c) in a pool having powder, liquid, or solid form. Step (c) of the method for storing digital information may involve generally forming a plurality of identifier nucleic acid molecules, each corresponding to a respective symbol position, without performing the forming of the molecules having first and second end molecules and a third molecule, as recited above.

In an aspect, the present disclosure provides a method for storing digital information into nucleic acid molecules, the method comprising: (a) receiving the digital information as a string of symbols, wherein each symbol in the string of symbols has a symbol value and a symbol position within the string of symbols; (b) forming a first identifier nucleic acid molecule by depositing M selected component nucleic acid molecules into a compartment, the M selected component nucleic acid molecules being selected from a set of distinct component nucleic acid molecules that are separated into M different layers, and physically assembling the M selected component nucleic acid molecules using click chemistry; (c) forming a plurality of identifier nucleic acid molecules, each corresponding to a respective symbol position; (d) collecting the identifier nucleic acid molecules in (b) and (c) in a pool having powder, liquid, or solid form; and (e) deleting data collected in the pool. In some implementations, step (c) comprises physically assembling a plurality of identifier nucleic acid molecules, each having first and second end molecules and a third molecule positioned between the first and second end molecules and corresponding to a respective symbol position, wherein at least one of the first end molecule, second end molecule, and third molecule of at least one additional identifier nucleic acid molecule is identical to a target molecule of the first identifier nucleic acid molecule in (b), so as to enable a single probe to select at least two identifier nucleic acid molecules corresponding to respective symbols having related symbol positions within the string of symbols, wherein physically assembling the M selected component nucleic acid molecules to form the identifier nucleic acid molecule in (b) comprises using click chemistry.

In some implementations, the method further comprises using sequence-specific probes to pull-down select identifier nucleic acid molecules from the pool in (d) to selectively delete data. In some implementations, the select identifier nucleic acid molecules are selectively deleted using CRISPR-based methods. In some implementations, the method further comprises obfuscating the identifier nucleic acid molecules in the pool in (d) to non-selectively delete data, by rendering it inaccessible, or difficult or impossible to read. In some implementations, the method further comprises using sonication, autoclaving, treatment with bleach, bases, acids, ethidium bromide or other DNA modification agents, irradiation, combustion, and non-specific nuclease digestion to degrade the identifier nucleic acid molecules from the pool in (d) to non-selectively delete data.

In an aspect, the present disclosure provides a method for storing digital information into nucleic acid molecules, the method comprising: (a) receiving the digital information as a string of symbols, wherein each symbol in the string of symbols has a symbol value and a symbol position within the string of symbols; (b) dividing the string of symbols into one or more blocks of size no greater than a fixed length; (c) forming a first identifier nucleic acid molecule by depositing M selected component nucleic acid molecules into a compartment, the M selected component nucleic acid molecules being selected from a set of distinct component nucleic acid molecules that are separated into M different layers, and physically assembling the M selected component nucleic acid molecules; (d) forming a plurality of identifier nucleic acid molecules, each corresponding to a respective symbol position; and (e) collecting the identifier nucleic acid molecules in (d) and (c) in a pool having powder, liquid, or solid form.

In some implementations, the plurality of identifier nucleic acid molecules in step (d) above each has first and second end molecules and a third molecule positioned between the first and second end molecules and corresponding to a respective symbol position, wherein at least one of the first end molecule, second end molecule, and third molecule of at least one additional identifier nucleic acid molecule is identical to a target molecule of the first identifier nucleic acid molecule in (b), so as to enable a single probe to select at least two identifier nucleic acid molecules corresponding to respective symbols having related symbol positions within the sting of symbols.

In some implementations, the method further comprises determining the size of each block based on the string of symbols, processing requirements, or an intended application of the digital information. In some implementations, the method further comprises computing a hash of each block. In some implementations, the method further comprises applying one or more error detection and correction to each block and computing one or more error protection bytes. In some implementations, the method further comprises mapping the one or more blocks to a set of codewords that optimizes chemical conditions during encoding or decoding. In some implementations, the set of codewords have a fixed weight such that a fixed number of identifier nucleic acid molecules are assembled in each reaction compartment in a writer system, and in approximately equal concentration within each reaction compartment and across reaction compartments.

In an aspect, the present disclosure provides a method performing a computation on digital information that has been stored into nucleic acid molecules. Importantly, that computation may be performed without having to read or decode the actual digital information from the pool of molecules. The computation may include any combination of Boolean logic gates, such as an AND, OR, NOT, or NAND operation. Specifically, the present disclosure provides a method for storing digital information into nucleic acid molecules, the method comprising: (a) receiving the digital information as a string of symbols, wherein each symbol in the string of symbols has a symbol value and a symbol position within the string of symbols; (b) forming a first identifier nucleic acid molecule by depositing M selected component nucleic acid molecules into a compartment, the M selected component nucleic acid molecules being selected from a set of distinct component nucleic acid molecules that are separated into M different layers, and physically assembling the M selected component nucleic acid molecules; (c) forming a plurality of identifier nucleic acid molecules, each corresponding to a respective symbol position; (d) collecting the identifier nucleic acid molecules in (b) and (c) in a pool having powder, liquid, or solid form; and (e) performing a computation involving a Boolean logical operation, including AND, OR, NOT, or NAND, on the string of symbols using the identifier nucleic acid molecules in (d), to produce a new pool of nucleic acid molecules. That new pool of nucleic acid molecules may represent the result, or output of the computation.

In some implementations the identifier nucleic acid molecules in (c) above each has first and second end molecules and a third molecule positioned between the first and second end molecules and corresponding to a respective symbol position, wherein at least one of the first end molecule, second end molecule, and third molecule of at least one additional identifier nucleic acid molecule is identical to a target molecule of the first identifier nucleic acid molecule in (b), so as to enable a single probe to select at least two identifier nucleic acid molecules corresponding to respective symbols having related symbol positions within the string of symbols.

In some implementations, the computation is performed on the pool of identifier nucleic acid molecules in (d) without decoding any of the identifier nucleic acid molecules to obtain any of the symbols in the string of symbols. In some implementations, performing the computation includes a series of chemical operations including hybridization and cleavage.

In some implementations, the string of symbols in (a) is denoted a and includes sub-bitstream s, and the plurality of identifier nucleic acid molecules in the pool in (d) are double stranded and denoted dsA, the method further comprising obtaining another pool of another plurality of identifier nucleic acid molecules, denoted dsB and representative of another string of symbols denoted b including sub-bitstream t, wherein the computation is performed on a sub-bitstream s and t by performing a series of steps on dsA and dsB. In some implementations, the series of steps on dsA and dsB includes performing an initialization step, comprising: converting the double stranded identifier nucleic acid molecules in dsA into positive single-stranded forms, denoted A; converting the double stranded identifier nucleic acid molecules in dsA into negative single-stranded forms, denoted A*, wherein A* is a reverse complement of A; converting the double stranded identifier nucleic acid molecules in dsB into positive single-stranded forms, denoted B; converting the double stranded identifier nucleic acid molecules in dsB into negative single-stranded forms, denoted B*, wherein B* is a reverse complement of B; selecting dsP as identifier nucleic acid molecules in dsA that correspond to s; selecting P as identifier nucleic acid molecules in A that correspond to s; selecting dsQ as identifier nucleic acid molecules in dsB that correspond to t; and selecting Q* as identifier nucleic acid molecules in B* that correspond to t.

In some implementations, the computation is an AND operation, and the series of steps on dsA and dsB further comprises: performing the AND operation between a and b by combining A and B*, hybridizing complementary nucleic acid molecules, and selecting fully complemented double stranded nucleic acid molecules as the new pool of nucleic acid molecules. In some implementations, the computation is an OR operation, and the series of steps on dsA and dsB further comprises: performing the AND operation between s and t by combining P and Q*, hybridizing complementary nucleic acid molecules, and selecting fully complemented double stranded nucleic acid molecules as the new pool of nucleic acid molecules.

In some implementations, selecting the fully complemented nucleic acid molecules comprises using chromatography, gel electrophoresis, single-strand specific endonucleases, single-strand specific exonuclease, or a combination thereof.

In some implementations, the computation is an OR operation, and the series of steps on dsA and dsB comprises performing the OR operation between a and b by combining dsA and dsB to produce the new pool of nucleic acid molecules. In some implementations, the computation is an OR operation, and the series of steps on dsA and dsB comprises performing the OR operation between s and t by combining dsP and dsQ to produce the new pool of nucleic acid molecules.

In some implementations, the method further comprises updating A or dsA to include the new pool of nucleic acid molecules, thereby allowing A or dsA to represent the output of the operation.

In an aspect, the present disclosure provides a method for storing digital information into nucleic acid molecules, the method comprising: (a) receiving the digital information as a string of symbols, wherein each symbol in the string of symbols has a symbol value and a symbol position within the string of symbols; (b) forming a first identifier nucleic acid molecule by depositing M selected component nucleic acid molecules into a compartment, the M selected component nucleic acid molecules being selected from a set of distinct component nucleic acid molecules that are separated into M different layers, and physically assembling the M selected component nucleic acid molecules; (c) forming a plurality of identifier nucleic acid molecules; and (c) partitioning the identifier nucleic acid molecules in (b) and (c) into separate bins, each bin corresponding to a different symbol value.

In some implementations, forming the first identifier nucleic acid molecule in (b) includes: (1) selecting, from a set of distinct component nucleic acid molecules that are separated into M different layers, one component nucleic acid molecule from each of the M layers; (2) depositing the M selected component nucleic acid molecules into a compartment; (3) physically assembling the M selected component nucleic acid molecules in (2) to form the first identifier nucleic acid molecule having first and second end molecules and a third molecule positioned between the first and second end molecules, such that the component nucleic acid molecules from first and second layers correspond to the first and second end molecules of the identifier nucleic acid molecule, and the component nucleic acid molecule in a third layer corresponds to the third molecule of the identifier nucleic acid molecule, to define a physical order of the M layers in the first identifier nucleic acid molecule. In some implementations, the symbol position of each symbol having a particular symbol value is recorded in a bin reserved for that value, the bin being the compartment in (2).

In an aspect, the present disclosure provides a method for storing digital information into nucleic acid molecules, the method comprising: (a) receiving the digital information as a string of symbols, wherein each symbol in the string of symbols has a symbol value and a symbol position within the string of symbols; (b) forming a first identifier nucleic acid molecule by depositing M selected component nucleic acid molecules into a compartment, the M selected component nucleic acid molecules being selected from a set of distinct component nucleic acid molecules that are separated into M different layers, and physically assembling the M selected component nucleic acid molecules; (c) forming a plurality of identifier nucleic acid molecules; (c) forming a plurality of identifier nucleic acid molecules, each corresponding to a respective symbol position; and (d) collecting the identifier nucleic acid molecules in (b) and (c) in a pool having powder, liquid, or solid form.

In some implementations, step (c) above includes forming the plurality of identifier nucleic acid molecules, each having first and second end molecules and a third molecule positioned between the first and second end molecules and corresponding to a respective symbol position, wherein at least one of the first end molecule, second end molecule, and third molecule of at least one additional identifier nucleic acid molecule is identical to a target molecule of the first identifier nucleic acid molecule in (b), so as to enable a single probe to select at least two identifier nucleic acid molecules corresponding to respective symbols having related symbol positions within the string of symbols.

In some implementations, an individual component of the M selected components comprises multiple parts wherein each part comprises a nucleic acid molecule and wherein each part is linked to the same identifier by one or more chemical methods. In some implementations, said multiple parts each serve separate functional purposes for different data storage operations. In some implementations, said functional purposes include ease of sequencing and ease of access by nucleic acid hybridization. In some implementations, forming the first identifier nucleic acid molecule comprises programmably mutating one or more bases in a parent identifier by applying base editors such as dCas9-deaminase.

In an aspect, the present disclosure provides a method for storing digital information into nucleic acid molecules, the method comprising: (a) receiving the digital information as a string of symbols, wherein each symbol in the string of symbols has a symbol value and a symbol position within the string of symbols; (b) forming a first identifier nucleic acid molecule by programmably mutating one or more bases in a parent identifier by applying base editors; (c) forming a plurality of identifier nucleic acid molecules, each identifier nucleic acid molecule corresponding to a respective symbol position; and (d) collecting the identifier nucleic acid molecules in (b) and (c) in a pool having powder, liquid, or solid form. In an example, one of the base editors applied in (b) is dCas9-deaminase.

In an aspect, the present disclosure provides a method for storing digital information that is produced from one or more random processes, into nucleic acid molecules, the method comprising: (a) receiving the digital information as a string of symbols, wherein each symbol in the string of symbols has a symbol value and a symbol position within the string of symbols; (b) forming a first identifier nucleic acid molecule by depositing M selected component nucleic acid molecules into a compartment, the M selected component nucleic acid molecules being selected from a set of distinct component nucleic acid molecules that are separated into M different layers, and physically assembling the M selected component nucleic acid molecules; (c) forming a plurality of identifier nucleic acid molecules, each corresponding to a respective symbol position; and (d) collecting the identifier nucleic acid molecules in (b) and (c) in a pool having powder, liquid, or solid form.

In some implementations, the present disclosure provides an application of the above method, or any of the above methods, in which the application comprises encryption of information, authentication of entities, or its use as a source of entropy in applications involving randomization. In some implementations, identifiers from one or more disjoint identifier libraries are used to uniquely identify entities or physical locations.

In an aspect, the present disclosure provides a method for encoding digital information in partitions of a number of random DNA species.

In an aspect, the present disclosure provides a method of generating random data by randomly sampling and sequencing DNA species from a large combinatorial pool of possible DNA species.

In an aspect, the present disclosure provides a method of generating and storing random data by randomly sampling and sequencing a subset of DNA species from a large combinatorial pool of possible DNA species.

In some implementations, said subset of DNA species is amplified to create multiple copies of each species. In some implementations, nucleic acid molecules for error checking and correction are added to said subset of DNA species to enable robust future readout. In some implementations, said subset of DNA species is barcoded with a unique molecule and combined in a pool of barcoded subsets of DNA species. In some implementations, a particular subset of DNA species in said pool of barcoded subsets of DNA species is accessible with input nucleic acid probes for PCR or nucleic acid capture.

In an aspect, the present disclosure provides a method of securing and authenticating an artifact with a system comprising: (1) DNA keys made up of subsets of DNA species from a defined set, and (2) a DNA reader that accepts keys and either searches for a matching key to unlock said artifact locally or returns a hashed token to access the artifact elsewhere. In some implementations, the method further comprises combinatorially assembling DNA fragments for biological applications.

In an aspect, the present disclosure provides a method for storing digital information into nucleic acid molecules, the method comprising: (a) receiving the digital information as a string of symbols, wherein each symbol in the string of symbols has a symbol value and a symbol position within the string of symbols; (b) forming a first identifier nucleic acid molecule by: (1) selecting, from a set of distinct component nucleic acid molecules that are separated into M different layers, one component nucleic acid molecule from each of the M layers; (2) depositing the M selected component nucleic acid molecules into a compartment; (3) physically assembling the M selected component nucleic acid molecules in (2) to form the first identifier nucleic acid molecule comprising a specified component, wherein the specified component comprises at least one target molecule, to allow access of the identifier containing the specified component; (c) physically assembling a plurality of additional identifier nucleic acid molecules, each having the specified component, wherein the specified component comprises the at least one target molecule of the first identifier nucleic acid molecule in (b), so as to enable a probe to select at least two identifier nucleic acid molecules corresponding to respective symbols having contiguous symbol positions within the string of symbols; and (d) collecting the identifier nucleic acid molecules in (b) and (c) in a pool having powder, liquid, or solid form.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 2A illustrates combining a rank object (or address object) with a byte-value object (or data object) to create an identifier; FIG. 2B illustrates an embodiment of the data at address method wherein the rank objects and byte-value objects are themselves combinatorial concatenations of other objects;

FIG. 3A illustrates encoding digital information using a rank object as an identifier; FIG. 3B illustrates an embodiment of the encoding method wherein the address objects are themselves combinatorial concatenations of other objects;

FIG. 6A illustrates the architecture of identifiers constructed using the product scheme; FIG. 6B illustrates an example of the combinatorial space of identifiers that may be constructed using the product scheme;

FIG. 10A schematically illustrates the use of template directed ligation to construct identifiers (e.g., nucleic acid molecules) from components (e.g., nucleic acid sequences); FIG. 10B shows a histogram of the copy numbers (abundances) of 256 distinct nucleic acid sequences that were each combinatorially assembled from six nucleic acid sequences (components) in one pooled template directed ligation reaction;

FIG. 11A illustrates the architecture of identifiers constructed using the permutation scheme; FIG. 11B illustrates an example of the combinatorial space of identifiers that may be constructed using the permutation scheme; FIG. 11C shows an example implementation of the permutation scheme with template directed ligation; FIG. 11D shows an example of how the implementation from FIG. 11C may be modified to construct identifiers with permuted and repeated components; FIG. 11E shows how the example implementation from FIG. 11D may lead to unwanted byproducts that may be removed with nucleic acid size selection; FIG. 11F shows another example of how to use template directed ligation and size selection to construct identifiers with permuted and repeated components; FIG. 11G shows an example of when size selection may fail to isolate a particular identifier from unwanted byproducts;

FIG. 12A illustrates the architecture of identifiers constructed using the MchooseK scheme; FIG. 12B illustrates an example of the combinatorial space of identifiers that may be constructed using the MchooseK scheme; FIG. 12C shows an example implementation of the MchooseK scheme using template directed ligation; FIG. 12D shows how the example implementation from FIG. 12C may lead to unwanted byproducts that may be removed with nucleic acid size selection;

FIG. 13A shows an example of the combinatorial space of identifiers that may be constructed using the partition scheme; FIG. 13B shows an example implementation of the partition scheme using template directed ligation;

FIG. 14A shows an example of the combinatorial space of identifiers that may be constructed using the USS scheme; FIG. 14B shows an example implementation of the USS scheme using template directed ligation;

FIG. 15A shows an example of the combinatorial space of identifiers that may be constructed using the component deletion scheme; FIG. 15B shows an example implementation of the component deletion scheme using double stranded targeted cleavage and repair;

FIG. 17A shows example methods for using polymerase chain reaction, affinity tagged probes, and degradation targeting probes to access identifiers containing a specified component; FIG. 17B shows example methods for using polymerase chain reaction to perform 'OR' or 'AND' operations to access identifiers containing multiple specified components; FIG. 17C shows example methods for using affinity tags to perform 'OR' or 'AND' operations to access identifiers containing multiple specified components;

FIG. 18A shows an example of encoding, writing, and reading 5,856 bits of data; FIG. 18b shows an example of encoding, writing, and reading 62,824 bits of data.

DETAILED DESCRIPTION

Figure 1:
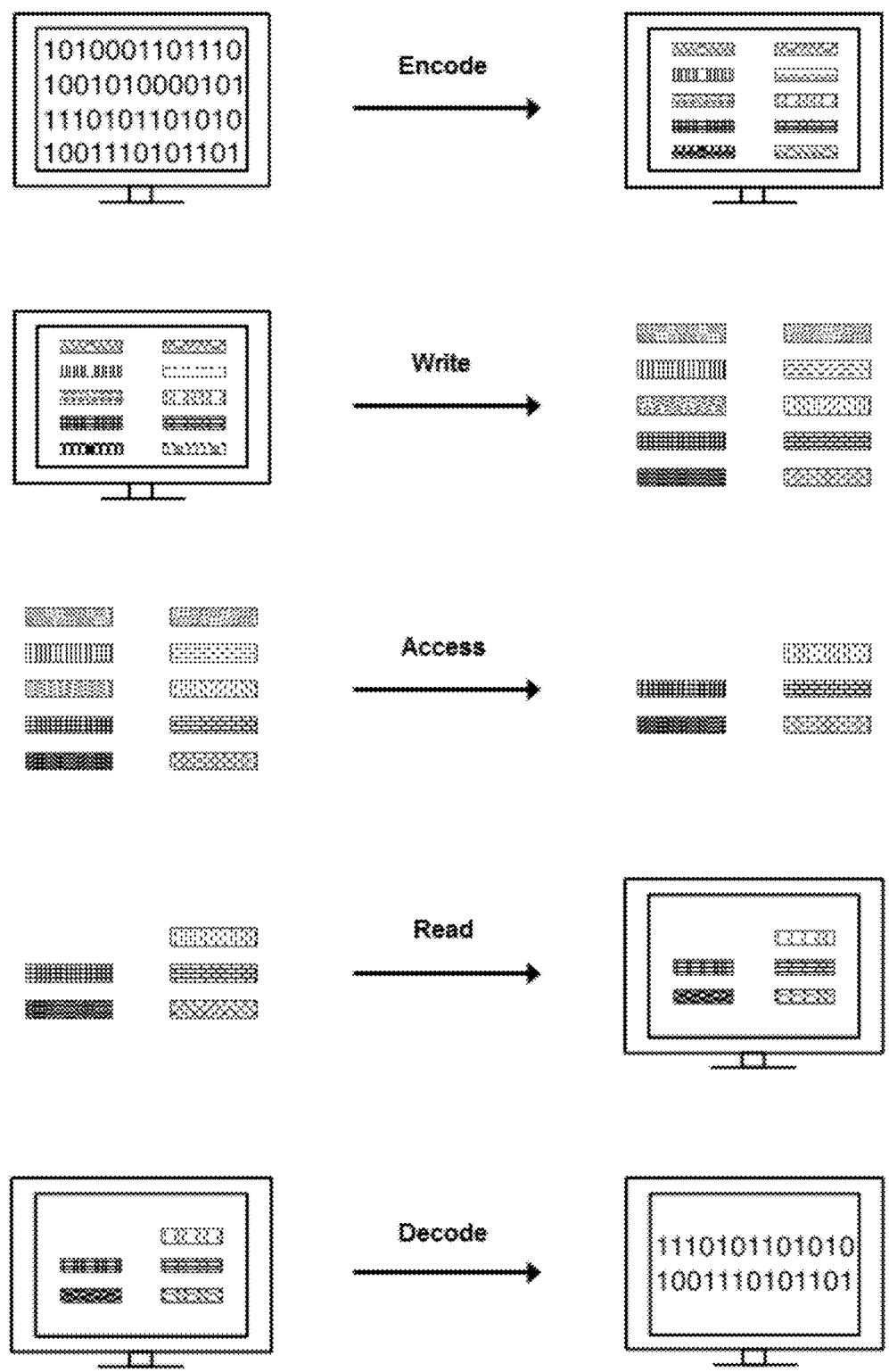
FIG. 1 schematically illustrates an overview of a process for encoding, writing, accessing, querying, reading, and decoding digital information stored in nucleic acid sequences.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "symbol," as used herein, generally refers to a representation of a unit of digital information. Digital information may be divided or translated into a string of symbols. In an example, a symbol may be a bit and the bit may have a value of '0' or '1'.

The term "distinct," or "unique," as used herein, generally refers to an object that is distinguishable from other objects in a group. For example, a distinct, or unique, nucleic acid sequence may be a nucleic acid sequence that does not have the same sequence as any other nucleic acid sequence. A distinct, or unique, nucleic acid molecule may not have the same sequence as any other nucleic acid molecule. The distinct, or unique, nucleic acid sequence or molecule may share regions of similarity with another nucleic acid sequence or molecule.

The term "component," as used herein, generally refers to a nucleic acid sequence. A component may be a distinct nucleic acid sequence. A component may be concatenated or assembled with one or more other components to generate other nucleic acid sequence or molecules.

The term "layer," as used herein, generally refers to group or pool of components. Each layer may comprise a set of distinct components such that the components in one layer are different from the components in another layer. Components from one or more layers may be assembled to generate one or more identifiers.

The term "identifier," as used herein, generally refers to a nucleic acid molecule or a nucleic acid sequence that represents the position and value of a bit-string within a larger bit-string. More generally, an identifier may refer to any object that represents or corresponds to a symbol in a string of symbols. In some embodiments, identifiers may comprise one or multiple concatenated components.

The term "combinatorial space," as used herein generally refers to the set of all possible distinct identifiers that may be generated from a starting set of objects, such as components, and a permissible set of rules for how to modify those objects to form identifiers. The size of a combinatorial space of identifiers made by assembling or concatenating components may depend on the number of layers of components, the number of components in each layer, and the particular assembly method used to generate the identifiers.

The term "identifier rank," as used herein generally refers to a relation that defines the order of identifiers in a set.

The term "identifier library," as used herein generally refers to a collection of identifiers corresponding to the symbols in a symbol suing representing digital information. In some embodiments, the absence of a given identifier in the identifier library may indicate a symbol value at a particular position. One or more identifier libraries may be combined in a pool, group, or set of identifiers. Each identifier library may include a unique barcode that identifies the identifier library.

The term "nucleic acid," as used herein, general refers to deoxyribonucleic acid (DNA), ribonucleic acid (RNA), or a variant thereof. A nucleic acid may include one or more subunits selected from adenosine (A), cytosine (C), guanine (G), thymine (T), and uracil (U), or variants thereof. A nucleotide can include A, C, G, T, or U, or variants thereof. A nucleotide can include any subunit that can be incorporated into a growing nucleic acid strand. Such subunit can be A, C, G, T, or U, or any other subunit that may be specific to one of more complementary A, C, T, or U, or complementary to a purine (i.e., A or G, or variant thereof) or pyrimidine (i.e., C, T, or U, or variant thereof). In some examples, a nucleic acid may be single-stranded or double stranded, in some cases, a nucleic acid is circular.

The terms "nucleic acid molecule" or "nucleic acid sequence," as used herein, generally refer to a polymeric form of nucleotides, or polynucleotide, that may have various lengths, either deoxyribonucleotides (DNA) or ribonucleotides (RNA), or analogs thereof. The term "nucleic acid sequence" may refer to the alphabetical representation of a polynucleotide; alternatively, the term may be applied to the physical polynucleotide itself. This alphabetical representation can be input into databases in a computer having a central processing unit and used for mapping nucleic acid sequences or nucleic acid molecules to symbols, or bits, encoding digital information. Nucleic acid sequences or oligonucleotides may include one or more non-standard nucleotide(s), nucleotide analog(s) and/or modified nucleotides.

An "oligonucleotide", as used herein, generally refers to a single-stranded nucleic acid sequence, and is typically composed of a specific sequence of four nucleotide bases: adenine (A); cytosine (C); guanine (G), and thymine (T) or uracil (U) when the polynucleotide is RNA.

Examples of modified nucleotides include, but are not limited to diaminopurine, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, 2,6-diaminopurine and the like. Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone. Nucleic acid molecules may also contain amine-modified groups, such as aminoallyl-dUTP (aa-dUTP) and aminohexylacrylamide-dCTP (aha-dCTP) to allow covalent attachment of amine reactive moieties, such as N-hydroxy succinimide esters (NHS).

The term "primer," as used herein, generally refers to a strand of nucleic acid that serves as a starting point for nucleic acid synthesis, such as polymerase chain reaction (PCR). In an example, during replication of a DNA sample, an enzyme that catalyzes replication starts replication at the 3'-end of a primer attached to the DNA sample and copies the opposite strand. See Chemical Methods Section D for more information on PCR, including details about primer design.

The term "polymerase" or "polymerase enzyme," as used herein, generally refers to any enzyme capable of catalyzing a polymerase reaction. Examples of polymerases include, without limitation, a nucleic acid polymerase. The polymerase can be naturally occurring or synthesized. An example polymerase is a Φ29 polymerase or derivative thereof. In some cases, a transcriptase or a ligase is used (i.e., enzymes which catalyze the formation of a bond) in conjunction with polymerases or as an alternative to polymerases to construct new nucleic acid sequences. Examples of polymerases include a DNA polymerase, a RNA polymerase, a thermostable polymerase, a wild-type polymerase, a modified polymerase, E. coli DNA polymerase I, T7 DNA polymerase, bacteriophage T4 DNA polymerase Φ29 (phi29) DNA polymerase, Taq polymerase, Tth polymerase, Tli polymerase, Pfu polymerase Pwo polymerase, VENT polymerase, DEEPVENT polymerase, Ex-Taq polymerase, LA-Taw polymerase, Sso polymerase Poc polymerase, Pab polymerase, Mth polymerase ES4 polymerase, Tru polymerase, Tac polymerase, Tne polymerase, Tma polymerase, Tca polymerase, Tih polymerase, Tfi polymerase, Platinum Taq polymerases, Tbr polymerase, Tfl polymerase, Pfutubo polymerase, Pyrobest polymerase, KOD polymerase, Bst polymerase, Sac polymerase, Klenow fragment polymerase with 3' to 5' exonuclease activity, and variants, modified products and derivatives thereof. See Chemical Methods Section D for additional polymerases that may be used with PCR as well as for details on how polymerase characteristics may affect PCR.

The term "species", as used herein, generally refers to one or more DNA molecule(s) of the same sequence. If "species" is used in a plural sense, then it may be assumed that every species in the plurality of species has a distinct sequence, though this may sometimes be made explicit by writing "distinct species" instead of "species".

Digital information, such as computer data, in the form of binary code can comprise a sequence or string of symbols. A binary code may encode or represent text or computer processor instructions using, for example, a binary number system having two binary symbols, typically 0 and 1, referred to as bits. Digital information may be represented in the form of non-binary code which can comprise a sequence of non-binary symbols. Each encoded symbol can be re-assigned to a unique bit string (or "byte"), and the unique bit string or byte can be arranged into strings of bytes or byte streams. A bit value for a given bit can be one of two symbols (e.g., 0 or 1). A byte, which can comprise a string of N bits, can have a total of $2^N$ unique byte-values. For example, a byte comprising 8 bits can produce a total of $2^8$ or 256 possible unique byte-values, and each of the 256 bytes can correspond to one of 256 possible distinct symbols, letters, or instructions which can be encoded with the bytes. Raw data (e.g., text tiles and computer instructions) can be represented as strings of bytes or byte streams. Zip files, or compressed data files comprising raw data can also be stored in byte streams, these files can be stored as byte streams in a compressed form, and then decompressed into raw data before being read by the computer.

Methods and systems of the present disclosure may be used to encode computer data or information in a plurality of identifiers, each of which may represent one or more bits of the original information. In some examples, methods and systems of the present disclosure encode data or information using identifiers that each represents two bits of the original information.

Previous methods for encoding digital information into nucleic acids have relied on base-by-base synthesis of the nucleic acids, which can be costly and time consuming. Alternative methods may improve the efficiency, improve the commercial viability of digital information storage by reducing the reliance on base-by-base nucleic acid synthesis for encoding digital information, and eliminate the de novo synthesis of distinct nucleic acid sequences for every new information storage request.

New methods can encode digital information (e.g., binary code) in a plurality of identifiers, or nucleic acid sequences, comprising combinatorial arrangements of components instead of relying on base-by-base or de-novo nucleic acid synthesis (e.g., phosphoramidite synthesis). As such, new strategies may produce a first set of distinct nucleic acid sequences (or components) for the first request of information storage, and can there-after re-use the same nucleic acid sequences (or components) for subsequent information storage requests. These approaches can significantly reduce the cost of DNA-based information storage by reducing the role of de-novo synthesis of nucleic acid sequences in the information-to-DNA encoding and writing process. Moreover, unlike implementations of base-by-base synthesis, such as phosphoramidite chemistry- or template-free polymerase-based nucleic acid elongation, which may use cyclical delivery of each base to each elongating nucleic acid, new methods of information-to-DNA writing using identifier construction from components are highly parallelizable processes that do not necessarily use cyclical nucleic acid elongation. Thus, new methods may increase the speed of writing digital information to DNA compared to older methods.

Methods for Encoding and Writing Information to Nucleic Acid Sequence(s)

In an aspect, the present disclosure provides methods for encoding information into nucleic acid sequences. A method for encoding information into nucleic acid sequences may comprise (a) translating the information into a string of symbols, (b) mapping the string of symbols to a plurality of identifiers, and (c) constructing an identifier library comprising at least a subset of the plurality of identifiers. An individual identifier of the plurality of identifiers may comprise one or more components. An individual component of the one or more components may comprise a nucleic acid sequence. Each symbol at each position in the string of symbols may correspond to a distinct identifier. The individual identifier may correspond to an individual symbol at an individual position in the string of symbols. Moreover, one symbol at each position in the string of symbols may correspond to the absence of an identifier. For example, in a string of binary symbols (e.g., bits) of '0's and '1's, each occurrence of '0' may correspond to the absence of an identifier.

In another aspect, the present disclosure provides methods for nucleic acid-based computer data storage. A method for nucleic acid-based computer data storage may comprise (a) receiving computer data, (b) synthesizing nucleic acid molecules comprising nucleic acid sequences encoding the computer data, and (c) storing the nucleic acid molecules having the nucleic acid sequences. The computer data may be encoded in at least a subset of nucleic acid molecules synthesized and not in a sequence of each of the nucleic acid molecules.

In another aspect, the present disclosure provides methods for writing and storing information in nucleic acid sequences. The method may comprise, (a) receiving or encoding a virtual identifier library that represents information, (b) physically constructing the identifier library, and (c) storing one or more physical copies of the identifier library in one or more separate locations. An individual identifier of the identifier library may comprise one or more components. An individual component of the one or more components may comprise a nucleic acid sequence.

In another aspect, the present disclosure provides methods for nucleic acid-based computer data storage. A method for nucleic acid-based computer data storage may comprise (a) receiving computer data, (b) synthesizing a nucleic acid molecule comprising at least one nucleic acid sequence encoding the computer data, and (c) storing the nucleic acid molecule comprising the at least one nucleic acid sequence. Synthesizing the nucleic acid molecule may be in the absence of base-by-base nucleic acid synthesis.

In another aspect, the present disclosure provides methods for writing and storing information in nucleic acid sequences. A method for writing and storing information in nucleic acid sequences may comprise, (a) receiving or encoding a virtual identifier library that represents information, (b) physically constructing the identifier library, and (c) storing one or more physical copies of the identifier library in one or more separate locations. An individual identifier of the identifier library may comprise one or more components. An individual component of the one or more components may comprise a nucleic acid sequence.

In another aspect, the present disclosure provides a method for storing digital information into nucleic acid sequences, the method comprising: (a) receiving the digital information as a string of symbols, wherein each symbol in the string of symbols has a symbol value and a symbol position within the string of symbols; (b) forming a first identifier nucleic acid sequence by: (1) selecting, from a set of distinct component nucleic acid sequences that are separated into M different layers, one component nucleic acid sequence from each of the M layers; (2) depositing the M selected component nucleic acid sequences into a compartment; (3) physically assembling the M selected component nucleic acid sequences in (2) to form the first identifier nucleic acid sequence having first and second end sequences and a third sequence positioned between the first and second end sequences, such that the component nucleic acid sequences from first and second layers correspond to the first and second end sequences of the identifier nucleic acid sequence, and the component nucleic acid sequence in a third layer corresponds to the third sequence of the identifier nucleic acid sequence, to define a physical order of the M layers in the first identifier nucleic acid sequence; (c) forming a plurality of additional identifier nucleic acid sequences, each (1) having first and second end sequences and a third sequence positioned between the first and second end sequences, and (2) corresponding to a respective symbol position, wherein at least one of the first end sequence, second end sequence, and third sequence of at least one additional identifier nucleic acid sequence is identical to a target sequence of the first identifier nucleic acid sequence in (b), so as to enable a probe to select at least two identifier nucleic acid sequences corresponding to respective symbols having contiguous symbol positions within the string of symbols, and (d) collecting the identifier nucleic acid sequences in (b) and (c) in a pool having powder, liquid, or solid form.

In another aspect, the present disclosure provides a method for storing digital information into nucleic acid sequences, the method comprising: (a) receiving the digital information as a string of symbols, wherein each symbol in the string of symbols has a symbol value and a symbol position within the string of symbols, wherein the digital information includes image data represented by a collection of vectors; (b) forming a first identifier nucleic acid sequence by depositing M selected component nucleic acid sequences into a compartment, the M selected component nucleic acid sequences being selected from a set of distinct component nucleic acid sequences that are separated into M different layers; (c) forming a plurality of identifier nucleic acid sequences, each having first and second end sequences and a third sequence positioned between the first and second end sequences and corresponding to a respective symbol position, wherein at least one of the first end sequence, second end sequence, and third sequence of at least one additional identifier nucleic acid sequence is identical to a target sequence of the first identifier nucleic acid sequence in (b), so as to enable a single probe to select at least two identifier nucleic acid sequences corresponding to respective symbols having related symbol positions within the string of symbols, and (d) collecting the identifier nucleic acid sequences in (b) and (c) in a pool having powder, liquid, or solid form, wherein storing the image data into nucleic acid sequences allows for any neighborhood of pixels to be queried for color values using a random access scheme.

In another aspect, the present disclosure provides a method for storing digital information into nucleic acid sequences, the method comprising: (a) receiving the digital information as a string of symbols, wherein each symbol in the string of symbols has a symbol value and a symbol position within the string of symbols; (b) forming a first identifier nucleic acid sequence by depositing M selected component nucleic acid sequences into a compartment, the M selected component nucleic acid sequences being selected from a set of distinct component nucleic acid sequences that are separated into M different layers; (c) physically assembling a plurality of identifier nucleic acid sequences, each having first and second end sequences and a third sequence positioned between the first and second end sequences and corresponding to a respective symbol position, wherein at least one of the first end sequence, second end sequence, and third sequence of at least one additional identifier nucleic acid sequence is identical to a target sequence of the first identifier nucleic acid sequence in (b), so as to enable a single probe to select at least two identifier nucleic acid sequences corresponding to respective symbols having related symbol positions within the string of symbols, and (d) collecting the identifier nucleic acid sequences in (b) and (c) in a pool having powder, liquid, or solid form.

In another aspect, the present disclosure provides a method for storing digital information into nucleic acid sequences, the method comprising: (a) receiving the digital information as a string of symbols, wherein each symbol in the string of symbols has a symbol value and a symbol position within the string of symbols; (b) dividing the string of symbols into one or more blocks of size no greater than a fixed length; (c) forming a first identifier nucleic acid sequence by depositing M selected component nucleic acid sequences into a compartment, the M selected component nucleic acid sequences being selected from a set of distinct component nucleic acid sequences that are separated into M different layers; (d) physically assembling a plurality of identifier nucleic acid sequences, each having first and second end sequences and a third sequence positioned between the first and second end sequences and corresponding to a respective symbol position, wherein at least one of the first end sequence, second end sequence, and third sequence of at least one additional identifier nucleic acid sequence is identical to a target sequence of the first identifier nucleic acid sequence in (b), so as to enable a single probe to select at least two identifier nucleic acid sequences corresponding to respective symbols having related symbol positions within the string of symbols, and (e) collecting the identifier nucleic acid sequences in (b) and (c) in a pool having powder, liquid, or solid form.

In another aspect, the present disclosure provides a method for storing digital information into nucleic acid sequences, the method comprising: (a) receiving the digital information as a string of symbols, wherein each symbol in the string of symbols has a symbol value and a symbol position within the string of symbols; (b) forming a first identifier nucleic acid sequence by depositing M selected component nucleic acid sequences into a compartment, the M selected component nucleic acid sequences being selected from a set of distinct component nucleic acid sequences that are separated into M different layers; (c) physically assembling a plurality of identifier nucleic acid sequences, each having first and second end sequences and a third sequence positioned between the first and second end sequences and corresponding to a respective symbol position, wherein at least one of the first end sequence, second end sequence, and third sequence of at least one additional identifier nucleic acid sequence is identical to a target sequence of the first identifier nucleic acid sequence in (b), so as to enable a single probe to select at least two identifier nucleic acid sequences corresponding to respective symbols having related symbol positions within the string of symbols; (d) collecting the identifier nucleic acid sequences in (b) and (c) in a pool having powder, liquid, or solid form; and (e) performing a computation involving a Boolean logical operation, including AND, OR, NOT, or NAND, on the string of symbols using the identifier nucleic acid sequences in (d), to produce a new pool of nucleic acid molecules.

In another aspect, the present disclosure provides a method for storing digital information into nucleic acid sequences, the method comprising: (a) receiving the digital information as a string of symbols, wherein each symbol in the string of symbols has a symbol value and a symbol position within the string of symbols; (b) forming a first identifier nucleic acid sequence by: (1) selecting, from a set of distinct component nucleic acid sequences that are separated into M different layers, one component nucleic acid sequence from each of the M layers; (2) depositing the M selected component nucleic acid sequences into a compartment; (c) physically assembling a plurality of identifier nucleic acid sequences, each having first and second end sequences and a third sequence positioned between the first and second end sequences and corresponding to a respective symbol position, wherein at least one of the first end sequence, second end sequence, and third sequence of at least one additional identifier nucleic acid sequence is identical to a target sequence of the first identifier nucleic acid sequence in (b), so as to enable a single probe to select at least two identifier nucleic acid sequences corresponding to respective symbols having related symbol positions within the string of symbols, and (d) collecting the identifier nucleic acid sequences in (b) and (c) in a pool having powder, liquid, or solid form.

In another aspect, the present disclosure provides a method for storing digital information into nucleic acid sequences, the method comprising: (a) receiving the digital information as a string of symbols, wherein each symbol in the string of symbols has a symbol value and a symbol position within the string of symbols; (b) forming a first identifier nucleic acid sequence by: (1) selecting, from a set of distinct component nucleic acid sequences that are separated into M different layers, one component nucleic acid sequence from each of the M layers; (2) depositing the M selected component nucleic acid sequences into a compartment; (3) physically assembling the M selected component nucleic acid sequences in (2) to form the first identifier nucleic acid sequence comprising a specified component, wherein the specified component comprises at least one target sequence, to allow access of the identifier containing the specified component; (c) physically assembling a plurality of additional identifier nucleic acid sequences, each having the specified component, wherein the specified component comprises the at least one target sequence of the first identifier nucleic acid sequence in (b), so as to enable a probe to select at least two identifier nucleic acid sequences corresponding to respective symbols having contiguous symbol positions within the string of symbols, and (d) collecting the identifier nucleic acid sequences in (b) and (c) in a pool having powder, liquid, or solid form.

FIG. 1 illustrates an overview process for encoding information into nucleic acid sequences, writing information to the nucleic acid sequences, reading information written to nucleic acid sequences, and decoding the read information. Digital information, or data, may be translated into one or more strings of symbols. In an example, the symbols are bits and each bit may have a value of either '0' or '1'. Each symbol may be mapped, or encoded, to an object (e.g., identifier) representing that symbol. Each symbol may be represented by a distinct identifier. The distinct identifier may be a nucleic acid molecule made up of components. The components may be nucleic acid sequences. The digital information may be written into nucleic acid sequences by generating an identifier library corresponding to the information. The identifier library may be physically generated by physically constructing the identifiers that correspond to each symbol of the digital information. All or any portion of the digital information may be accessed at a time. In an example, a subset of identifiers is accessed from an identifier library. The subset of identifiers may be read by sequencing and identifying the identifiers. The identified identifiers may be associated with their corresponding symbol to decode the digital data.

A method for encoding and reading information using the approach of FIG. 1 can, for example, include receiving a bit stream and mapping each one-bit (bit with bit-value of '1') in the bit stream to a distinct nucleic acid identifier using an identifier rank or a nucleic acid index. Constructing a nucleic acid sample pool, or identifier library, comprising copies of the identifiers that correspond to bit values of 1 (and excluding identifiers for bit values of 0). Reading the sample can comprise using molecular biology methods (e.g., sequencing, hybridization, PCR, etc), determining which identifiers are represented in the identifier library, and assigning bit-values of '1' to the bits corresponding to those identifiers and bit-values of '0' elsewhere (again referring to the identifier rank to identify the bits in the original bit-stream that each identifier corresponds to), thus decoding the information into the original encoded bit stream.

Encoding a string of N distinct bits, can use an equivalent number of unique nucleic acid sequences as possible identifiers. This approach to information encoding may use de-novo synthesis of identifiers (e.g., nucleic acid molecules) for each new item of information (string of N bits) to store. In other instances, the cost of newly synthesizing identifiers (equivalent in number to or less than N) for each new item of information to store can be reduced by the one-time de-novo synthesis and subsequent maintenance of all possible identifiers, such that encoding new items of information may involve mechanically selecting and mixing together pre-synthesized (or pre-fabricated) identifiers to form an identifier library. In other instances, both the cost of (1) de-novo synthesis of up to N identifiers for each new item of information to store or (2) maintaining and selecting from N possible identifiers for each new item of information to store, or any combination thereof may be reduced by synthesizing and maintaining a number (less than N, and in some cases much less than N) of nucleic acid sequences and then modifying these sequences through enzymatic reactions to generate up to N identifiers for each new item of information to store.

The identifiers may be rationally designed and selected for ease of read, write, access, copy, and deletion operations. The identifiers may be designed and selected to minimize write errors, mutations, degradation, and read errors. See Chemical Methods Section on the rational design of DNA sequences that comprise synthetic nucleic acid libraries (such as identifier libraries)

Figure 2A:
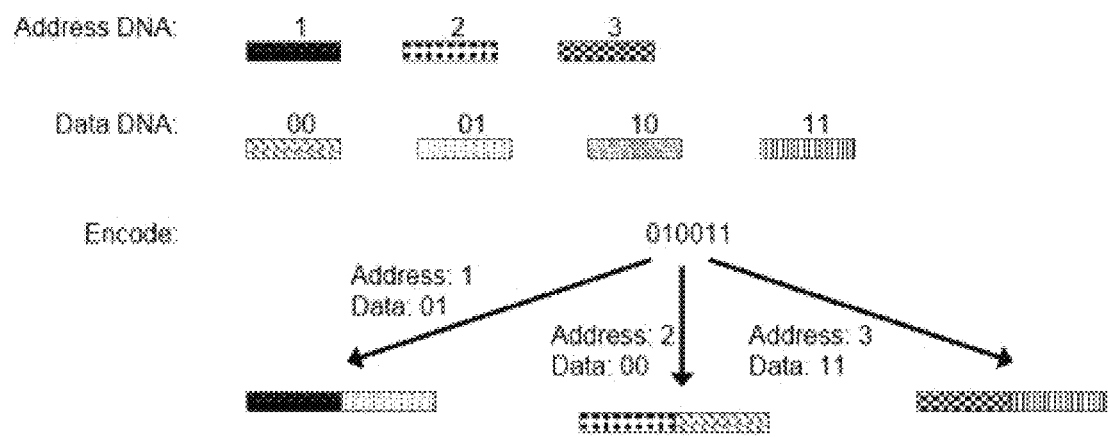
FIGS. 2A and 2B schematically illustrate an example method of encoding digital data, referred to as "data at address", using objects or identifiers (e.g., nucleic acid molecules)
Figure 2B:
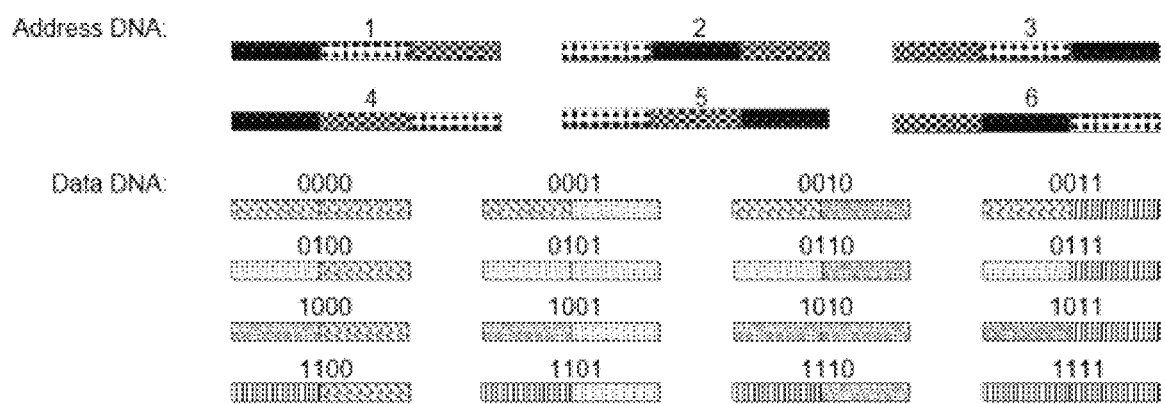

FIGS. 2A and 2B schematically illustrate an example method, referred to as "data at address", of encoding digital data in objects or identifiers (e.g., nucleic acid molecules). FIG. 2A illustrates encoding a bit stream into an identifier library wherein the individual identifiers are constructed by concatenating or assembling a single component that specifies an identifier rank with a single component that specifies a byte-value. In general, the data at address method uses identifiers that encode information modularly by comprising two objects: one object, the "byte-value object" (or "data object"), that identifies a byte-value and one object, the "rank object" (or "address object"), that identifies the identifier rank (or the relative position of the byte in the original bit-stream). FIG. 2B illustrates an example of the data at address method wherein each rank object may be combinatorially constructed from a set of components and each byte-value object may be combinatorially constructed from a set of components. Such combinatorial construction of rank and byte-value objects enables more information to be written into identifiers than if the objects where made from the single components alone (e.g., FIG. 2A).

Figure 3A:
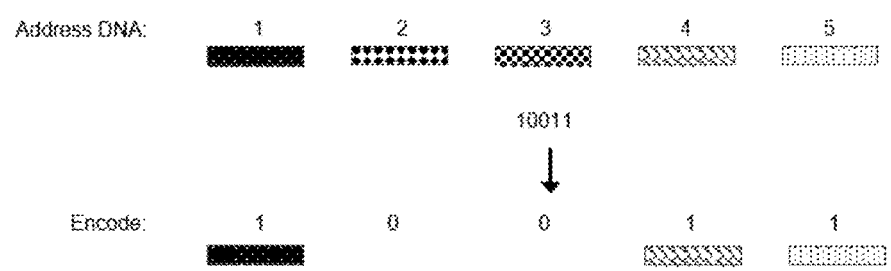
FIGS. 3A and 3B schematically illustrate an example method of encoding digital information using objects or identifiers (e.g., nucleic acid sequences)
Figure 3B:
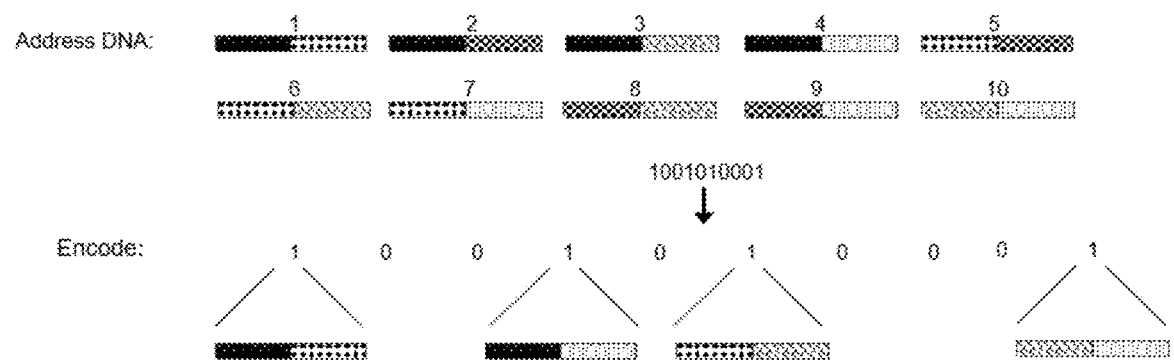

FIGS. 3A and 3B schematically illustrate another example method of encoding digital information in objects or identifiers (e.g., nucleic acid sequences). FIG. 3A illustrates encoding a bit stream into an identifier library wherein identifiers are constructed from single components that specify identifier rank. The presence of an identifier at a particular rank (or address) specifies a bit-value of '1' and the absence of an identifier at a particular rank (or address) specifies a bit-value of '0'. This type of encoding may use identifiers that solely encode rank (the relative position of a bit in the original bit stream) and use the presence or absence of those identifiers in an identifier library to encode a bit-value of '1' or '0', respectively. Reading and decoding the information may include identifying the identifiers present in the identifier library, assigning bit-values of '1' to their corresponding ranks and assigning bit-values of '0' elsewhere. FIG. 3B illustrates an example encoding method where each identifier may be combinatorially constructed from a set of components such that each possible combinatorial construction specifies a rank. Such combinatorial construction enables more information to be written into identifiers than if the identifiers where made from the single components alone (e.g., FIG. 3A). For example, a component set may comprise five distinct components. The five distinct components may be assembled to generate ten distinct identifiers, each comprising two of the five components. The ten distinct identifiers may each have a rank (or address) that corresponds to the position of a bit in a bit stream. An identifier library may include the subset of those ten possible identifiers that corresponds to the positions of bit-value '1', and exclude the subset of those ten possible identifiers that corresponds to the positions of the bit-value '0' within a bit stream of length ten.

Figure 4:
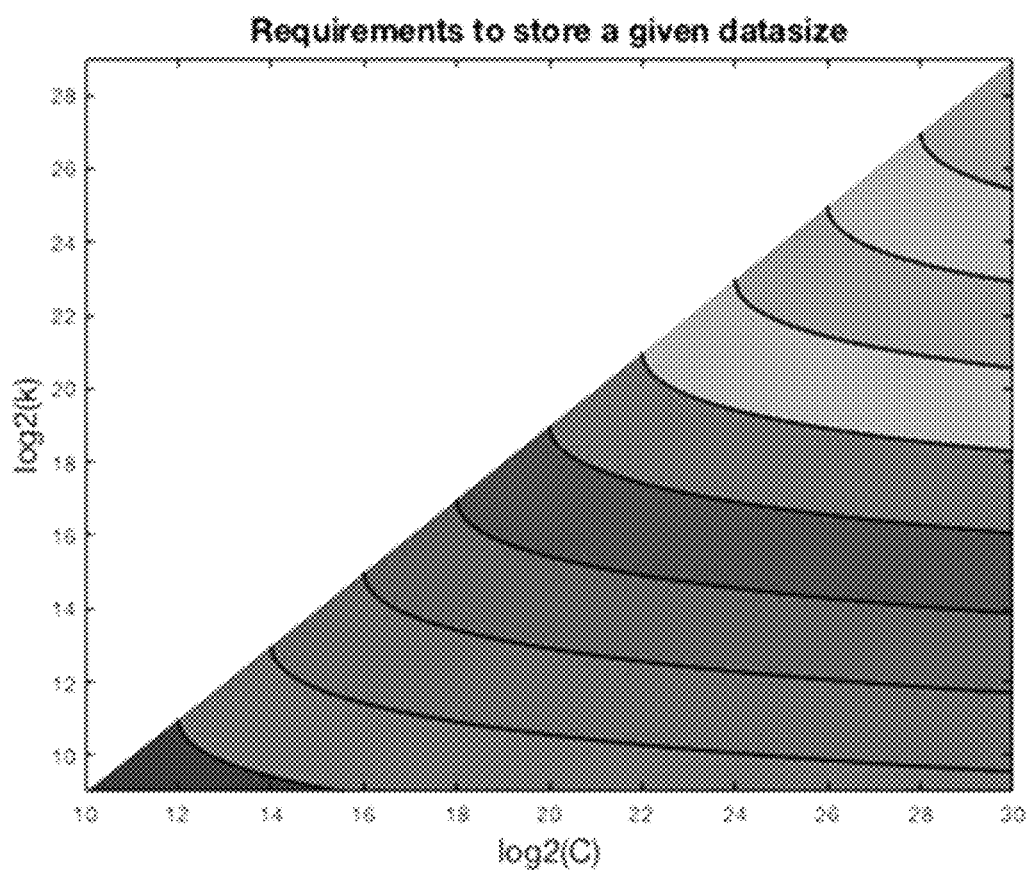
FIG. 4 shows a contour plot, in log space, of a relationship between the combinatorial space of possible identifiers (C, x-axis) and the average number of identifiers (k, y-axis) that may be constructed to store information of a given size (contour lines)

FIG. 4 shows a contour plot, in log space, of a relationship between the combinatorial space of possible identifiers (C, x-axis) and the average number of identifiers (k, y-axis) to be physically constructed in order to store information of a given original size in bits (D, contour lines) using the encoding method shown in FIGS. 3A and 3B. This plot assumes that the original information of size D is re-coded into a string of C bits (where C may be greater than D) where a number of bits, k has a bit-value of '1'. Moreover, the plot assumes that information-to-nucleic-acid encoding is performed on the re-coded bit string and that identifiers for positions where the bit-value is are constructed and identifiers for positions where the bit-value is '0' are not constructed. Following the assumptions, the combinatorial space of possible identifiers has size C to identify every position in the re-coded bit string, and the number of identifiers used to encode the bit string of size D is such that $D=\log_2(Cchoosek)$, where Cchoosek may be the mathematical formula for the number of ways to pick k unordered outcomes from C possibilities. Thus, as the combinatorial space of possible identifiers increases beyond the size (in bits)) of a given item of information, a decreasing number of physically constructed identifiers may be used to store the given information.

Figure 5:
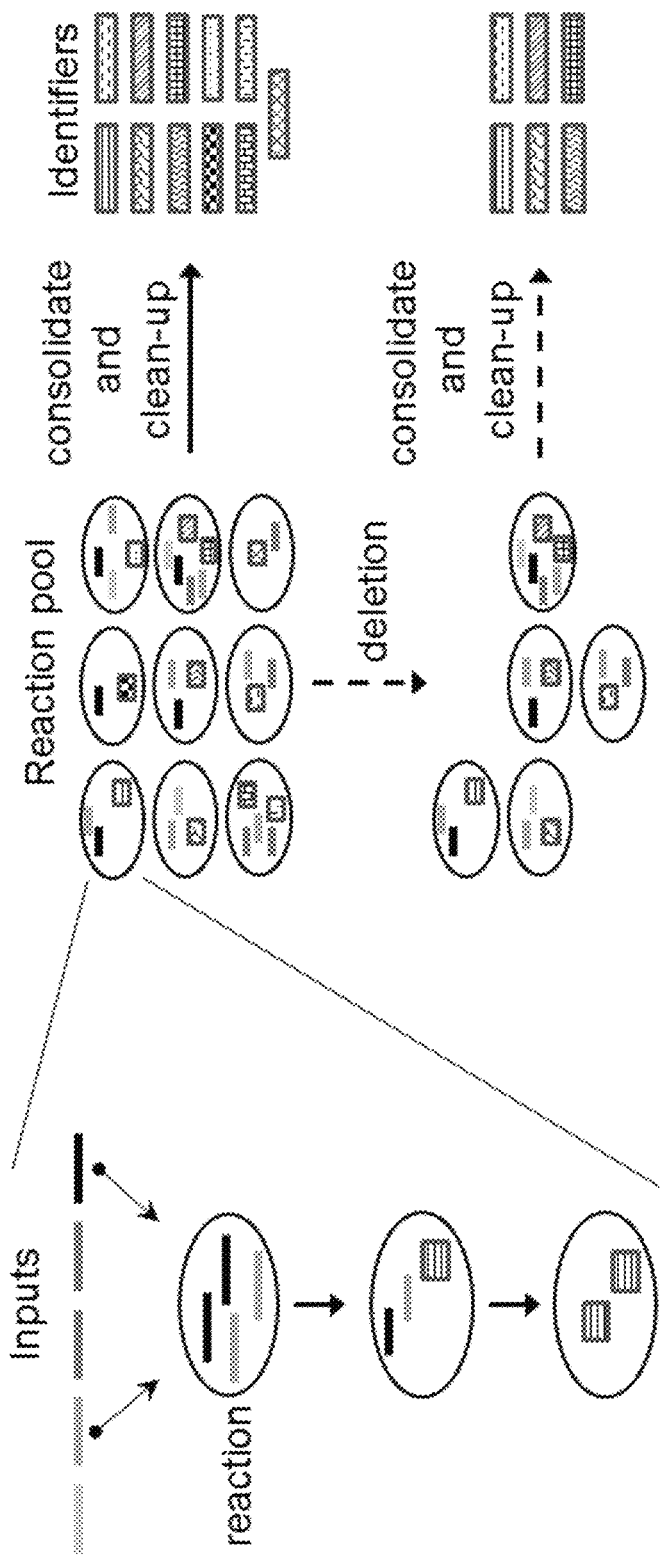
FIG. 5 schematically illustrates an overview of a method for writing information to nucleic acid sequences (e.g., deoxyribonucleic acid)

FIG. 5 shows an overview method for writing information into nucleic acid sequences. Prior to writing the information, the information may be translated into a string of symbols and encoded into a plurality of identifiers. Writing the information may include setting up reactions to produce possible identifiers. A reaction may be set up by depositing inputs into a compartment. The inputs may comprise nucleic acids, components, templates, enzymes, or chemical reagents. The compartment may be a well, a tube, a position on a surface, a chamber in a microfluidic device, or a droplet within an emulsion. Multiple reactions may be set up in multiple compartments. Reactions may proceed to produce identifiers through programmed temperature incubation or cycling. Reactions may be selectively or ubiquitously removed (e.g., deleted). Reactions may also be selectively or ubiquitously interrupted, consolidated, and purified to collect their identifiers in one pool. Identifiers from multiple identifier libraries may be collected in the same pool. An individual identifier may include a barcode or a tag to identify to which identifier library it belongs. Alternatively, or in addition to, the barcode may include metadata for the encoded information. Supplemental nucleic acids or identifiers may also be included in an identifier pool together with an identifier library. The supplemental nucleic acids or identifiers may include metadata for the encoded information or serve to obfuscate or conceal the encoded information.

An identifier rank (e.g., nucleic acid index) can comprise a method or key for determining the ordering of identifiers. The method can comprise a look-up table with all identifiers and their corresponding rank. The method can also comprise a look up table with the rank of all components that constitute identifiers and a function for determining the ordering of any identifier comprising a combination of those components. Such a method may be referred to as lexicographical ordering and may be analogous to the manner in which words in a dictionary are alphabetically ordered. In the data at address encoding method, the identifier rank (encoded by the rank object of the identifier) may be used to determine the position of a byte (encoded by the byte-value object of the identifier) within a bit stream. In an alternative method, the identifier rank (encoded by the entire identifier itself) for a present identifier may be used to determine the position of bit-value of '1' within a bit stream.

A key may assign distinct bytes to unique subsets of identifiers (e.g., nucleic acid molecules) within a sample. For example, in a simple form, a key may assign each bit in a byte to a unique nucleic acid sequence that specifies the position of the bit, and then the presence or absence of that nucleic acid sequence within a sample may specify the bit-value of 1 or 0, respectively. Reading the encoded information from the nucleic acid sample can comprise any number of molecular biology techniques including sequencing, hybridization, or PCR. In some embodiments, reading the encoded dataset may comprise reconstructing a portion of the dataset or reconstructing the entire encoded dataset from each nucleic acid sample. When the sequence may be read the nucleic acid index can be used along with the presence or absence of a unique nucleic acid sequence and the nucleic acid sample can be decoded into a bit stream (e.g., each string of bits, byte, bytes, or string of bytes).

Identifiers may be constructed by combinatorially assembling component nucleic acid sequences. For example, information may be encoded by taking a set of nucleic acid molecules (e.g., identifiers) from a defined group of molecules (e.g., combinatorial space). Each possible identifier of the defined group of molecules may be an assembly of nucleic acid sequences (e.g., components) from a prefabricated set of components that may be divided into layers. Each individual identifier may be constructed by concatenating one component from every layer in a fixed order. For example, if there are M layers and each layer may have n components, then up to $C=n^M$ unique identifiers may be constructed and up to $2^C$ different items of information, or C bits, may be encoded and stored. For example, storage of a megabit of information may use $1\times10^6$ distinct identifiers or a combinatorial space of size $C=1\times10^6$. The identifiers in this example may be assembled from a variety of components organized in different ways. Assemblies may be made from $M=2$ prefabricated layers, each containing $n=1\times10^3$ components. Alternatively, assemblies may be made from $M=3$ layers, each containing $n=1\times10^2$ components. In some implementations, assemblies may be made from $M=2$, $M=3$, $M=4$, $M=5$ or more layers. As this example illustrates, encoding the same amount of information using a larger number of layers may allow for the total number of components to be smaller. Using a smaller number of total components may be advantageous in terms of writing cost.

In an example, one can start with two sets of unique nucleic acid sequences or layers, X and Y, each with x and y components (e.g., nucleic acid sequences), respectively. Each nucleic acid sequence from X can be assembled to each nucleic acid sequence from Y. Though the total number of nucleic acid sequences maintained in the two sets may be the sum of x and y, the total number of nucleic acid molecules, and hence possible identifiers, that can be generated may be the product of x and y. Even more nucleic acid sequences (e.g., identifiers) can be generated if the sequences from X can be assembled to the sequences of Y in any order. For example, the number of nucleic acid sequences (e.g., identifiers) generated may be twice the product of x and y if the assembly order is programmable. This set of all possible nucleic acid sequences that can be generated may be referred to as XY. The order of the assembled units of unique nucleic acid sequences in XY can be controlled using nucleic acids with distinct 5' and 3' ends, and restriction digestion, ligation, polymerase chain reaction (PCR), and sequencing may occur with respect to the distinct 5' and 3' ends of the sequences. Such an approach can reduce the total number of nucleic acid sequences (e.g., components) used to encode N distinct bits, by encoding information in the combinations and orders of their assembly products. For example, to encode 100 bits of information, two layers of 10 distinct nucleic acid molecules (e.g., component) may be assembled in a fixed order to produce 10*10 or 100 distinct nucleic acid molecules (e.g., identifiers), or one layer of 5 distinct nucleic acid molecules (e.g., components) and another layer of 10 distinct nucleic acid molecules (e.g., components) may be assembled in any order to produce 100 distinct nucleic acid molecules (e.g., identifiers).

Nucleic acid sequences (e.g., components) within each layer may comprise a unique (or distinct) sequence, or barcode, in the middle, a common hybridization region on one end, and another common hybridization region on another other end. The barcode may contain a sufficient number of nucleotides to uniquely identify every sequence within the layer. For example, there are typically four possible nucleotides for each base position within a barcode. Therefore, a three base barcode may uniquely identify $4^3=64$ nucleic acid sequences. The barcodes may be designed to be randomly generated. Alternatively, the barcodes may be designed to avoid sequences that may create complications to the construction chemistry of identifiers or sequencing. Additionally, barcodes may be designed so that each may have a minimum hamming distance from the other barcodes, thereby decreasing the likelihood that base-resolution mutations or read errors may interfere with the proper identification of the barcode. See Chemical Methods Section H on the rational design of DNA sequences.

The hybridization region on one end of the nucleic acid sequence (e.g., component) may be different in each layer, but the hybridization region may be the same for each member within a layer. Adjacent layers are those that have complementary hybridization regions on their components that allow them to interact with one another. For example, any component from layer X may be able to attach to any component from layer Y because they may have complementary hybridization regions. The hybridization region on the opposite end may serve the same purpose as the hybridization region on the first end. For example, any component from layer Y may attach to any component of layer X on one end and any component of layer Z on the opposite end.

Figure 6A:
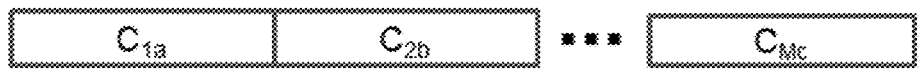
FIGS. 6A and 6B illustrate an example method, referred to as the "product scheme", for constructing identifiers (e.g., nucleic acid molecules) by combinatorially assembling distinct components (e.g., nucleic acid sequences)
Figure 6B:
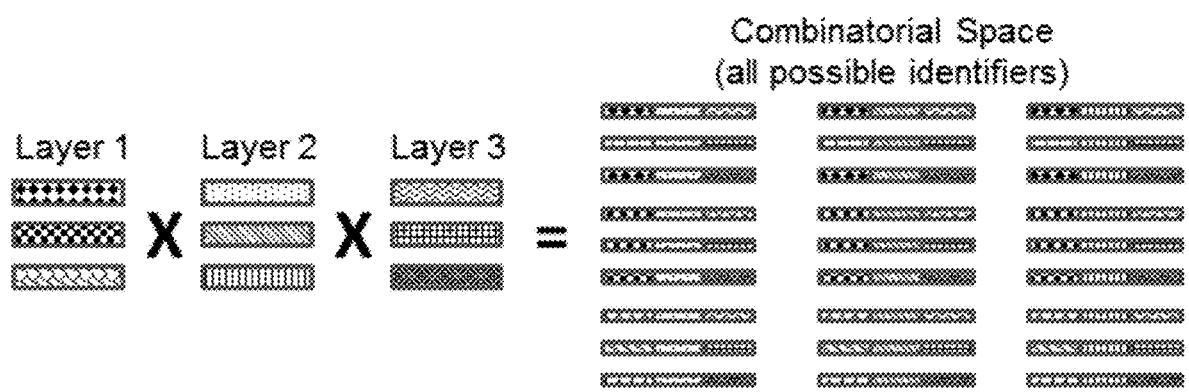

FIGS. 6A and 6B illustrate an example method, referred to as the "product scheme", for constructing identifiers (e.g., nucleic acid molecules) by combinatorially assembling a distinct component (e.g., nucleic acid sequence) from each layer in a fixed order. FIG. 6A illustrates the architecture of identifiers constructed using the product scheme. An identifier may be constructed by combining a single component from each layer in a fixed order. For M layers, each with N components, there are $N^M$ possible identifiers. FIG. 6B illustrates an example of the combinatorial space of identifiers that may be constructed using the product scheme. In an example, a combinatorial space may be generated from three layers each comprising three distinct components. The components may be combined such that one component from each layer may be combined in a fixed order. The entire combinatorial space for this assembly method may comprise twenty-seven possible identifiers.

FIGS. 7-10 illustrate chemical methods for implementing the product scheme (see FIG. 6). Methods depicted in FIGS. 7-10, along with any other methods for assembling two or more distinct components in a fixed order may be used, for example, to produce any one or more identifiers in an identifier library. Identifiers may be constructed using any of the implementation methods described in FIGS. 7-10, at any time during the methods or systems disclosed herein. In some instances, all or a portion of the combinatorial space of possible identifiers may be constructed before digital information is encoded or written, and then the writing process may involve mechanically selecting and pooling the identifiers (that encode the information) from the already existing set. In other instances, the identifiers may be constructed after one or more steps of the data encoding or writing process may have occurred (i.e., as information is being written).

Enzymatic reactions may be used to assemble components from the different layers or sets. Assembly can occur in a one pot reaction because components (e.g., nucleic acid sequences) of each layer have specific hybridization or attachment regions for components of adjacent layers. For example, a nucleic acid sequence (e.g., component) X1 from layer X, a nucleic acid sequence Y1 from layer Y, and a nucleic acid sequence Z1 from layer Z may form the assembled nucleic acid molecule (e.g., identifier) X1Y1Z1. Additionally, multiple nucleic acid molecules (e.g., identifiers) may be assembled in one reaction by including multiple nucleic acid sequences from each layer. For example, including both Y1 and Y2 in the one pot reaction of the previous example may yield two assembled products (e.g., identifiers), X1Y1Z1 and X1Y2Z1. This reaction multiplexing may be used to speed up writing time for the plurality of identifiers that are physically constructed. See Chemical Methods Section H for detail about the rational design of DNA sequences as it pertains to assembly efficiency. Assembly of the nucleic acid sequences may be performed in a time period that is less than or equal to about 1 day, 12 hours, 10 hours, 9 hours, 8 hours, 7 hours, 6 hours, 5 hours, 4 hours, 3 hours, 2 hours, or 1 hour. The accuracy of the encoded data may be at least about or equal to about 90%, 95%, 96%, 97%, 98%, 99%, or greater.

Figure 7:
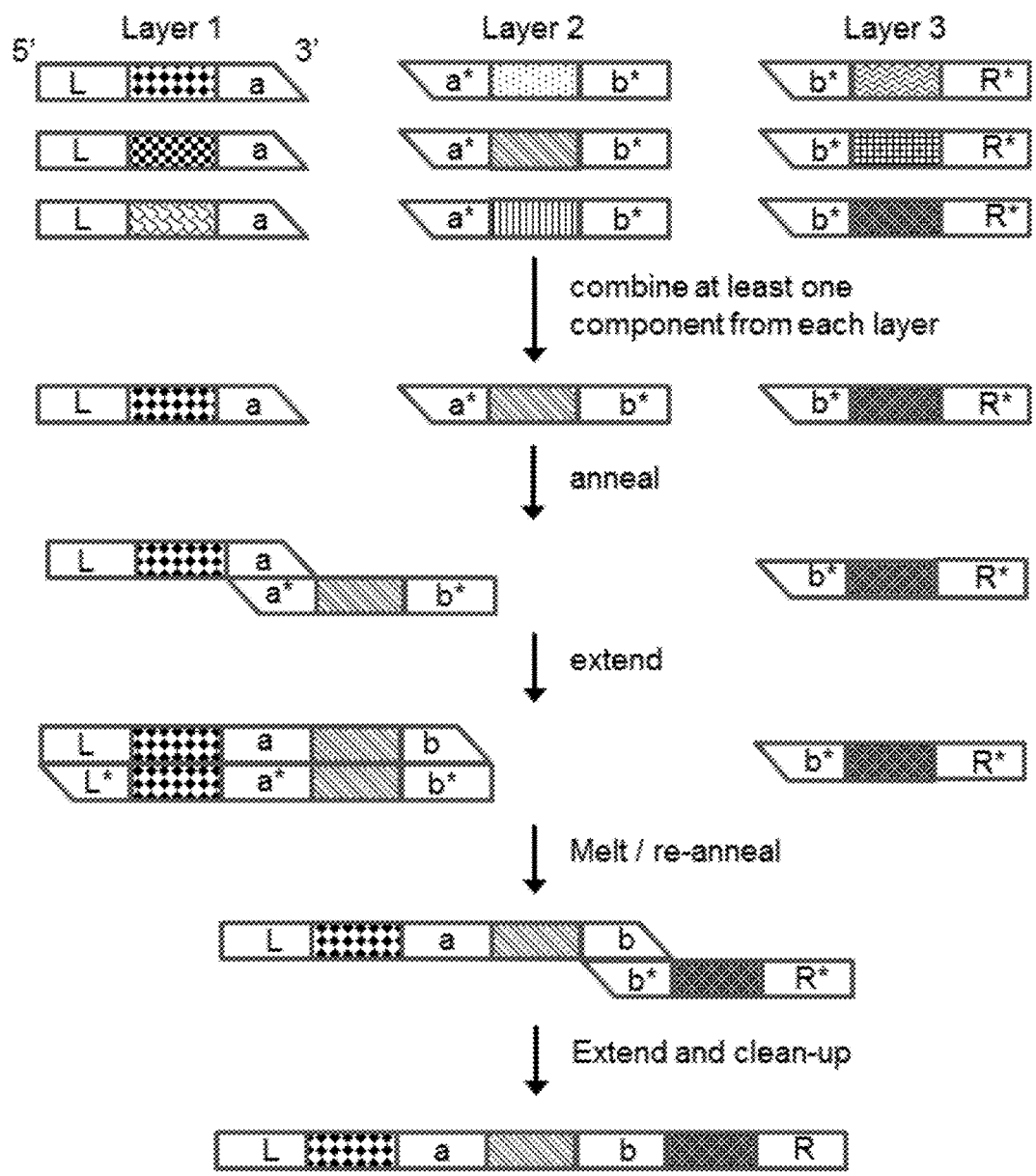
FIG. 7 schematically illustrates the use of overlap extension polymerase chain reaction to construct identifiers (e.g., nucleic acid molecules) from components (e.g., nucleic acid sequences)

Identifiers may be constructed in accordance with the product scheme using overlap extension polymerase chain reaction (OEPCR), as illustrated in FIG. 7. Each component in each layer may comprise a double-stranded or single stranded (as depicted in the figure) nucleic acid sequence with a common hybridization region on the sequence end that may be homologous and/or complementary to the common hybridization region on the sequence end of components from an adjacent layer. An individual identifier may be constructed by concatenating one component (e.g., unique sequence) from a layer X (or layer 1) comprising components $X_1$-$X_A$, a second component (e.g., unique sequence) from a layer Y (or layer 2) comprising $Y_1$-$Y_A$, and a third component (e.g., unique sequence) from layer Z (or layer 3) comprising $Z_1$-$Z_B$. The components from layer X may have a 3' end that shares complementarity with the 3' end on components from layer Y. Thus single-stranded components from layer X and Y may be annealed together at the 3' end and may be extended using PCR to generate a double-stranded nucleic acid molecule. The generated double-stranded nucleic-acid molecule may be melted to generate a 3' end that shares complementarity with a 3' end of a component from layer Z. A component from layer Z may be annealed with the generated nucleic acid molecule and may be extended to generate a unique identifier comprising a single component from layers X, Y, and Z in a fixed order. See Chemical Methods Section A about OEPCR. DNA size selection (e.g., with gel extraction, see Chemical Methods Section E) or polymerase chain reaction (PCR) with primers flanking the outer most layers (see Chemical Methods Section D) may be implemented to isolate fully assembled identifier products from other byproducts that may form in the reaction. Sequential nucleic acid capture with two probes, one for each of the two outermost layers, may also be implemented to isolate fully assembled identifier products from other byproducts that may form in the reaction (see Chemical Methods Section F).

Figure 8:
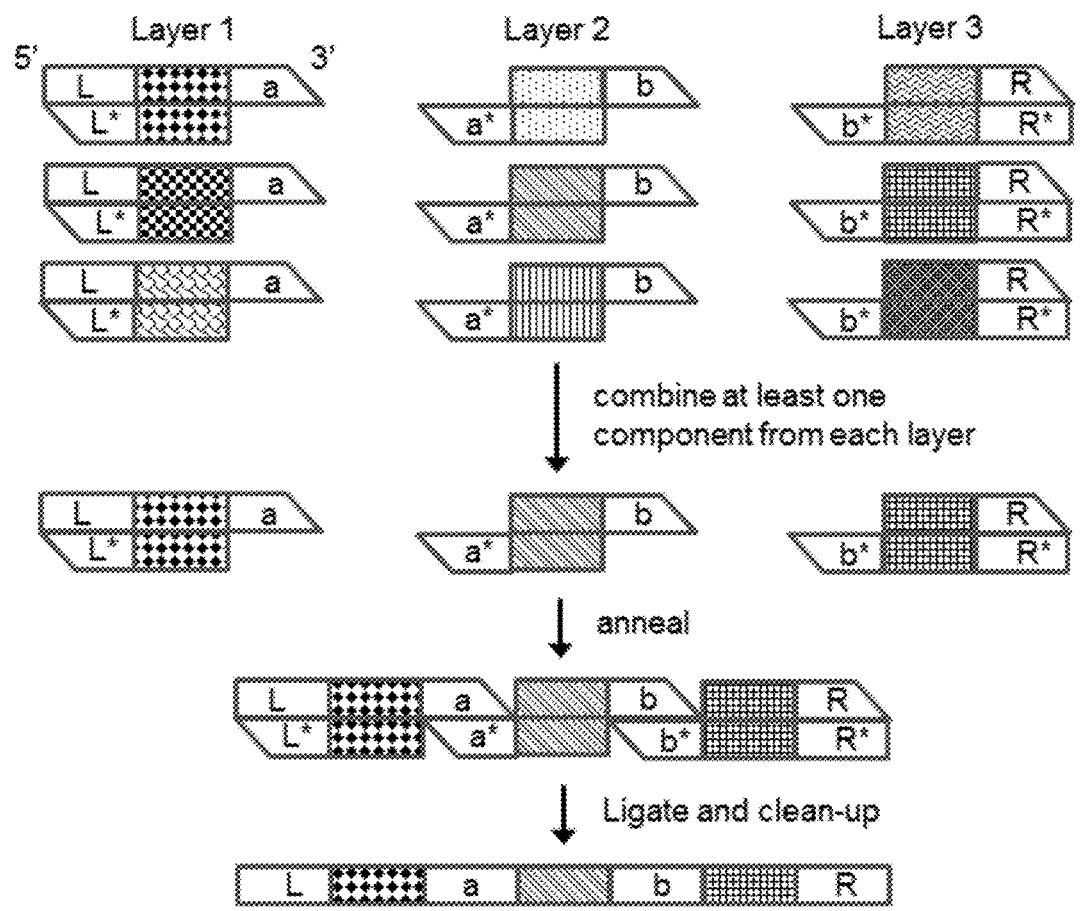
FIG. 8 schematically illustrates the use of sticky end ligation to construct identifiers (e.g., nucleic acid molecules) from components (e.g., nucleic acid sequences)

Identifiers may be assembled in accordance with the product scheme using sticky end ligation, as illustrated in FIG. 8. Three layers, each comprising double stranded components (e.g., double stranded DNA (dsDNA)) with single-stranded 3' overhangs, can be used to assemble distinct identifiers. For example, identifiers comprising one component from the layer X (or layer 1) comprising components $X_1$-$X_A$, a second component from the layer Y (or layer 2) comprising $Y_1$-$Y_B$, and a third component from the layer Z (or layer 3) comprising $Z_1$-$Z_C$. To combine components from layer X with components from layer Y, the components in layer X can comprise a common 3' overhang, FIG. 8 labeled a, and the components in layer Y can comprise a common, complementary 3' overhang, a*. To combine components from layer Y with components from layer Z, the elements in layer Y can comprise a common 3' overhang, FIG. 8 labeled b, and the elements in layer Z can comprise a common, complementary 3' overhang, b*. The 3' overhang in layer X components can be complementary to the 3' end in layer Y components and the other 3' overhang in layer Y components can be complementary to the 3' end in layer Z components allowing the components to hybridize and ligate. As such, components from layer X cannot hybridize with other components from layer X or layer Z, and similarly components from layer Y cannot hybridize with other elements from layer Y. Furthermore, a single component from layer Y can ligate to a single component of layer X and a single component of layer Z, ensuring the formation of a complete identifier. See Chemical Methods Section B about sticky end ligation. DNA size selection (e.g., with gel extraction, see Chemical Methods Section E) or polymerase chain reaction (PCR) with primers flanking the outer most layers (see Chemical Methods Section D) may be implemented to isolate identifier products from other byproducts that may form in the reaction. Sequential nucleic acid capture with two probes, one for each of the two outermost layers, may also be implemented to isolate identifier products from other byproducts that may form in the reaction (see Chemical Methods Section F).

Figure 20:
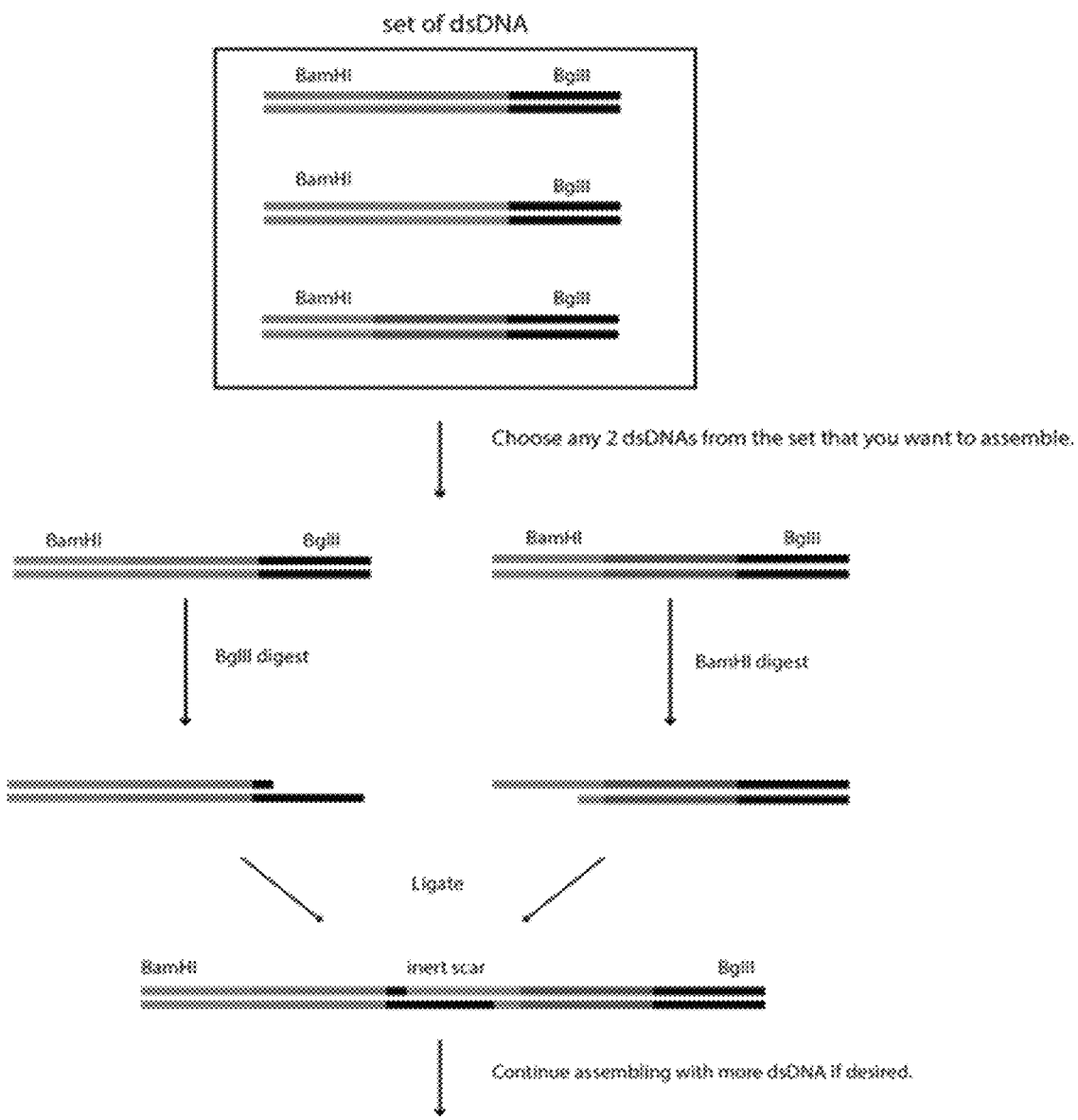
FIG. 20 shows an example scheme of assembly any two selected double-stranded components from a single parent set of double-stranded components.

The sticky ends for sticky end ligation may be generated by treating the components of each layer with restriction endonucleases (see Chemical Methods Section C for more information about restriction enzyme reactions). In some embodiments, the components of multiple layers may be generated from one "parent" set of components. For example, an embodiment wherein a single parent set of double-stranded components may have complementary restrictions sites on each end (e.g., restriction sites for BamHI and BglII). Any two components may be selected for assembly, and individually digested with one or the other complementary restriction enzymes (e.g., BglII or BamHI) resulting in complementary sticky ends that can be ligated together resulting in an inert scar. The product nucleic acid sequence may comprise the complementary restriction sites on each end (e.g., BamHI on the 5' end and BglII on the 3' end), and can be further ligated to another component from the parent set following the same process. This process may cycle indefinitely (FIG. 20). If the parent comprises N components, then each cycle may be equivalent to adding an extra layer of N components to the product scheme.

A method for using ligation to construct a sequence of nucleic acids comprising elements from set X (e.g., set 1 of dsDNA) and elements from set Y (e.g., set 2 of dsDNA) can comprise the steps of obtaining or constructing two or more pools (e.g., set 1 of dsDNA and set 2 of dsDNA) of double stranded sequences wherein a first set (e.g., set 1 of dsDNA) comprises a sticky end (e.g., a) and a second set (e.g., set 2 of dsDNA) comprises a sticky end (e.g., a*) that is complementary to the sticky end of the first set. Any DNA from the first set (e.g., set 1 of dsDNA) and any subset of DNA from the second set (e.g., set 2 of dsDNA) can me combined and assembled and then ligated together to form a single double stranded DNA with an element from the first set and an element from the second set.

Figure 9:
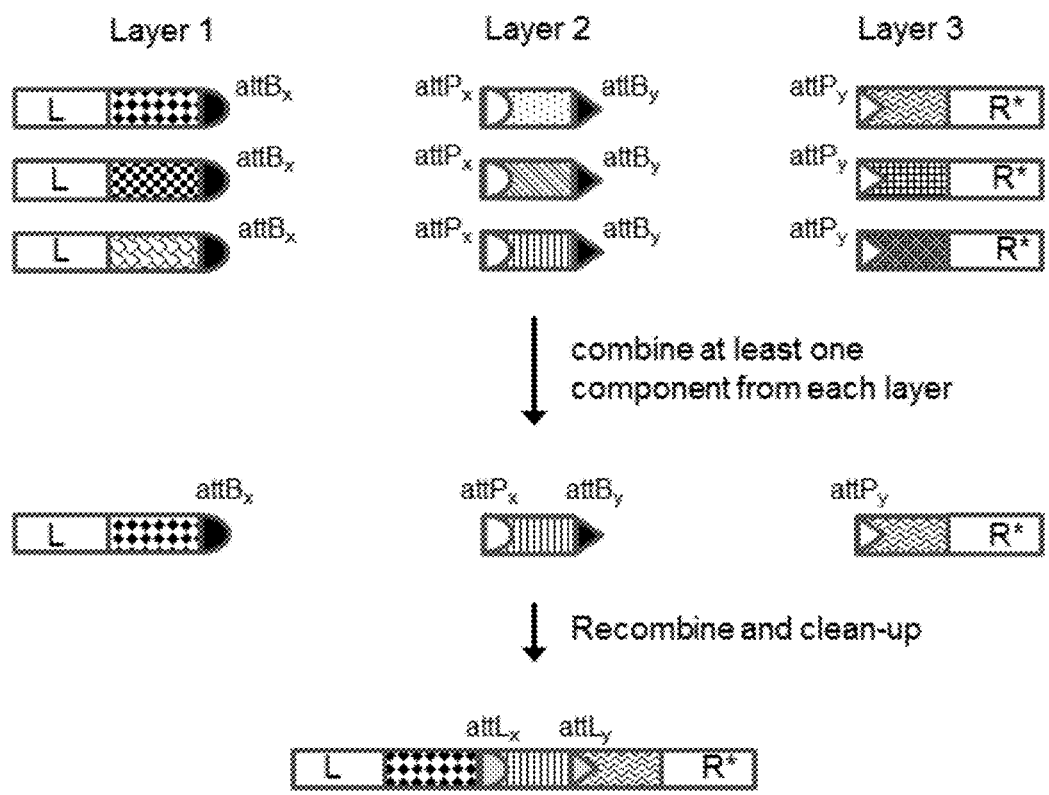
FIG. 9 schematically illustrates the use of recombinase assembly to construct identifiers (e.g., nucleic acid molecules) from components (e.g., nucleic acid sequences)

Identifiers may be assembled in accordance with the product scheme using site specific recombination, as illustrated in FIG. 9. Identifiers may be constructed by assembling components from three different layers. The components in layer X (or layer 1) may comprise double-stranded molecules with an $attB_x$ recombinase site on one side of the molecule, components from layer Y (or layer 2) may comprise double-stranded molecules with an $attP_x$ recombinase site on one side and an $attB_y$ recombinase site on the other side, and components in layer Z (or layer 3) may comprise an $attP_y$ recombinase site on one side of the molecule. attB and attP sites within a pair, as indicate by their subscripts, are capable of recombining in the presence of their corresponding recombinase enzyme. One component from each layer may be combined such that one component from layer X associates with one component from layer Y, and one component from layer Y associates with one component from layer Z. Application of one or more recombinase enzymes may recombine the components to generate a double-stranded identifier comprising the ordered components. DNA size selection (for example with gel extraction) or PCR with primers flanking the outer most layers may be implemented to isolate identifier products from other byproducts that may form in the reaction. In general, multiple orthogonal attB and attP pairs may be used, and each pair may be used to assemble a component from an extra layer. For the large-serine family of recombinases, up to six orthogonal attB and attP pairs may be generated per recombinases, and multiple orthogonal recombinases may be implemented as well. For example, thirteen layers may be assembled by using twelve orthogonal attB and attP pairs, six orthogonal pairs from each of two large serine recombinases, such as BxbI and PhiC31. Orthogonality of attB and attP pairs ensures that an attB site from one pair does not react with an attP site from another pair. This enables components from different layers to be assembled in a fixed order. Recombinase-mediated recombination reactions may be reversible or irreversible depending on the recombinase system implemented. For example, the large serine recombinase family catalyzes irreversible recombination reactions without requiring any high energy cofactors, whereas the tyrosine recombinase family catalyzes reversible reactions.

Figure 10A:
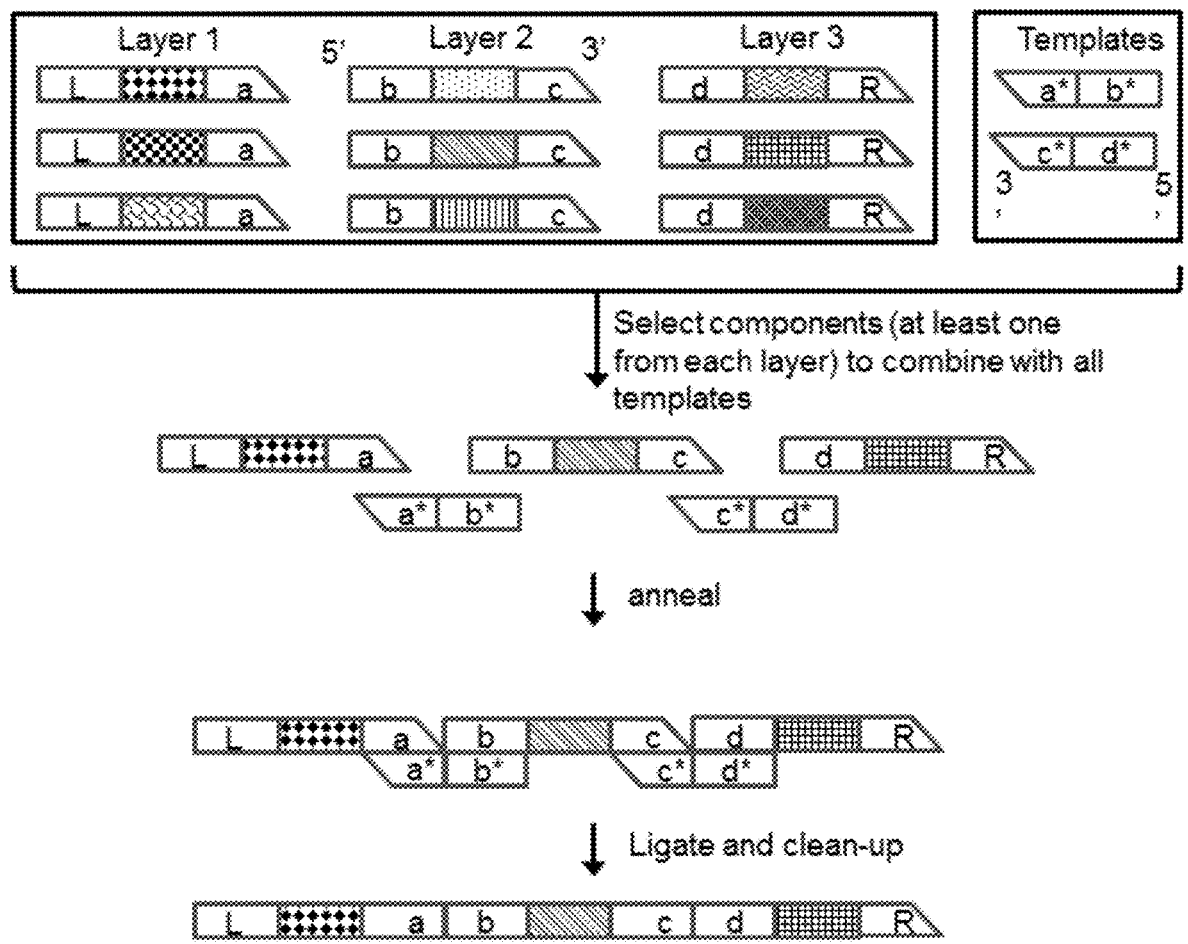
FIGS. 10A and 10B demonstrates template directed ligation.

Identifiers may be constructed in accordance with the product scheme using template directed ligation (TDL), as shown in FIG. 10A. Template directed ligation utilizes single stranded nucleic acid sequences, referred to as "templates" or "staples", to facilitate the ordered ligation of components to form identifiers. The templates simultaneously hybridize to components from adjacent layers and hold them adjacent to each other (3' end against 5' end) while a ligase ligates them. In the example from FIG. 10A, three layers or sets of single-stranded components are combined. A first layer of components (e.g., layer X or layer 1) that share common sequences a on their 3' end, which are complementary to sequences a*; a second layer of components (e.g., layer Y or layer 2) that share common sequences b and c on their 5' and 3' ends respectively, which are complementary to sequences b* and c*; a third layer of components (e.g., layer Z or layer 3) that share common sequence d on their 5' end, which may be complementary to sequences d*; and a set of two templates or "staples" with the first staple comprising the sequence a*b* (5' to 3') and the second staple comprising a sequence c*d* ('5 to 3'). In this example, one or more components from each layer may be selected and mixed into a reaction with the staples, which, by complementary annealing may facilitate the ligation of one component from each layer in a defined order to form an identifier. See Chemical Methods Section B about TDL. DNA size selection (e.g., with gel extraction, see Chemical Methods Section E) or polymerase chain reaction (PCR) with primers flanking the outer most layers (see Chemical Methods Section D) may be implemented to isolate identifier products from other byproducts that may form in the reaction. Sequential nucleic acid capture with two probes, one for each of the two outermost layers, may also be implemented to isolate identifier products from other byproducts that may form in the reaction (see Chemical Methods Section F).

Figure 10B:
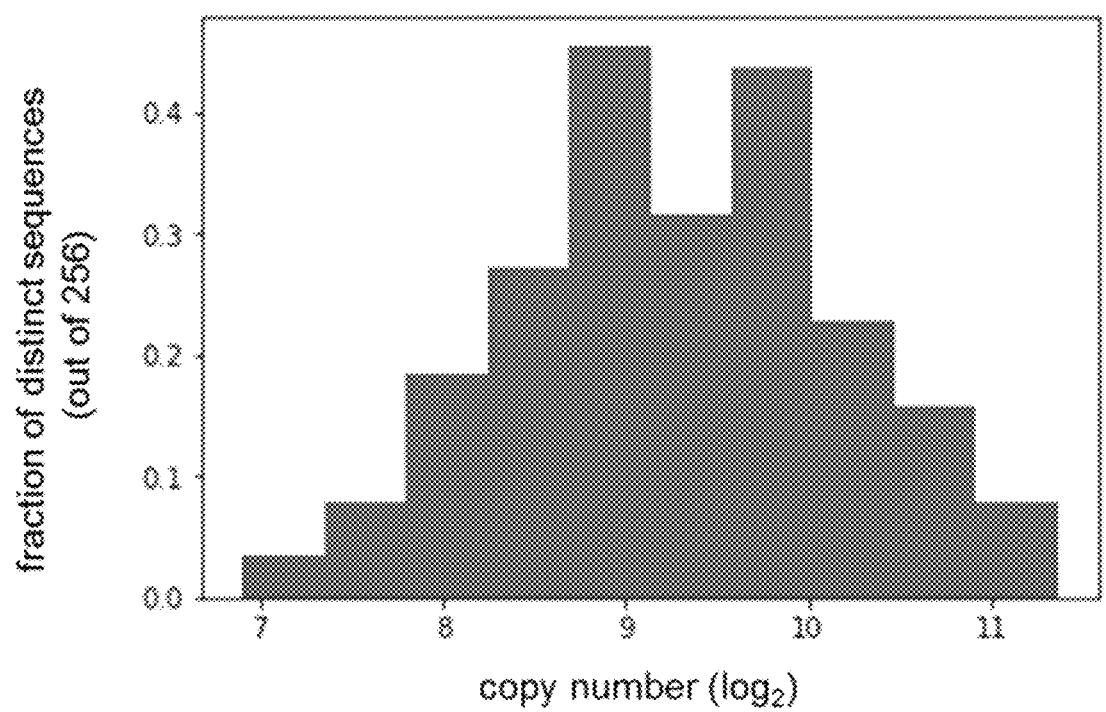

FIG. 10B shows a histogram of the copy numbers (abundances) of 256 distinct nucleic acid sequences that were each assembled with 6-layer TDL. The edge layers (first and final layers) each had one component, and each of the internal layers (remaining 4 four layers) had four components. Each edge layer component was 28 bases including a 10 base hybridization region. Each internal layer component was 30 bases including a 10 base common hybridization region on the 5' end, a 10 base variable (barcode) region, and a 10 base common hybridization region on the 3' end. Each of the three template strands was 20 bases in length. All 256 distinct sequences were assembled in a multiplex fashion with one reaction containing all of the components and templates, T4 Polynucleotide Kinase (for phosphorylating the components), and T4 Ligase, ATP, and other proper reaction reagents. The reaction was incubated at 37 degrees for 30 minutes and then room temperature for 1 hour. Sequencing adapters were added to the reaction product with PCR, and the product was sequenced with an Illumina MiSeq instrument. The relative copy number of each distinct assembled sequence out of 192910 total assembled sequence reads is shown. Other embodiments of this method may use double stranded components, where the components are initially melted to form single stranded versions that can anneal to the staples. Other embodiments or derivatives of this method (i.e., TDL) may be used to construct a combinatorial space of identifiers more complex than what may be accomplished in the product scheme.

Identifiers may be constructed in accordance with the product scheme using various other chemical implementations including golden gate assembly, gibson assembly, and ligase cycling reaction assembly.

Figure 11A:
FIGS. 11A-11G schematically illustrate an example method, referred to as the "permutation scheme", for constructing identifiers (e.g., nucleic acid molecules) with permuted components (e.g., nucleic acid sequences)
Figure 11B:
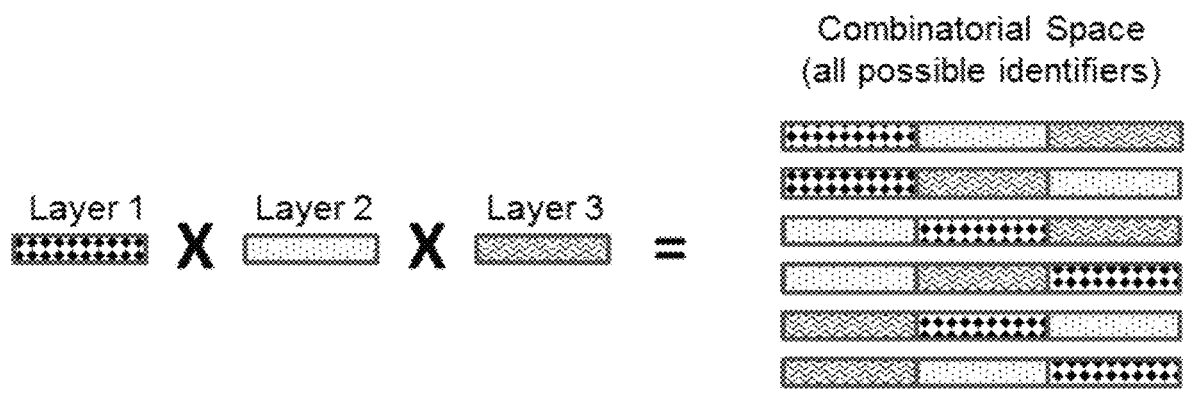

FIGS. 11A and 11B schematically illustrate an example method, referred to as the "permutation scheme", for constructing identifiers (e.g., nucleic acid molecules) with permuted components (e.g., nucleic acid sequences). FIG. 11A illustrates the architecture of identifiers constructed using the permutation scheme. An identifier may be constructed by combining a single component from each layer in a programmable order. FIG. 11B illustrates an example of the combinatorial space of identifiers that may be constructed using the permutation scheme. In an example, a combinatorial space of size six may be generated from three layers each comprising one distinct component. The components may be concatenated in any order. In general, with M layers, each with N components, the permutation scheme enables a combinatorial space $N^M M!$ total identifiers.

Figure 11C:
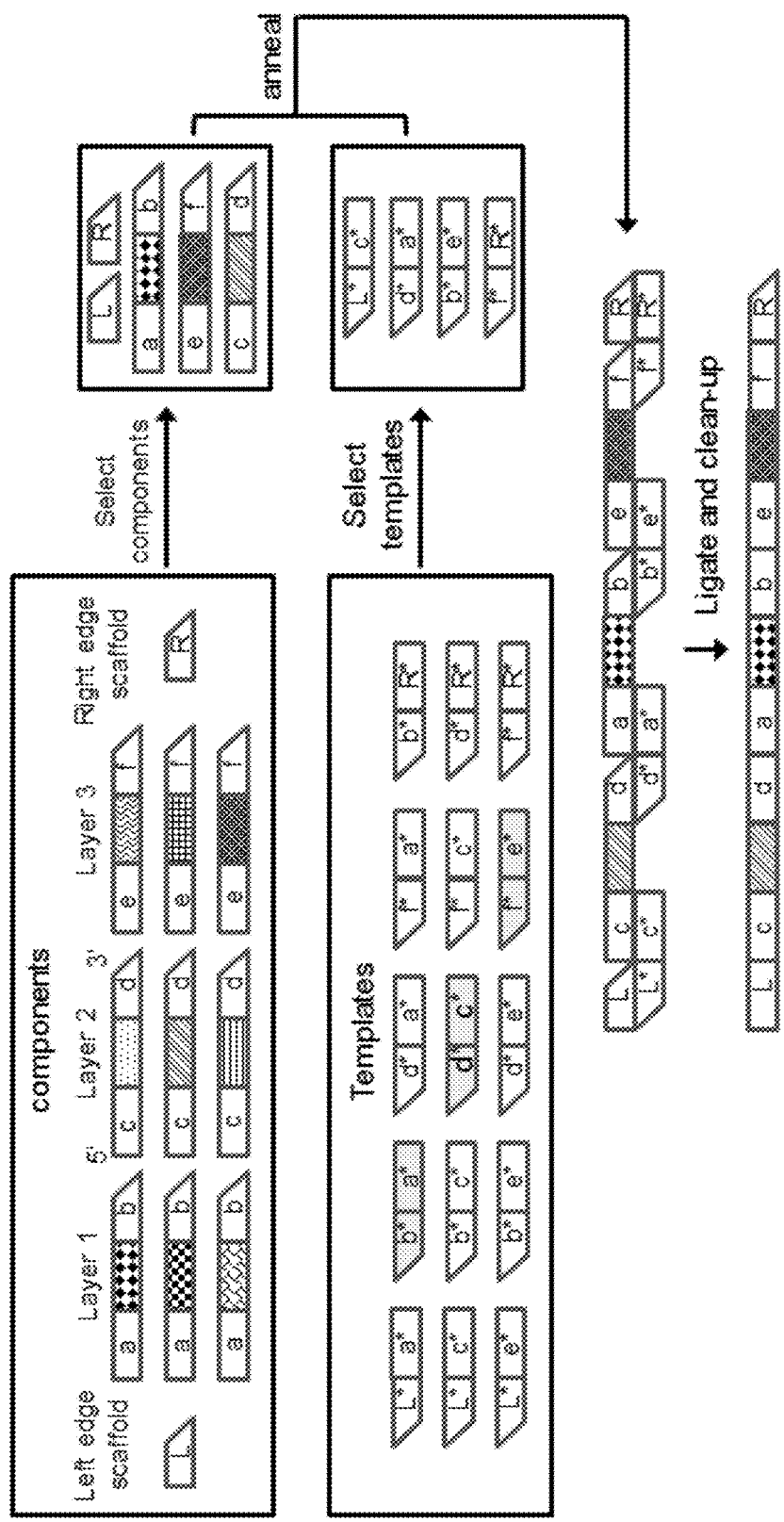

FIG. 11C illustrates an example implementation of the permutation scheme with template directed ligation (TDL, see Chemical Methods Section B). Components from multiple layers are assembled in between fixed left end and right end components, referred to as edge scaffolds. These edge scaffolds are the same for all identifiers in the combinatorial space and thus may be added as part of the reaction master mix for the implementation. Templates or staples exist for any possible junction between any two layers or scaffolds such that the order in which components from different layers are incorporated into an identifier in the reaction depends on the templates selected for the reaction. In order to enable any possible permutation of layers for M layers, there may be $M^2+2M$ distinct selectable staples for every possible junction (including junctions with the scaffolds). M of those templates (shaded in grey) form junctions between layers and themselves and may be excluded for the purposes of permutation assembly as described herein. However, their inclusion can enable a larger combinatorial space with identifiers comprising repeat components as illustrated in FIGS. 11D-G. DNA size selection (e.g., with gel extraction, see Chemical Methods Section E) or polymerase chain reaction (PCR) with primers flanking the outer most layers (see Chemical Methods Section D) may be implemented to isolate identifier products from other byproducts that may form in the reaction. Sequential nucleic acid capture with two probes, one for each of the two outermost layers, may also be implemented to isolate identifier products from other byproducts that may form in the reaction (see Chemical Methods Section F).

Figure 11D:
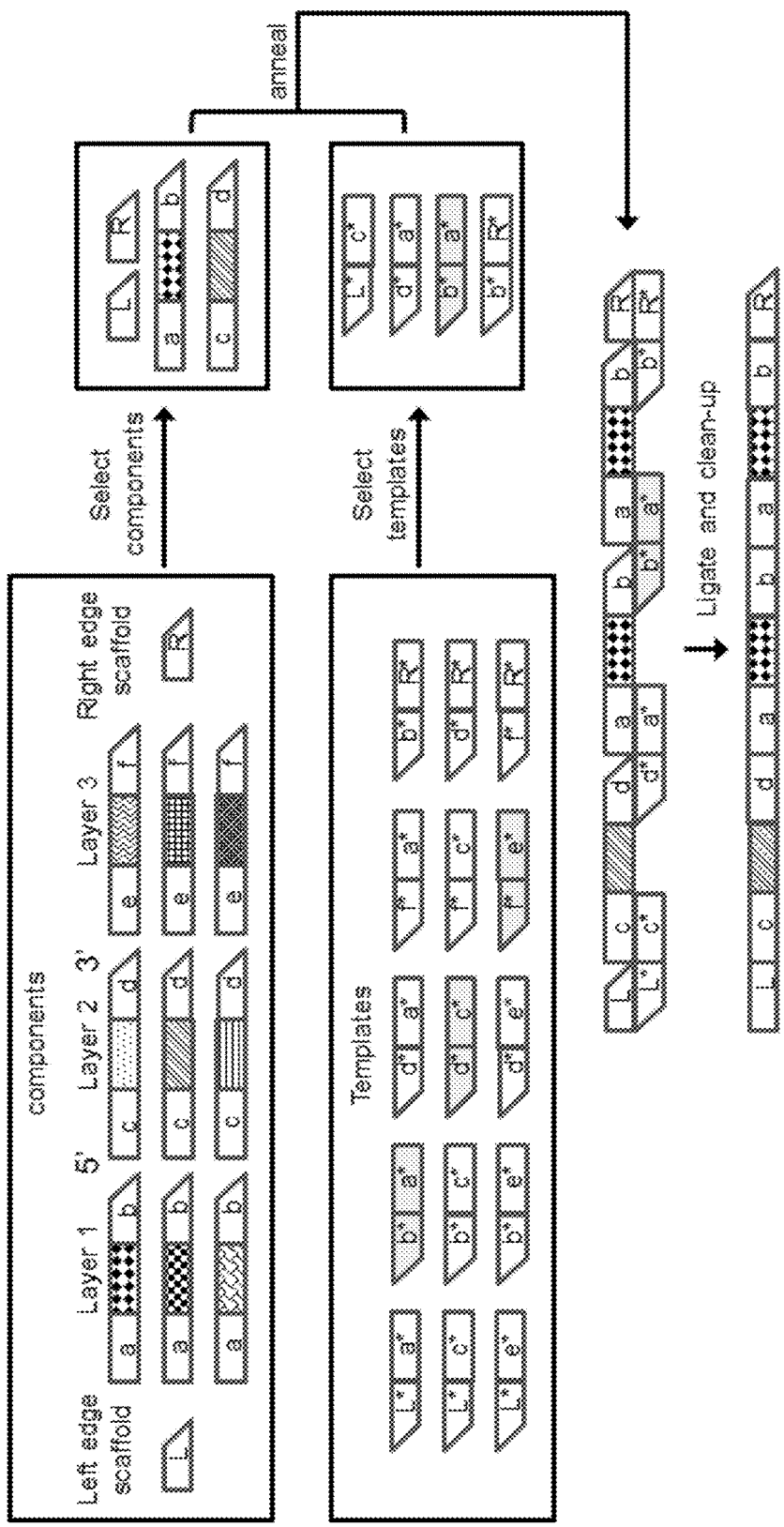
Figure 11E:
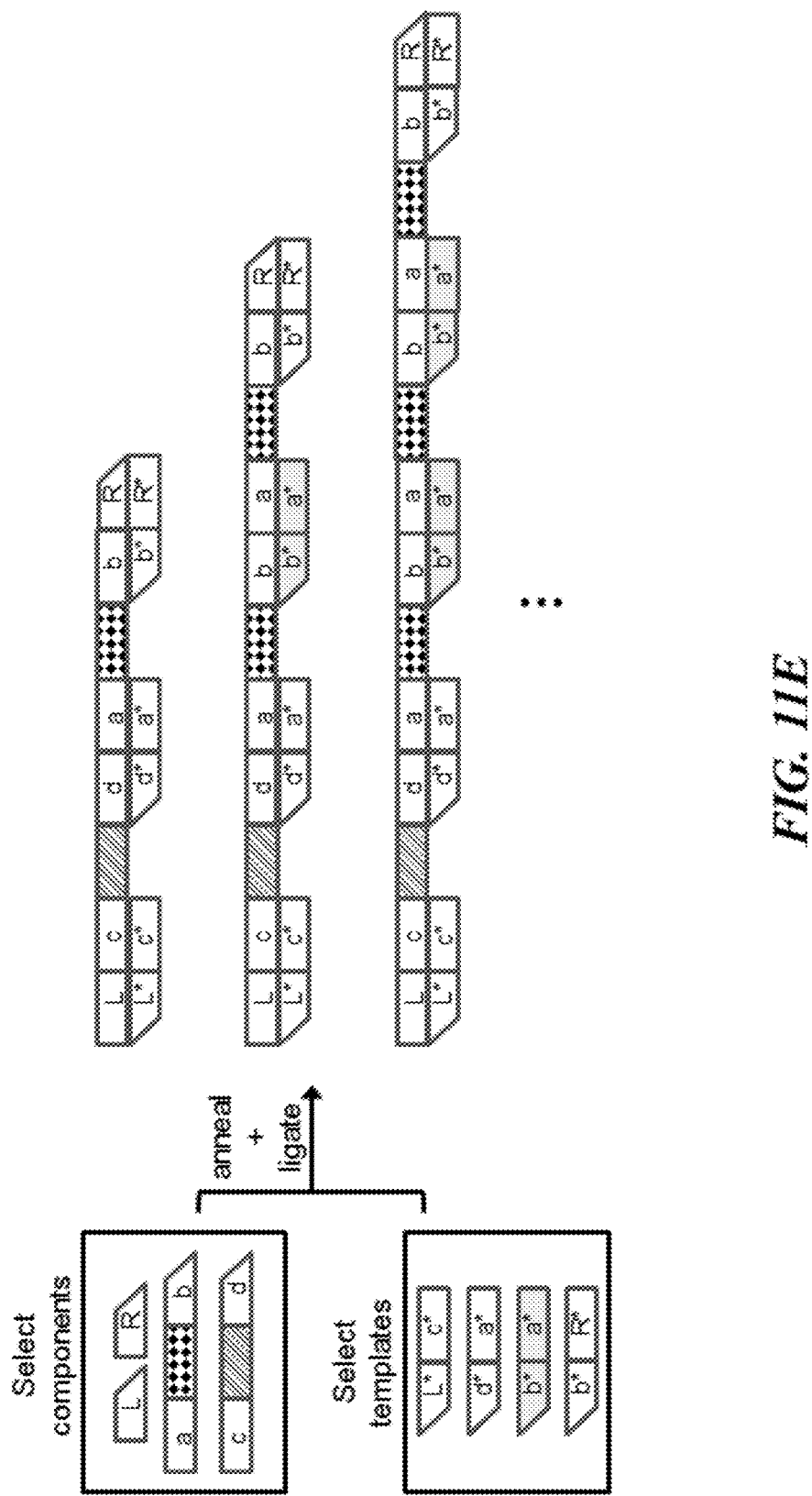
Figure 11F:
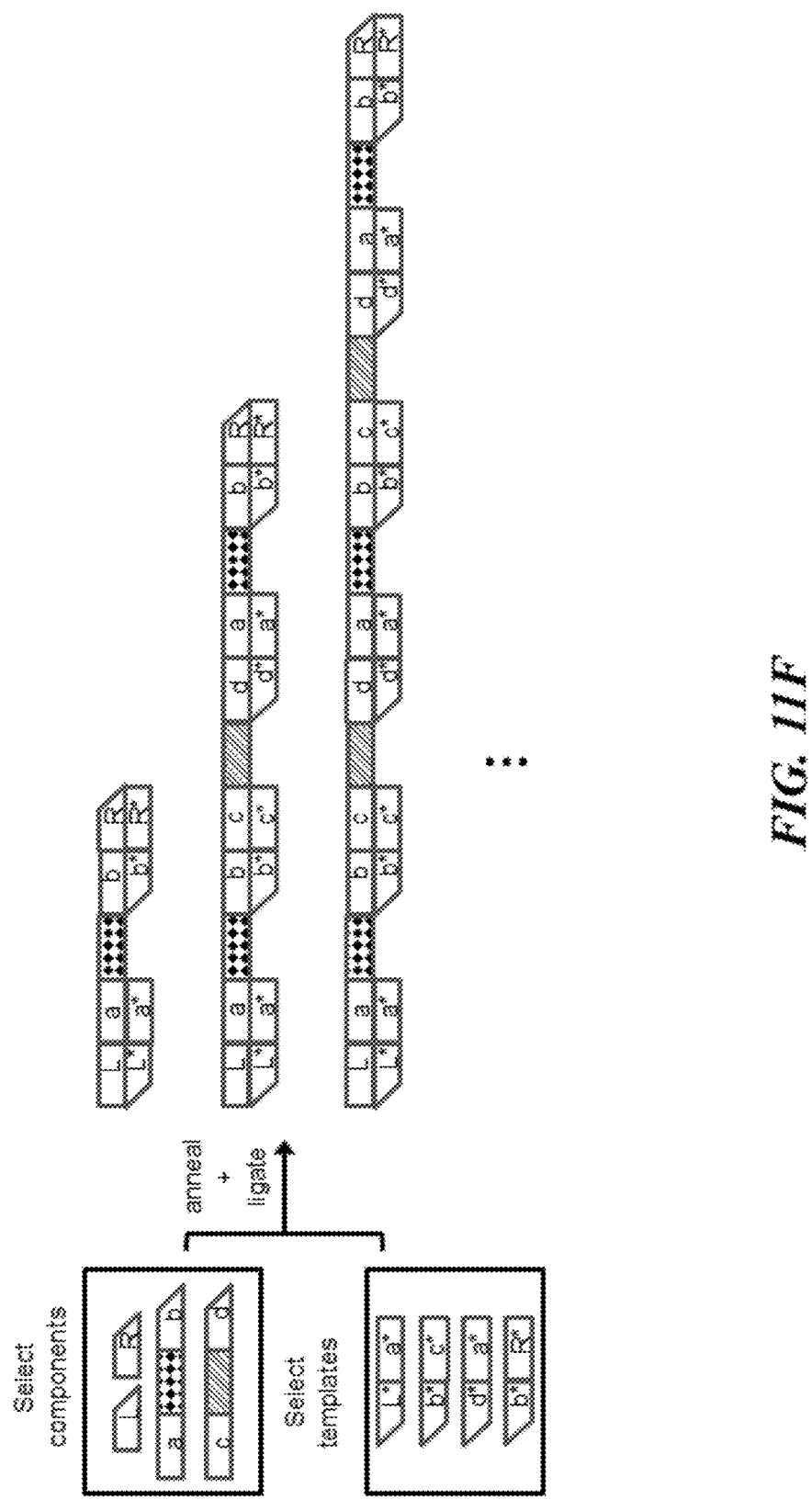
Figure 11G:
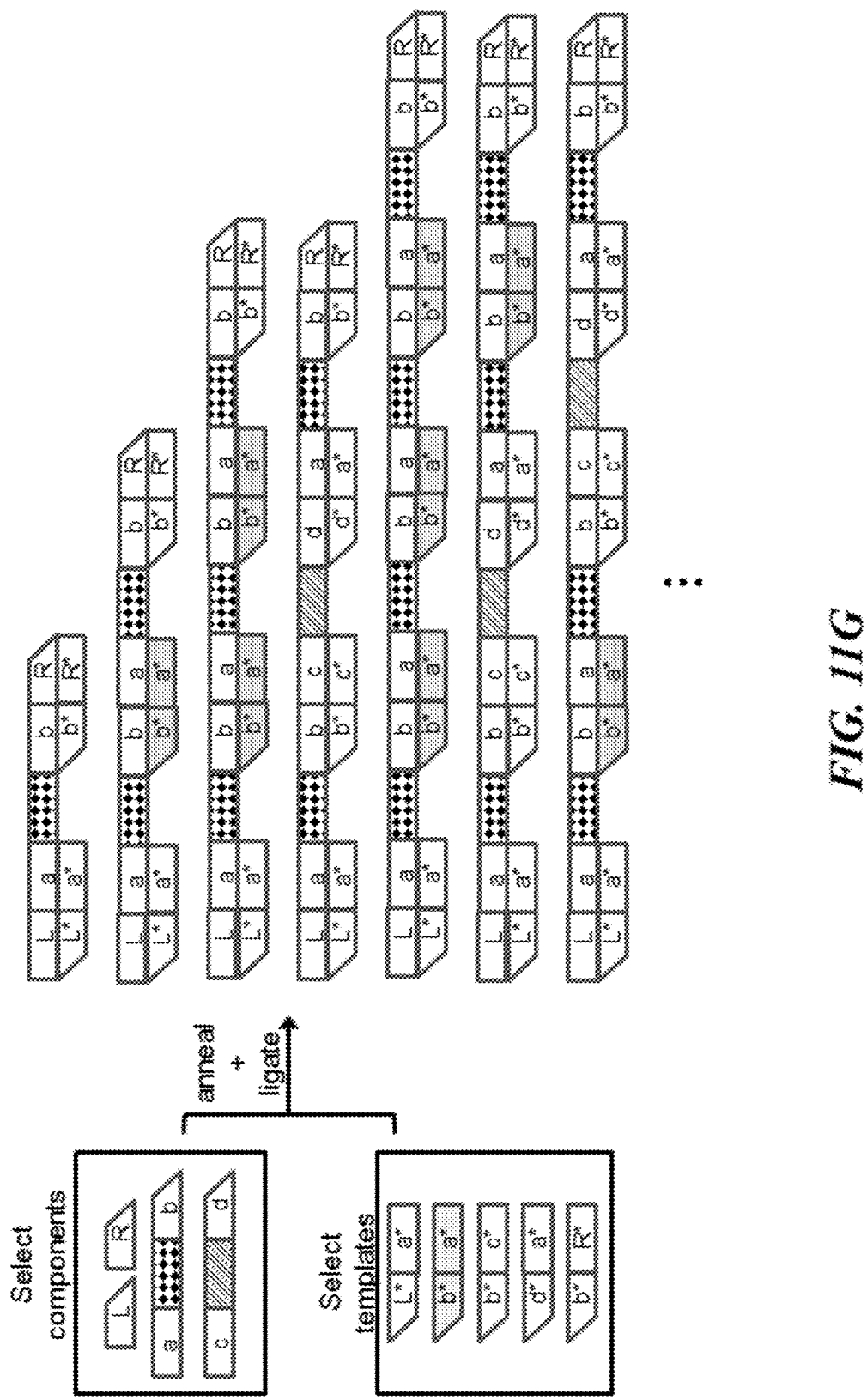

FIGS. 11D-G illustrate example methods of how the permutation scheme may be expanded to include certain instances of identifiers with repeated components. FIG. 11D shows an example of how the implementation form FIG. 11C may be used to construct identifiers with permuted and repeated components. For example, an identifier may comprise three total components assembled from two distinct components. In this example, a component from a layer may be present multiple times in an identifier. Adjacent concatenations of the same component may be achieved by using a staple with adjacent complementary hybridization regions for both the 3' end and 5' end of the same component, such as the a*b* (5' to 3') staple in the figure. In general, for M layers, there are M such staples. Incorporation of repeated components with this implementation may generate nucleic acid sequences of more than one length (i.e., comprising one, two, three, four, or more components) that are assembled between the edge scaffolds, as demonstrated in FIG. 11E. FIG. 11E shows how the example implementation from FIG. 11D may lead to non-targeted nucleic acid sequences, besides the identifier, that are assembled between the edge scaffolds. The appropriate identifier cannot be isolated from non-targeted nucleic acid sequence with PCR because they share the same primer binding sites on the edge. However, in this example, DNA size selection (e.g., with gel extraction) may be implemented to isolate the targeted identifier (e.g., the second sequence from the top) from the non-targeted sequences since each assembled nucleic acid sequence can be designed to have a unique length (e.g., if all components have the same length). See Chemical Methods Section E about size-selection. FIG. 11F shows another example where constructing an identifier with repeated components may generate multiple nucleic acid sequences with equal edge sequences but distinct lengths in the same reaction. In this method, templates that assemble a components in one layer with components in other layers in an alternating pattern may be used. As with the method shown in FIG. 11E, size selection may be used to select identifiers of the designed length. FIG. 11G shows an example where constructing an identifier with repeated components may generate multiple nucleic acid sequences with equal edge sequences and for some nucleic acid sequences (e.g., the third and fourth from the top and the sixth and seventh from the top), equal lengths. In this example, those nucleic acid sequences that share equal lengths may be excluded from both being individual identifiers as it may not be possible to construct one without also constructing the other, even if PCR and DNA size selection are implemented.

Figure 12A:
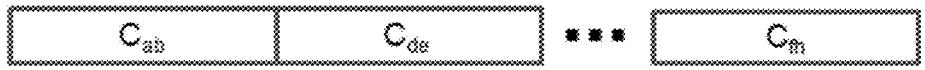
FIGS. 12A-12D schematically illustrate an example method, referred to as the "MchooseK" scheme, for constructing identifiers (e.g., nucleic acid molecules) with any number, K, of assembled components (e.g., nucleic acid sequences) out of a larger number, M, of possible components.
Figure 12B:
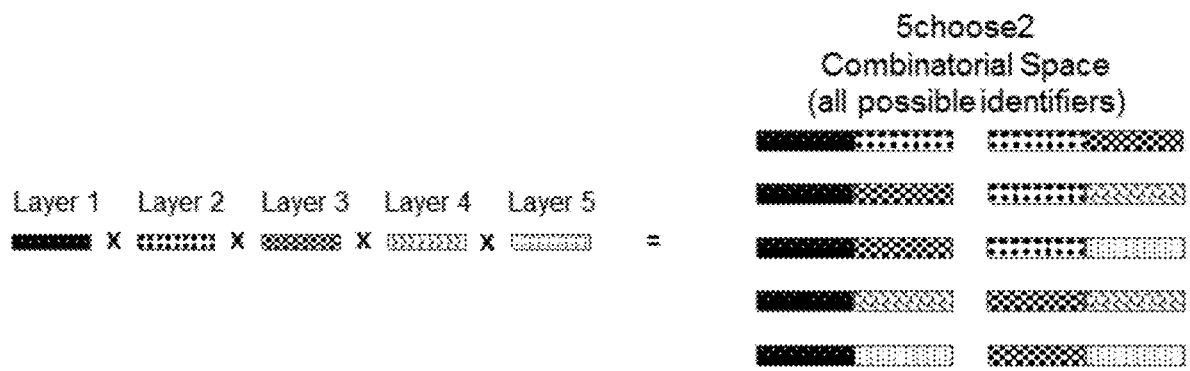

FIGS. 12A-12D schematically illustrate an example method, referred to as the "MchooseK scheme", for constructing identifiers (e.g., nucleic acid molecules) with any number, K, of assembled components nucleic acid sequences) out of a larger number, M, of possible components. FIG. 12A illustrates the architecture of identifiers constructed using the MchooseK scheme. Using this method identifiers are constructed by assembling one component form each layer in any subset of all layers (e.g., choose components from k layers out of M possible layers). FIG. 12B illustrates an example of the combinatorial space of identifiers that may be constructed using the MchooseK scheme. In this assembly scheme the combinatorial space may comprise $N^K$chooseK possible identifiers for M layers, N components per layer, and an identifier length of K components. In an example, if there are five layers each comprising one component, then up to ten distinct identifiers may be assemble each comprising two components each.

Figure 12C:
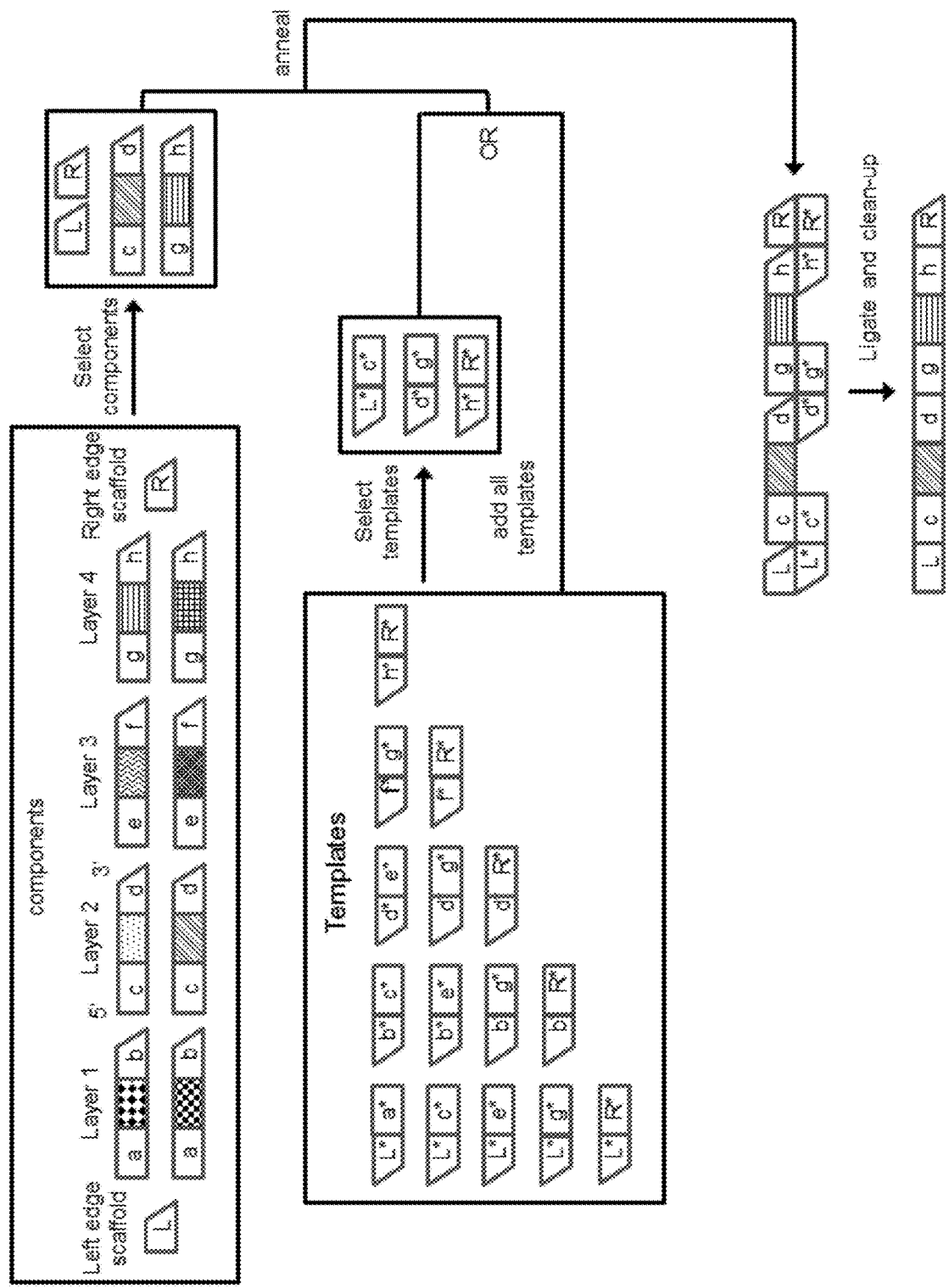
Figure 12D:
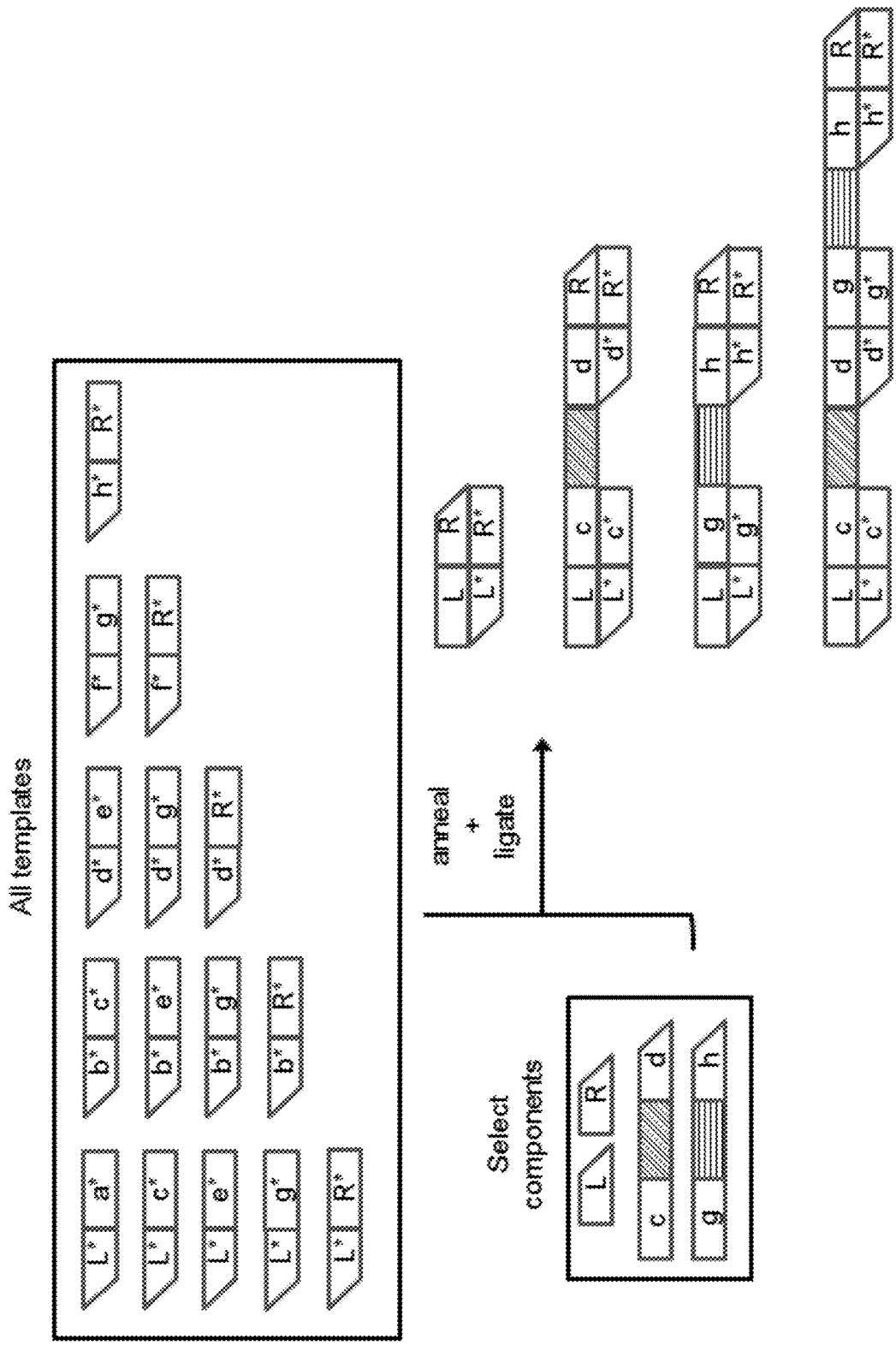

The MchooseK scheme may be implemented using template directed ligation (See Chemical Methods Section B), as shown in FIG. 12C. As with the TDL implementation for the permutation scheme (FIG. 11C), components in this example are assembled between edge scaffolds that may or may not be included in the reaction master mix. Components may be divided into M layers, for example M=4 layers with predefined rank from 2 to M, where the left edge scaffold may be rank 1 and the right edge scaffold may be rank M+1. Templates comprise nucleic acid sequences for the 3' to 5' ligation of any two components with lower rank to higher rank, respectively. There are $((M+1)^2+M+1)/2$ such templates. An individual identifier of any K components from distinct layers may be constructed by combining those selected components in a ligation reaction with the corresponding K+1 staples used to bring the K components together with the edge scaffolds in their rank order. Such a reaction set up may yield the nucleic acid sequence corresponding to the target identifier between the edge scaffolds. Alternatively, a reaction mix comprising all templates may be combined with the select components to assemble the target identifier. This alternative method may generate various nucleic acid sequences with the same edge sequences but distinct lengths (if all component lengths are equal), as illustrated in FIG. 12D. The target identifier (bottom) may be isolated from byproduct nucleic acid sequences by size. See Chemical Methods Section E about nucleic acid size-selection.

Figure 13A:
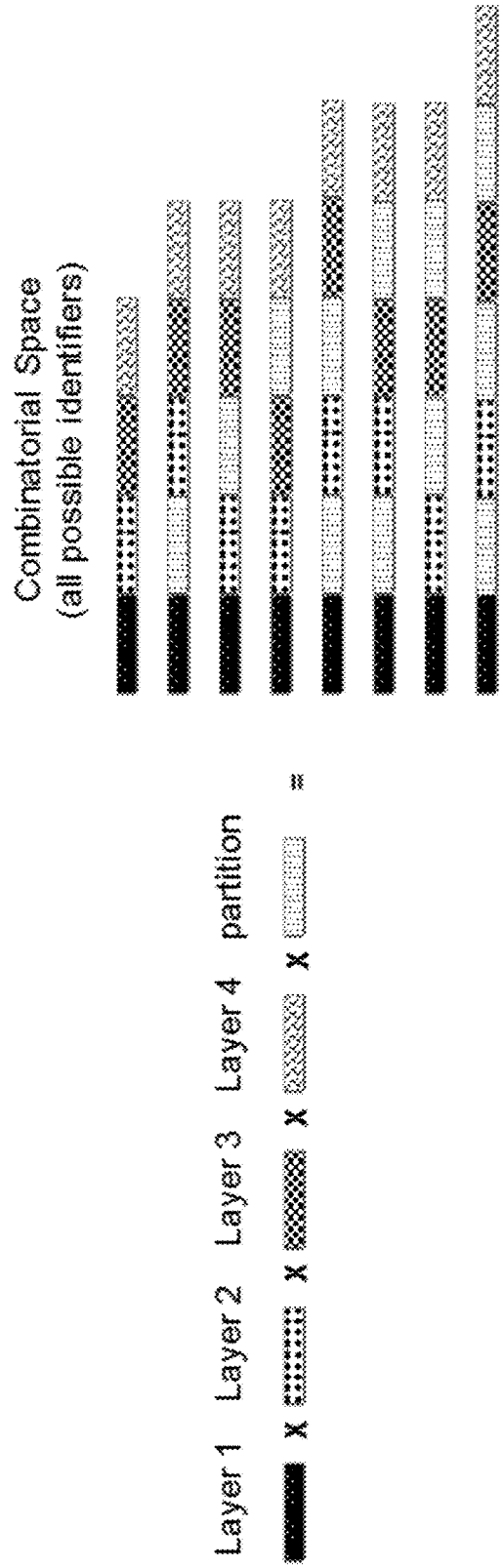
FIGS. 13A and 13B schematically illustrates an example method, referred to as the "partition scheme" for constructing identifiers with partitioned components.
Figure 13B:
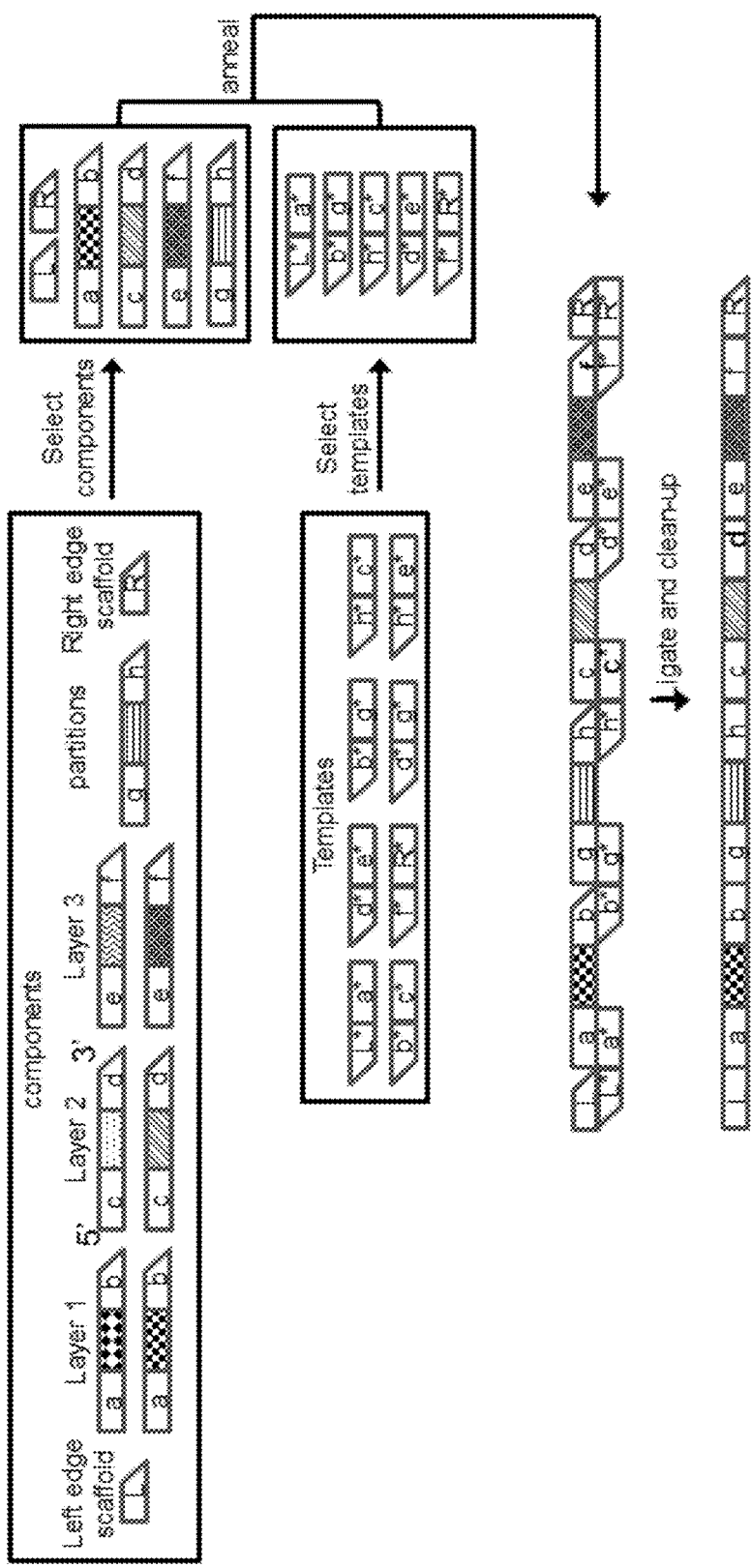

FIGS. 13A and 13B schematically illustrate an example method, referred to as the "partition scheme" for constructing identifiers with partitioned components. FIG. 13A shows an example of the combinatorial space of identifiers that may be constructed using the partition scheme. An individual identifier may be constructed by assembling one component from each layer in a fixed order with the optional placement of any partition (specially classified component) between any two components of different layers. For example, a set of components may be organized into one partition component and four layers containing one component each. A component from each layer may be combined in a fixed order and a single partition component may be assembled in various locations between layers. An identifier in this combinatorial space may comprise no partition components, a partition component between the components from the first and second layer, a partition between the components from the second and third layer, and so on to make a combinatorial space of eight possible identifiers. In general, with M layers, each with N components, and p partition components, there are $N^K(p+1)^{M-1}$ possible identifiers that may be constructed. This method may generate identifiers of various lengths.

FIG. 13B shows an example implementation of the partition scheme using template directed ligation (See Chemical Methods Section B). Templates comprise nucleic acid sequences for ligating together one component from each of M layers in a fixed order. For each partition component, additional pairs of templates exist that enable the partition component to ligate in between the components from any two adjacent layers. For example a pair of templates such that one template (with sequence g*b* (5' to 3') for example) in a pair enables the 3' end of layer 1 (with sequence b) to ligate to the 5' end of the partition component (with sequence g) and such that the second template in the pair (with sequence c*h* (5' to 3') for example) enables the 3' end of the partition component (with sequence h) to ligate to the 5' end of layer 2 (with sequence c). To insert a partition between any two components of adjacent layers, the standard template for ligating together those layers may be excluded in the reaction and the pair of templates for ligating the partition in that position may be selected in the reaction. In the current example, targeting the partition component between layer 1 and layer 2 may use the pair of templates c*h* (5' to 3') and g*b* (5' to 3') to select for the reaction rather than the template c*b* (5' to 3'). Components may be assembled between edge scaffolds that may be included in the reaction mix (along with their corresponding templates for ligating to the first and Mth layers, respectively). In general, a total of around M−1+2*p*(M−1) selectable templates may be used for this method for M layers and p partition components. This implementation of the partition scheme may generate various nucleic acid sequences in a reaction with the same edge sequences but distinct lengths. The target identifier may be isolated from byproduct nucleic acid sequences by DNA size selection. Specifically, there may be exactly one nucleic acid sequence product with exactly M layer components. If the layer components are designed large enough compared to the partition components, it may be possible to define a universal size selection region whereby the identifier (and none of the non-targeted byproducts) may be selected regardless of the particular partitioning of the components within the identifier, thereby allowing for multiple partitioned identifiers from multiple reactions to be isolated in the same size selection step. See Chemical Methods Section E about nucleic acid size-selection.

Figure 14A:
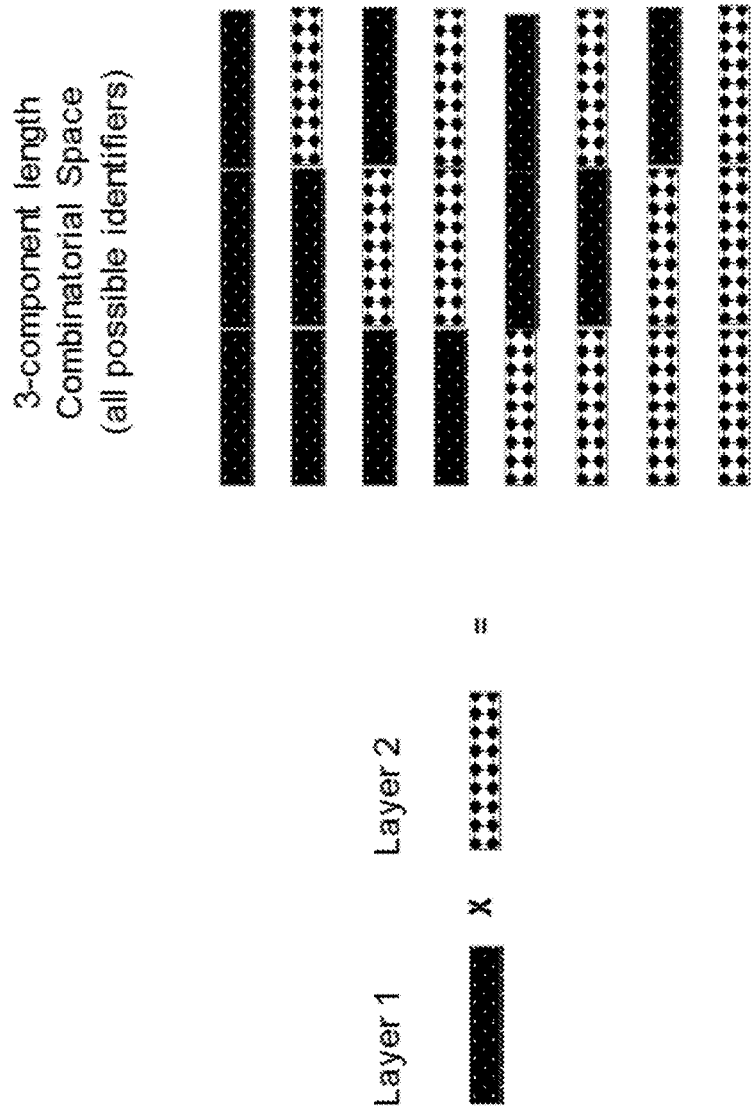
FIGS. 14A and 14B schematically illustrates an example method, referred to as the "unconstrained string" (or USS) scheme, for constructing identifiers made up of any string of components from a number of possible components.
Figure 14B:
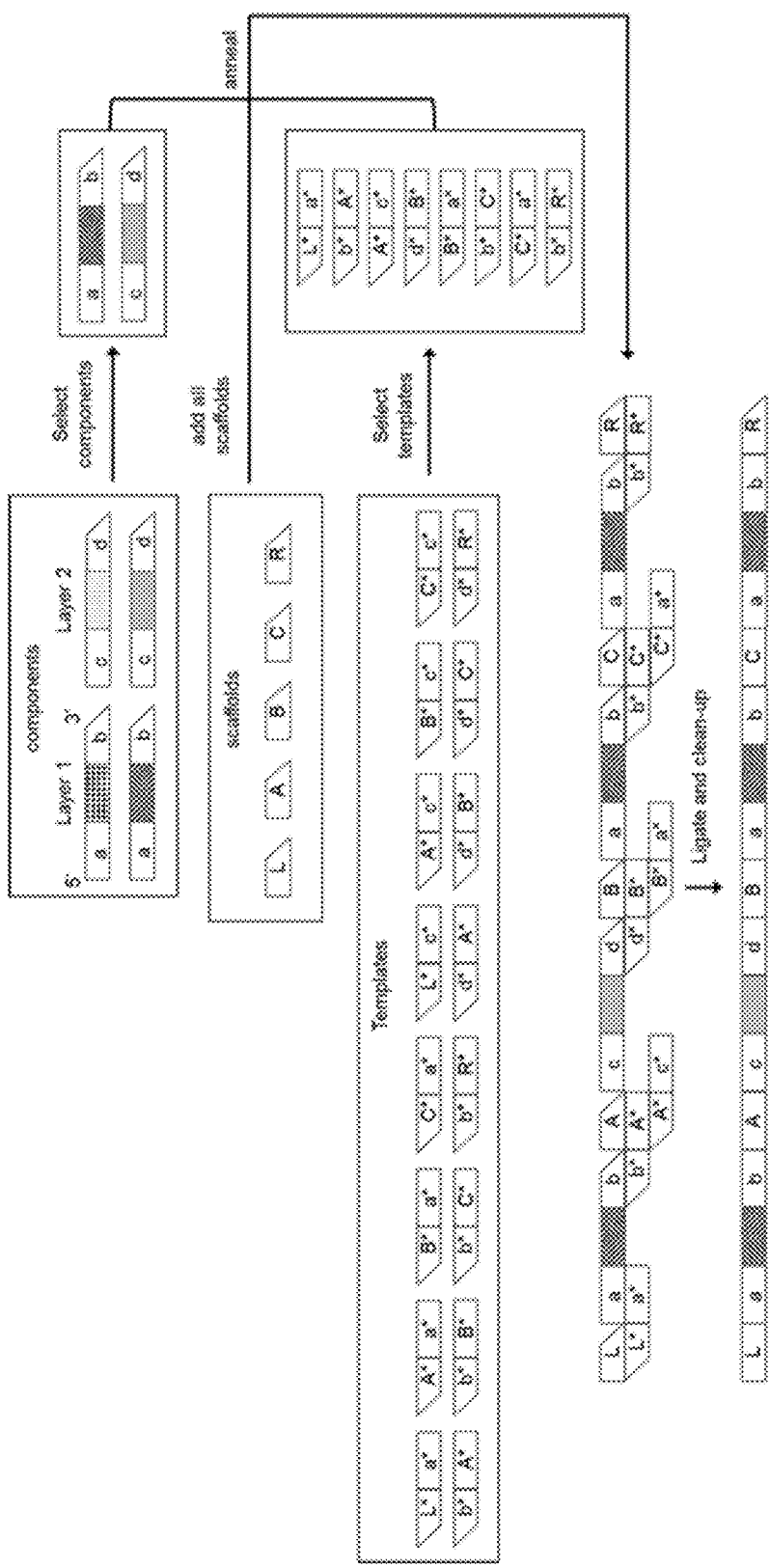

FIGS. 14A and 14B schematically illustrates an example method, referred to as the "unconstrained string scheme" or "USS", for constructing identifiers made up of any string of components from a number of possible components. FIG. 14A shows an example of the combinatorial space of 3-component (or 4-scaffold) length identifiers that may be constructed using the unconstrained string scheme. The unconstrained string scheme constructs an individual identifier of length K components with one or more distinct components each taken from one or more layers, where each distinct component can appear at any of the K component positions in the identifier (allowing for repeats). For example, for two layers, each comprising one component, there are eight possible 3-component length identifiers. In general, with M layers, each with one component, there are $M^K$ possible identifiers of length K components. FIG. 14B shows an example implementation of the unconstrained string scheme using template directed ligation (see Chemical Methods Section B). In this method, K+1 single-stranded and ordered scaffold DNA components (including two edge scaffolds and K−1 internal scaffolds) are present in the reaction mix. An individual identifier comprises a single component ligated between every pair of adjacent scaffolds. For example, a component ligated between scaffolds A and B, a component ligated between scaffolds C and D, and so on until all K adjacent scaffold junctions are occupied by a component. In a reaction, selected components from different layers are introduced to scaffolds along with selected pairs of staples that direct them to assemble onto the appropriate scaffolds. For example, the pair of staples a*L* (5' to 3') and A*b* (5' to 3') direct the layer 1 component with a 5' end region 'a' and 3' end region 'b' to ligate in between the L and A scaffolds. In general, with M layers and K+1 scaffolds, 2*M*K selectable staples may be used to construct any USS identifier of length K. Because the staples that connect a component to a scaffold on the 5' end are disjoint from the staples that connect the same component to a scaffold on the 3' end, nucleic acid byproducts may form in the reaction with equal edge scaffolds as the target identifier, but with less than K components (less than K+1 scaffolds) or with more than K components (more than K+1 scaffolds). The targeted identifier may form with exactly K components (K+1 scaffolds) and may therefore be selectable through techniques like DNA size selection if all components are designed to be equal in length and all scaffolds are designed to be equal in length. See Chemical Methods Section E on nucleic acid size selection. In certain embodiments of the unconstrained string scheme where there may be one component per layer, that component may solely comprise a single distinct nucleic acid sequence that fulfills all three roles of (1) an identification barcode, (2) a hybridization region for staple-mediated ligation of the 5' end to a scaffold, and (3) a hybridization region for staple mediated ligation of the 3' end to a scaffold.

The internal scaffolds illustrated in FIG. 14B may be designed such that they use the same hybridization sequence for both the staple-mediated 5' ligation of the scaffold to a component and the staple-mediated 3' ligation of the scaffold to another (not necessarily distinct) component. Thus the depicted one-scaffold, two-staple stacked hybridization events in FIG. 14B represent the statistical back-and-forth hybridization events that occur between the scaffold and each of the staples, thus enabling both 5' component ligation and 3' component ligation. In other embodiments of the unconstrained string scheme, the scaffold may be designed with two concatenated hybridization regions—a distinct 3' hybridization region for staple-mediated 3' ligation and a distinct 5' hybridization region for staple-mediated 5' ligation.

Figure 15A:
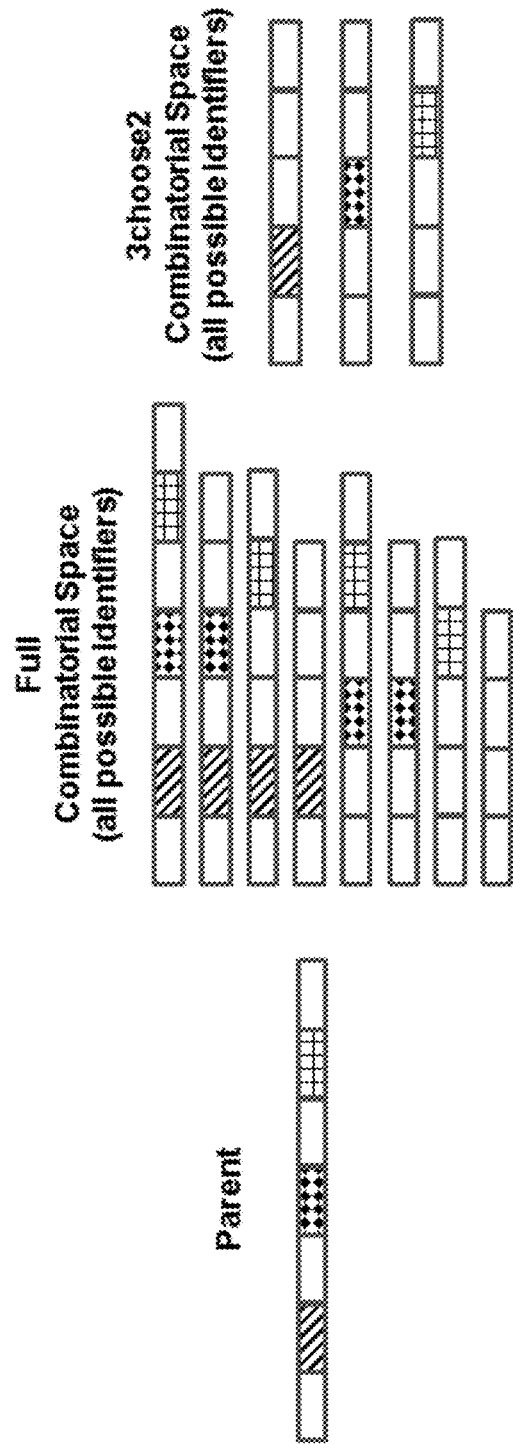
FIGS. 15A and 15B schematically illustrates an example method, referred to as "component deletion" for constructing identifiers by removing components from a parent identifier.
Figure 15B:
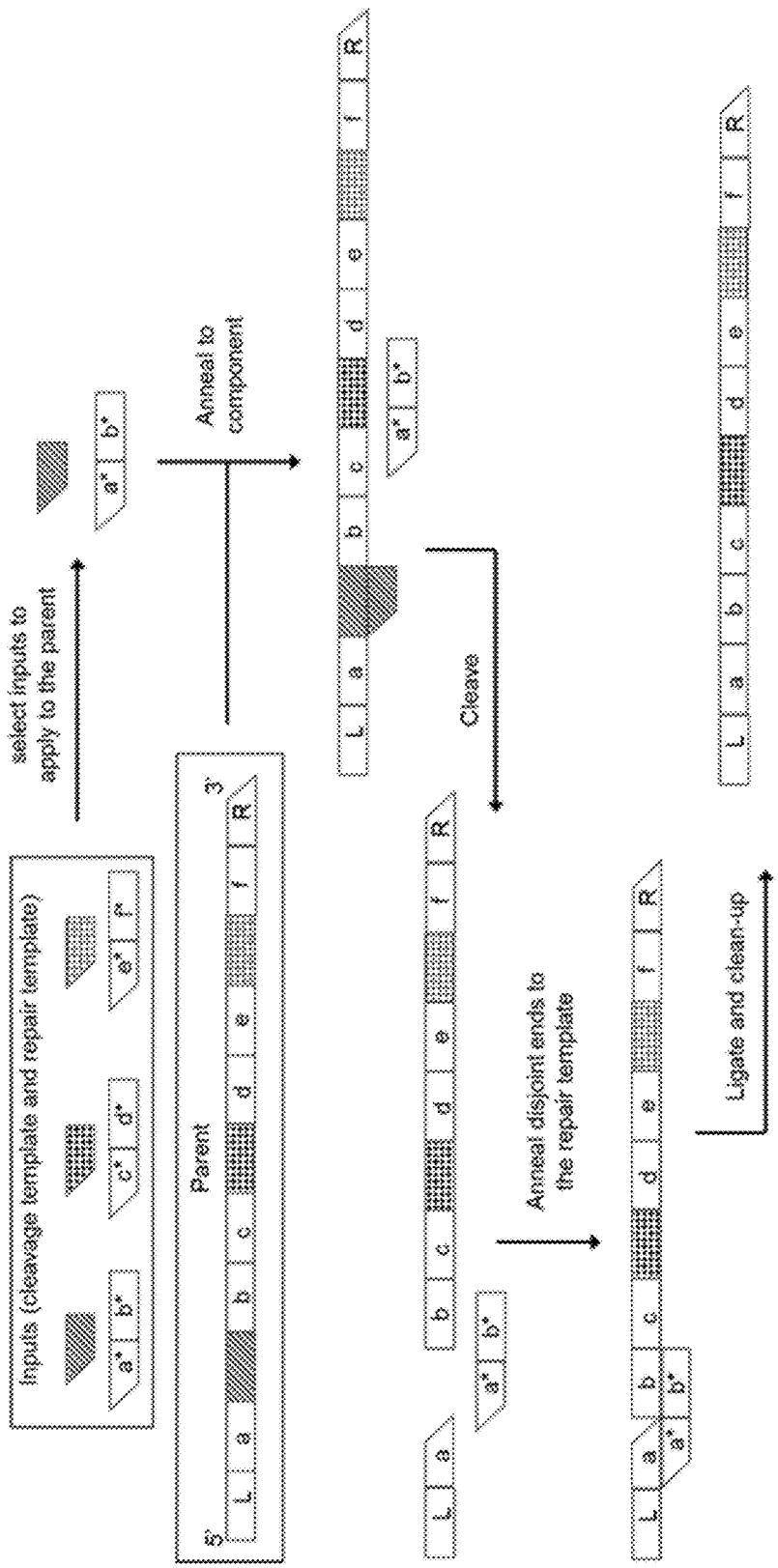

FIGS. 15A and 15B schematically illustrate an example method, referred to as the "component deletion scheme", for constructing identifiers by deleting nucleic acid sequences (or components) from a parent identifier. FIG. 15A shows an example of the combinatorial spaces of possible identifiers that may be constructed using the component deletion scheme. In this example, a parent identifier may comprise multiple components. A parent identifier may comprise more than or equal to about 2, 3, 4, 5, 6, 7, 8, 9, 10, 20, 30, 40, 50 or more components. An individual identifier may be constructed by selectively deleting any number of components from N possible components, leading to a "full" combinatorial space of size $2^N$, or by deleting a fixed number of K components from N possible components, thus leading to an "NchooseK" combinatorial space of size NchooseK. In an example with a parent identifier with 3 components, the full combinatorial space may be 8 and the 3choose2 combinatorial space may be 3.

FIG. 15B shows an example implementation of the component deletion scheme using double stranded targeted cleavage and repair (DSTCR). The parent sequence may be a single stranded DNA substrate comprising components flanked by nuclease-specific target sites (which can be 4 or less bases in length), and where the parent may be incubated with one or more double-strand-specific nucleases corresponding to the target sites. An individual component may be targeted for deletion with a complementary single stranded. DNA (or cleavage template) that binds the component DNA (and flanking nuclease sites) on the parent, thus forming a stable double stranded sequence on the parent that may be cleaved on both ends by the nucleases. Another single stranded DNA (or repair template) hybridizes to the resulting disjoint ends of the parent (between which the component sequence had been) and brings them together for ligation, either directly or bridged by a replacement sequence, such that the ligated sequences on the parent no longer contain active nuclease-targeted sites. We refer to this method as "Double Stranded Targeted Cleavage" (DSTC). Size selection may be used to select for identifiers with a certain number of deleted components. See Chemical Methods Section E about nucleic acid size-selection.

Alternatively, or in addition to, the parent identifier may be a double or single stranded nucleic acid substrate comprising components separated by spacer sequences such that no two components are flanked by the same sequence. The parent identifier may be incubated with Cas9 nuclease. An individual component may be targeted for deletion with guide ribonucleic acids (the cleavage templates) that bind to the edges of the component and enable Cas9-mediated cleavage at its flanking sites. A single stranded nucleic acid (the repair template) may hybridize to the resulting disjoint ends of the parent identifier (e.g., between the ends where the component sequence had been), thus bringing them together for ligation. Ligation may be done directly or by bridging the ends with a replacement sequence, such that the ligated sequences on the parent no longer contain spacer sequences that can be targeted by Cas9. We refer to this method as "sequence specific targeted cleavage and repair" or "SSTCR".

Identifiers may be constructed by inserting components into a parent identifier using a derivative of DSTCR. A parent identifier may be single stranded nucleic acid substrate comprising nuclease-specific target sites (which can be 4 or less bases in length), each embedded within a distinct nucleic acid sequence. The parent identifier may be incubated with one or more double-strand-specific nucleases corresponding to the target sites. An individual target site on the parent identifier may be targeted for component insertion with a complementary single stranded nucleic acid (the cleavage template) that binds the target site and the distinct surrounding nucleic acid sequence on the parent identifier, thus forming a double stranded site. The double-stranded site may be cleaved by a nuclease. Another single stranded nucleic acid (the repair template) may hybridize to the resulting disjoint ends of the parent identifier and bring them together for ligation, bridged by a component sequence, such that the ligated sequences on the parent no longer contain active nuclease-targeted sites. Alternatively a derivative of SSTCR may be used to insert components into a parent identifier. The parent identifier may be a double or single-stranded nucleic acid and the parent may be incubated with a Cas9 nuclease. A distinct site on the parent identifier may be targeted for cleavage with a guide RNA (the cleavage template). A single stranded nucleic acid (the repair template) may hybridize to the disjoint ends of the parent identifier and bring them together for ligation, bridged by a component sequence, such that the ligated sequences on the parent identifier no longer contain active nuclease-targeted sites. Size selection may be used to select for identifiers with a certain number of component insertions.

Figure 16:
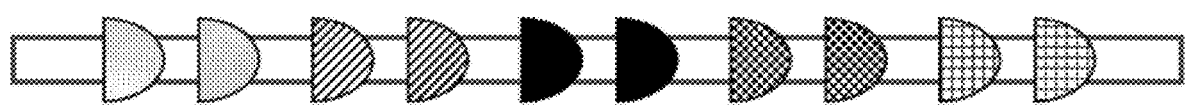
FIG. 16 schematically illustrates a parent identifier with recombinase recognition sites where further identifiers may be constructed by applying recombinases to the parent identifier.

FIG. 16 schematically illustrates a parent identifier with recombinase recognition sites. Recognition sites of different patterns can be recognized by different recombinases. All recognition sites for a given set of recombinases are arranged such that the nucleic acids in between them may be excised if the recombinase is applied. The nucleic acid strand shown in FIG. 16 can adopt $2^5=32$ different sequences depending on the subset of recombinases that are applied to it. In some embodiments, as depicted in FIG. 16, unique molecules can be generated using recombinases to excise, shift, invert, and transpose segments of DNA to create different nucleic acid molecules. In general, with N recombinases there can be $2^N$ possible identifiers built from a parent. In some embodiments, multiple orthogonal pairs of recognition sites from different recombinases may be arranged on a parent identifier in an overlapping fashion such that the application of one recombinase affects the type of recombination event that occurs when a downstream recombinase is applied (see Roquet et al., Synthetic recombinase-based state machines in living cells, Science 353 (6297): aad8559 (2016), which is entirely incorporated herein by reference). Such a system may be capable of constructing a different identifier for every ordering of N recombinases, N!. Recombinases may be of the tyrosine family such as Flp and Cre, or of the large serine recombinase family such as PhiC31, BxbI, TP901, or A118. The use of recombinases from the large serine recombinase family may be advantageous because they facilitate irreversible recombination and therefore may produce identifiers more efficiently than other recombinases.

In some instances, a single nucleic acid sequence can be programmed to become many distinct nucleic acid sequences by applying numerous recombinases in a distinct order. Approximately $\sim e^1 M!$ distinct nucleic acid sequences may be generated by applying M recombinases in different subsets and orders thereof, when the number of recombinases, may be less than or equal to 7 for the large serine recombinase family. When the number of recombinases, M, may be greater than 7, the number of sequences that can be produced approximates $3.9^M$, see e.g., Roquet et al., Synthetic recombinase-based state machines in living cells, Science 353 (6297): aad8559 (2016), which is entirely incorporated herein by reference. Additional methods for producing different DNA sequences from one common sequence can include targeted nucleic acid editing enzymes such as CRISPR-Cas, TALENS, and Zinc Finger Nucleases. Sequences produced by recombinases, targeted editing enzymes or the like can be used in conjunction with any of the previous methods, for example methods disclosed in any of the figures and disclosure in the present application.

If the bit-stream of information to be encoded is larger than that which can be encoded by any single nucleic acid molecule, then the information can be split and indexed with nucleic acid sequence barcodes. Moreover, any subset of size k nucleic acid molecules from the set of N nucleic acid molecules can be chosen to produce $\log_2(N choose k)$ bits of information. Barcodes may be assembled onto the nucleic acid molecules within the subsets of size k to encode even longer bit streams. For example, M barcodes may be used to produce $M*\log_2(N choose k)$ bits of information. Given a number, N, of available nucleic acid molecules in a set and a number, M, of available barcodes, subsets of size $k=k_0$ may be chosen to minimize the total number of molecules in a pool to encode a piece of information. A method for encoding digital information can comprise steps for breaking up the bit stream and encoding the individual elements. For example, a bit stream comprising 6 bits can be split into 3 components each component comprising two bits. Each two bit component can be barcoded to form an information cassette, and grouped or pooled together to form a hyperpool of information cassettes.

Barcodes can facilitate information indexing when the amount of digital information to be encoded exceeds the amount that can fit in one pool alone. Information comprising longer strings of bits and/or multiple bytes can be encoded by layering the approach disclosed in FIG. 3, for example, by including a tag with unique nucleic acid sequences encoded using the nucleic acid index. Information cassettes or identifier libraries can comprise nitrogenous bases or nucleic acid sequences that include unique nucleic acid sequences that provide location and bit-value information in addition to a barcode or tag which indicates the component or components of the bit stream that a given sequence corresponds to. Information cassettes can comprise one or more unique nucleic acid sequences as well as a barcode or tag. The barcode or tag on the information cassette can provide a reference for the information cassette and any sequences included in the information cassette. For example, the tag or barcode on an information cassette can indicate which portion of the bit stream or bit component of the bit steam the unique sequence encodes information for (e.g., the bit value and bit position information for).

Using barcodes, more information in bits can be encoded in a pool than the size of the combinatorial space of possible identifiers. A sequence of 10 bits, for example, can be separated into two sets of bytes, each byte comprising 5 bits. Each byte can be mapped to a set of 5 possible distinct identifiers. Initially, the identifiers generated for each byte can be the same, but they may be kept in separate pools or else someone reading the information may not be able to tell which byte a particular nucleic acid sequence belongs to. However each identifier can be barcoded or tagged with a label that corresponds to the byte for which the encoded information applies (e.g., barcode one may be attached to sequences in the nucleic acid pool to provide the first five bits and barcode two may be attached to sequences in the nucleic acid pool to provide the second five bits), and then the identifiers corresponding to the two bytes can be combined into one pool (e.g, "hyper-pool" or one or more identifier libraries). Each identifier library of the one or more combined identifier libraries may comprise a distinct barcode that identifies a given identifier as belonging to a given identifier library. Methods for adding a barcode to each identifier in an identifier library can comprise using PCR, Gibson, ligation, or any other approach that enables a given barcode (e.g., barcode 1) to attach to a given nucleic acid sample pool (e.g., barcode 1 to nucleic acid sample pool 1 and barcode 2 to nucleic acid sample pool 2). The sample from the hyper-pool can be read with sequencing methods, and sequencing information can be parsed using the barcode or tag. A method using identifier libraries and barcodes with a set of M barcodes and N possible identifiers (the combinatorial space) can encode a stream of bits with a length equivalent to the product of M and N.

In some embodiments, identifier libraries may be stored in an array of wells. The array of wells may be defined as having n columns and q rows and each well may comprise two or more identifier libraries in a hyper-pool. The information encoded in each well may constitute one large contiguous item of information of size n×q larger than the information contained in each of the wells. An aliquot may be taken from one or more of the wells in the array of wells and the encoding may be read using sequencing, hybridization, or PCR.

A nucleic acid sample pool, hyper-pool, identifier library, group of identifier libraries, or a well, containing a nucleic acid sample pool or hyper-pool may comprise unique nucleic acid molecules (e.g., identifiers) corresponding to bits of information and a plurality of supplemental nucleic acid sequences. The supplemental nucleic acid sequences may not correspond to encoded data (e.g., do not correspond to a bit value). The supplemental nucleic acid samples may mask or encrypt the information stored in the sample pool. The supplemental nucleic acid sequences may be derived from a biological source or synthetically produced. Supplemental nucleic acid sequences derived from a biological source may include randomly fragmented nucleic acid sequences or rationally fragmented sequences. The biologically derived supplemental nucleic acids may hide or obscure the data-containing nucleic acids within the sample pool by providing natural genetic information along with the synthetically encoded information, especially if the synthetically encoded information (e.g., the combinatorial space of identifiers) is made to resemble natural genetic information (e.g., a fragmented genome). In an example, the identifiers are derived from a biological source and the supplemental nucleic acids are derived from a biological source. A sample pool may contain multiple sets of identifiers and supplemental nucleic acid sequences. Each set of identifiers and supplemental nucleic acid sequences may be derived from different organisms. In an example, the identifiers are derived from one or more organisms and the supplemental nucleic acid sequences are derived from a single, different organism. The supplemental nucleic acid sequences may also be derived from one or more organism and the identifiers may be derived from a single organism that is different from the organism that the supplemental nucleic acids are derived from. Both the identifiers and the supplemental nucleic acid sequences may be derived from multiple different organisms. A key may be used to distinguish the identifiers from the supplemental nucleic acid sequences.

The supplemental nucleic acid sequences may store metadata about the written information. The metadata may comprise extra information for determining and/or authorizing the source of the original information and or the intended recipient of the original information. The metadata may comprise extra information about the format of the original information, the instruments and methods used to encode and write the original information, and the date and time of writing the original information into the identifiers. The metadata may comprise additional information about the format of the original information, the instruments and methods used to encode and write the original information, and the date and time of writing the original information into nucleic acid sequences. The metadata may comprise additional information about modifications made to the original information after writing the information into nucleic acid sequences. The metadata may comprise annotations to the original information or one or more references to external information. Alternatively, or in addition to, the metadata may be stored in one or more barcodes or tags attached to the identifiers.

The identifiers in an identifier pool may have the same, similar, or different lengths than one another. The supplemental nucleic acid sequences may have a length that is less than, substantially equal to, or greater than the length of the identifiers. The supplemental nucleic acid sequences may have an average length that is within one base, within two bases, within three bases, within four bases, within five bases, within six bases, within seven bases, within eight bases, within nine bases, within ten bases, or within more bases of the average length of the identifiers. In an example, the supplemental nucleic acid sequences are the same or substantially the same length as the identifiers. The concentration of supplemental nucleic acid sequences may be less than, substantially equal to, or greater than the concentration of the identifiers in the identifiers library. The concentration of the supplemental nucleic acids may be less than or equal to about 1%, 10%, 20%, 40%, 60%, 80%, 100, %; 125%, 150%, 175%, 200%, 1000%, $1\times10^4$%, $1\times10^5$%, $1\times10^6$%, $1\times10^7$%, $1\times10^8$% or less than the concentration of the identifiers. The concentration of the supplemental nucleic acids may be greater than or equal to about 1%, 10%, 20%, 40%, 60%, 80%, 100, %, 125%, 150%, 175%, 200%, 1000%, $1\times10^4$%, $1\times10^5$%, $1\times10^6$%, $1\times10^7$%, $1\times10^8$% or more than the concentration of the identifiers. Larger concentrations may be beneficial for obfuscation or concealing data. In an example, the concentration of the supplemental nucleic acid sequences are substantially greater (e.g., $1\times10^8$% greater) than the concentration of identifiers in an identifier pool.

Methods for Copying and Accessing Data Stored in Nucleic Acid Sequences

In another aspect, the present disclosure provides methods for copying information encoded in nucleic acid sequence(s). A method for copying information encoded in nucleic acid sequence(s) may comprise (a) providing an identifier library and (b) constructing one or more copies of the identifier library. An identifier library may comprise a subset of a plurality of identifiers from a larger combinatorial space. Each individual identifier of the plurality of identifiers may correspond to an individual symbol in a string of symbols. An identifier may comprise one or more components. A component may comprise a nucleic acid sequence.

In another aspect, the present disclosure provides methods for accessing information encoded in nucleic acid sequences. A method for accessing information encoded in nucleic acid sequences may comprise (a) providing an identifier library, and (b) extracting a portion or a subset of the identifiers present in the identifier library from the identifier library. An identifier library may comprise a subset of a plurality of identifiers from a larger combinatorial space. Each individual identifier of the plurality of identifiers may correspond to an individual symbol in a string of symbols. An identifier may comprise one or more components. A component may comprise a nucleic acid sequence.

Information may be written into one or more identifier libraries as described elsewhere herein. Identifiers may be constructed using any method described elsewhere herein. Stored data may be copied by generating copies of the individual identifiers in an identifier library or in one or more identifier libraries. A portion of the identifiers may be copied or an entire library may be copied. Copying may be performed by amplifying the identifiers in an identifier library. When one or more identifier libraries are combined, a single identifier library or multiple identifier libraries may be copied. If an identifier library comprises supplemental nucleic acid sequences, the supplemental nucleic acid sequences may or may not be copied.

Identifiers in an identifier library may be constructed to comprise one or more common primer binding sites. The one or more binding sites may be located at the edges of each identifier or interweaved throughout each identifier. The primer binding site may allow for an identifier library specific primer pair or a universal primer pair to bind to and amplify the identifiers. All the identifiers within an identifier library or all the identifiers in one or more identifier libraries may be replicated multiple times by multiple PCR cycles. Conventional PCR may be used to copy the identifiers and the identifiers may be exponentially replicated with each PCR cycle. The number of copies of an identifier may increase exponentially with each PCR cycle. Linear PCR may be used to copy the identifiers and the identifiers may be linearly replicated with each PCR cycle. The number of identifier copies may increase linearly with each PCR cycle. The identifiers may be ligated into a circular vector prior to PCR amplification. The circle vector may comprise a barcode at each end of the identifier insertion site. The PCR primers for amplifying identifiers may be designed to prime to the vector such that the barcoded edges are included with the identifier in the amplification product. During amplification, recombination between identifiers may result in copied identifiers that comprise non-correlated barcodes on each edge. The non-correlated barcodes may be detectable upon reading the identifiers. Identifiers containing non-correlated barcodes may be considered false positives and may be disregarded during the information decoding process. See Chemical Methods Section D.

Information may be encoded by assigning each bit of information to a unique nucleic acid molecule. For example, three sample sets (X, Y, and Z) each containing two nucleic acid sequences may assemble into eight unique nucleic acid molecules and encode eight bits of data:

N1=X1Y1Z1
N2=X1Y1Z2
N3=X1Y2Z1
N4=X1Y2Z2
N5=X2Y1Z1
N6=X2Y1Z2
N7=X2Y2Z1
N8=X2Y2Z2

Each bit in a string may then be assigned to the corresponding nucleic acid molecule (e.g., N1 may specify the first bit, N2 may specify the second bit, N3 may specify the third bit, and so forth). The entire bit string may be assigned to a combination of nucleic acid molecules where the nucleic acid molecules corresponding to bit-values of '1' are included in the combination or pool. For example, in UTF-8 codings, the letter 'K' may be represented by the 8-bit string code 01001011 which may be encoded by the presence of four nucleic acid molecules (e.g., X1Y1Z2, X2Y1Z1, X2Y2Z1, and X2Y2Z2 in the above example).

The information may be accessed through sequencing or hybridization assays. For example, primers or probes may be designed to bind to common regions or the barcoded region of the nucleic acid sequence. This may enable amplification of any region of the nucleic acid molecule. The amplification product may then be read by sequencing the amplification product or by a hybridization assay. In the above example encoding the letter 'K', if the first half of the data is of interest a primer specific to the barcode region of the X1 nucleic acid sequence and a primer that binds to the common region of the Z set may be used to amplify the nucleic acid molecules. This may return the sequence Y1Z2, which may encode for 0100. The substring of that data may also be accessed by further amplifying the nucleic acid molecules with a primer that binds to the barcode region of the Y1 nucleic acid sequence and a primer that binds to the common sequence of the Z set. This may return the Z2 nucleic acid sequence, encoding the substring 01. Alternatively, the data may be accessed by checking for the presence or absence of a particular nucleic acid sequence without sequencing. For example, amplification with a primer specific to the Y2 barcode may generate amplification products for the Y2 barcode, but not for the Y1 barcode. The presence of Y2 amplification product may signal a bit value of '1'. Alternatively, the absence of Y amplification products may signal a bit value of '0'.

PCR based methods can be used to access and copy data from identifier or nucleic acid sample pools. Using common primer binding sites that flank the identifiers in the pools or hyper-pools, nucleic acids containing information can be readily copied. Alternatively, other nucleic acid amplification approaches such as isothermal amplification may also be used to readily copy data from sample pools or hyper-pools (e.g., identifier libraries). See Chemical Methods Section D on nucleic acid amplification. In instances where the sample comprises hyper-pools, a particular subset of information (e.g., all nucleic acids relating to a particular barcode) can be accessed and retrieved by using a primer that binds the specific barcode at one edge of the identifier in the forward orientation, along with another primer that binds a common sequence on the opposite edge of the identifier in a reverse orientation. Various read-out methods can be used to pull information from the encoded nucleic acid; for example microarray (or any sort of fluorescent hybridization), digital PCR, quantitative PCR (qPCR), and various sequencing platforms can be further used to read out the encoded sequences and by extension digitally encoded data.

Figure 17A:
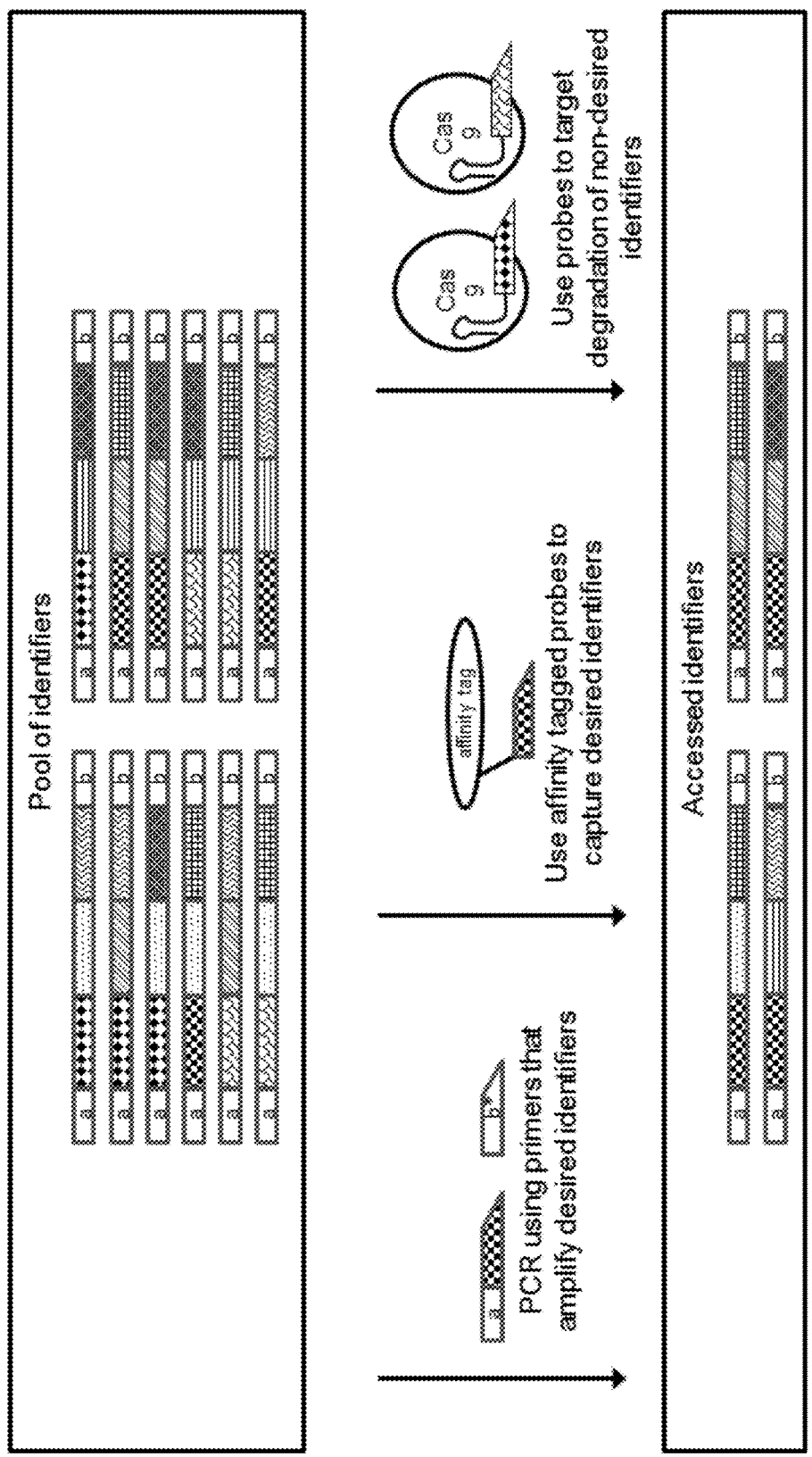
FIGS. 17A-17C schematically illustrate an overview of example methods for accessing portions of information stored in nucleic acid sequences by accessing a number of particular identifiers from a larger number of identifiers.
Figure 17B:
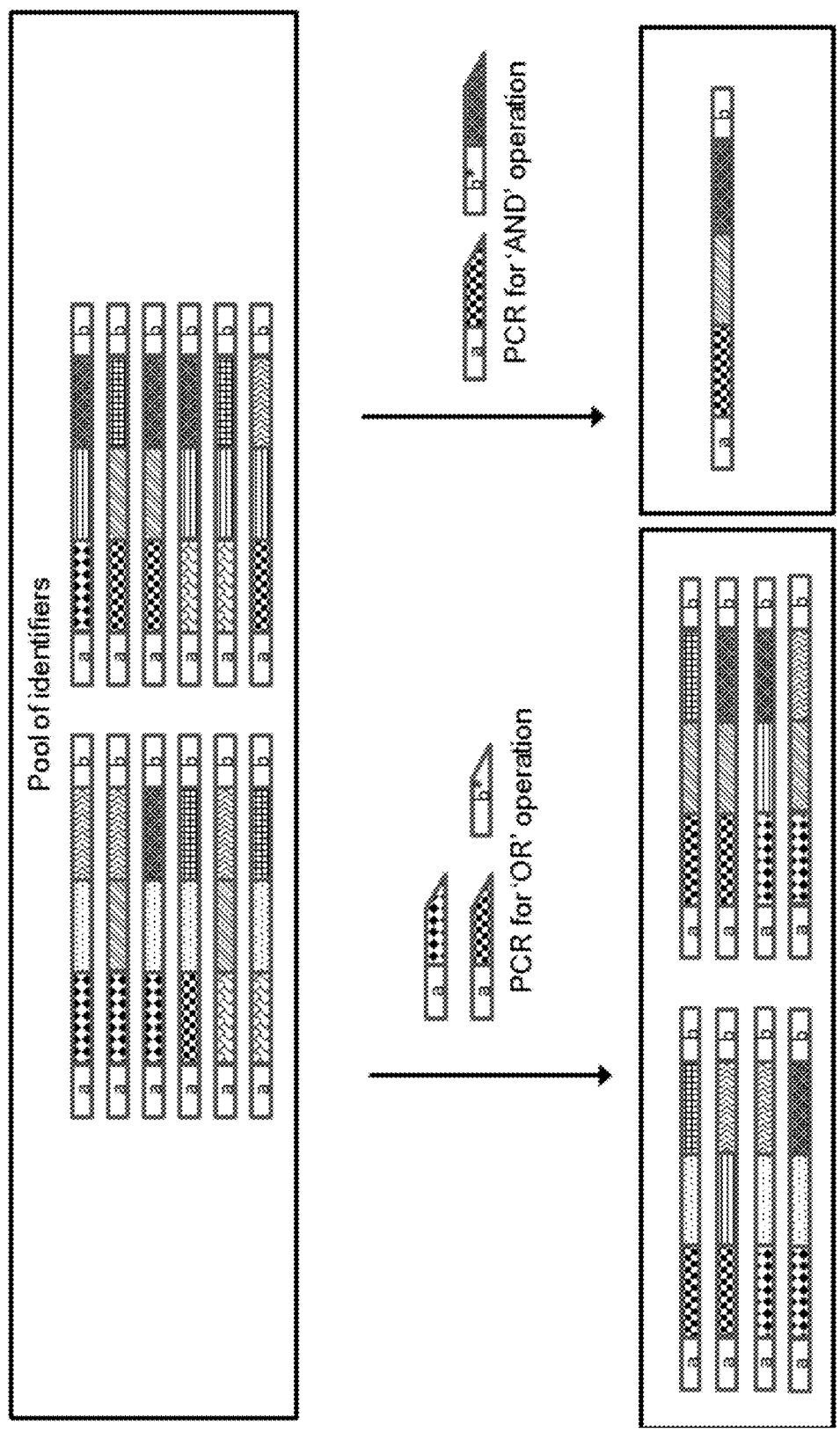
Figure 17C:
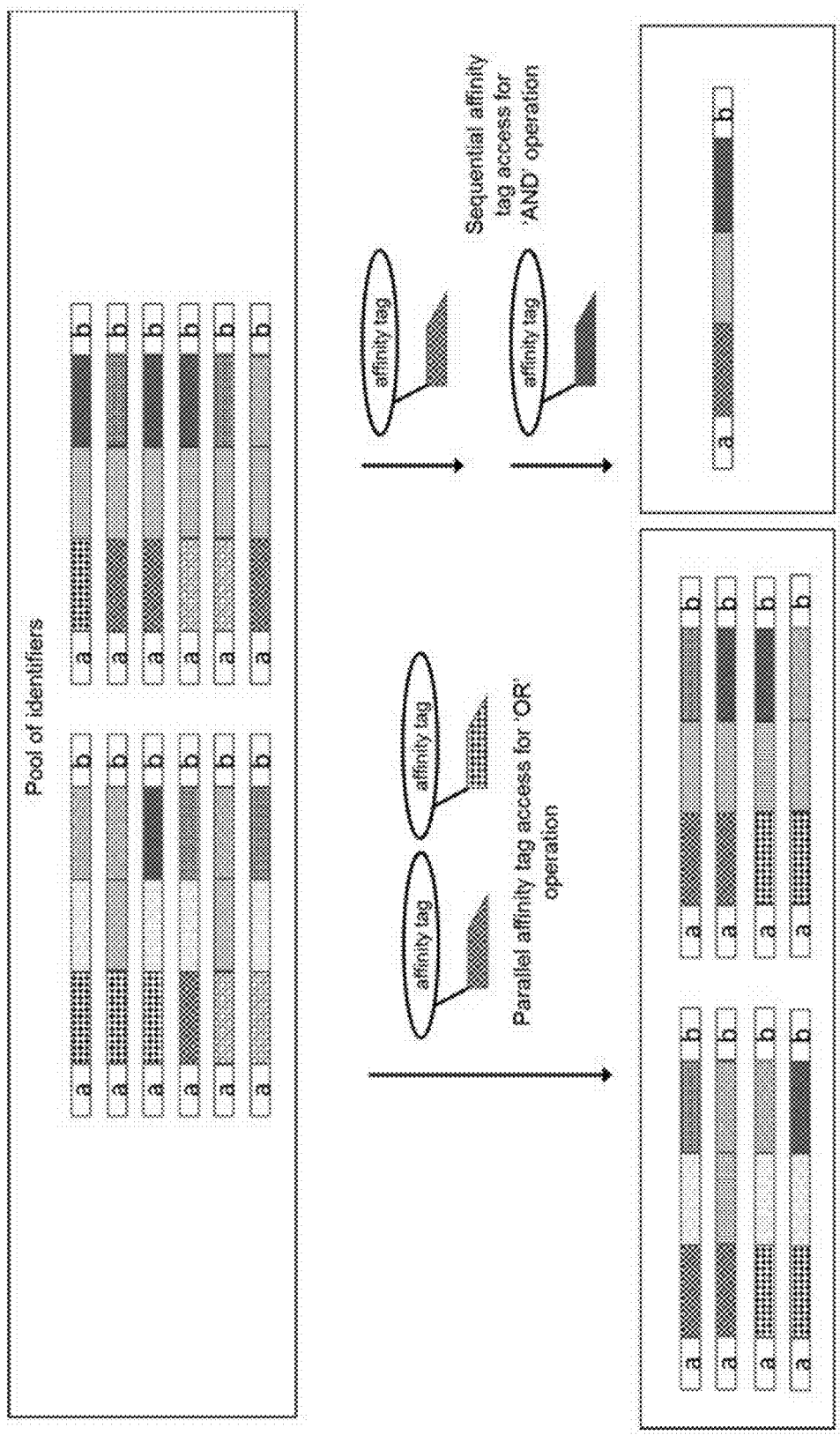

Accessing information stored in nucleic acid molecules (e.g., identifiers) may be performed by selectively removing the portion of non-targeted identifiers from an identifier library or a pool of identifiers or, for example, selectively removing all identifiers of an identifier library from a pool of multiple identifier libraries. As used herein, "access" and "query" can be used interchangeably. Accessing data may also be performed by selectively capturing targeted identifiers from an identifier library or pool of identifiers. The targeted identifiers may correspond to data of interest within the larger item of information. A pool of identifiers may comprise supplemental nucleic acid molecules. The supplemental nucleic acid molecules may contain metadata about the encoded information or may be used to encrypt or mask the identifiers corresponding to the information. The supplemental nucleic acid molecules may or may not be extracted while accessing the targeted identifiers. FIGS. 17A-17C schematically illustrate an overview of example methods for accessing portions of information stored in nucleic acid sequences by accessing a number of particular identifiers from a larger number of identifiers. FIG. 17A shows example methods for using polymerase chain reaction, affinity tagged probes, and degradation targeting probes to access identifiers containing a specified component. For PCR-based access, a pool of identifiers (e.g., identifier library) may comprise identifiers with a common sequence at each end, a variable sequence at each end, or one of a common sequence or a variable sequence at each end. The common sequences or variable sequences may be primer binding sites. One or more primers may bind to the common or variable regions on the identifier edges. The identifiers with primers bound may be amplified by PCR. The amplified identifiers may significantly outnumber the non-amplified identifiers. During reading, the amplified identifiers may be identified. An identifier from an identifier library may comprise sequences on one or both of its ends that are distinct to that library, thus enabling a single library to be selectively accessed from a pool or group of more than one identifier libraries.

For affinity-tag based access, a process which may be referred to as nucleic acid capture, the components that constitute the identifiers in a pool may share complementarity with one or more probes. The one or more probes may bind or hybridize to the identifiers to be accessed. The probe may comprise an affinity tag. The affinity tags may be captured on a solid-phase substrate such as a membrane, a well, a column, or a bead. When using a bead as the solid-phase substrate, the affinity tag may bind to a bead, generating a complex comprising a bead, at least one probe, and at least one identifier. The beads may be magnetic, and together with a magnet, the beads may collect and isolate the identifiers to be accessed. The identifiers may be removed from the beads under denaturing conditions prior to reading. Alternatively, or in addition to, the beads may collect the non-targeted identifiers and sequester them away from the rest of the pool that can get washed into a separate vessel and read. When using a column, the affinity tag may bind to the column. The identifiers to be accessed may bind to the column for capture. Column-bound identifiers may subsequently be eluted or denatured from the column prior to reading. Alternatively, the non-targeted identifiers may be selectively targeted to the column while the targeted identifiers may flow through the column. The identifiers bound to a solid-phase substrate may be removed from the solid-phase substrate, for example, by exposure to conditions such as acid, base, oxidation, reduction, heat, light, metal ion catalysis, displacement or elimination chemistry, or by enzymatic cleavage. In certain embodiments, the identifiers to be accessed may be attached to a solid support through a cleavable linkage moiety. For example, the solid-phase substrate may be functionalized to provide cleavable linkers for covalent attachment to the targeted identifiers. The linker moiety may be of six or more atoms in length. In some embodiments, the cleavable linker may be a TOPS (two oligonucleotides per synthesis) linker, an amino linker, chemically cleavable linker, or a photocleavable linker. Accessing the targeted identifiers may comprise applying one or more probes to a pool of identifiers simultaneously or applying one or more probes to a pool of identifiers sequentially. See Chemical Methods Section F on nucleic acid capture.

For degradation based access, the components that constitute the identifiers in a pool may share complementarity with one or more degradation-targeting probes. The probes may bind to or hybridize with distinct components on the identifiers. The probe may be a target for a degradation enzyme, such as an endonuclease. In an example, one or more identifier libraries may be combined. A set of probes may hybridize with one of the identifier libraries. The set of probes may comprise RNA and the RNA may guide a Cas9 enzyme. A Cas9 enzyme may be introduced to the one or more identifier libraries. The identifiers hybridized with the probes may be degraded by the Cas9 enzyme. The identifiers to be accessed may not be degraded by the degradation enzyme. In another example, the identifiers may be single-stranded and the identifier library may be combined with a single-strand specific endonuclease(s), such as the S1 nuclease, that selectively degrades identifiers that are not to be accessed. Identifiers to be accessed may be hybridized with a complementary set of identifiers to protect them from degradation by the single-strand specific endonuclease(s). The identifiers to be accessed may be separated from the degradation products by size selection, such as size selection chromatography (e.g., agarose gel electrophoresis). Alternatively, or in addition, identifiers that are not degraded may be selectively amplified (e.g., using PCR) such that the degradation products are not amplified. The non-degraded identifiers may be amplified using primers that hybridize to each end of the non-degraded identifiers and therefore not to each end of the degraded or cleaved identifiers.

FIG. 17B shows example methods for using polymerase chain reaction to perform 'OR' or 'AND' operations to access identifiers containing multiple components. In an example, if two forward primers bind distinct sets of identifiers on the left end, then an 'OR' amplification of the union of those sets of identifiers may be accomplished by using the two forward primers together in a multiplex PCR reaction with a reverse primer that binds all of the identifiers on the right end. In another example, if one forward primer binds a set of identifiers on the left end and one reverse primer binds a set of identifiers on the right end, then an 'AND' amplification of the intersection of those two sets of identifiers may be accomplished by using the forward primer and the reverse primer together as a primer pair in a PCR reaction.

FIG. 17C shows example methods for using affinity tags to perform 'OR' or 'AND' operations to access identifiers containing multiple components. In an example, if affinity probe 'P1' captures all identifiers with component 'C1' and another affinity probe 'P2' captures all identifiers with component 'C2', then the set of all identifiers with C1 or C2 can be captured by using P1 and P2 simultaneously (corresponding to an 'OR' operation). In another example with the same components and probes, the set of all identifiers with C1 and C2 can be captures by using P1 and P2 sequentially (corresponding to an 'AND' operation).

Methods for Reading Information Stored in Nucleic Acid Sequences

In another aspect, the present disclosure provides methods for reading information encoded in nucleic acid sequences. A method for reading information encoded in nucleic acid sequences may comprise (a) providing an identifier library, (b) identifying the identifiers present in the identifier library, (c) generating a string of symbols from the identifiers present in the identifier library, and (d) compiling information from the string of symbols. An identifier library may comprise a subset of a plurality of identifiers from a combinatorial space. Each individual identifier of the subset of identifiers may correspond to an individual symbol in a string of symbols. An identifier may comprise one or more components. A component may comprise a nucleic acid sequence.

Information may be written into one or more identifier libraries as described elsewhere herein. Identifiers may be constructed using any method described elsewhere herein. Stored data may be copied and accessed using any method described elsewhere herein.

The identifier may comprise information relating to a location of the encoded symbol, a value of the encoded symbol, or both the location and the value of the encoded symbol. An identifier may include information relating to a location of the encoded symbol and the presence or absence of the identifier in an identifier library may indicate the value of the symbol. The presence of an identifier in an identifier library may indicate a first symbol value (e.g., first bit value) in a binary string and the absence of an identifier in an identifier library may indicate a second symbol value (e.g., second bit value) in a binary string. In a binary system, basing a bit value on the presence or absence of an identifier in an identifier library may reduce the number of identifiers assembled and, therefore, reduce the write time. In an example, the presence of an identifier may indicate a bit value of '1' at the mapped location and the absence of an identifier may indicate a bit value of '0' at the mapped location.

Generating symbols (e.g., bit values) for a piece of information may include identifying the presence or absence of the identifier that the symbol (e.g., bit) may be mapped or encoded to. Determining the presence or absence of an identifier may include sequencing the present identifiers or using a hybridization array to detect the presence of an identifier. In an example, decoding and reading the encoded sequences may be performed using sequencing platforms. Examples of sequencing platforms are described in U.S. patent application Ser. No. 14/465,685 filed Aug. 21, 2014, entitled "METHOD OF NUCLEIC ACID AMPLIFICATION", and published as U.S. Patent Publication No.: 2014-0371100 A1 on Dec. 18, 2014; U.S. patent application Ser. No. 13/886,234 filed May 2, 2013, entitled "METHOD OF NUCLEIC ACID AMPLIFICATION", and published as U.S. Patent Publication No.: 2013-0231254 A1 on Sep. 5, 2013; and U.S. patent application Ser. No. 12/400,593 filed Mar. 9, 2009, entitled "METHODS AND APPARATUSES FOR ANALYZING POLYNUCLEOTIDE SEQUENCES", and published as U.S. Patent Publication No.: US 2009-0253141 A1 on Oct. 8, 2009, each of which is entirely incorporated herein by reference.

In an example, decoding nucleic acid encoded data may be achieved by base-by-base sequencing of the nucleic acid strands, such as Illumina® Sequencing, or by utilizing a sequencing technique that indicates the presence or absence of specific nucleic acid sequences, such as fragmentation analysis by capillary electrophoresis. The sequencing may employ the use of reversible terminators. The sequencing may employ the use of natural or non-natural (e.g., engineered) nucleotides or nucleotide analogs. Alternatively or in addition to, decoding nucleic acid sequences may be performed using a variety of analytical techniques, including but not limited to, any methods that generate optical, electrochemical, or chemical signals. A variety of sequencing approaches may be used including, but not limited to, polymerase chain reaction (PCR), digital PCR, Sanger sequencing, high-throughput sequencing, sequencing-by-synthesis, single-molecule sequencing, sequencing-by-ligation, RNA-Seq (Illumina), Next generation sequencing, Digital Gene Expression (Helicos), Clonal Single MicroArray (Solexa), shotgun sequencing, Maxim-Gilbert sequencing, or massively-parallel sequencing.

Various read-out methods can be used to pull information from the encoded nucleic acid. In an example, microarray (or any sort of fluorescent hybridization), digital PCR, quantitative PCR (qPCR), and various sequencing platforms can be further used to read out the encoded sequences and by extension digitally encoded data.

An identifier library may further comprise supplemental nucleic acid sequences that provide metadata about the information, encrypt or mask the information, or that both provide metadata and mask the information. The supplemental nucleic acids may be identified simultaneously with identification of the identifiers. Alternatively, the supplemental nucleic acids may be identified prior to or after identifying the identifiers. In an example, the supplemental nucleic acids are not identified during reading of the encoded information. The supplemental nucleic acid sequences may be indistinguishable from the identifiers. An identifier index or a key may be used to differentiate the supplemental nucleic acid molecules from the identifiers.

The efficiency of encoding and decoding data may be increased by recoding input bit strings to enable the use of fewer nucleic acid molecules. For example, if an input string is received with a high occurrence of '111' substrings, which may map to three nucleic acid molecules (e.g., identifiers) with an encoding method, it may be recoded to a '000' substring which may map to a null set of nucleic acid molecules. The alternate input substring of '000' may also be recoded to '111'. This method of recoding may reduce the total amount of nucleic acid molecules used to encode the data because there may be a reduction in the number of '1's in the dataset. In this example, the total size of the dataset may be increased to accommodate a codebook that specifies the new mapping instructions. An alternative method for increasing encoding and decoding efficiency may be to recede the input string to reduce the variable length. For example, '111' may be recoded to '00' which may shrink the size of the dataset and reduce the number of '1's in the dataset.

The speed and efficiency of decoding nucleic acid encoded data may be controlled (e.g., increased) by specifically designing identifiers for ease of detection. For example, nucleic acid sequences (e.g., identifiers) that are designed for ease of detection may include nucleic acid sequences comprising a majority of nucleotides that are easier to call and detect based on their optical, electrochemical, chemical, or physical properties, Engineered nucleic acid sequences may be either single or double stranded. Engineered nucleic acid sequences may include synthetic or unnatural nucleotides that improve the detectable properties of the nucleic acid sequence. Engineered nucleic acid sequences may comprise all natural nucleotides, all synthetic or unnatural nucleotides, or a combination of natural, synthetic, and unnatural nucleotides. Synthetic nucleotides may include nucleotide analogues such as peptide nucleic acids, locked nucleic acids, glycol nucleic acids, and threose nucleic acids. Unnatural nucleotides may include dNaM, an artificial nucleoside containing a 3-methoxy-2-naphthly group, and d5SICS, an artificial nucleoside containing a 6-methylisoquinoline-1-thione-2-yl group. Engineered nucleic acid sequences may be designed for a single enhanced property, such as enhanced optical properties, or the designed nucleic acid sequences may be designed with multiple enhanced properties, such as enhanced optical and electrochemical properties or enhanced optical and chemical properties. See Chemical Methods Section H on DNA design.

Engineered nucleic acid sequences may comprise reactive natural, synthetic, and unnatural nucleotides that do not improve the optical, electrochemical, chemical, or physical properties of the nucleic acid sequences. The reactive components of the nucleic acid sequences may enable the addition of a chemical moiety that confers improved properties to the nucleic acid sequence. Each nucleic acid sequence may include a single chemical moiety or may include multiple chemical moieties. Example chemical moieties may include, but are not limited to, fluorescent moieties, chemiluminescent moieties, acidic or basic moieties, hydrophobic or hydrophilic moieties, and moieties that alter oxidation state or reactivity of the nucleic acid sequence.

A sequencing platform may be designed specifically for decoding and reading information encoded into nucleic acid sequences. The sequencing platform may be dedicated to sequencing single or double stranded nucleic acid molecules. The sequencing platform may decode nucleic acid encoded data by reading individual bases (e.g., base-by-base sequencing) or by detecting the presence or absence of an entire nucleic acid sequence (e.g., component) incorporated within the nucleic acid molecule (e.g., identifier). The sequencing platform may include the use of promiscuous reagents, increased read lengths, and the detection of specific nucleic acid sequences by the addition of detectable chemical moieties. The use of more promiscuous reagents during sequencing may increase reading efficiency by enabling faster base calling which in turn may decrease the sequencing time. The use of increased read lengths may enable longer sequences of encoded nucleic acids to be decoded per read. The addition of detectable chemical moiety tags may enable the detection of the presence or absence of a nucleic acid sequence by the presence or absence of a chemical moiety. For example, each nucleic acid sequence encoding a bit of information may be tagged with a chemical moiety that generates a unique optical, electrochemical, or chemical signal. The presence or absence of that unique optical, electrochemical, or chemical signal may indicate a '0' or a '1' bit value. The nucleic acid sequence may comprise a single chemical moiety or multiple chemical moieties. The chemical moiety may be added to the nucleic acid sequence prior to use of the nucleic acid sequence to encode data. Alternatively or in addition to, the chemical moiety may be added to the nucleic acid sequence after encoding the data, but prior to decoding the data. The chemical moiety tag may be added directly to the nucleic acid sequence or the nucleic acid sequence may comprise a synthetic or unnatural nucleotide anchor and the chemical moiety tag may be added to that anchor.

Unique codes may be applied to minimize or detect encoding and decoding errors. Encoding and decoding errors may occur from false negatives (e.g., a nucleic acid molecule or identifier not included in a random sampling). An example of an error detecting code may be a checksum sequence that counts the number of identifiers in a contiguous set of possible identifiers that is included in the identifier library. While reading the identifier library, the checksum may indicate how many identifiers from that contiguous set of identifiers to expect to retrieve, and identifiers can continue to be sampled for reading until the expected number is met. In some embodiments, a checksum sequence may be included for every contiguous set of R identifiers where R can be equal in size or greater than 1, 2, 5, 10, 50, 100, 200, 500, or 1000 or less than 1000, 500, 200, 100, 50, 10, 5, or 2. The smaller the value of R, the better the error detection. In some embodiments, the checksums may be supplemental nucleic acid sequences. For example, a set comprising seven nucleic acid sequences (e.g., components) may be divided into two groups, nucleic acid sequences for constructing identifiers with a product scheme (components X1-X3 in layer X and Y1-Y3 in layer Y), and nucleic acid sequences for the supplemental checksums (X4-X7 and Y4-Y7). The checksum sequences X4-X7 may indicate whether zero, one, two, or three sequences of layer X are assembled with each member of layer Y. Alternatively, the checksum sequences Y4-Y7 may indicate whether zero, one, two, or three sequences of layer Y are assembled with each member of layer X. In this example, an original identifier library with identifiers {X1Y1, X1Y3, X2Y1, X2Y2, X2Y3} may be supplemented to include checksums to become the following pool: {X1Y1, X1Y3, X2Y1, X2Y2, X2Y3, X1Y6, X2Y7, X3Y4, X6Y1, X5Y2, X6Y3}. The checksum sequences may also be used for error correction. For example, absence of X1Y1 from the above dataset and the presence of X1Y6 and X6Y1 may enable inference that the X1Y1 nucleic acid molecule is missing from the dataset. The checksum sequences may indicate whether identifiers are missing from a sampling of the identifier library or an accessed portion of the identifier library. In the case of a missing checksum sequence, access methods such as PCR or affinity tagged probe hybridization may amplify and/or isolate it, in some embodiments, the checksums may not be supplemental nucleic acid sequences. They checksums may be coded directly into the information such that they are represented by identifiers.

Noise in data encoding and decoding may be reduced by constructing identifiers palindromically, for example, by using palindromic pairs of components rather than single components in the product scheme. Then the pairs of components from different layers may be assembled to one another in a palindromic manner (e.g., YXY instead of XY for components X and Y). This palindromic method may be expanded to larger numbers of layers (e.g., ZYXYZ instead of XYZ) and may enable detection of erroneous cross reactions between identifiers.

Adding supplemental nucleic acid sequences in excess (e.g., vast excess) to the identifiers may prevent sequencing from recovering the encoded identifiers. Prior to decoding the information, the identifiers may be enriched from the supplemental nucleic acid sequences. For example, the identifiers may be enriched by a nucleic acid amplification reaction using primers specific to the identifier ends. Alternatively, or in addition to, the information may be decoded without enriching the sample pool by sequencing (e.g., sequencing by synthesis) using a specific primer. In both decoding methods, it may be difficult to enrich or decode the information without having a decoding key or knowing something about the composition of the identifiers. Alternative access methods may also be employed such as using affinity tag based probes.

Systems for Encoding Binary Sequence Data

A system for encoding digital information into nucleic acids (e.g., DNA) can comprise systems, methods and devices for converting files and data (e.g., raw data, compressed zip files, integer data, and other forms of data) into bytes and encoding the bytes into segments or sequences of nucleic acids, typically DNA, or combinations thereof.

In an aspect, the present disclosure provides systems for encoding binary sequence data using nucleic acids. A system for encoding binary sequence data using nucleic acids may comprise a device and one or more computer processors. The device may be configured to construct an identifier library. The one or more computer processors may be individually or collectively programmed to (i) translate the information into a sting of symbols, (ii) map the string of symbols to the plurality of identifiers, and (iii) construct an identifier library comprising at least a subset of a plurality of identifiers. An individual identifier of the plurality of identifiers may correspond to an individual symbol of the string of symbols. An individual identifier of the plurality of identifiers may comprise one or more components. An individual component of the one or more components may comprise a nucleic acid sequence.

In another aspect, the present disclosure provides systems for reading binary sequence data using nucleic acids. A system for reading binary sequence data using nucleic acids may comprise a database and one or more computer processors. The database may store an identifier library encoding the information. The one or more computer processors may be individually or collectively programmed to (i) identify the identifiers in the identifier library, (ii) generate a plurality of symbols from identifiers identified in (i), and (iii) compile the information from the plurality of symbols. The identifier library may comprise a subset of a plurality of identifiers. Each individual identifier of the plurality of identifiers may correspond to an individual symbol in a string of symbols. An identifier may comprise one or more components. A component may comprise a nucleic acid sequence.

Non-limiting embodiments of methods for using the system to encode digital data can comprise steps for receiving digital information in the form of byte streams. Parsing the byte streams into individual bytes, mapping the location of a bit within the byte using a nucleic acid index (or identifier rank), and encoding sequences corresponding to either bit values of 1 or bit values of 0 into identifiers. Steps for retrieving digital data can comprise sequencing a nucleic acid sample or nucleic acid pool comprising sequences of nucleic acid (e.g., identifiers) that map to one or more bits, referencing an identifier rank to confirm if the identifier is present in the nucleic acid pool and decoding the location and bit-value information for each sequence into a byte comprising a sequence of digital information.

Systems for encoding, writing, copying, accessing, reading, and decoding information encoded and written into nucleic acid molecules may be a single integrated unit or may be multiple units configured to execute one or more of the aforementioned operations. A system for encoding and writing information into nucleic acid molecules (e.g., identifiers) may include a device and one or more computer processors. The one or more computer processors may be programmed to parse the information into strings of symbols (e.g., strings of bits). The computer processor may generate an identifier rank. The computer processor may categorize the symbols into two or more categories. One category may include symbols to be represented by a presence of the corresponding identifier in the identifier library and the other category may include symbols to be represented by an absence of the corresponding identifiers in the identifier library. The computer processor may direct the device to assemble the identifiers corresponding to symbols to be represented to the presence of an identifier in the identifier library.

The device may comprise a plurality regions, sections, or partitions. The reagents and components to assemble the identifiers may be stored in one or more regions, sections, or partitions of the device. Layers may be stored in separate regions of section of the device. A layer may comprise one or more unique components. The component in one layer may be unique from the components in another layer. The regions or sections may comprise vessels and the partitions may comprise wells. Each layer may be stored in a separate vessel or partition. Each reagent or nucleic acid sequence may be stored in a separate vessel or partition. Alternatively, or in addition to, reagents may be combined to form a master mix for identifier construction. The device may transfer reagents, components, and templates from one section of the device to be combined in another section. The device may provide the conditions for completing the assembly reaction. For example, the device may provide heating, agitation, and detection of reaction progress. The constructed identifiers may be directed to undergo one or more subsequent reactions to add barcodes, common sequences, variable sequences, or tags to one or more ends of the identifiers. The identifiers may then be directed to a region or partition to generate an identifier library. One or more identifier libraries may be stored in each region, section, or individual partition of the device. The device may transfer fluid (e.g., reagents, components, templates) using pressure, vacuum, or suction.

The identifier libraries may be stored in the device or may be moved to a separate database. The database may comprise one or more identifier libraries. The database may provide conditions for long term storage of the identifier libraries (e.g., conditions to reduce degradation of identifiers). The identifier libraries may be stored in a powder, liquid, or solid form. Aqueous solutions of identifiers may be lyophilized for more stable storage (see Chemical Methods Section G for more information about lyophilization). Alternatively, identifiers may be stored in the absence of oxygen (e.g. anaerobic storage conditions). The database may provide Ultra-Violet light protection, reduced temperature (e.g., refrigeration or freezing), and protection from degrading chemicals and enzymes. Prior to being transferred to a database, the identifier libraries may be lyophilized or frozen. The identifier libraries may include ethylenediaminetetraacetic acid (EDTA) to inactivate nucleases and/or a buffer to maintain the stability of the nucleic acid molecules.

The database may be coupled to, include, or be separate from a device that writes the information into identifiers, copies the information, accesses the information, or reads the information. A portion of an identifier library may be removed from the database prior to copying, accessing or reading. The device that copies the information from the database may be the same or a different device from that which writes the information. The device that copies the information may extract an aliquot of an identifier library from the device and combine that aliquot with the reagents and constituents to amplify a portion of or the entire identifier library. The device may control the temperature, pressure, and agitation of the amplification reaction. The device may comprise partitions and one or more amplification reaction may occur in the partition comprising the identifier library. The device may copy more than one pool of identifiers at a time.

The copied identifiers may be transferred from the copy device to an accessing device. The accessing device may be the same device as the copy device. The access device may comprise separate regions, sections, or partitions. The access device may have one or more columns, bead reservoirs, or magnetic regions for separating identifiers bound to affinity tags (see Chemical Methods Section F about nucleic acid capture). Alternatively, or in addition to, the access device may have one or more size selection units. A size selection unit may include agarose peel electrophoresis or any other method for size selecting nucleic acid molecules (see Chemical Methods Section E for more information about nucleic acid size-selection). Copying and extraction may be performed in the same region of a device or in different regions of a device (see Chemical Methods Section D about nucleic acid amplification).

The accessed data may be read in the same device or the accessed data may be transferred to another device. The reading device may comprise a detection unit to detect and identify the identifiers. The detection unit may be part of a sequencer, hybridization array, or other unit for identifying the presence or absence of an identifier. A sequencing platform may be designed specifically for decoding and reading information encoded into nucleic acid sequences. The sequencing platform may be dedicated to sequencing single or double stranded nucleic acid molecules. The sequencing platform may decode nucleic acid encoded data by reading individual bases base-by-base sequencing) or by detecting the presence or absence of an entire nucleic acid sequence e.g, component) incorporated within the nucleic acid molecule (e.g., identifier). Alternatively, the sequencing platform may be a system such as Illumina® Sequencing or fragmentation analysis by capillary electrophoresis. Alternatively or in addition to, decoding nucleic acid sequences may be performed using a variety of analytical techniques implemented by the device, including but not limited to, any methods that generate optical, electrochemical, or chemical signals.

Information storage in nucleic acid molecules may have various applications including, but not limited to, long term information storage, sensitive information storage, and storage of medical information. In an example, a person's medical information (e.g., medical history and records) may be stored in nucleic acid molecules and carried on his or her person. The information may be stored external to the body (e.g., in a wearable device) or internal to the body (e.g., in a subcutaneous capsule). When a patient is brought into a medical office or hospital, a sample may be taken from the device or capsule and the information may be decoded with the use of a nucleic acid sequencer. Personal storage of medical records in nucleic acid molecules may provide an alternative to computer and cloud based storage systems. Personal storage of medical records in nucleic acid molecules may reduce the instance or prevalence of medical records being hacked. Nucleic acid molecules used for capsule-based storage of medical records may be derived from human genomic sequences. The use of human genomic sequences may decrease the immunogenicity of the nucleic acid sequences in the event of capsule failure and leakage.

Computer Systems

Figure 19:
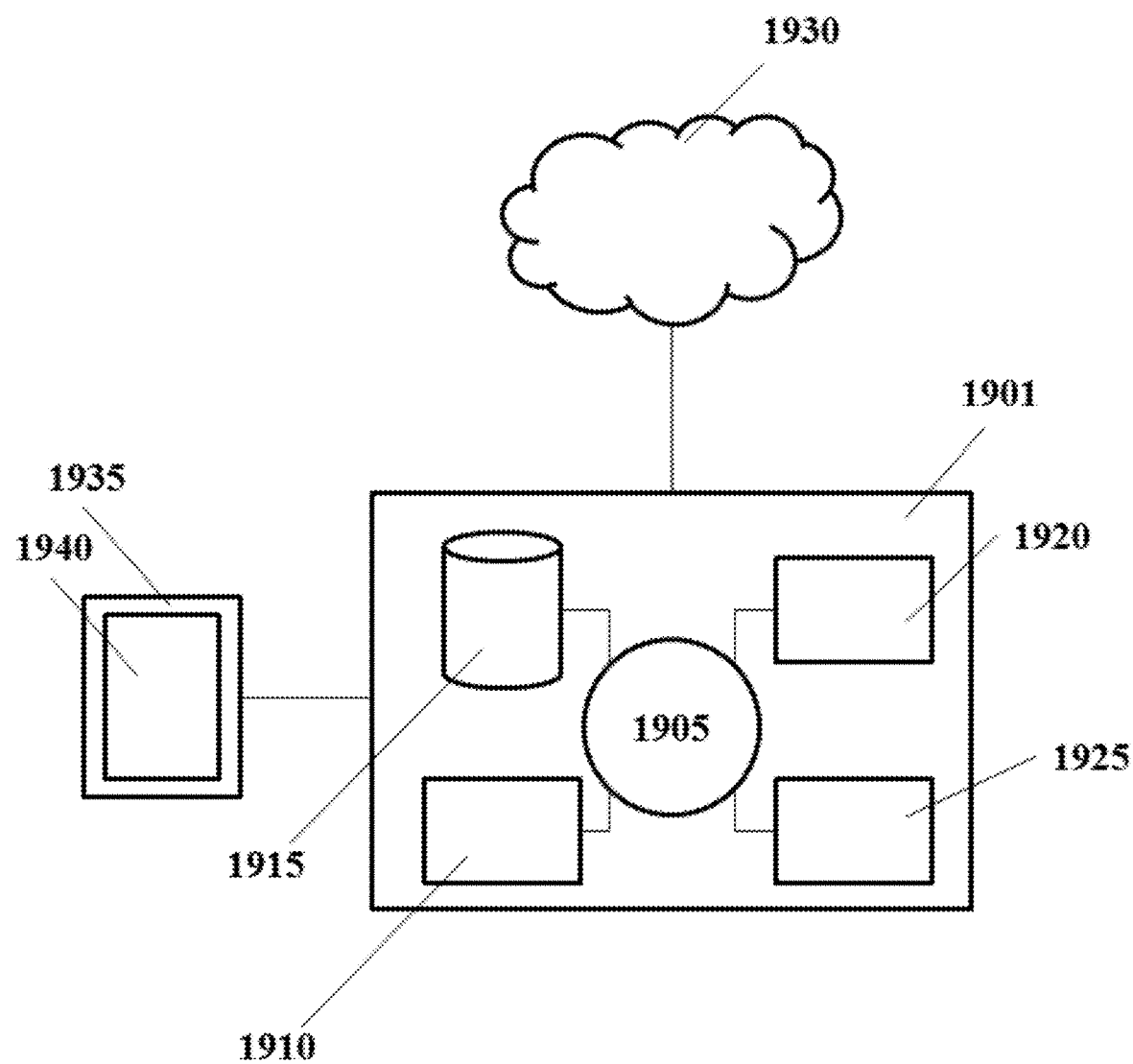
FIG. 19 shows a computer system that is programmed or otherwise configured to implement methods provided herein.

The present disclosure provides computer systems that are programmed to implement methods of the disclosure. FIG. 19 shows a computer system 1901 that is programmed or otherwise configured to encode digital information into nucleic acid sequences and/or read (e.g., decode) information derived from nucleic acid sequences. The computer system 1901 can regulate various aspects of the encoding and decoding procedures of the present disclosure, such as, for example, the bit-values and bit location information for a given bit or byte from an encoded bitstream or byte stream.

The computer system 1901 includes a central processing unit (CPU, also "processor" and "computer processor" herein) 1905, which can be a single core or multi core processor, or a plurality of processors for parallel processing. The computer system 1901 also includes memory or memory location 1910 (e.g., random-access memory, read-only memory, flash memory), electronic storage unit 1915 (e.g., hard disk), communication interface 1920 (e.g., network adapter) for communicating with one or more other systems, and peripheral devices 1925, such as cache, other memory, data storage and/or electronic display adapters. The memory 1910, storage unit 1915, interface 1920 and peripheral devices 1925 are in communication with the CPU 1905 through a communication bus (solid lines), such as a motherboard. The storage unit 1915 can be a data storage unit (or data repository) for storing data. The computer system 1901 can be operatively coupled to a computer network ("network") 1930 with the aid of the communication interface 1920. The network 1930 can be the Internet, an internet and/or extranet, or an intranet and/or extranet that is in communication with the Internet. The network 1930 in some cases is a telecommunication and/or data network. The network 1930 can include one or more computer servers, which can enable distributed computing, such as cloud computing. The network 1930, in some cases with the aid of the computer system 1901, can implement a peer-to-peer network, which may enable devices coupled to the computer system 1901 to behave as a client or a server.

The CPU 1905 can execute a sequence of machine-readable instructions, which can be embodied in a program or software. The instructions may be stored in a memory location, such as the memory 1910. The instructions can be directed to the CPU 1905, which can subsequently program or otherwise configure the CPU 1905 to implement methods of the present disclosure. Examples of operations performed by the CPU 1905 can include fetch, decode, execute, and writeback.

The CPU 1905 can be part of a circuit, such as an integrated circuit. One or more other components of the system 1901 can be included in the circuit. In some cases, the circuit is an application specific integrated circuit (ASIC).

The storage unit 1915 can store files, such as drivers, libraries and saved programs. The storage unit 1915 can store user data, e.g., user preferences and user programs. The computer system 1901 in some cases can include one or more additional data storage units that are external to the computer system 1901, such as located on a remote server that is in communication with the computer system 1901 through an intranet or the Internet.

The computer system 1901 can communicate with one or more remote computer systems through the network 1930. For instance, the computer system 1901 can communicate with a remote computer system of a user or other devices and or machinery that may be used by the user in the course of analyzing data encoded or decoded in a sequence of nucleic acids (e.g., a sequencer or other system for chemically determining the order of nitrogenous bases in a nucleic acid sequence). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1901 via the network 1930.

Methods as described herein can be implemented by way of machine (e.g., computer processor) executable code stored on an electronic storage location of the computer system 1901, such as, for example, on the memory 1910 or electronic storage unit 1915. The machine executable or machine readable code can be provided in the form of software. During use, the code can be executed by the processor 1905. In some cases, the code can be retrieved from the storage unit 1915 and stored on the memory 1910 for ready access by the processor 1905. In some situations, the electronic storage unit 1915 can be precluded, and machine-executable instructions are stored on memory 1910.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 1901, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1901 can include or be in communication with an electronic display 1935 that comprises a user interface WO 1940 for providing, for example, sequence output data including chromatographs, sequences as well as bits, bytes, or bit streams encoded by or read by a machine or computer system that is encoding or decoding nucleic acids, raw data, files and compressed or decompressed zip files to be encoded or decoded into DNA stored data. Examples of UI's include, without limitation, a graphical user interface (GUI) and web-based user interface. Methods and systems of the present disclosure can be implemented by way of one or more algorithms. An algorithm can be implemented by way of software upon execution by the central processing unit 1905. The algorithm can, for example, be used with a DNA index and raw data or zip file compressed or decompressed data, to determine a customized method for coding digital information from the raw data or zip file compressed data, prior to encoding the digital information.

Chemical Methods Section

A. Overlap Extension PCR (OEPCR) Assembly

In OEPCR, components are assembled in a reaction comprising polymerase and dNTPs (deoxynucleotide tri phosphates comprising dATP, dTTP, dCTP, dGTP or variants or analogs thereof). Components can be single stranded or double stranded nucleic acids. Components to be assembled adjacent to each other may have complementary 3' ends, complementary 5' ends, or homology between one component's 5' end and the adjacent component's 3' end. These end regions, termed "hybridization regions", are intended to facilitate the formation of hybridized junctions between the components during OEPCR, wherein the 3' end of one input component (or it's complement) is hybridized to the 3' end of its intended adjacent component (or it's complement). An assembled double-stranded product can then be formed by polymerase extension. This product may then be assembled to more components through subsequent hybridization and extension. FIG. 7 illustrates an example schematic of OEPCR for assembling three nucleic acids.

In some embodiments, the OEPCR may comprise cycling between three temperatures: a melting temperature, an annealing temperature, and an extension temperature. The melting temperature is intended to turn double stranded nucleic acids into single stranded nucleic acids, as well as remove the formation of secondary structures or hybridizations within a component or between components. Typically the melting temperature is high, for example above 95 degrees Celsius. In some embodiments the melting temperature may be at least 96, 97, 98, 99, 100, 101, 102, 103, 104, or 105 degrees Celsius. In other embodiments the melting temperature may be at most 95, 94, 93, 92, 91, or 90 degrees Celsius. A higher melting temperature may improve dissociation of nucleic acids and their secondary structures, but may also cause side effects such as the degradation of nucleic acids or the polymerase. Melting temperatures may be applied to the reaction for at least 1, 2, 3, 4, 5 seconds, or above, such as 30 seconds, 1 minute, 2 minutes, or 3 minutes.

The annealing temperature is intended to facilitate the formation of hybridization between complementary 3' ends of intended adjacent components (or their complements). In some embodiments, the annealing temperature may match the calculated melting temperature of the intended hybridized nucleic acid formation. In other embodiments, the annealing temperature may be within 10 degrees Celsius or more of said melting temperature. In some embodiments, the annealing temperature may be at least 25, 30, 50, 55, 60, 65, or 70 degrees Celsius. The melting temperature may depend on the sequence of the intended hybridization region between components. Longer hybridization regions have higher melting temperatures, and hybridization regions with higher percent content of Guanine or Cytosine nucleotides may have higher melting temperatures. It may therefore be possible to design components for OEPCR reactions intended to assemble optimally at particular annealing temperatures. Annealing temperatures may be applied to the reaction for at least 1, 5, 10, 15, 20, 25, or 30 seconds, or above.

The extension temperature is intended to initiate and facilitate the nucleic acid chain elongation of hybridized 3' ends catalyzed by one or more polymerase enzymes. In some embodiments, the extension temperature may be set at the temperature in which the polymerase functions optionally in terms of nucleic acid binding strength, elongation speed, elongation stability, or fidelity. In some embodiments, the extension temperature may be at least 30, 40, 50, 60, or 70 degrees Celsius, or above. Annealing temperatures may be applied to the reaction for at least 1, 5, 10, 15, 20, 25, 30, 40, 50, or 60 seconds or above. Recommended extension times may be around 15 to 45 seconds per kilobase of expected elongation.

In some embodiments of OEPCR, the annealing temperature and the extension temperature may be the same. Thus a 2-step temperature cycle may be used instead of a 3-step temperature cycle. Examples of combined annealing and extension temperatures include 60, 65, or 72 degrees Celsius.

In some embodiments, OEPCR may be performed with one temperature cycle. Such embodiments may involve the intended assembly of just two components. In other embodiments, OEPCR may be performed with multiple temperature cycles. Any give nucleic acid in OEPCR may only assemble to at most one other nucleic acid in one cycle. This is because assembly (or extension or elongation) only occurs at the 3' end of a nucleic acid and each nucleic acid only has one 3' end. Therefore, the assembly of multiple components may require multiple temperature cycles. For example, assembling four components may involve 3 temperature cycles. Assembling 6 components may involve 5 temperature cycles. Assembling 10 components may involve 9 temperature cycles. In some embodiments, using more temperature cycles than the minimum required may increase assembly efficiency. For example using four temperature cycles to assemble two components may yield more product than only using one temperature cycle. This is because the hybridization and elongation of components is a statistical event that occurs with a fraction of the total number of components in each cycle. So the total fraction of assembled components may increase with increased cycles.

In addition to temperature cycling considerations, the design of the nucleic acid sequences in OEPCR may influence the efficiency of their assembly to one another. Nucleic acids with long hybridization regions may hybridize more efficiently at a given annealing temperature compared with nucleic acids with short hybridization regions. This is because a longer hybridized product contains a larger number of stable base-pairs and may therefore be a more stable overall hybridized product than a shorter hybridized product. Hybridization regions may have a length of at least 1, 2, 3 4, 5, 6, 7, 8, 9, 10, or more bases.

Hybridization regions with high guanine or cytosine content may hybridize more efficiently at a given temperature than hybridization regions with low guanine or cytosine content. This is because guanine forms a more stable basepair with cytosine than adenine does with thymine. Hybridization regions may have a guanine or cytosine content (also known as GC content) of anywhere between 0% and 100%.

In addition to hybridization region length and GC content, there are many more aspects of the nucleic acid sequence design that may affect the efficiency of the OEPCR. For example, the formation of undesired secondary structures within a component may interfere with its ability to form a hybridization product with its intended adjacent component. These secondary structures may include hairpin loops. The types of possible secondary structures and their stability (for example meting temperature) for a nucleic acid may be predicted based on the sequence. Design space search algorithms may be used to determine nucleic acid sequences that meet proper length and GC content criteria for efficient OEPCR, while avoiding sequences with potentially inhibitory secondary structures. Design space search algorithms may include genetic algorithms, heuristic search algorithms, meta-heuristic search strategies like tabu search, branch-and-bound search algorithms, dynamic programming-based algorithms, constrained combinatorial optimization algorithms, gradient descent-based algorithms, randomized search algorithms, or combinations thereof.

Likewise, the formation of homodimers (nucleic acid molecules that hybridize with nucleic acid molecules of the same sequence) and unwanted heterodimers (nucleic acid sequences that hybridize with other nucleic acid sequences aside from their intended assembly partner) may interfere with OEPCR. Similar to secondary structures within a nucleic acid, the formation of homodimers and heterodimers may be predicted and accounted for during nucleic acid design using computation methods and design space search algorithms.

Longer nucleic acid sequences or higher GC content may create increased formation of unwanted secondary structures, homodimers, and heterodimers with the OEPCR.

Therefore, in some embodiments, the use of shorter nucleic acid sequences or lower GC content may lead to higher assembly efficiency. These design principles may counteract the design strategies of using long hybridization regions or high GC content for more efficient assembly. As such, in some embodiments, OEPCR may be optimized by using long hybridization regions with high GC content but short non-hybridization regions with low GC content. The overall length of nucleic acids may be at least 10, 20, 30, 40, 50, 60, 70, 80, 90, or 100 bases, or above. In some embodiments, there may be an optimal length and optimal GC content for the hybridization regions of nucleic acids where the assembly efficiency is optimized.

A larger number of distinct nucleic acids in an OEPCR reaction may interfere with the expected assembly efficiency. This is because a larger number of distinct nucleic acid sequences may create a higher probability for undesirable molecular interactions, particularly in the form of heterodimers. Therefore in some embodiments of OEPCR that assemble large numbers of components, nucleic acid sequence constraints may become more stringent for efficient assembly.

Primers for amplifying the anticipated final assembled product may be included in an OEPCR reaction. The OEPCR reaction may then be performed with more temperature cycles to improve the yield of the assembled product, not just by creating more assemblies between the constituent components, but also by exponentially amplifying the full assembled product in the manner of conventional PCR (see Chemical Methods Section D).

Additives may be included in the OEPCR reaction to improve assembly efficiency. For example, the addition of Betaine, Dimethyl sulfoxide (DMSO), non-ionic detergents. Formamide, Magnesium, Bovine Serum Albumin (BSA), or combinations thereof. Additive content (weight per volume) may be at least 0%, 1%, 5%, 10%, 20%, or more.

Various polymerases may be used for OEPCR. The polymerase can be naturally occurring or synthesized. An example polymerase is a Φ29 polymerase or derivative thereof. In some cases, a transcriptase or a ligase is used (i.e., enzymes which catalyze the formation of a bond) in conjunction with polymerases or as an alternative to polymerases to construct new nucleic acid sequences. Examples of polymerases include a DNA polymerase, a RNA polymerase, a thermostable polymerase, a wild-type polymerase, a modified polymerase, E. coli DNA polymerase I, T7 DNA polymerase, bacteriophage T4 DNA polymerase Φ29 (phi29) DNA polymerase, Taq polymerase, Tth polymerase, Tli polymerase, Pfu polymerase Pwo polymerase, VENT polymerase, DEEPVENT polymerase, Ex-Taq polymerase, LA-Taw polymerase, Sso polymerase Poc polymerase, Pab polymerase, Mth polymerase ES4 polymerase, Tru polymerase, Tac polymerase, Tne polymerase, Tma polymerase, Tca polymerase, Tih polymerase, Tfi polymerase, Platinum Taq polymerases, Tbr polymerase, Phusion polymerase, KAPA polymerase, Q5 polymerase, Tfl polymerase, Pfutubo polymerase, Pyrobest polymerase, KOD polymerase, Bst polymerase, Sac polymerase, Klenow fragment polymerase with 3' to 5' exonuclease activity, and variants, modified products and derivatives thereof. Different polymerases may be stable and function optimally at different temperatures. Moreover, different polymerases have different properties. For example, some polymerases, such a Phusion polymerase, may exhibit 3' to 5' exonuclease activity, which may contribute to higher fidelity during nucleic acid elongation. Some polymerases may displace leading sequences during elongation, while others may degrade them or halt elongation. Some polymerases, like Taq, incorporate an adenine base at the 3' end of nucleic acid sequences. This process is referred to as A-tailing and may be inhibitory to OEPCR as the addition of an Adenine base may disrupt the designed 3' complementarity between intended adjacent components.

OEPCR may also be referred to as polymerase cycling assembly (or PCA).

B. Ligation Assembly

In ligation assembly, separate nucleic acids are assembled in a reaction comprising one or more ligase enzymes and additional co-factors. Co-factors may include Adenosine Tri-Phosphate (ATP), Dithiothreitol (DTT), or Magnesium ion ($Mg^{2+}$). During ligation, the 3'-end of one nucleic acid strand is covalently linked to the 5' end of another nucleic acid strand, thus forming an assembled nucleic acid. Components in a ligation reaction may be blunt-ended double stranded DNA (dsDNA), single stranded DNA (ssDNA), or partially hybridized single-stranded DNA. Strategies that bring the ends of nucleic acids together increase the frequency of viable substrate for ligase enzymes, and thus may be used for improving the efficiency of ligase reactions. Blunt-ended dsDNA molecules tend to form hydrophobic stacks on which ligase enzymes may act, but a more successful strategy for bringing nucleic acids together may be to use nucleic acid components with either 5' or 3' single-stranded overhangs that have complementarity for the overhangs of components to which they are intended to assemble. In the latter instance, more stable nucleic acid duplexes may form due to base-base hybridization.

When a double stranded nucleic acid has an overhang strand on one end, the other strand on the same end may be referred to as a "cavity". Together, a cavity and overhang form a "sticky end", also known as a "cohesive-end". A sticky end may be either a 3' overhang and a 5' cavity, or a 5' overhang and a 3' cavity. The sticky-ends between two intended adjacent components may be designed to have complementarity such that the overhang of both sticky ends hybridize such that each overhang ends directly adjacent to the beginning of the cavity on the other component. This forms a "nick" (a double stranded DNA break) that may be "sealed" (covalently linked through a phosphodiester bond) by the action of a ligase. See FIG. 8 for an example schematic of sticky end ligation for assembling three nucleic acids. Either the nick on one strand or the other, or both, may be sealed. Thermodynamically, the top and bottom strand of a molecule that forms a sticky end may move between associated and dissociated states, and therefore the sticky end may be a transient formation. Once, however, the nick along one strand of a sticky end duplex between two components is sealed, that covalent linkage remains even if the members of the opposite strand dissociate. The linked strand may then become a template to which the intended adjacent members of the opposite strand can bind and once again form a nick that may be sealed.

Sticky ends may be created by digesting dsDNA with one or more endonucleases. Endonucleases (that may be referred to as restriction enzymes) may target specific sites (that may be referred to as restriction sites) on either or both ends of dsDNA molecule, and create a staggered cleavage (sometimes referred to as a digestion) thus leaving a sticky end. See Chemical Methods Section C on restriction digests. The digest may leave a palindromic overhang (an overhang with a sequence that is the reverse complement of itself). If so, then two components digested with the same endonuclease may form complimentary sticky ends along which they may be assembled with a ligase. The digestion and ligation may occur together in the same reaction if the endonuclease and ligase are compatible. The reaction may occur at a uniform temperature, such as 4, 10, 16, 25, or 37 degrees Celsius. Or the reaction may cycle between multiple temperatures, such as between 16 degrees Celsius and 37 degrees Celsius. Cycling between multiple temperatures may enable the digestion and ligation to each proceed at their respective optimal temperatures during different parts of the cycle.

It may be beneficial to perform the digestion and ligation in separate reactions. For example, if the desired ligases and the desired endonucleases function optimally at different conditions. Or, for example, if the ligated product forms a new restriction site for the endonuclease. In these instances, it may be better to perform the restriction digest and then the ligation separately, and perhaps it may be further beneficial to remove the restriction enzyme prior to ligation. Nucleic acids may be separated from enzymes through phenol-chloroform extraction, ethanol precipitation, magnetic bead capture, and/or silica membrane adsorption, washing, and elution. Multiple endonucleases may be used in the same reaction, though care should be taken to ensure that the endonucleases do not interfere with each other and function under similar reaction conditions. Using two endonucleases, one may create orthogonal (non-complementary)sticky ends on both ends of a dsDNA component.

Endonuclease digestion will leave sticky ends with phosphorylated 5' ends. Ligases may only function on phosphorylated 5' ends, and not on non-phosphorylated 5' ends. As such, there may not be any need for an intermediate 5' phosphorylation step in between digestion and ligation. A digested dsDNA component with a palindromic overhang on its sticky end may ligate to itself. To prevent self-ligation, it may be beneficial to dephosphorylate said dsDNA component prior to ligation.

Multiple endonucleases may target different restriction sites, but leave compatible overhangs (overhangs that are the reverse complement of each other). The product of ligation of sticky ends created with two such endonucleases may result in an assembled product that does not contain a restriction site for either endonuclease at the site of ligation. Such endonucleases form the basis of assembly methods, such as biobricks assembly, that may programmably assemble multiple components using just two endonucleases by performing repetitive digestion-ligation cycles. FIG. 20 illustrates an example of a digestion-ligation cycle using endonucleases BamHI and BglII with compatible overhangs.

In some embodiments, the endonucleases used to create sticky ends may be type IIS restriction enzymes. These enzymes cleave a fixed number of bases away from their restriction sites in a particular direction, therefore the sequence of the overhangs that they generate may be customized. The overhang sequences need not be palindromic. The same type IIS restriction enzyme may be used to create multiple different sticky ends in the same reaction, or in multiple reactions. Moreover, one or multiple type IIS restriction enzymes may be used to create components with compatible overhangs in the same reaction, or in multiple reactions. The ligation site between two sticky ends generated by type IIS restriction enzymes may be designed such that it does not form a new restriction site. In addition, the type IIS restriction enzyme sites may be placed on a dsDNA such that the restriction enzyme cleaves off its own restriction site when it generates a component with a sticky end. Therefore the ligation product between multiple components generated from type IIS restriction enzymes may not contain any restriction sites.

Type IIS restriction enzymes may be mixed in a reaction together with ligase to perform the component digestion and ligation together. The temperature of the reaction may be cycled between two or more values to promote optimal digestion and ligation. For example, the digestion may be performed optimally at 37 degrees Celsius and the ligation may be performed optimally at 16 degrees Celsius. More generally, the reaction may cycle between temperature values of at least 0, 5, 10, 15, 20, 25, 30, 35, 40, 45, 50, 55, 60, or 65 degrees Celsius or above. A combined digestion and ligation reaction may be used to assemble at least 2, 3, 4, 5, 6, 7, 8, 9, 10, 11, 12, 13, 14, 15, 16, 17, 18, 19, or 20 components, or more. Examples of assembly reactions that leverage Type IIS restriction enzymes to create sticky ends include Golden Gate Assembly (also known as Golden Gate Cloning) or Modular Cloning (also known as MoClo).

In some embodiments of ligation, exonucleases may be used to create components with sticky ends. 3' exonucleases may be used to chew back the 3' ends from dsDNA, thus creating 5' overhangs. Likewise, 5' exonucleases may be used to chew back the 5' ends from dsDNA thus creating 3' overhangs. Different exonucleases may have different properties. For example, exonucleases may differ in the direction of their nuclease activity (5' to 3' or 3' to 5'), whether or not they act on ssDNA, whether they act on phosphorylated or non-phosphorylated 5' ends, whether or not they are able to initiate on a nick, or whether or not they are able to initiate their activity on 5' cavities, 3' cavities, 5' overhangs, or 3' overhangs. Different types of exonucleases include Lambda exonuclease, $RecJ_f$, Exonuclease III, Exonuclease I, Exonuclease T, Exonuclease V, Exonuclease VIII, Exonuclease VII, Nuclease BAL_31, T5 Exonuclease, and I7 Exonuclease.

Exonuclease may be used in a reaction together with ligase to assemble multiple components. The reaction may occur at a fixed temperature or cycle between multiple temperatures, each ideal for the ligase or the exonuclease, respectively. Polymerase may be included in an assembly reaction with ligase and a 5'-to-3' exonuclease. The components in such a reaction may be designed such that components intended to assemble adjacent to each other share homologous sequences on their edges. For example, a component X to be assembled with component Y may have a 3' edge sequence of the form 5'-z-3', and the component Y may have a 5' edge sequence of the form 5'-z-3', where z is any nucleic acid sequence. We refer to homologous edge sequences of such a form as 'gibson overlaps'. As the 5' exonuclease chews back the 5' end of dsDNA components with gibson overlaps it creates compatible 3' overhangs that hybridize to each other. The hybridized 3' ends may then be extended by the action of polymerase to the end of the template component, or to the point where the extended 3' overhang of one component meets the 5' cavity of the adjacent component, thereby forming a nick that may be sealed by a ligase. Such an assembly reaction where polymerase, ligase, and exonuclease are used together is often referred to as "Gibson assembly". Gibson assembly may be performed by using T5 exonuclease, Phusion polymerase, and Taq ligase, and incubating the reaction at 50 degrees Celsius. In said instance, the use of the thermophilic ligase, Taq, enables the reaction to proceed at 50 degrees Celsius, a temperature suitable for all three types of enzymes in the reaction.

The term "Gibson assembly" may generally refer to any assembly reaction involving polymerase, ligase, and exonuclease. Gibson assembly may be used to assemble at least 2, 3, 4, 5, 6, 7, 8, 9, 10, or more components. Gibson assembly may occur as a one-step, isothermal reaction or as a multi-step reaction with one or more temperature incubations. For example, Gibson assembly may occur at temperatures of at least 30, 40, 50, 60, or 70 degrees, or less. The incubation time for a Gibson assembly may be at least 1, 5, 10, 20, 40, or 80 minutes.

Gibson assembly reactions may occur optimally when gibson overlaps between intended adjacent components are a certain length and have sequence features, such as sequences that avoid undesirable hybridization events such as hairpins, homodimers, or unwanted heterodimers. Generally, gibson overlaps of at least 20 bases are recommended. But Gibson overlaps may be at least 1, 2, 3, 5, 10, 20, 30, 40, 50, 60, 100, or more bases in length. The GC content of a gibson overlap may be anywhere from 0% to 100%.

Though Gibson assembly is commonly described with a 5' exonuclease, the reaction may also occur with a 3' exonuclease. As the 3' exonuclease chews back the 3' end of dsDNA components, the polymerase counteracts the action by extending the 3' end. This dynamic process may continue until the 5' overhang (created by the exonuclease) of two components (that share a gibson overlap) hybridize and the polymerase extends the 3' end of one component far enough to meet the 5' end of its adjacent component, thus leaving a nick that may be sealed by a ligase.

Figure 21:
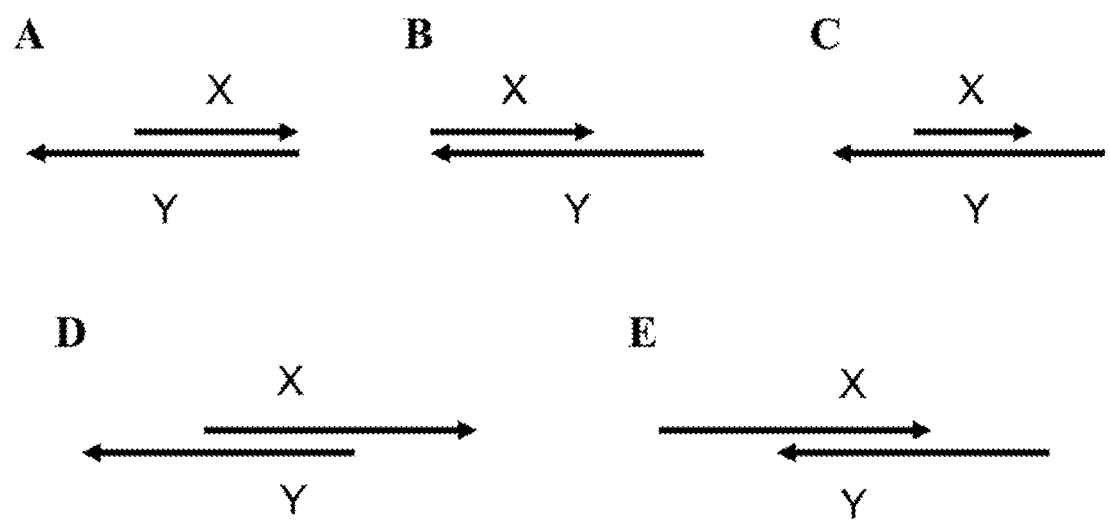
FIG. 21 shows possible sticky-end component structures made from two oligos, X and Y.

In some embodiments of ligation, components with sticky ends may be created synthetically, as opposed to enzymatically, by mixing together two single stranded nucleic acids, or oligos, that do not share full complementarity. For example, two oligos, oligo X and oligo Y, may be designed to only fully hybridize along a contiguous string of complementary bases that form a substring of a larger string of bases that make up the entirety of either one or both oligos. This complementary string of bases is referred to as the "index region". If the index region occupies the entirety of oligo X and only the 5' end of oligo Y, then the oligos together form a component with a blunt end on one side and a sticky end on the other with a 3' overhang from oligo Y (FIG. 21A). If the index region occupies the entirety of oligo X and only the 3' end of oligo Y, then the oligos together form a component with a blunt end on one side and a sticky end on the other with a 5' overhang from oligo Y (FIG. 21B). If the index region occupies the entirety of oligo X and neither end of oligo Y (implying that the index region is embedded within the middle of oligo Y), then the oligos together form a component with a sticky end on one side with a 3' overhang from oligo Y and on the other side with a 5' overhang from oligo Y (FIG. 21C). If the index region occupies only the 5' end of oligo X and only the 5' end of oligo Y, then the oligos together form a component with a sticky end on one side with a 3' overhang from oligo Y and on the other side with a 3' overhang from oligo X (FIG. 21D). If the index region occupies only the 3' end of oligo X and only the 3' end of oligo Y, then the oligos together form a component with a sticky end on one side with a 5' overhang from oligo Y and on the other side with a 5' overhang from oligo X (FIG. 21E). In the aforementioned examples, the sequences of the overhangs are defined by the oligo sequences outside of the index region. These overhang sequences may be referred to as hybridization regions as they are the regions along which components hybridize for ligation.

The index region and hybridization region(s) of oligos in sticky-end ligation may be designed to facilitate the proper assembly of components. Components with long overhangs may hybridize more efficiently with each other at a given annealing temperature compared with components with short overhangs. Overhangs may have a length of at least 1, 2, 3 4, 5, 6, 78, 9, 10, 15, 20, 30, or more bases.

Components with overhangs that contain high guanine or cytosine content may hybridize more efficiently to their complementary component at a given temperature than components with overhangs that contain low guanine or cytosine content. This is because guanine forms a more stable base-pair with cytosine than adenine does with thymine. Overhangs may have a guanine or cytosine content (also known as GC content) of anywhere between 0% and 100%.

As with overhang sequences, the GC content and length of the index region of an oligo may also affect ligation efficiency. This is because sticky-end components may assemble more efficiently if the top and bottom strand of each component are stably bound. Therefore, index regions may be designed with higher GC content, longer sequences, and other features that promote higher melting temperatures. However, there are many more aspects of the oligo design, for both the index region and overhang sequence(s), that may affect the efficiency of the ligation assembly. For example, the formation of undesired secondary structures within a component may interfere with its ability to form an assembled product with its intended adjacent component. This may occur due to either secondary structures in the index region, in the overhang sequence, or in both. These secondary structures may include hairpin loops. The types of possible secondary structures and their stability (for example meting temperature) for an oligo may be predicted based on the sequence. Design space search algorithms may be used to determine oligo sequences that meet proper length and GC content criteria for the formation of effective components, while avoiding sequences with potentially inhibitory secondary structures. Design space search algorithms may include genetic algorithms, heuristic search algorithms, meta-heuristic search strategies like tabu search, branch-and-bound search algorithms, dynamic programming-based algorithms, constrained combinatorial optimization algorithms, gradient descent-based algorithms, randomized search algorithms, or combinations thereof.

Likewise, the formation of homodimers (oligos that hybridize with oligos of the same sequence) and unwanted heterodimers (oligos that hybridize with other oligos aside from their intended assembly partner) may interfere with ligation. Similar to secondary structures within a component, the formation of homodimers and heterodimers may be predicted and accounted for during oligo design using computation methods and design space search algorithms.

Longer oligo sequences or higher GC content may create increased formation of unwanted secondary structures, homodimers, and heterodimers within the ligation reaction. Therefore, in some embodiments, the use of shorter oligos or lower GC content may lead to higher assembly efficiency. These design principles may counteract the design strategies of using long oligos or high GC content for more efficient assembly. As such, there may be an optimal length and optimal GC content for the oligos that make up each component such that the ligation assembly efficiency is optimized. The overall length of oligos to be used in ligation may be at least 10, 20, 30, 40, 50, 60, 70, 80, 90, or 100 bases, or above. The overall GC content of oligos to be used in ligation may be anywhere between 0% and 100%.

In addition to sticky end ligation, ligation may also occur between single-stranded nucleic acids using staple (or template or bridge) strands. This method may be referred to as staple strand ligation (SSL), template directed ligation (TDL), or bridge strand ligation. See FIG. 10A for an example schematic of TDL for assembling three nucleic acids. In TDL, two single stranded nucleic acids hybridize adjacently onto a template, thus forming a nick that may be sealed by a ligase. The same nucleic acid design considerations for sticky end ligation also apply to TDL. Stronger hybridization between the templates and their intended complementary nucleic acid sequences may lead to increased ligation efficiency. Therefore sequence features that improve the hybridization stability (or melting temperature) on each side of the template may improve ligation efficiency. These features may include longer sequence length and higher GC content. The length of nucleic acids in TDL, including templates, may be at least 5, 10, 20, 30 40, 50, 60, 70, 80, 90, or 100 bases, or above. The GC content of nucleic acids, including templates, may be anywhere between 0% and 100%.

In TDL, as with sticky end ligation, care may be taken to design component and template sequences that avoid unwanted secondary structures by using nucleic acid structure-predicting software with sequence space search algorithms. As the components in TDL may be single stranded instead of double stranded, there may be higher incidence of unwanted secondary structures (as compared to sticky end ligation) due to the exposed bases.

TDL may also be performed with blunt-ended dsDNA components. In such reactions, in order for the staple strand to properly bridge two single-stranded nucleic acids, the staple may first need to displace or partially displace the full single-stranded complements. To facilitate the TDL reaction with dsDNA components, the dsDNA may initially be melted with incubation at a high temperature. The reaction may then be cooled thus allowing staple strands to anneal to their proper nucleic acid complements. This process may be made even more efficient by using a relatively high concentration of template compared to dsDNA components, thus enabling the templates to outcompete the proper full-length ssDNA complements for binding. Once two ssDNA strands get assembled by their template and a ligase, that assembled nucleic acid may then become a template for the opposite full-length ssDNA complements. Therefore, ligation of blunt-ended dsDNA with TDL may be improved through multiple rounds of melting (incubation at higher temperatures) and annealing (incubation at lower temperatures). This process may be referred to as Ligase Cyling Reaction, or LCR. Proper melting and annealing temperatures depend on the nucleic acid sequences. Melting and annealing temperatures may be at least 4, 10, 20, 20, 30, 40, 50, 60, 70, 80, 90, or 100 degrees Celsius. The number of temperature cycles may be at least 1, 5, 10, 15, 20, 15, 30, or more.

All ligations may be performed in fixed temperature reactions or in multi-temperature reactions. Ligation temperatures may be at least 0, 4, 10, 20, 20, 30, 40, 50, or 60 degrees Celsius or above. The optimal temperature for ligase activity may differ depending on the type of ligase. Moreover, the rate at which components adjoin or hybridize in the reaction may differ depending on their nucleic acid sequences. Higher incubation temperatures may promote faster diffusion and therefore increase the frequency with which components temporarily adjoin or hybridize. However increased temperature may also disrupt hydrogen bonds between base pairs and therefore decrease the stability of those adjoined or hybridized component duplexes. The optimal temperature for ligation may depend on the number of nucleic acids to be assembled, the sequences of those nucleic acids, the type of ligase, as well as other factors such as reaction additives. For example, two sticky end components with 4-base complementary overhangs may be assembled faster at 4 degrees Celsius with T4 ligase than at 25 degrees Celsius with T4 ligase. But two sticky-end components with 25-base complementary overhangs may assemble faster at 25 degrees Celsius with T4 ligase than at 4 degrees Celsius with T4 ligase, and perhaps faster than ligation with 4-base overhangs at any temperature. In some embodiments of ligation, it may be beneficial to heat and slowly cool the components for annealing prior to ligase addition.

Ligation may be used to assemble at least 2, 3, 4, 5, 6, 7, 8, 9, 10, 11, 12, 13, 14, 15, 16, 17, 18, 19, 20, or more nucleic acids. Ligation incubation times may be at most 30 seconds, 1 minute, 2 minutes, 5 minutes, 10 minutes, 20 minutes, 30 minutes, 1 hour, or longer. Longer incubation times may improve ligation efficiency.

Ligation may require nucleic acids with 5' phosphorylated ends. Nucleic acid components without 5' phosphorylated ends may be phosphorylated in a reaction with polynucleotide kinase, such as T4 polynucleotide kinase (or T4 PNK). Other co-factors may be present in the reaction such as ATP, magnesium ion, or DTT. Polynucleotide kinase reactions may occur at 37 degrees Celsius for 30 minutes. Polynucleotide kinase reaction temperatures may be at least 4, 10, 20, 20, 30, 40, 50, or 60 degrees Celsius. Polynucleotide kinase reaction incubation timees may be at most, 1 minute, 5 minutes, 10 minutes, 20 minutes, 30 minutes, 60 minutes, or more. Alternatively, the nucleic acid components may be synthetically (as opposed to enzymatically) designed and manufactured with a modified 5' phosphorylation. Only nucleic acids being assembled on their 5' ends may require phosphorylation. For example, templates in TDL may not be phosphorylated as they are not intended to be assembled.

Additives may be included in a ligation reaction to improve ligation efficiency. For example, the addition of Dimethyl sulfoxide (DMSO), polyethylene glycol (PEG), 1,2-Propanediol (1,2-Prd), glycerol, Tween-20 or combinations thereof. PEG6000 may be a particularly effective ligation enhancer. PEG6000 may increase ligation efficiency by acting as a crowding agent. For example, the PEG6000 may form aggregated nodules that take up space in the ligase reaction solution and bring the ligase and components to closer proximity. Additive content (weight per volume) may be at least 0%, 1%, 5%, 10%, 20%, or more.

Various ligases may be used for ligation. The ligases can be naturally occurring or synthesized. Examples of ligases include T4 DNA Ligase, T7 DNA Ligase, T3 DNA Ligase, Taq DNA Ligase, 9°N™ DNA Ligase, E. coli DNA Ligase, and SplintR DNA Ligase. Different ligases may be stable and function optimally at different temperatures. For example, Taq DNA Ligase is thermostable and T4 DNA Ligase is not. Moreover, different ligases have different properties. For example, T4 DNA Ligase may ligate blunt-ended dsDNA while T7 DNA Ligase may not.

Ligation may be used to attach sequencing adapters to a library of nucleic acids. For example, the ligation may be performed with common sticky ends or staples at the ends of each member of the nucleic acid library. If the sticky end or staple at one end of the nucleic acids is distinct from that of the other end, then the sequencing adapters may be ligated asymmetrically. For example, a forward sequencing adapter may be ligated to one end of the members of the nucleic acid library and a reverse sequencing adapter may be ligate to the other end of the members of the nucleic acid library. Alternatively, blunt-ended ligation may be used to attach adapters to a library of blunt-ended double-stranded nucleic acids. Fork adapters may be used to asymmetrically attach adapters to a nucleic acid library with either blunt ends or sticky ends that are equivalent at each end (such as A-tails).

Ligation may be inhibited by heat inactivation (for example incubation at 65 degrees Celsius for at least 20 minutes), addition of a denaturant, or addition of a chelator such as EDTA.

C. Restriction Digest

Restriction digests are reactions in which restriction endonucleases (or restriction enzymes) recognize their cognate restriction site on nucleic acids and subsequently cleave (or digest) the nucleic acids containing said restriction site. Type I, type II, type III, or type IV restriction enzymes may be used for restriction digests. Type II restriction enzymes may be the most efficient restriction enzymes for nucleic acid digestions. Type II restriction enzymes may recognize palindromic restriction sites and cleave nucleic acids within the recognition site. Examples of said restriction enzymes (and their restriction sites) include AatII (GACGTC), AfeI (AGCGCT), ApaI (GGGCCC), DpnI (GATC), EcoRI (GAATTC), NgeI (GCTAGC), and many more. Some restriction enzymes, such as DpnI and AfeI, may cut their restriction sites in the center, thus leaving blunt-ended dsDNA products. Other restriction enzymes, such as EcoRI and AatII, cut their restriction sites off-center, thus leaving dsDNA products with sticky ends (or staggered ends). Some restriction enzymes may target discontinuous restriction sites. For example, the restriction enzyme AlwNI recognizes the restriction site CAGNNNCTG, where N may be either A, T, C, or G. Restriction sites may be at least 2, 4, 6, 8, 10, or more bases long.

Some Type II restriction enzymes cleave nucleic acids outside of their restriction sites. The enzymes may be sub-classified as either Type IIS or Type IIG restriction enzymes. Said enzymes may recognize restriction sites that are non-palindromic. Examples of said restriction enzymes include BbsI, that recognizes GAAAC and creates a staggered cleavage 2 (same strand) and 6 (opposite strand) bases further downstream. Another example includes BsaI, that recognizes GGTCTC and creates a staggered cleavage 1 (same strand) and 5 (opposite strand) bases further downstream. Said restriction enzymes may be used for golden gate assembly or modular cloning (MoClo). Some restriction enzymes, such as BcgI (a Type IIG restriction enzyme) may create a staggered cleavage on both ends of its recognition site. Restriction enzymes may cleave nucleic acids at least 1, 5, 10, 15, 20, or more bases away from their recognition sites. Because said restriction enzymes may create staggered cleavages outside of their recognitions sites, the sequences of the resulting nucleic acid overhangs may be arbitrarily designed. This is as opposed to restriction enzymes that create staggered cleavages within their recognition sites, where the sequence of a resulting nucleic acid overhang is coupled to the sequence of the restriction site. Nucleic acid overhangs created by restriction digests may be at least 1, 2, 3, 4, 5, 6, 7, 8, or more bases long. When restriction enzymes cleave nucleic acids, the resulting 5' ends contain a phosphate.

One or more nucleic acid sequences may be included in a restriction digest reaction. Likewise, one or more restriction enzymes may be used together in a restriction digest reaction. Restriction digests may contain additives and cofactors including potassium ion, magnesium ion, sodium ion, BSA, S-Adenosyl-L-methionine (SAM), or combinations thereof. Restriction digest reactions may be incubated at 37 degrees Celsius for one hour. Restriction digest reactions may be incubated in temperatures of at least 0, 10, 20, 30, 40, 50, or 60 degrees Celsius. Optimal digest temperatures may depend on the enzymes. Restriction digest reactions may be incubated for at most 1, 10, 30, 60, 90, 120, or more minutes. Longer incubation times may result in increased digestion.

D. Nucleic Acid Amplification

Nucleic acid amplification may be executed with polymerase chain reaction, or PCR. In PCR, a starting pool of nucleic acids (referred to as the template pool or template) may be combined with polymerase, primers (short nucleic acid probes), nucleotide tri phosphates (such as dATP, dTTP, dCTP, dGTP, and analogs or variants thereof), and additional cofactors and additives such as betaine, DMSO, and magnesium ion. The template may be single stranded or double stranded nucleic acids. The primer may be a short nucleic acid sequence built synthetically to complement and hybridize to a target sequence in the template pool. The primer may bind each identifier nucleic acid sequence comprising the target sequence in the template pool to select only those identifier nucleic acid sequences which comprise the target sequence. Typically, there are two primers in a PCR reaction, one to complement a primer binding site on the top strand of a target template, and another to complement a primer binding site on the bottom strand of the target template downstream of the first binding site. The 5'-to-3' orientation in which these primers bind their target must be facing each other in order to successfully replicate and exponentially amplify the nucleic acid sequence in between them. Though "PCR" may typically refer to reactions specifically of said form, it may also be used more generally to refer to any nucleic acid amplification reaction.

In some embodiments, PCR may comprise cycling between three temperatures: a melting temperature, an annealing temperature, and an extension temperature. The melting temperature is intended to turn double stranded nucleic acids into single stranded nucleic acids, as well as remove the formation of hybridization products and secondary structures. Typically the melting temperature is high, for example above 95 degrees Celsius. In some embodiments the melting temperature may be at least 96, 97, 98, 99, 100, 101, 102, 103, 104, or 105 degrees Celsius. In other embodiments the melting temperature may be at most 95, 94, 93, 92, 91, or 90 degrees Celsius. A higher melting temperature will improve dissociation of nucleic acids and their secondary structures, but may also cause side effects such as the degradation of nucleic acids or the polymerase. Melting temperatures may be applied to the reaction for at least 1, 2, 3, 4, 5 seconds, or above, such as 30 seconds, 1 minute, 2 minutes, or 3 minutes. A longer initial melting temperature step may be recommended for PCR with complex or long template.

The annealing temperature is intended to facilitate the formation of hybridization between the primers and their target templates. In some embodiments, the annealing temperature may match the calculated melting temperature of the primer. In other embodiments, the annealing temperature may be within 10 degrees Celsius or more of said melting temperature. In some embodiments, the annealing temperature may be at least 25, 30, 50, 55, 60, 65, or 70 degrees Celsius. The melting temperature may depend on the sequence of the primer. Longer primers may have higher melting temperatures, and primers with higher percent content of Guanine or Cytosine nucleotides may have higher melting temperatures. It may therefore be possible to design primers intended to assemble optimally at particular annealing temperatures. Annealing temperatures may be applied to the reaction for at least 1, 5, 10, 15, 20, 25, or 30 seconds, or above. To help ensure annealing, the primer concentrations may be at high or saturating amounts. Primer concentrations may be 500 nanomolar (nM). Primer concentrations may be at most 1 nM, 10 nM, 100 nM, 1000 nM, or more.

The extension temperature is intended to initiate and facilitate the 3' end nucleic acid chain elongation of primers catalyzed by one or more polymerase enzymes. In some embodiments, the extension temperature may be set at the temperature in which the polymerase functions optimally in terms of nucleic acid binding strength, elongation speed, elongation stability, or fidelity. In some embodiments, the extension temperature may be at least 30, 40, 50, 60, or 70 degrees Celsius, or above. Annealing temperatures may be applied to the reaction for at least 1, 5, 10, 15, 20, 25, 30, 40, 50, or 60 seconds or above. Recommended extension times may be approximately 15 to 45 seconds per kilobase of expected elongation.

In some embodiments of PCR, the annealing temperature and the extension temperature may be the same. Thus a 2-step temperature cycle may be used instead of a 3-step temperature cycle. Examples of combined annealing and extension temperatures include 60, 65, or 72 degrees Celsius.

In some embodiments, PCR may be performed with one temperature cycle. Such embodiments may involve turning targeted single stranded template nucleic into double stranded nucleic acid. In other embodiments, PCR may be performed with multiple temperature cycles. If the PCR is efficient, it is expected that the number of target nucleic acid molecules will double each cycle, thereby creating an exponential increase in the number of targeted nucleic acid templates from the original template pool. The efficiency of PCR may vary. Therefore, the actual percent of targeted nucleic acid that is replicated each round may be more or less than 100%. Each PCR cycle may introduce undesirable artifacts such as mutated and recombined nucleic acids. To curtail this potential detriment, a polymerase with high fidelity and high processivity may be used. In addition, a limited number of PCR cycles may be used. PCR may involve at most 1, 5, 10, 15, 20, 25, 30, 35, 40, 45, or more cycles.

In some embodiments, multiple distinct target nucleic acid sequences may be amplified together in one PCR. If each target sequence has common primer binding sites, then all nucleic acid sequences may be amplified with the same set of primers. Alternatively, PCR may comprise multiple primers intended to each target distinct nucleic acids. Said PCR may be referred to as multiplex PCR. PCR may involve at most 1, 2, 3, 4, 5, 6, 7, 8, 9, 10, or more distinct primers. In PCR with multiple distinct nucleic acid targets, each PCR cycle may change the relative distribution of the targeted nucleic acids. For example, a uniform distribution may become skewed or non-uniformly distributed. To curtail this potential detriment, optimal polymerases (e.g., with high fidelity and sequence robustness) and optimal PCR conditions may be used. Factors such as annealing and extension temperature and time may be optimized. In addition, a limited number of PCR cycles may be used.

In some embodiments of PCR, a primer with base mismatches to its targeted primer binding site in the template may be used to mutate the target sequence. In some embodiments of PCR, a primer with an extra sequence on its 5' end (known as an overhang) may be used to attach a sequence to its targeted nucleic acid. For example, primers containing sequencing adapters on their 5' ends may be used to prepare and/or amplify a nucleic acid library for sequencing. Primers that target sequencing adapters may be used to amplify nucleic acid libraries to sufficient enrichment for certain sequencing technologies.

In some embodiments, linear-PCR (or asymmetric-PCR) is used wherein primers only target one strand (not both strands) of a template. In linear-PCR the replicated nucleic acid from each cycle is not complemented to the primers, so the primers do not bind it. Therefore, the primers only replicate the original target template with each cycle, hence the linear (as opposed to exponential) amplification. Though the amplification from linear-PCR may not be as fast as conventional (exponential) PCR, the maximal yield may be greater. Theoretically, the primer concentration in linear-PCR may not become a limiting factor with increased cycles and increased yield as it would with conventional PCR. Linear-After-The-Exponential-PCR (or LATE-PCR) is a modified version of linear-PCR that may be capable of particularly high yields.

In some embodiments of nucleic acid amplification, the process of melting, annealing, and extension may occur at a single temperature. Such PCR may be referred to as isothermal PCR. Isothermal PCR may leverage temperature-independent methods for dissociating or displacing the fully-complemented strands of nucleic acids from each other in favor of primer binding. Strategies include loop-mediated isothermal amplification, strand displacement amplification, helicase-dependent amplification, and nicking enzyme amplification reaction. Isothermal nucleic acid amplification may occur at temperatures of at most 20, 30, 40, 50, 60, or 70 degrees Celsius or more.

In some embodiments, PCR may further comprise a fluorescent probe or dye to quantify the amount of nucleic acid in a sample. For example, the dye may interpolate into double stranded nucleic acids. An example of said dye is SYBR Green. A fluorescent probe may also be a nucleic acid sequence attached to a fluorescent unit. The fluorescent unit may be release upon hybridization of the probe to a target nucleic acid and subsequent modification from an extending polymerase unit. Examples of said probes include Taqman probes. Such probes may be used in conjunction with PCR and optical measurement tools (for excitation and detection) to quantify nucleic acid concentration in a sample. This process may be referred to as quantitative PCR (qPCR) or real-time PCR (rtPCR).

In some embodiments, a PCR may be performed on single a molecule template (in a process that may be referred to as single-molecule PCR), rather than on a pool of multiple template molecules. For example, emulsion-PCR (ePCR) may be used to encapsulate single nucleic acid molecules within water droplets within an oil emulsion. The water droplets may also contain PCR reagents, and the water droplets may be held in a temperature-controlled environment capable of requisite temperature cycling for PCR. This way, multiple self-contained PCR reactions may occur simultaneously in high throughput. The stability of oil emulsions may be improved with surfactants. The movement of droplets may be controlled with pressure through microfluidic channels. Microfluidic devices may be used to create droplets, split droplets, merge droplets, inject material intro droplets, and to incubate droplets. The size of water droplets in oil emulsions may be at least 1 picoliter (pL), 10 pL, 100 pL, 1 nanoliter (nL), 10 nL, 100 nL, or more.

In some embodiments, single-molecule PCR may be performed one a solid-phase substrate. Examples include the Illumina solid-phase amplification method or variants thereof. The template pool may be exposed to a solid-phase substrate, wherein the solid phase substrate may immobilize templates at a certain spatial resolution. Bridge amplification may then occur within the spatial neighborhood of each template thereby amplifying single molecules in a high throughput fashion on the substrate.

High-throughput, single-molecule PCR may be useful for amplifying a pool of distinct nucleic acids that may interfere with each other. For example, if multiple distinct nucleic acids share a common sequence region, then recombination between the nucleic acids along this common region may occur during the PCR reaction, resulting in new, recombined nucleic acids. Single-molecule PCR would prevent this potential amplification error as it compartmentalizes distinct nucleic acid sequences from each other so they may not interact. Single-molecule PCR may be particularly useful for preparing nucleic acids for sequencing. Single-molecule PCR mat also be useful for absolute quantitation of a number of targets within a template pool. For example, digital PCR (or dPCR), uses the frequency of distinct single-molecule PCR amplification signals to estimate the number of starting nucleic acid molecules in a sample.

In some embodiments of PCR, a group of nucleic acids may be non-discriminantly amplified using primers for primer binding sites common to all nucleic acids. For example, primers for primer binding sites flank all nucleic acids in a pool. Synthetic nucleic acid libraries may be created or assembled with these common sites for general amplification. However, in some embodiments, PCR may be used to selectively amplify a targeted subset of nucleic acids from a pool, for example, by using primers with primer binding sites that only appear on said targeted subset of nucleic acids. Synthetic nucleic acid libraries may be created or assembled such that nucleic acids belonging to potential sub-libraries of interest all share common primer binding sites on their edges (common within the sub-library but distinct from other sub-libraries) for selective amplification of the sub-library from the more general library. In some embodiments, PCR may be combined with nucleic acid assembly reactions (such as ligation or OEPCR) to selectively amplify fully assembled or potentially fully assembled nucleic acids from partially assembled or mis-assembled (or unintended or undesirable) bi-products. For example, the assembly may involve assembling a nucleic acid with a primer binding site on each edge sequence such that only a full assembled nucleic product would contain the requisite two primer binding sites for amplification. In said example, a partially assembled product may contain neither or only one of the edge sequences with the primer binding sites, and therefore should not be amplified. Likewise a mis-assembled (or unintended or undesirable) product may contain neither or only one of the edge sequences, or both edge sequences but in the incorrect orientation or separated by an incorrect amount of bases. Therefore said mis-assembled product should either not amplify or amplify to create a product of incorrect length. In the latter case the amplified mis-assembled product of incorrect length may be separated from the amplified fully assembled product of correct length by nucleic acid size selection methods (see Chemical Methods Section E), such as DNA electrophoresis in an agarose gel followed by gel extraction.

Additives may be included in the PCR to improve the efficiency of nucleic acid amplification. For example, the addition of Betaine, Dimethyl sulfoxide (DMSO), non-ionic detergents, Formamide, Magnesium, Bovine Serum Albumin (BSA), or combinations thereof. Additive content (weight per volume) may be at least 0%, 1%, 5%, 10%, 20%, or more.

Various polymerases may be used for PCR. The polymerase can be naturally occurring or synthesized. An example polymerase is a Φ29 polymerase or derivative thereof. In some cases, a transcriptase or a ligase is used (i.e., enzymes which catalyze the formation of a bond) in conjunction with polymerases or as an alternative to polymerases to construct new nucleic acid sequences. Examples of polymerases include a DNA polymerase, a RNA polymerase, a thermostable polymerase, a wild-type polymerase, a modified polymerase, E. coli DNA polymerase I, T7 DNA polymerase, bacteriophage T4 DNA polymerase Φ29 (phi29) DNA polymerase, Taq polymerase, Tth polymerase, Tli polymerase, Pfu polymerase Pwo polymerase, VENT polymerase, DEEPVENT polymerase, Ex-Taq polymerase, LA-Taw polymerase, Sso polymerase Poc polymerase, Pab polymerase, Mth polymerase ES4 polymerase, Tru polymerase, Tac polymerase, Tne polymerase, Tma polymerase, Tca polymerase, Tih polymerase, Tfi polymerase, Platinum Taq polymerases, Tbr polymerase, Phusion polymerase, KAPA polymerase, Q5 polymerase, Tfl polymerase, Pfutubo polymerase, Pyrobest polymerase, KOD polymerase, Bst polymerase, Sac polymerase, Klenow fragment polymerase with 3' to 5' exonuclease activity, and variants, modified products and derivatives thereof. Different polymerases may be stable and function optimally at different temperatures. Moreover, different polymerases have different properties. For example, some polymerases, such a Phusion polymerase, may exhibit 3' to 5' exonuclease activity, which may contribute to higher fidelity during nucleic acid elongation. Some polymerases may displace leading sequences during elongation, while others may degrade them or halt elongation. Some polymerases, like Taq, incorporate an adenine base at the 3' end of nucleic acid sequences. Additionally, some polymerases may have higher fidelity and processivity than others and may be more suitable to PCR applications, such as sequencing preparation, where it is important for the amplified nucleic acid yield to have minimal mutations and where it is important for the distribution of distinct nucleic acids to maintain uniform distribution throughout amplification.

E. Size Selection

Nucleic acids of a particular size may be selected from a sample using size-selection techniques. In some embodiments, size-selection may be performed using gel electrophoresis or chromatography. Liquid samples of nucleic acids may be loaded onto one terminal of a stationary phase or gel (or matrix). A voltage difference may be placed across the gel such that the negative terminal of the gel is the terminal at which the nucleic acid samples are loaded and the positive terminal of the gel is the opposite terminal. Since the nucleic acids have a negatively charged phosphate backbone, they can migrate across the gel to the positive terminal. The size of the nucleic acid can determine its relative speed of migration through the gel. Therefore nucleic acids of different sizes will resolve on the gel as they migrate. Voltage differences may be 100V or 120V. Voltage differences may be at most 50V, 100V, 150V, 200V, 250V, or more. Larger voltage differences may increase the speed of nucleic acid migration and size resolution. However, larger voltage differences may also damage the nucleic acids or the gel. Larger voltage differences may be recommended for resolving nucleic acids of larger sizes. Typical migration times may be between 15 minutes and 60 minutes. Migration times may be at most 10 minutes, 30 minutes, 60 minutes, 90 minutes, 120 minutes, or more. Longer migration times, similar to higher voltage, may lead to better nucleic acid resolution but may lead to increased nucleic acid damage.

Longer migration times may be recommended for resolving nucleic acids of larger sizes. For example, a voltage difference of 120V and a migration time of 30 minutes may be sufficient for resolving a 200-base nucleic acid from a 250-base nucleic acid.

The properties of the gel, or matrix, may affect the size-selection process. Gels typically comprise a polymer substance, such as agarose or polyacrylamide, dispersed in a conductive buffer such as TAE (Tris-acetate-EDTA) or TBE (Tris-borate-EDTA). The content (weight per volume) of the substance (e.g. agarose or acrylamide) in the gel may be at most 0.5%, 1%, 2%, 3%, 5%, 10%, 15%, 20%, 25%, or higher. Higher content may decrease migration speed. Higher content may be preferable for resolving smaller nucleic acids. Agarose gels may be better for resolving double stranded DNA (dsDNA). Polyacrylamide gels may be better for resolving single stranded DNA (ssDNA). The preferred gel composition may depend on the nucleic acid type and size, the compatibility of additives (e.g., dyes, stains, denaturing solutions, or loading buffers) as well as the anticipate downstream applications (e.g., gel extraction then ligation, PCR, or sequencing). Agarose gels may be simpler for gel extraction than polyacrylamide gels. TAE, though not as good a conductor as TBE, may also be better for gel extraction because borate (an enzyme inhibitor) carry-over in the extraction process may inhibit downstream enzymatic reactions.

Gels may further comprise a denaturing solution such as SDS (sodium dodecyl sulfate) or urea. SDS may be used, for example, to denature proteins or to separate nucleic acids from potentially bound proteins. Urea may be used to denature secondary structures in DNA. For example, urea may convert dsDNA into ssDNA, or urea may convert a folded ssDNA (for example a hairpin) to a non-folded ssDNA. Urea-polyacrylamide gels (further comprising TBE) may be used for accurately resolving ssDNA.

Samples may be incorporate into gels with different formats. In some embodiments, gels may contain wells in which samples may be loaded manually. One gel may have multiple wells for running multiple nucleic acids samples. In other embodiments, the gels may be attached to microfluidic channels that automatically load the nucleic acid sample(s). Each gel may be downstream of several microfluidic channels, or the gels themselves may each occupy separate microfluidic channels. The dimensions of the gel may affect the sensitivity of nucleic acid detection (or visualization). For example, thin gels or gels inside of microfluidic channels (such as in bioanalyzers or tapestations) may improve the sensitivity of nucleic acid detection. The nucleic acid detection step may be important for selecting and extracting a nucleic acid fragment of the correct size.

A ladder may be loaded into a gel for nucleic acid size reference. The ladder may contain markers of different sizes to which the nucleic acid sample may be compared. Different ladders may have different size ranges and resolutions. For example a 50 base ladder may have markers at 50, 100, 150, 200, 250, 300, 350, 400, 450, 500, 550, and 600 bases. Said ladder may be useful for detecting and selecting nucleic acids within the size range of 50 and 600 bases. The ladder may also be used as a standard for estimating the concentration of nucleic acids of different sizes in a sample.

Nucleic acid samples and ladders may be mixed with loading buffer to facilitate the gel electrophoresis (or chromatography) process. Loading buffer may contain dyes and markers to help track the migration of the nucleic acids. Loading buffer may further comprise reagents (such as glycerol) that are denser than the running buffer (e.g., TAE or TBE), to ensure that nucleic acid samples sink to the bottom of the sample loading wells (which may be submerged in the buffer). Loading buffer may further comprise denaturing agents such as SDS or urea. Loading buffer may further comprise reagents for improving the stability of nucleic acids. For example, loading buffer may contain EDTA to protect nucleic acids from nucleases.

In some embodiments, the gel may comprise a stain that binds the nucleic acid and that may be used to optically detect nucleic acids of different sizes. Stains may be specific for dsDNA, ssDNA, or both. Different stains may be compatible with different gel substances. Some stains may require excitation from a source light (or electromagnetic wave) in order to visualize. The source light may be UV (ultraviolet) or blue light. In some embodiments, stains may be added to the gel prior to electrophoresis. In other embodiments, stains may be added to the gel after electrophoresis. Examples of stains include Ethidium Bromide (EtBr), SYBR Safe, SYBR Gold, silver stain, or methylene blue. A reliable method for visualizing dsDNA of a certain size, for example, may be to use an agarose TAE gel with a SYBR Safe or EtBr stain. A reliable method for visualizing ssDNA of a certain size, for example, may be to use a urea-polyacrylamide TBE gel with a methylene blue or silver stain.

In some embodiments, the migration of nucleic acids through gels may be driven by other methods besides electrophoresis. For example, gravity, centrifugation, vacuums, or pressure may be used to drive nucleic acids through gels so that they may resolve according to their size.

Nucleic acids of a certain size may be extracted from gels using a blade or razor to excise the band of gel containing the nucleic acid. Proper optical detection techniques and DNA ladders may be used to ensure that the excision occurs precisely at a certain hand and that the excision successfully excludes nucleic acids that may belong to different, undesirable size bands. The gel band may be incubated with buffer to dissolve it, thus releasing the nucleic acids into the buffer solution. Heat or physical agitation may speed the dissolution. Alternatively, the gel band may be incubated in buffer long enough to allow diffusion of the DNA into the buffer solution without requiring gel dissolution. The buffer may then be separated from the remaining solid-phase gel, for example by aspiration or centrifugation. The nucleic acids may then be purified from the solution using standard purification or buffer-exchange techniques, such as phenol-chloroform extraction, ethanol precipitation, magnetic bead capture, and/or silica membrane adsorption, washing, and elution. Nucleic acids may also be concentrated in this step.

As an alternative to gel excision, nucleic acids of a certain size may be separated from a gel by allowing them to run off the gel. Migrating nucleic acids may pass through a basin (or well) either embedded in the gel or at the end of the gel. The migration process may be timed or optically monitored such that when the nucleic acid group of a certain size enters the basin, the sample is collected from the basin. The collection may occur, for example, by aspiration. The nucleic acids may then be purified from the collected solution using standard purification or buffer-exchange techniques, such as phenol-chloroform extraction, ethanol precipitation, magnetic bead capture, and/or silica membrane adsorption, washing, and elution. Nucleic acids may also be concentrated in this step.

Other methods for nucleic acid size selection may include mass-spectrometry or membrane-based filtration. In some embodiments of membrane-based filtration, nucleic acids are passed through a membrane (for example a silica membrane) that may preferentially bind to either dsDNA, ssDNA, or both. The membrane may be designed to preferentially capture nucleic acids of at least a certain size. For example, membranes may be designed to filter out nucleic acids of less than 20, 30, 40, 50, 70, 90, or more bases. Said membrane-based, size-selection techniques may not be as stringent as gel electrophoresis or chromatography.

F. Nucleic Acid Capture

Affinity-tagged nucleic acids may be used as sequence specific probes for nucleic acid capture. The probe may be designed to complement a target sequence within a pool of nucleic acids. Subsequently, the probe may be incubated with the nucleic acid pool and hybridized to its target. The incubation temperature may be below the melting temperature of the probe to facilitate hybridization. The incubation temperature may be up to 5, 10, 15, 20, 25, or more degrees Celsius below the melting temperature of the probe. The hybridized target may be captured to a solid-phase substrate that specifically binds the affinity tag. The solid-phase substrate may be a membrane, a well, a column, or a bead. Multiple rounds of washing may remove all non-hybridized nucleic acids from the targets. The washing may occur at a temperature below the melting temperature of the probe to facilitate stable immobilization of target sequences during the wash. The washing temperature may be up to 5, 10, 15, 20, 25, or more degrees Celsius below the melting temperature of the probe. A final elution step may recover the nucleic acid targets from the solid phase-substrate, as well as from the affinity tagged probes. The elution step may occur at a temperature above the melting temperature of the probe to facilitate the release of nucleic acid targets into an elution buffer. The elution temperature may be up to 5, 10, 15, 20, 25, or more degrees Celsius above the melting temperature of the probe.

In certain embodiments, the oligonucleotides bound to a solid-phase substrate may be removed from the solid-phase substrate, for example, by exposure to conditions such as acid, base, oxidation, reduction, heat, light, metal ion catalysis, displacement or elimination chemistry, or by enzymatic cleavage. In certain embodiments, the oligonucleotides may be attached to a solid support through a cleavable linkage moiety. For example, the solid support may be functionalized to provide cleavable linkers for covalent attachment to the targeted oligonucleotides. In some embodiments, the linker moiety may be of six or more atoms in length. In some embodiments, the cleavable linker may be a TOPS (two oligonucleotides per synthesis) linker, an amino linker, or a photocleavable linker.

In some embodiments, biotin may be used as an affinity tag that is immobilized by streptavidin on a solid-phase substrate. Biotinylated oligonucleotides, for use as nucleic acid capture probes, may be designed and manufactured. Oligonucleotides may be biotinylated on the 5' or 3' end. They may also be biotinylated internally on thymine residues. Increased biotin on an oligo may lead to stronger capture on the streptavidin substrate. A biotin on the 3' end of an oligo may block the oligo from extending during PCR. The biotin tag may be a variant of standard biotin. For example, the biotin variant may be biotin-TEG (triethylene glycol), dual biotin, PC biotin, DesthioBiotin-TEG, and biotin Azide. Dual biotin may increase the biotin-streptavidin affinity. Biotin-TEG attaches the biotin group onto a nucleic acid separated by a TEG linker. This may prevent the biotin from interfering with the function of the nucleic acid probe, for example its hybridization to the target. A nucleic acid biotin linker may also be attached to the probe. The nucleic acid linker may comprise nucleic acid sequences that are not intended to hybridize to the target.

The biotinylated nucleic acid probe may be designed with consideration for how well it may hybridize to its target. Nucleic acid probes with higher designed melting temperatures may hybridize to their targets more strongly. Longer nucleic acid probes, as well as probes with higher GC content, may hybridize more strongly due to increased melting temperatures. Nucleic acid probes may have a length of a least 5, 10, 15, 20, 30, 40, 50, or 100 bases, or more. Nucleic acid probes may have a GC content anywhere between 0 and 100%. Care may be taken to ensure that the melting temperature of the probe does not exceed the temperature tolerance of the streptavidin substrate. Nucleic acid probes may be designed to avoid inhibitory secondary structures such as hairpins, homodimers, and heterodimers with off-target nucleic acids. There may be a tradeoff between probe melting temperature and off-target binding. There may be an optimal probe length and GC content at which melting temperature is high and off-target binding is low. A synthetic nucleic acid library may be designed such that its nucleic acids comprise efficient probe binding sites.

The solid-phase streptavidin substrate may be magnetic beads. Magnetic beads may be immobilized using a magnetic strip or plate. The magnetic strip or plate may be brought into contact with a container to immobilize the magnetic beads to the container. Conversely, the magnetic strip or plate may be removed from a container to release the magnetic beads from the container wall into a solution. Different bead properties may affect their application. Beads may have varying sizes. For example beads may be anywhere between 1 and 3 micrometers (um) in diameter. Beads may have a diameter of at most 1, 2, 3, 4, 5, 10, 15, 20, or more micrometers. Bead surfaces may be hydrophobic or hydrophilic. Beads may be coated with blocking proteins, for example BSA. Prior to use, beads may be washed or pre-treated with additives, such as blocking solution to prevent them from non-specifically binding nucleic acids.

A biotinylated probe may be coupled to the magnetic streptavidin beads prior to incubation with the nucleic acid sample pool. This process may be referred to as direct capture. Alternatively, the biotinylated probe may be incubated with the nucleic acid sample pool prior to the addition of magnetic streptavidin beads. This process may be referred to as indirect capture. The indirect capture method may improve target yield. Shorter nucleic acid probes may require a shorter amount of time to couple to the magnetic beads.

Optimal incubation of the nucleic acid probe with the nucleic acid sample may occur at a temperature that is 1 to 10 degrees Celsius or more below the melting temperature of the probe. Incubation temperatures may be at most 5, 10, 20, 30, 40, 50, 60, 70, 80, or more degrees Celsius. The recommended incubation time may be 1 hour. The incubation time may be at most 1, 5, 10, 20, 30, 60, 90, 120, or more minutes. Longer incubation times may lead to better capture efficiency. An additional 10 minutes of incubation may occur after the addition of the streptavidin beads to allow biotin-streptavidin coupling. This additional time may be at most 1, 5, 10, 20, 30, 60, 90, 120, or more minutes. Incubation may occur in buffered solution with additives such as sodium ion.

Hybridization of the probe to its target may be improved if the nucleic acid pool is single-stranded nucleic acid (as opposed to double-stranded). Preparing a ssDNA pool from a dsDNA pool may entail performing linear-PCR with one primer that commonly binds the edge of all nucleic acid sequences in the pool. If the nucleic acid pool is synthetically created or assembled, then this common primer binding site may be included in the synthetic design. The product of the linear-PCR will be ssDNA, More starting ssDNA template for the nucleic acid capture may be generated with more cycles of linear-PCR, See Chemical Methods Section D on PCR.

After the nucleic acid probes are hybridized to their targets and coupled to magnetic streptavidin beads, the beads may be immobilized by a magnet and several rounds of washing may occur. Three to five washes may be sufficient to remove non-target nucleic acids, but more or less rounds of washing may be used. Each incremental wash may further decrease non-targeted nucleic acids, but it may also decrease the yield of target nucleic acids. To facilitate proper hybridization of the target nucleic acids to the probe during the wash step, a low incubation temperature may be used. Temperatures as low as 60, 50, 40, 30, 20, 10, or 5 degrees Celsius or less may be used. The washing buffer may comprise Tris buffered solution with sodium ion.

Optimal elution of the hybridized targets from the magnetic bead-coupled probes may occur at a temperature that is equivalent to or more than the melting temperature of the probe. Higher temperatures will facilitate the dissociation of the target to the probe. Elution temperatures may be at most 30, 40, 50, 60, 70, 80, or 90 degrees Celsius, or more. Elution incubation time may be at most 1, 5, 10, 30, 60 or more minutes. Typical incubation times may be approximately 5 minutes, but longer incubation times may improve yield. Elution buffer may be water or tris-buffered solution with additives such as EDTA.

Nucleic acid capture of target sequences containing at least one or more of a set of distinct sites may be performed in one reaction with multiple distinct probes for each of those sites. Nucleic acid capture of target sequences containing every member of a set of distinct sites may be performed in a series of capture reactions, one reaction for each distinct site using a probe for that particular site. The target yield after a series of capture reactions may be low, but the captured targets may subsequently be amplified with PCR. If the nucleic acid library is synthetically designed, then the targets may be designed with common primer binding sites for PCR.

Synthetic nucleic acid libraries may be created or assembled with common probe binding sites for general nucleic acid capture. These common sites may be used to selectively capture fully assembled or potentially fully assembled nucleic acids from assembly reactions, thereby filtering out partially assembled or mis-assembled (or unintended or undesirable) bi-products. For example, the assembly may involve assembling a nucleic acid with a probe binding site on each edge sequence such that only a fully assembled nucleic product would contain the requisite two probe binding sites necessary to pass through a series of two capture reactions using each probe. In said example, a partially assembled product may contain neither or only one of the probe sites, and therefore should not ultimately be captured. Likewise a mis-assembled (or unintended or undesirable) product may contain neither or only one of the edge sequences. Therefore said mis-assembled product may not ultimately be captured. For increased stringency, common probe binding sites may be included on each component of an assembly. A subsequent series of nucleic acid capture reactions using a probe for each component may isolate only fully assembled product (containing each component) from any bi-products of the assembly reaction. Subsequent PCR may improve target enrichment, and subsequent size-selection may improve target stringency.

In some embodiments, nucleic acid capture may be used to selectively capture a targeted subset of nucleic acids from a pool. For example, by using probes with binding sites that only appear on said targeted subset of nucleic acids. Synthetic nucleic acid libraries may be created or assembled such that nucleic acids belonging to potential sub-libraries of interest all share common probe binding sites (common within the sub-library but distinct from other sub-libraries) for the selective capture of the sub-library from the more general library.

G. Lyophilization

Lyophilization is a dehydration process. Both nucleic acids and enzymes may be lyophilized. Lyophilized substances may have longer lifetimes. Additives such as chemical stabilizers may be used to maintain functional products (e.g., active enzymes) through the lyophilization process. Disaccharides, such as sucrose and trehalose, may be used as chemical stabilizers.

H. DNA Design

The sequences of nucleic acids (e.g., components) for building synthetic libraries (e.g., identifier libraries) may be designed to avoid synthesis, sequencing, and assembly complications. Moreover, they may be designed to decrease the cost of building the synthetic library and to improve the lifetime over which the synthetic library may be stored.

Nucleic acids may be designed to avoid long strings of homopolymers (or repeated base sequences) that may be difficult to synthesize. Nucleic acids may be designed to avoid homopolymers of length greater than 2, 3, 4, 5, 6, 7 or more. Moreover, nucleic acids may be designed to avoid the formation of secondary structures, such as hairpin loops, that may inhibit their synthesis process. For example, predictive software may be used to generate nucleic acid sequences that do not form stable secondary structures. Nucleic acids for building synthetic libraries may be designed to be short. Longer nucleic acids may be more difficult and expensive to synthesize. Longer nucleic acids may also have a higher chance of mutations during synthesis. Nucleic acids (e.g., components) may be at most 5, 10, 15, 20, 25, 30, 40, 50, 60 or more bases.

Nucleic acids to become components in an assembly reaction may be designed to facilitate that assembly reaction. See Chemical Methods Section A and B for more information on nucleic acid sequence considerations for OEPCR and ligation-based assembly reactions, respectively. Efficient assembly reactions typically involve hybridization between adjacent components. Sequences may be designed to promote these on-target hybridization events while avoiding potential off-target hybridizations. Nucleic acid base modifications, such as locked nucleic acids (LNAs), may be used to strengthen on-target hybridization. These modified nucleic acids may be used, for example, as staples in staple strand ligation or as sticky ends in sticky-strand ligation. Other modified bases that may be used for building synthetic nucleic acid libraries (or identifier libraries) include 2,6-Diaminopurine, 5-Bromo dU, deoxyUridine, inverted dT, inverted diDeoxy-T, Dideoxy-C, 5-Methyl dC, deoxylnosine, Super T, Super G, or 5-Nitroindole. Nucleic acids may contain one or multiple of the same or different modified bases. Some of the said modified bases are natural base analogs (for example, 5-Methyl dC and 2,6-Diaminopurine) that have higher melting temperatures and may therefore be useful for facilitating specific hybridization events in assembly reactions. Some of the said modified bases are universal bases (for example, 5-Nitroindole) that can bind to all natural bases and may therefore be useful for facilitating hybridization with nucleic acids that may have variable sequences within desirable binding sites. In addition to their beneficial roles in assembly reactions, these modified bases may be useful in primers (e.g., for PCR) and probes (e.g., for nucleic acid capture) as they may facilitate the specific binding of primers and probes to their target nucleic acids within a pool of nucleic acids. See Chemical Methods Section D and F for more nucleic acid design considerations with regard to nucleic acid amplification (or PCR) and nucleic acid capture, respectively.

Nucleic acids may be designed to facilitate sequencing. For example, nucleic acids may be designed to avoid typical sequencing complications such as secondary structure, stretches of homopolymers, repetitive sequences, and sequences with too high or too low of a GC content. Certain sequencers or sequencing methods may be error prone. Nucleic acid sequences (or components) that make up synthetic libraries (e.g., identifier libraries) may be designed with certain hamming distances from each other. This way, even when base resolution errors occur at a high rate in sequencing, the stretches of error-containing sequences may still be mapped back to their most likely nucleic acid (or component). Nucleic acid sequences may be designed with hamming distances of at least 1, 2, 3, 4, 5, 6, 7, 8, 9, 10, 11, 12, 13, 14, 15 or more base mutations. Alternative distance metrics from hamming distance may also be used to define a minimum requisite distance between designed nucleic acids.

Some sequencing methods and instruments may require input nucleic acids to contain particular sequences, such as adapter sequences or primer-binding sites. These sequences may be referred to as "method-specific sequences". Typical preparatory workflows for said sequencing instruments and methods may involve assembling the method-specific sequences to the nucleic acid libraries. However, if it is known ahead of time that a synthetic nucleic acid library (e.g., identifier library) will be sequenced with a particular instrument or method, then these method-specific sequences may be designed into the nucleic acids components) that comprise the library (e.g., identifier library). For example, sequencing adapters may be assembled onto the members of a synthetic nucleic acid library in the same reaction step as when the members of a synthetic nucleic acid library are themselves assembled from individual nucleic acid components.

Nucleic acids may be designed to avoid sequences that may facilitate DNA damage. For example, sequences containing sites for site-specific nucleases may be avoided. As another example, UVB (ultraviolet-B) light may cause adjacent thymines to form pyrimidine dimers which may then inhibit sequencing and PCR. Therefore, if a synthetic nucleic acid library is intended to be stored in an environment exposed to UVB, then it may be beneficial to design its nucleic acid sequences to avoid adjacent thymines (i.e., TT).

All information contained within the Chemical Methods section is intended to support and enable the technologies, methods, protocols, systems, and processes described herein.

Methods of Assembling Identifiers from Components with Azide-Alkyne Modifications Two or more nucleic acid components may be ligated together to create an identifier using either chemical and/or biological ligation methods. In some embodiments, there may be advantages with chemical ligation methods, such as "click chemistry", versus biological methods, such as enzymatic ligation.

Click chemistry or Copper-Catalyzed Azide-Alkyne Cycloaddition (CuAAC) is a variant of the Huisgen 1,3-dipolar cycloaddition reaction. In the reaction, an alkyne and azide group react to form a triazole phosphodiester mimic. Current methods use Cu(I) ion to increase the specificity, rate, and yield of this reaction. The reaction may be fast with some alkynes reporting reaction completion times of approximately one minute. Reaction times may be 30, 60, 90, 120, 150, or 180 seconds or more. The reaction may also be robust, showing tolerance to a broad pH range.

Chemical ligation using click chemistry may occur between two single-stranded nucleic acid components with the help of a template (or staple or splint) oligonucleotide. Alternatively, chemical ligation may also occur between double-stranded nucleic acid components if there is a complementary overhang (or sticky end) in common. Chemical ligation with click chemistry may be used to construct identifiers according to the product scheme (FIG. 6), permutation scheme (FIG. 11), MchooseK scheme (FIG. 12), partition scheme (FIG. 13), or unconstrained string scheme (FIG. 14) described in the preceding.

Ligation of components using click chemistry requires one component to have at least one alkyne group and another component to have at least one azide group. Either modification may be placed at the 5' or 3' end of one nucleic acid component as long as the complementary modification is placed on the adjacent component such that the 3' end of one component ligates to the 5' end of the other.

Several different types of alkyne-azide linkages may be used in click chemistry. Alkyne-azide linkages that are compatible with molecular biology methods, such as PCR, may be particularly well suited for generating identifiers. If a particular pool of identifiers comprises one or more alkyne-azide linkages, then the identifiers may be copied to their natural forms (with phosphodiester bonds between bases) using PCR.

Methods of Assembling Identifiers from Multi-Part Components

The components that comprise identifiers may be divided into two or more parts with different functions. For example, each component may have two parts: one longer part intended for hybridizing to nucleic acid probes for data access, and another shorter part intended for sequencing read out. The two parts may be disjoint and intended to assemble onto an identifier at each edge, such that the final identifier product has two functionally different regions. One region on one side intended for chemical access, and one region on the other side intended for sequencing.

Figure 22:
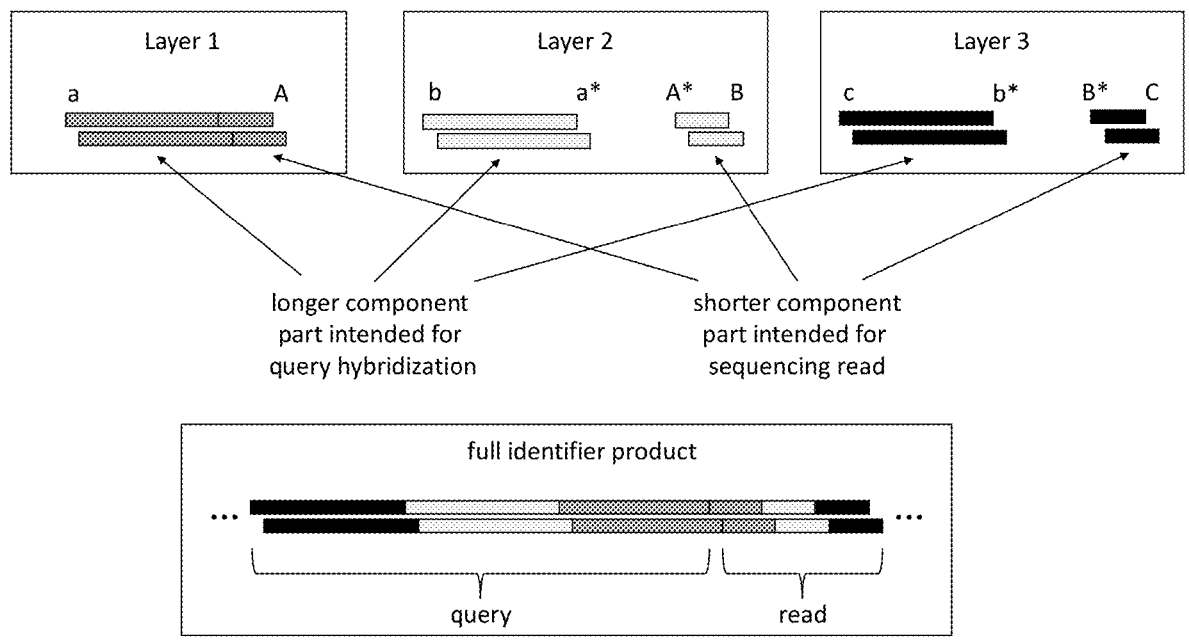
FIG. 22 shows an example of building identifiers from components with multiple functional parts.

FIG. 22 gives an example schematic of this concept for sticky end ligation assembly of identifiers, where components from each layer come together according to the product scheme. The first layer nucleates the identifier assembly process with a joint 2-part component, and the subsequent layers comprise disjoint 2-part components that assemble onto the identifier from both edges. The symbols above the sticky ends represent their sequences. Sticky ends with different symbols are orthogonal. An asterisk next to a symbol represents the reverse complement. For example, 'a' and 'a*' are reverse complements of each other and will therefore hybridize to form a product during ligation.

Methods of Building Identifiers with Base Editors

Base editors may be used to programmably mutate bases located at particular loci within a parent identifier to construct new identifiers. In one embodiment, a base editor may be a dCas9 protein fused to a cytidine deaminase, which converts Cystosine (C) to Uracil (U). Parent identifiers may be designed with several orthogonal target loci for guide RNAs (gRNAs) to bind. A target locus may contain one or more Cytosines within the activity range of a bound dCas9-deaminase at that locus. The activity range may be 1, 2, 3, 4, 5, 6 or more bases within the locus. Subsequent incubation of the parent identifier with dCas9-deaminase and a subset of gRNAs for particular loci may result in one or more Cystosine-to-Uracil mutations at each of those targeted loci. Further, DNA polymerase recognizes a Uracil as a Thymine, so performing PCR on the mutated identifier may result in the complementary mutations as well (Guanine to Adenine). A parent identifier with N orthogonal target loci may be programmably converted to $2^N$ distinct daughter identifier sequences by applying dCas9-deaminase and different subsets of N gRNAs (each targeting a distinct locus on the parent). Hence the combinatorial space of possible identifiers constructed in this scheme may store N bits of information for N gRNA inputs.

In some embodiments, any given target locus of the parent sequences may contain targeted cytosines on both the top and bottom strand to promote increased mutation efficiency. Moreover, each locus must be adjacent to a PAM site for efficient gRNA targeting to occur. However, the PAM sequence may vary depending on the use of different engineered Cas9 variants.

A dCas9-deaminase fusion may comprise a linker sequence between the two fused proteins. The optimal linker length may be 16 amino acids long for efficient targeted mutations. Linker length may be at least 0, 1, 5, 10, 15, 20, 25 or more amino acids in length. One of multiple Cytidine deaminases may be used. Examples of Cytidine deaminases include APOBEC1, AID, CDA1, or APOBEC3G. An active Cas9 nickase may be used instead of dCas9, but then it may be necessary to include DNA repair enzymes in the identifier construction reaction as well.

In another embodiment of constructing identifiers with base editors, an Adenine deaminase fused to dCas9 (as opposed to, or in addition to, a Cytidine deaminase fused to dCas9) may be used to mutate Adenine to Inosine at defined loci of a parent identifier accessible by a gRNA. The Inosine is interpreted as a Guanine by DNA polymerase. Therefore, PCR of a base edited locus may result in a complementary Thymine to Cytosine mutation on the opposite strand.

Methods of Deleting Information Stored in DNA

The ability to reliably delete (or erase) data stored using nucleic acids may be beneficial for security, privacy, and regulatory reasons. Erasing data may involve breaking the covalent bonds within nucleic acids, irreversibly modifying nucleic acids to disrupt their ability to be sequenced, encapsulating or adsorbing them in irreversible ways, or adding more nucleic acids or other materials to render the original collection of nucleic acids unreadable or unfeasible to read. These methods may be performed in a selective or non-selective way. The selection process may be separate from the deletion process. For example, starting with an identifier library, sequence specific probes may be used to pull-down subsets of identifiers for deletion. As another example, purification of select identifiers by size or mass-to-charge ratio may be done in conjunction with other selective or non-selective deletion methods.

Selective methods for nucleic acid deletion from a library include the use of sequence specific probes to pull-down subsets of nucleic acids for deletion, the use of CRISPR-based methods to cleave select nucleic acids containing one or more target sequences, and the use of purification techniques to select nucleic acids by size or mass-to-charge ratio.

Non-selective methods for deleting information-encoding nucleic acids from a library include sonication, autoclaving, treatment with bleach, bases, acids, ethidium bromide or other DNA modification agents, irradiation (for example with ultraviolet light), combustion, and non-specific nuclease digestion (in vitro or in vivo) such as with DNase I. Other methods may be used obfuscate, hide, or physically protect the nucleic acids from access or sequencing. The methods may include encapsulation, dilution, addition of random nucleic acids to obfuscate the original nucleic acids, and addition of other agents that prevent downstream sequencing of the nucleic acids. In one embodiment, the data stored in nucleic acids may be obfuscated with amplification by an error-prone polymerase, for example, a polymerase with a lack of proofreading functionality.

For data stored in nucleic acids with a defined period of value, it may be beneficial to use methods that automatically delete the data at a specified point in time. For example, data may be scheduled for deletion after a mandatory regulatory period. As another example, data may be scheduled for deletion if it is being transferred and it does not reach its destination on time. In one embodiment, scheduled deletion of nucleic acids may involve the use of degradation agents that work at a defined rate or instantly at a specified point in time. In another embodiment, scheduled deletion of nucleic acids may involve the use of a nucleic acid capsule or protective casing that degrades over time. In another embodiment, nucleic acids may be held at different temperatures or different environments to promote different rates of degradation. For example, high temperatures or high humidity for increased degradation rates. In another embodiment, nucleic acids may be converted to less stable forms for faster degradation. For example, DNA may be converted to the less stable RNA.

Verification of nucleic acid deletion may be achieved with sequencing, PCR, or quantitative PCR.

Methods of Designing and Ranking Identifiers for Efficient Random Access

The systems and methods described herein allow for efficient random access retrieval of any distribution of bits from an encoded and stored information. Fractions of encoded information may be retrieved efficiently if the data is stored with component specific primers used on edge layers (or end sequences) to amplify a targeted subset of identifiers in a library. Efficient access may include reducing the number of PCR steps necessary to retrieve a selected portion of information from stored data. For example, in set of data stored using the methods described herein an identifier may be accessed in less than L/2 sequential PCR steps, where L is the number of layers that comprise identifiers. The identifier architecture and identifier ranking system affect the random access properties of the identifier pool. The rank of an identifier corresponds to the position of the bit that it represents. The identifier rank may be determined lexicographically from the order of each possible component that may appear in each layer, which may be defined strategically. For example, layers on the edges of the identifiers may be assigned a higher priority than layers in the middle of identifiers, so that random access (e.g., with PCR primers that bind the edge layers of the identifiers) will return identifiers with consecutive rankings corresponding to a contiguous or related stretch of encoded bits. A higher "priority" is akin to a lower depth of access e.g., a high priority element is easier to access than a low priority element.

The identifier architecture and identifier ranking system allow for random access of particular subsets of identifiers from the identifier pool. In some implementations, each identifier nucleic acid sequence in the identifier pool corresponds to a symbol value and symbol position within a string of symbols. Further, the presence or absence of an identifier nucleic acid sequence in the pool may be representative of the symbol value of the corresponding respective symbol position within the string of symbols.

Figure 23A:
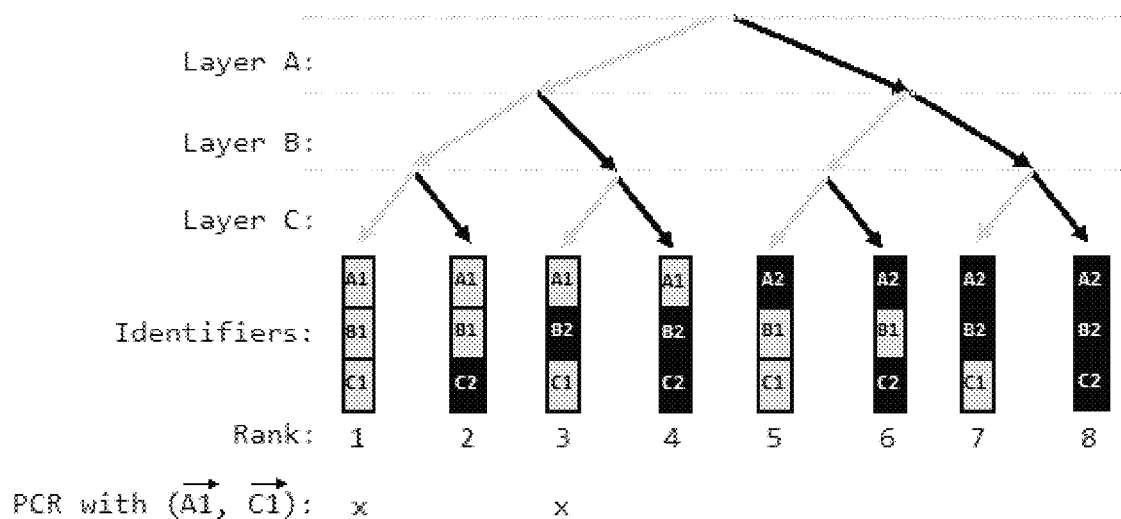
FIG. 23A-23B show an example effect of identifier rank on PCR-based random access.
Figure 23B:
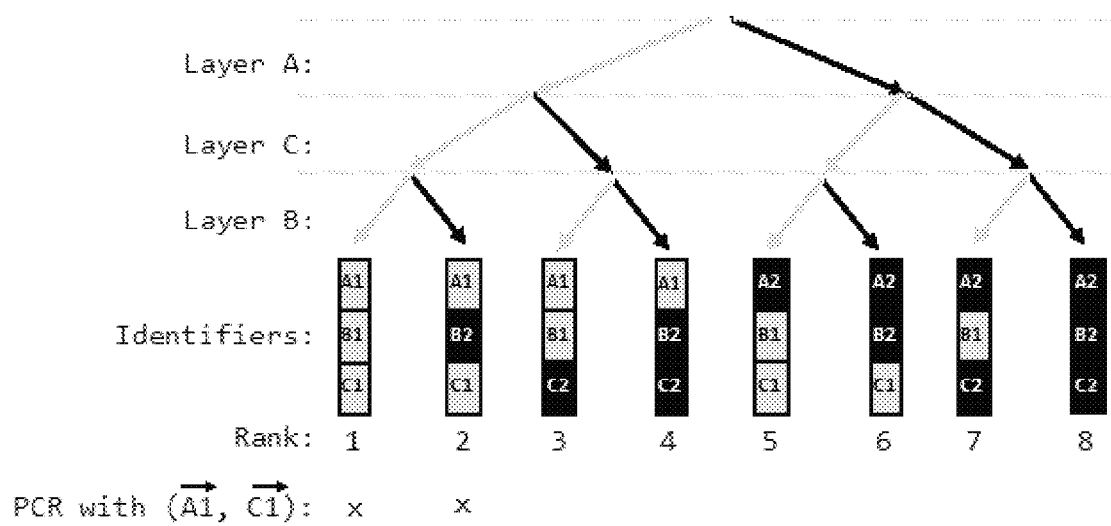

In certain implementations, symbols having contiguous symbol position encode similar digital information. As used herein similar digital information may include data of the same structure (i.e., image data or strings of binary code). Similar digital information may also refer to the data contained within the information. For example, all image data locations encoded with a particular intensity of red may be grouped together in contiguous symbol positions. Alternatively, symbols having contiguous symbol positions may not encode similar digital information. For instance, contiguous symbol positions may correspond to various features in the data (i.e., image data) such as an x-coordinate, a y-coordinate, or an intensity value or a range of intensity values. FIG. 23 shows an example of identifiers produced by the product scheme of three layers, A, B, and C, where each layer has two components, 1 and 2. Components from each of the three layers A, B, and C assemble in that order. The rank of each identifier may be determined by assigning each layer a particular order and then assigning each component within each layer a particular order, and then ordering the identifiers lexicographically. FIG. 23A demonstrates the resulting rank from defining the lexicographical ordering of the layers in the same way that they are ordered in the physical identifier. If such an identifier pool were to be queried with a PCR reaction using primers that bind the edges of the identifiers (for example, component A1 and component C1) then the accessed identifiers would have non-continuous ranks, making it impossible to randomly access a continuous string of bits with one PCR reaction. In certain implementations described herein, the edges of the identifiers (for example, component A1 and component C1) are referred to as "end sequences" or "end molecules." However, it would often be ideal to randomly access a contiguous stretch of bits (represented by continuously ranked identifiers) as the bits within a contiguous stretch often encode related information. Each of the bits within a contiguous stretch of bits may be accessed using a probe to hybridize to the target end sequence of each identifier nucleic acid sequence in the plurality of identifier nucleic acid sequences to select identifier nucleic acid sequences which correspond to respective symbols having contiguous symbol positions. FIG. 23B demonstrates how the lexicographical order of layers A, B and C may be changed to enable query of a contiguous stretch of bits with one PCR reaction using primers that bind the edges (or end sequences) of the identifiers. The strategy is not to use the same lexicographical ordering of layers as the physical ordering of layers. Instead, the strategy is to assign a higher priority lexicographical order to layers on the edges (or end sequences) of the identifiers and a lower priority order to layers in the middle of the identifiers.

Figure 24A:
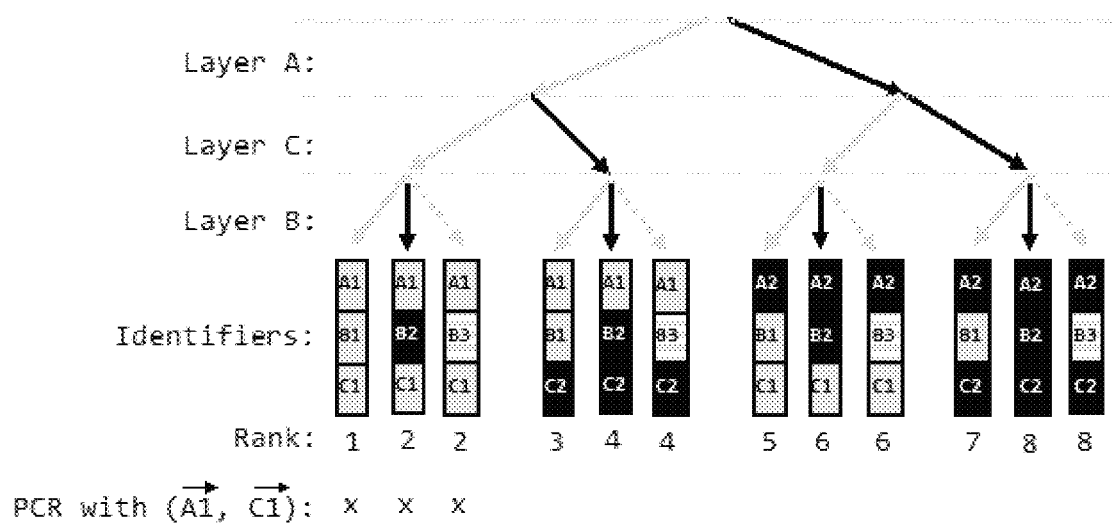
FIG. 24A-24B show an example effect of identifier architectures with non-uniform component distributions on PCR-based random access.
Figure 24B:
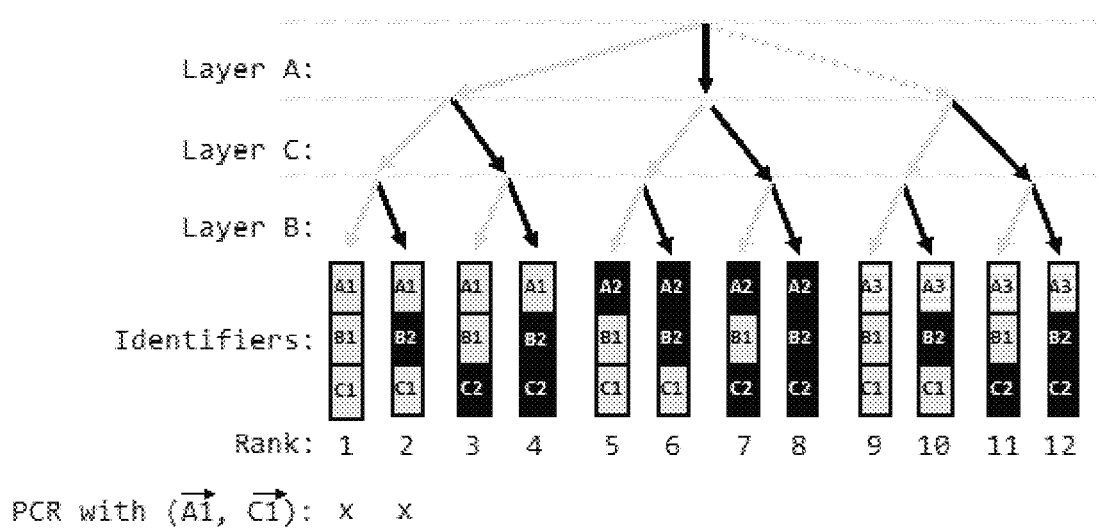

The distribution of components in a partition scheme underlying a combinatorial space may impact the number of symbols that may be accessed in a PCR reaction. FIG. 24 shows an example of identifiers produced by the product scheme of three layers, A, B, and C, where there is a non-uniform distribution of components across layers. Specifically, two layers have two components, 1 and 2, and one layer has three components 1, 2, and 3. In accordance with the aforementioned identifier ranking principle, the lexicographical order of the layers is A, C, then B, even though the physical ordering is A, B, then C. This is so that random access with PCR primers that bind the edge layers (or end sequences) of the identifiers will return identifiers with consecutive rankings (corresponding to a contiguous stretch of bits). Specifically, the first and second end sequences of certain identifier nucleic acid sequences are shared between multiple identifier nucleic acid sequences that correspond to contiguous stretches of bits. FIG. 24A demonstrates that when more components are placed in the middle layer(s) of an identifier, a PCR query (with primers that each bind an edge component (or end sequence)) may result in a larger pool of accessed identifiers. Correspondingly, more bits may be accessed at a time. FIG. 24B demonstrates that when more components are placed on the edge layers) (or end sequence(s)) of an identifier, an equivalent PCR query may result in a smaller pool of accessed identifiers. Correspondingly, the bits may be accessed with higher resolution.

Figure 25:
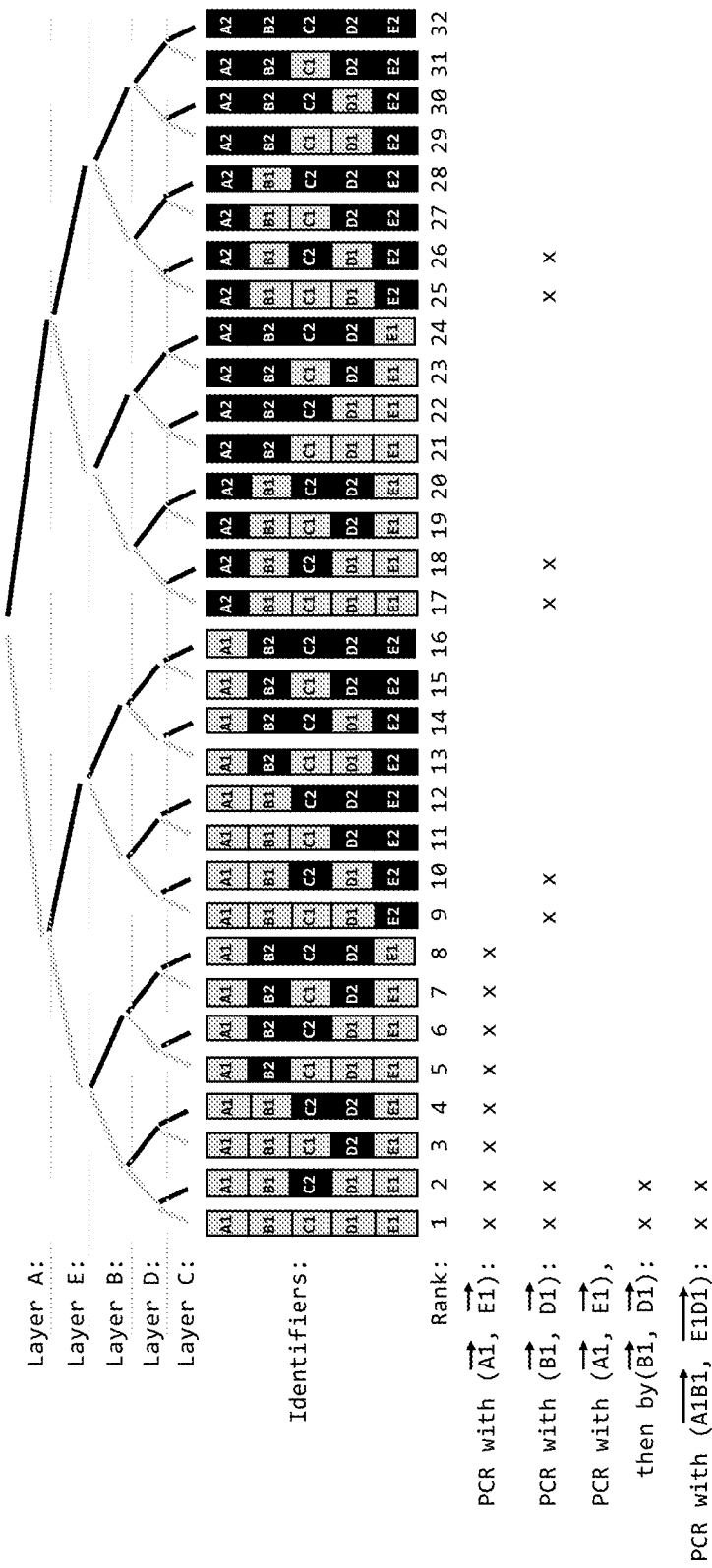
FIG. 25 shows an example effect of increasing layers in the identifier architecture on PCR-based random access.

The number of layers in a product scheme for constructing identifiers may also have an impact on the number of symbols that may be accessed per PCR query. FIG. 25 shows an example of identifiers produced by the product scheme of five layers, A, B, C, D, and E, where each layer has two components, 1 and 2. Furthering the aforementioned identifier ranking principle, the lexicographical order of the layers assigns highest priority to the outermost layers (A and E), next highest priority to the second-to-outermost layers (B and D), and lowest priority to the middle layer (layer C). As used herein, priority refers to the depth (or level) of data access, with high priority corresponding to shallow depth and low priority corresponding to deep depth. For instance, access of a book (i.e., layers A and E) from a volume of books would be considered the highest priority, access of a chapter within the book would be considered the next highest priority (i.e., layers B and D), and access of a paragraph within the chapter of the book would be considered the lowest priority (i.e., layer C). If there were more layers, the lexicographical ordering of layers would continue in this manner so that fewer PCR queries may be used to retrieve contiguous or related stretches of bits. All identifiers associated with components in the outermost layers (A1 and E1) may be queried in one PCR reaction. Further higher resolution (i.e., lower priority or deeper) queries may then be performed with an additional PCR reaction using primers that bind components in the second-to-outermost layers (B1 and D1). If there were more layers in the identifier architecture, sequential PCR reactions may continue in this manner to achieve higher and higher resolution queries. However, as an alternative to using two sequential PCR reactions to query all identifiers associated with 4 components, A1, B1, D1, and E1. It is possible (especially if the components are designed to have short enough sequences) that PCR primers may be designed to bind A1-B1 together and E1-D1 together, but neither component on its own, so that the resulting PCR query would access the same identifiers as if A1 and E1 followed by B1 and D1 were PCR queried sequentially.

Methods of Encoding Information with DNA and Multiple Bins

Information may be encoded with DNA identifiers using a "multi-bin scheme". In one implementation of such a scheme, there are b bins, each holding a disjoint set of identifiers. Each bin is labeled with a unique $[\log_2 b]$ bit symbol, which may be referred to herein as a label or bin label. A bitstream of l bits is divided into $l/\log_2 b$ "words", where each word has length $[\log_2 b]$ bits. Any word w may be a bin label.

Specifically, the multi-bin scheme may be a "multi-bin positional encoding scheme". In this multi-bin scheme, a unique identifier is constructed to denote the position of each word w in the bitstream, and is placed into the unique bin with label w. In this multi-bin implementation of the scheme, $l/\log_2 b$ identifiers are created to encode l bits of information, and each bit is encoded by exactly one identifier present in exactly one bin. We refer to this as the "multi-bin positional encoding scheme".

The multi-bin positional encoding scheme described above may be described by the following example. Consider 35 bins, each bin labeled by a distinct symbol of the English alphabet, including punctuation. Encoding a paragraph of English text is accomplished in the following way. For each symbol x, all occurrences of x are identified in the paragraph. Their integer addresses are obtained by numbering each letter in the text in ascending order. All the identifiers corresponding to the addresses of some specific symbol x are created and collected into a single bin labeled x. Thus, all the locations in the text where x occurs are represented by identifiers in the bin labeled x.

Figure 26:
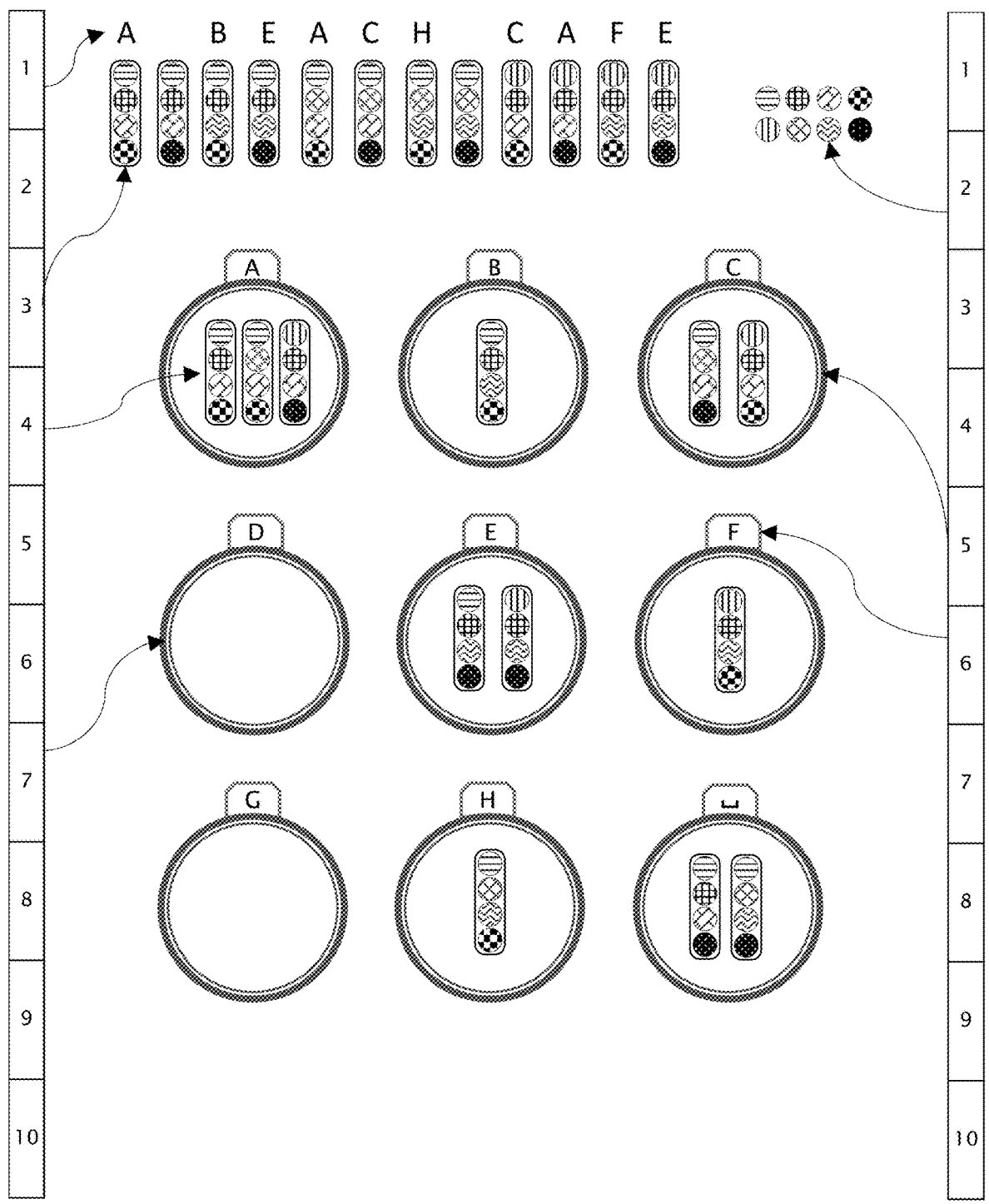
FIG. 26 shows an example of a multi-bin positional encoding scheme over an alphabet of nine symbols.

FIG. 26 illustrates an example of the multi-bin positional encoding scheme, where the position of each type of symbol in a symbol stream is recorded in a bin reserved for that type of symbol. The figure shows an example phrase "A BEACH CAFÉ" labeled 1. We assume in this example a nine letter alphabet comprising nine types of symbols "A", "B", "C", "D", "E", "F", "G", "H", and ⎵ (representing a space). Each symbol in this alphabet is assigned a distinct bin corresponding to the respective symbol and named by that symbol. For example of empty bin "D" is indicated by label 7. For example, the label of bin "F" is shown by label 6. A phrase to be encoded is divided into symbols from the alphabet and mapped in one-to-one correspondence with an identifier library, as shown by label 3. Each occurrence of a symbol triggers the addition of the corresponding identifier to the bin reserved for that symbol. For example, bin A contains three identifiers (label 4) because the symbol "A" occurs three times in the phrase to be encoded ("A̲ BE̲A̲CH CA̲FÉ", emphasis added). Moreover, the three identifiers in bin "A" mark the positions of the occurrences of that symbol. Bins "D" and "G" are empty because the letters "B" and "G" do not occur the mapped phrase ("A BEACH CAFÉ").

In another implementation of a multi-bin scheme, a bitstream of l bits is encoded implicitly in the distribution of identifiers to b bins labeled 1, 2, . . . , b. In this scheme, a mapping is designed between the set of all bits reams of length l bits and the set of all distributions of d identifiers into b bins. A distribution of d identifiers to b bins is a vector of integer labels $(b_1, b_2, \ldots, b_d)$ such that $0 \le b_i < b$: each nonnegative integer $b_i$ is the label of the unique bin assigned to the i-th identifier. Since each assigned bin label may be chosen freely from b possible labels, there are $b^d$ possible distributions.

Figure 27:
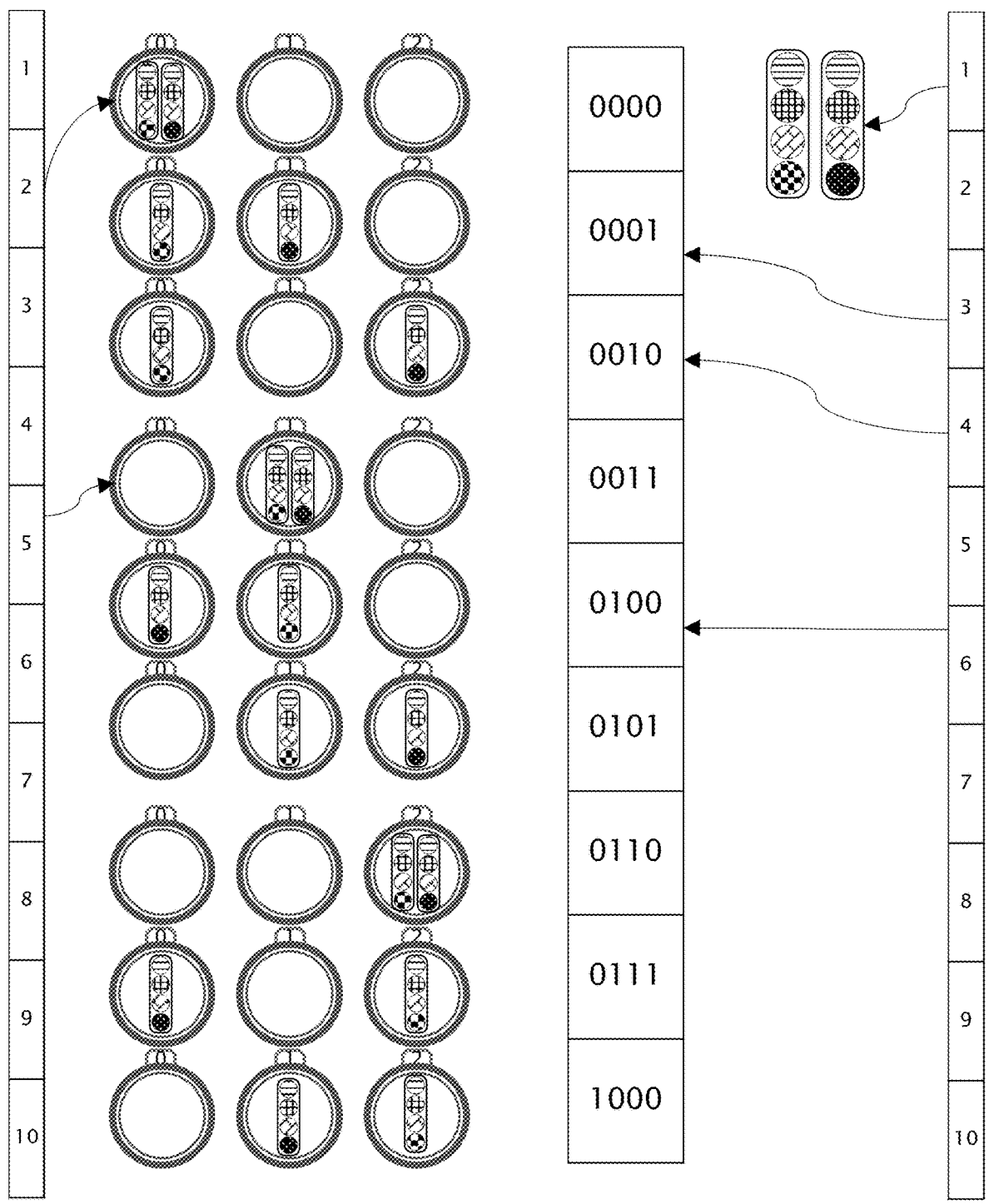
FIG. 27 shows an example of a multi-bin identifier distribution encoding scheme with an identifier library of two identifiers and a bin set of three bins allowing encoding any of nine possible messages of four-bit strings.

FIG. 27 illustrates an example of the multi-bin scheme based on the use of identifier distributions for encoding information. FIG. 27 shows an example with an identifier library of two identifiers (labeled 1) and a bin collection of three named bins (0, 1, 2). Each row of bins (each row comprising the three named bins 0, 1, 2) shows an example of a distribution of the two identifiers partitioned into the three bins. The table (labeled 6) shows the fixed but arbitrary bitstream mapped to each distribution. For example, the fourth row of three bins (labeled 5) shows a distribution in which the two identifiers are placed into the bin named 1, while the 0 and 2 bins are empty. This distribution is arbitrarily mapped to the bitstream 0011. Similarly, he second row of three bins shows a distribution in which the two identifiers are placed into bins named 0 and 1, while the third bin is left empty. This distribution is mapped to the bitstream 0001 (labeled 3). The he next row shows a distribution in which the bin named 1 is left empty. This corresponds to the bitstream 0010. Given any such bitstream, its corresponding distribution is constructed, and preserved. In this way, any bitstream may be encoded using this multi-bin identifier distribution scheme, using a sufficient number of bins and identifiers.

In another embodiment of a multi-bin scheme, an identifier may be present in more than one bin. In this scheme, a bitstream of l bits is encoded implicitly in the distribution of identifiers to bins labeled 1, 2, . . . , b. In this scheme, each bin contains a subset of identifiers. Thus, in this scheme, a mapping is designed between the set of all bitstreams of length l bits and the set of all b-subsets of the set of all identifier subsets. By a b-subset, we mean a set containing b elements. For example, if there are a total of d identifiers in a combinatorial space, then the set of all identifier subsets contains $2^d$ sets, which we denote by D. The scheme uses a mapping between all bitstreams of length l and any subset of D containing b sets, and can encode a bitstream of length no greater than $\log_2 2^{db}$. In another embodiment, each bin contains a distinct subset: in this case the scheme can encode a bitstream of length no greater than $\log_2$ $$\binom{2^d}{b}.$$

Figure 28:
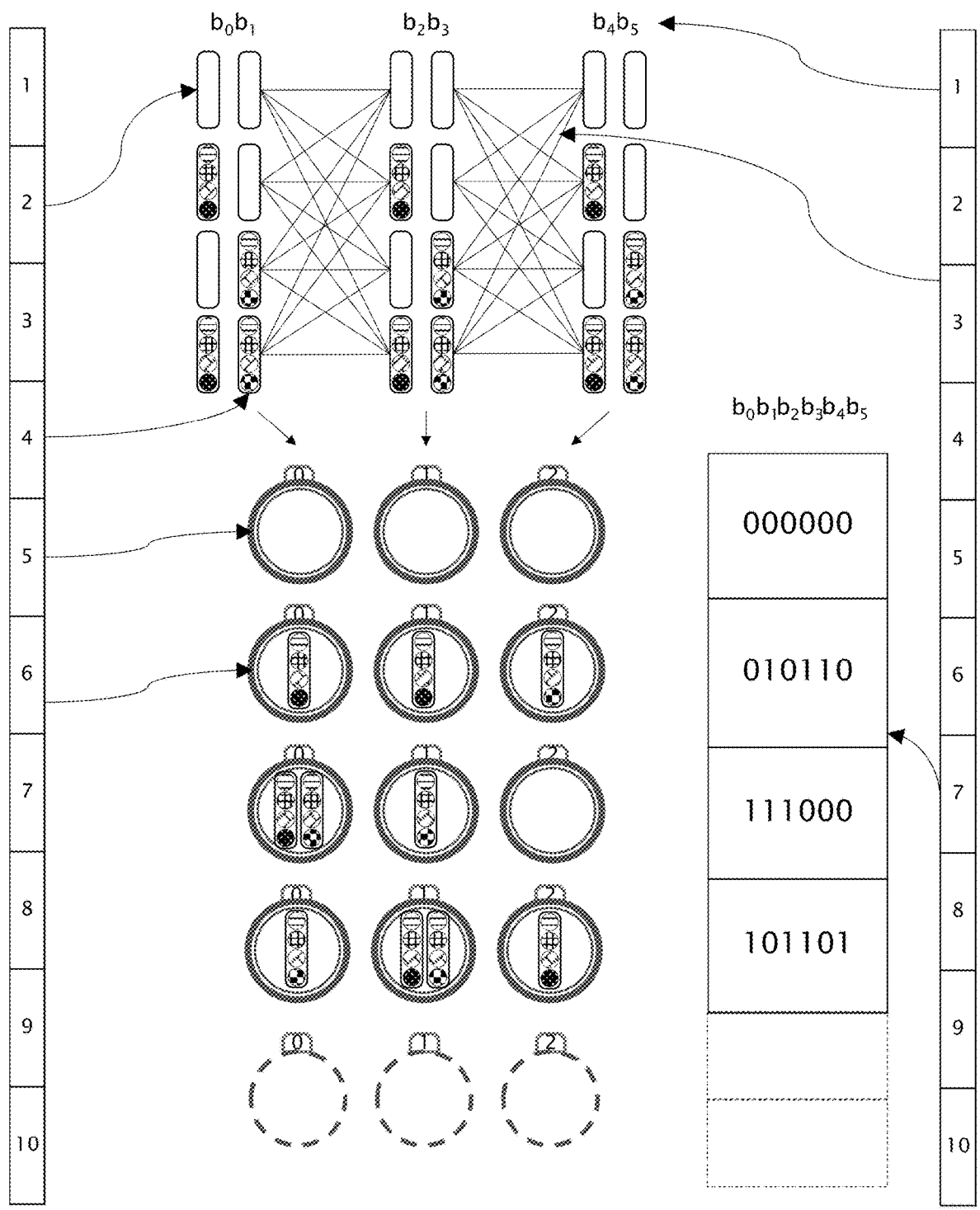
FIG. 28 shows an example of a multi-bin identifier distribution encoding scheme with reuse of identifiers with a library of two identifiers and a bin set of three bins allowing encoding any of 64 possible messages of six-bit strings.

FIG. 28 illustrates an example of the multi-bin scheme based on the use of identifier distributions for encoding information, where an identifier may appear in more than one bin. We refer to this scheme as Identifier Distributions with Reuse. FIG. 28 shows an example involving an identifier library of two identifiers (labeled 8 and 9) and three bins (bins 0, 1, 2). The two identifiers and three bins are used to code six bits $(b_0 b_1 b_2 b_3 b_4 b_5$, wherein each $b_x$ corresponds to a single bit in a bitstream and x denotes the position of the respective bit in the bitstream). The top of the figure shows the possible subsets of identifiers corresponding to bits $b_0 b_1$ (labeled 4), $b_2 b_3$, and $b_4 b_5$, respectively. Any subset of identifiers may be included into any bin. Each bin of the three bins may thus include four options: no identifiers, a single identifier (labeled 8), the other identifier (labeled 9), or both identifiers (8 and 9). Since this example involves three bins, each subset is shown thrice, in each row (label 2). Each of the three bins may include exactly one subset, but all subset triples are acceptable. This is illustrated by the lines (label 3) connecting the subsets: each path from left to right corresponds to a collection of subsets to be included in the three bins. Each distribution of identifiers is mapped to a specific bitstream, as shown in the table (labeled 7). In one embodiment, the bitstream may be inferred by naming the subsets as 00, 01, 10, and 11 for each bin. Thus, for example, the distribution shown by label 5 would correspond to the bitstream 000000 because it chooses to include the empty subset of identifiers in each of the three bins, and this subset is named 00. Similarly, the distribution shown by label 6 would correspond to the bitstream 010110, because it chooses to include subset 01 in bin 0, subset 01 in bin 1 and subset 10 in bin 2. The figure shows a few more examples out of the 64 possible distributions (alluded to by the dashed items in the figure).

Multi-bin encoding schemes may have applications in secure archival of data because decoding data encoded with such schemes may requires access to and decoding of all bins. For example, to map a multi-bin encoded identifier library back to the source bitstream, it may be necessary to obtain the identifier sets present in each bin because multi-bin schemes map a bitstream to distinct distributions of identifiers in multiple bins making it not possible in general to decode any significant substring of the source bitstream from a proper subset of bins.

In another embodiment, a source bitstream may be encoded using a multi-bin scheme using multiple orthogonal identifier libraries. The resulting multi-bin libraries may be combined in a way that enables decoding from any subset of bins of some minimum cardinality. For example, a source bitstream may be encoded using five orthogonal libraries and three bins each. The resulting 15 bins may then be combined in a way than enables the decoding of the bitstream from any subset of the three bins. In practice, a bin may be a physical location such as a tube, a well, or a spot on a substrate.

In some embodiments, a bin may be a physical location such as a tube, a well, or a spot on a substrate. In other embodiments a bin may be a more abstract association shared by all identifiers in a collection, such as a particular barcode sequence.

Methods of Encoding Information with DNA and Integer Partitioning

Figure 29:
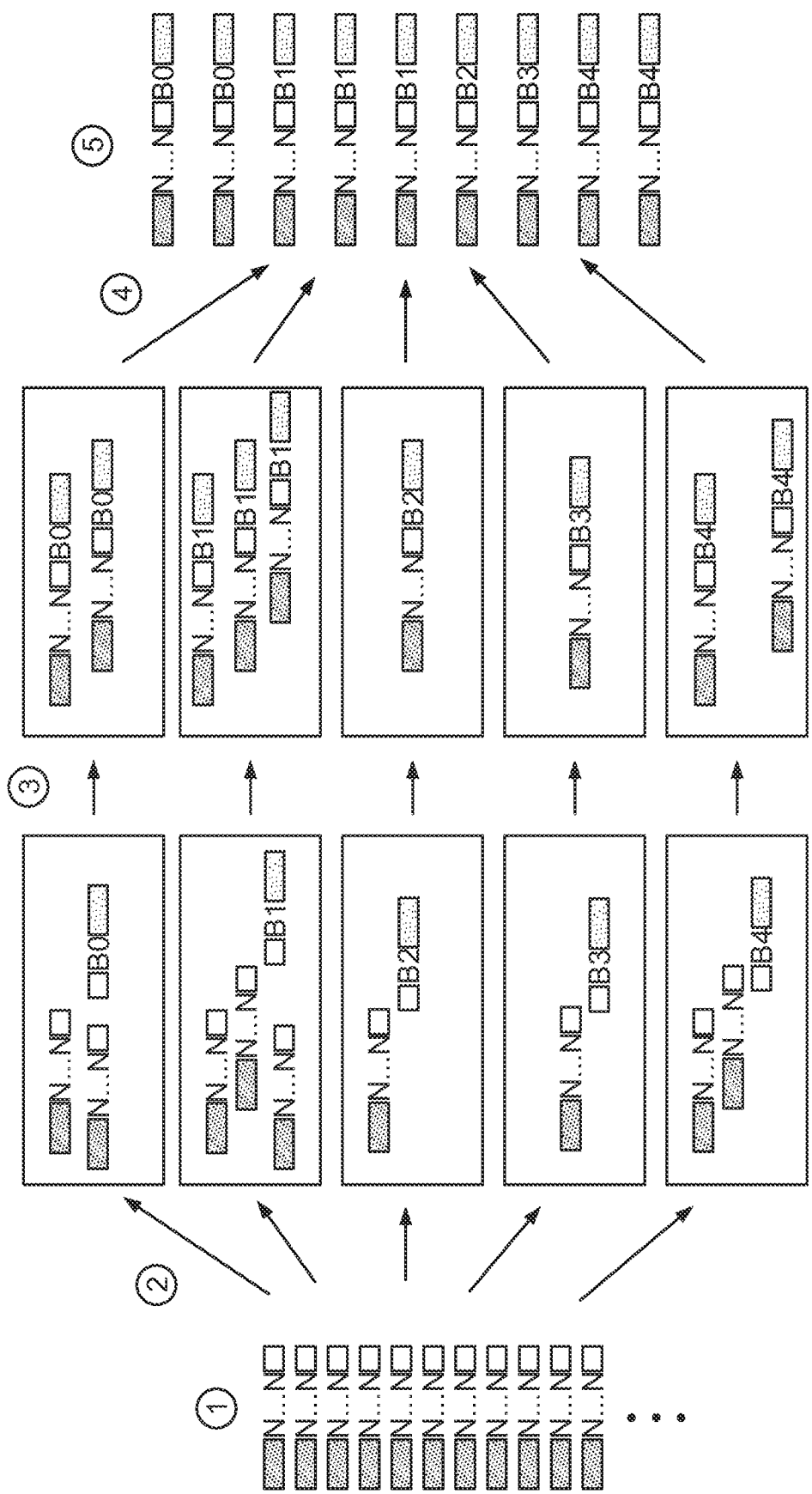
FIG. 29 show an example of encoding information in DNA with integer partitioning.

We use the term "integer partition" method, to refer to an encoding strategy that stores information in the partitioning of random sequences of DNA. FIG. 29 illustrates an embodiment of the integer partition method as outlined by five steps. DNA is depicted as strings comprising grey or black bars and symbols. Each depicted DNA represents a distinct species. A "species" is defined as one or more DNA molecule(s) of the same sequence. If "species" is used in a plural sense, then it may be assumed that every species in the plurality of species has a distinct sequence, though this may sometimes be made explicit by writing "distinct species" instead of "species".

In Step 1 of the method embodiment, we start with a pool of a very large number of species, each referred to as a "count". The counts may be designed to have common sequences on the edges (the black and light grey bars) and then distinct sequences in the middle (N . . . N). Degenerate oligonucleotide synthesis strategies may be used to manufacture this starting pool of counts in a rapid and inexpensive manner. In Step 2 counts are partitioned to bins (rectangles present in Step 2). It does not matter which count gets partitioned to which bin; all that matters is the number of counts that get partitioned to each bin. So partitioning may occur by sampling a single count at random from the starting pool and then assigning it to a particular bin (e.g., one of the five bins present in Step 2). A single count may be sampled from the pool in a small droplet. Bins are reaction containers. For example, bins may be chambers in a microfluidic channel or positions on a substrate. The counts may be assigned to chambers through microfluidic devices or to positions on a substrate through printing. Each bin contains a distinct DNA species, referred to as a barcode. The barcodes may be designed to have common sequences on the edges (the light and dark grey bars) and distinct sequences in the middle (B0, B1, B2, B3, B4 . . . ) that identify each bin. In Step 3, a common edge sequence of the barcodes assembles to a common edge sequence of the counts. For example, the common edge sequences of the barcodes may be configured to assemble through sticky end ligation or Gibson assembly. In Step 4, assembled DNA molecules from each bin are consolidated into a final pool for storage, denoted as Step 5. The species in the final pool contain all of the information about how the counts were partitioned to each bin. This information may be recovered by sequencing. In the given example, sequencing data may imply that 9 counts were partitioned into 5 bins such that the first bin (B0) has two counts, the second bin (B1) has three counts, the third bin (B2) has one count, the fourth bin (B3) has one count, and the fifth bin (B4) has two counts. This is equivalent to mathematically rewriting the integer "9" as the ordered summation "2+3+1+1+2", which is known as a "composition". If the parameters of this method are fixed to always have a total of 9 counts and 5 bins, then the particular composition recorded in this example contains log 2(13choose4) bits of information since there were 13choose4 possible compositions possible. At any point in this process, multiple copies of each species may exist or be created (for example with PCR) without interfering with the information being stored. This enables the final pool to be amplified, both to protect against degradation and to facilitate sequencing.

Generally, if an integer partition system has fixed parameter values of n partitioned counts and k bins, then the method may be implemented to store $\log_2[(n+k-1)\text{choose}(k-1)]$ bits of information. Mathematically, we say that the information measures the number of "weak compositions" of the system. However, this is only if the barcode sequence of each bin is known. If the barcode sequence of each bin is unknown (for example, if the barcode is itself a random sequence), then the method may still be implemented to store $\log_2[\Sigma_{j=1}^{j=k} Pj(n)]$, where Pj(n) is the number of partitions of n into exactly j parts.

Methods of Data Pipeline Design for Encoding Information in DNA

Figure 30:
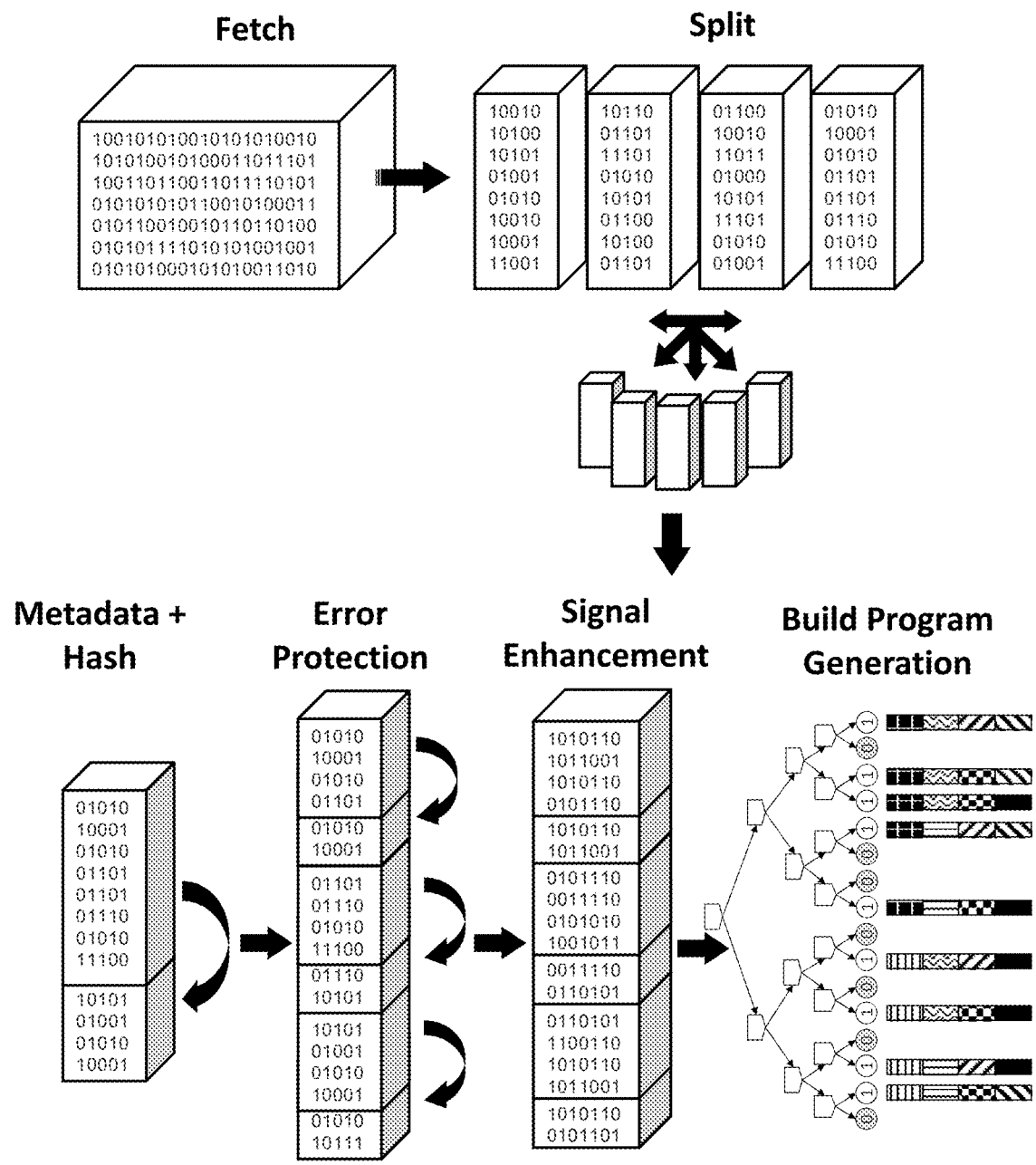
FIG. 30 shows an example of an encoding pipeline comprising algorithmic modules for preparing and converting a source bitstream into a build program specification to be interpreted by a Writer.

An input bitstream to be written into DNA is processed by a computational encoding-decoding pipeline, abbreviated as a "codec". FIG. 30 shows a high level block diagram of an example encoding portion of the codec. Upon receiving a source bitstream and a request to write it to DNA, the codec divides the source bitstream into one or more blocks of size no greater than a fixed length, known as the block size. The codec determines an appropriate block size based on the source bitstream (i.e. string of symbols), processing requirements, and the intended application of the content of the bitstream (i.e. digital information). For example, a 100 Gbit bitstream may be divided into 100 blocks of length 1 Gbit each, or 1000 blocks of length 100 Mbit each, or divided in some other way.

The codec may use one or more hashing algorithms to compute a hash of each block. It may append the hash and other metadata, for example, block length and block address, to the block.

The codec may apply one or more error detection and correction algorithms to each block and compute one or more error protection bytes. The codec may then combine the original block with the error protection information to obtain an error-protected block. For example, the codec may apply convolution coding to bits in the block and Reed-Solomon or erasure coding to chunks of bytes in the block and append the Reed-Solomon or erasure error protection bytes to each chunk of the block. The codec may append error protection metadata to each block.

In computing error protection information, the codec may choose a specific algebraic field size to conduct error protection calculations. The field size may dictate a source word length, which may be an arbitrary number of bits such as 4, 8, 12, 16, 20, 24, 28, 32, 36, 40, 44, 48, 64, or 128 bits. Source words are contiguous strings of bits (of a fixed length) that comprise the source bitstream. The codec may choose a specific field size and word length based on computational complexity and error protection considerations. For example, an 8-bit word length may be computationally efficient, but a 16-bit word length may offer better error protection. The codec may use a search algorithm to identify an optimal set of parameter values based on one or more objective functions. For example, the codec may use the number of independent reaction compartments within a writer hardware system, or the number of unique identifiers needed to encode a bitstream under a specific configuration of parameter values, or some other function, or some combination of functions, as a cost function.

The codec may further apply another encoding step to an error protected block to improve writing or reading performance. The codec may map each word in an error protected block to a new codeword. The codec may use a search algorithm to generate a set of codewords with a specific set of properties. For example, the codec may generate codewords that are of variable lengths, or have the same fixed number of "1" bit values, or codewords that have a specified Hamming distance from each other, or some combination of such features. The codec may use a set of parameters including the source word length, writer hardware speed, and total number of available components, in determining the best codeword length, weight, Hamming distance, or other features of the codewords. The codec may include another layer of error detection or correction information with these codewords. For example, the codec may generate codewords of length with exactly k "1" bit values where two of the bits, known as the high or low bit, serve as parity bits: the high bit is set when then parity bit is 1, otherwise the low bit is set. One or more pairs of such error protection bits may protect various parts of the codeword.

The codec may choose a specific set of codewords to ensure optimized chemical conditions during encoding or decoding. For example, the codec may generate codewords of a fixed weight to ensure that a fixed and identical number of identifiers are assembled in each reaction compartment in a writer system, and in an approximately equal concentration within each compartment and across compartments. The codec may choose codeword length and a partition scheme such that each reaction compartment assembles the same number of identifiers and encodes an integral number of codewords.

The codec may choose to encode some or all bits in a source bitstream using multiple sets of identifiers. The identifiers may conic from orthogonal identifier libraries or may belong to the same identifier library. The identifiers may encode the source bitstream or combinations of bits from the source bitstream. Using multiple sets of identifiers encoding combinations of bits, the codec may be able to decrease the size of the sample needed to reliably decode all the bits.

The codec may produce one or more output blocks for each source block. The output block may describe the set of identifiers to be assembled as a list or some other type of data structure including a tree. The codec may produce one or more command files that command a device to assemble the specified identifiers. For example, the codec may produce command files that control a liquid handling robot or a inkjet printer with inks containing components. The codec may communicate with the device and optimize the block files based on information from the device. For example, the device may report an assembly error rate and the codec may produce new block files that have higher error protection performance. The codec may transmit block files or commands as files or over a network. The codec may execute its computational processes over one or more computers.

Methods of Specifying Instructions to an Information Writer

We refer to any system that builds identifier libraries as a "Writer". For example, some embodiments of a Writer may use print-based methods to collocate components for construction of identifiers. Print-based methods may involve the use of one or more printheads, each capable of printing one or more nucleic acid molecules onto a substrate.

The identifier library to be assembled is specified and transmitted to the Writer via a set of specification files. A block data file specifies the set of identifiers to be generated by the Writer. The block data file may be compressed using a data compression algorithm. The identifiers comprising a block may be specified in the form of a serialized data structure such as, but not limited to, a tree, a trie, a list, or a bitmap.

For example, an identifier library to be generated using the product scheme may be specified with a block metadata file containing the component library partition scheme (the manner in which components are divided into layers in the identifier architecture), and a list of names of the possible components to be used in each layer. The block data file may contain the identifiers to be generated organized as a serialized trie data structure in which each path from the root to the leaf of the trie represents an identifier and each node along the path specifies the component name to be used in that layer of that identifier. The block data file may comprise a serialization of this trie by traversing it in order starting with the root, and visiting the left child node of each node, before visiting the node itself, and then visiting its right child node.

Figure 31:
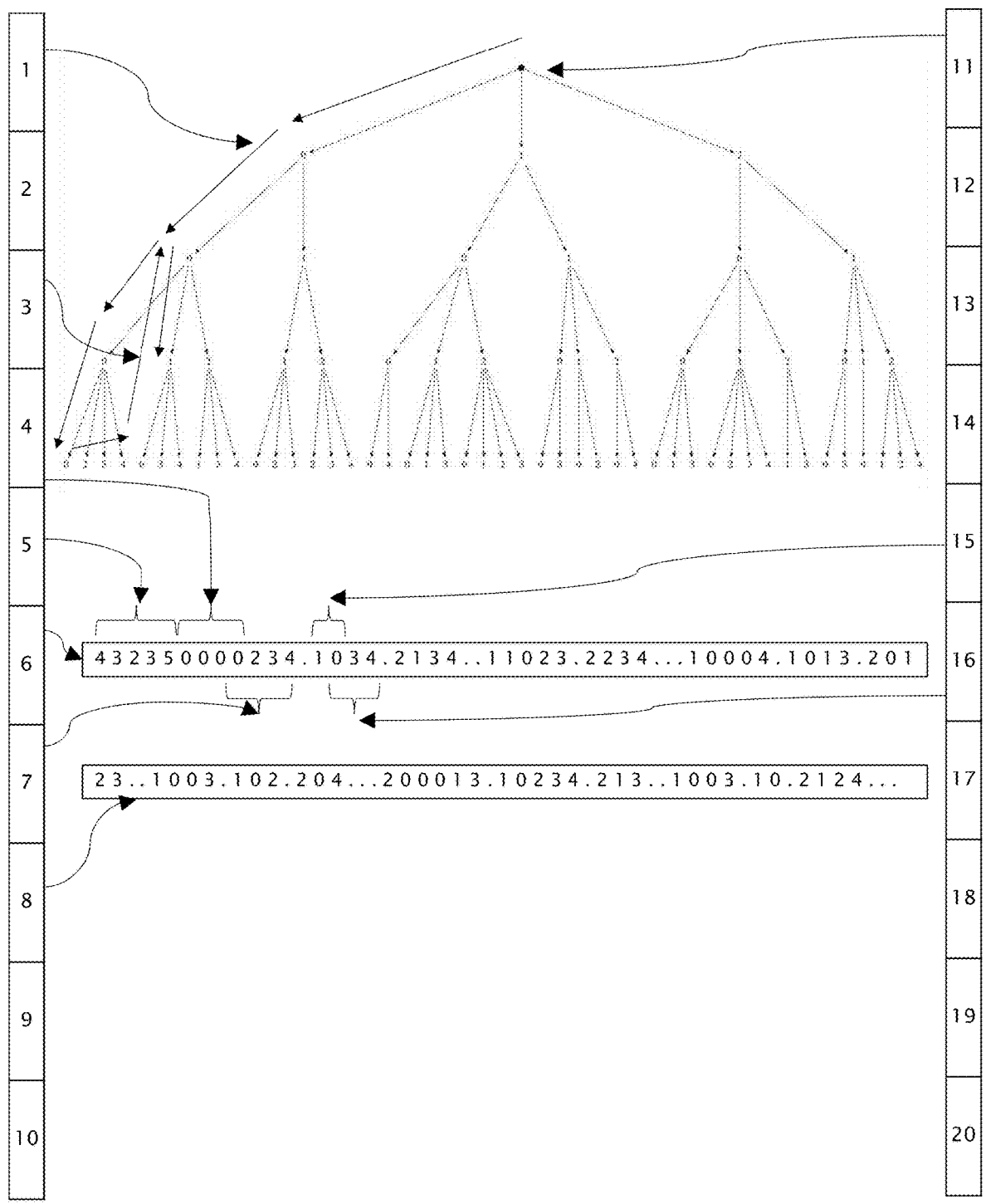
FIG. 31 shows an instance of one embodiment of a data structure for representing an identifier library in a serialized format.

FIG. 31 illustrates an embodiment of a data structure and serialization for representing an identifier library. An identifier library encoding some bitstream is shown (label 11). Each path from the root of the tree to any leaf represents a single identifier, with the components in the identifier specified by the names of the nodes encountered along the path. Label 6 shows a serialized representation of the data structure primarily comprising component names and delimiters. The serialized form begins with a specification of the constructor-specific partition scheme (label 5). In this case, a product construct is used with four layers, containing 3, 2, 3, and 5 components in each of the respective layers. The remaining items in the serialization sketch out paths in the data structure, like the one labeled 1. The segment labeled 4 in the serialization sketches a path that starts at the root of the tree and descends down node 0 in the first layer, then node 0 in the second layer, node 0 in the third layer, and to the leaf 0 in the last layer. Because the partition scheme has four layers, the algorithm deduces that a complete identifier may be output at this stage. More generally, this segment of the serialization (labeled 7) specifies all the alternative components in the final layer. When all the alternatives to be included in the identifier library in a specific layer have been listed, a delimiter (a period in this example) is included in the serialization to ark this state. This triggers the algorithm to ascend up a layer, as shown in the path in the tree (labeled 3). The next segment of component identifiers in the serialization (labeled 16) describes the next set of identifiers. In this way, an entire identifier library may be represented in a flat serial file in a compact manner.

Methods of Computing with Identifiers

It may be possible to perform computations on data encoded in an identifier library using chemical operations. It may be advantageous to do so because such operations may be performed on any subset of an entire archive, or the entire archive, in a parallelized manner. Additionally, the computations may be performed in vitro without decoding the data thus ensuring secrecy while allowing computation. In some implementations, computations involving Boolean logical operations such as AND, OR, NOT, NAND and more are performed on bitstreams encoded using identifiers that represent each bit position, where the presence of an identifier encodes the bit-value of '1' and the absence of an identifier encodes the bit-value of '0'.

In some implementations, all identifiers are constructed as single stranded nucleic acid molecules (or initially as double stranded nucleic acid molecules and then isolated into single stranded form). For any single stranded identifier x, an identifier is denoted as a reverse complement of x by x*. For any set of single stranded identifiers S, we denote the set of reverse complements of each identifier in S as S*. We denote by U the set of all possible single-stranded identifiers in a library, and by U* the set of its reverse complements. We call these sets the universe and universe*. By $U_s$ and $U_s^*$, we denote a second pair of universe and universe* sets, such that each identifier in these sets is augmented with an additional nucleic acid sequence, known as a search region, that may be targeted or selected by chemical methods.

Computation on a given identifier library may be implemented by a sequence of chemical operations, involving hybridization and cleavage. Abstractions of these operations are described below. Each operation takes as an input a pool of identifiers, performs an operation, and returns as an output a pool of identifiers.

As an introductory example, a first library L1 and a second library L2 may each contain eight bits, as shown in the table below. The results of a bit-by-bit "OR" operation between the two libraries and a bit-by-bit "AND" operation between the two libraries are also shown. The details of these operations (and additional operations) performed by chemical steps will be described in further detail below.

TABLE 1

| Bits | L1 | L2 | OR | AND |
|------|----|----|----|-----|
| b0 | 1 | 0 | 1 | 0 |
| b1 | 0 | 0 | 0 | 0 |
| b2 | 1 | 1 | 1 | 1 |
| b3 | 1 | 0 | 1 | 0 |
| b4 | 0 | 1 | 1 | 0 |
| b5 | 1 | 1 | 1 | 1 |
| b6 | 0 | 1 | 1 | 0 |
| b7 | 0 | 0 | 0 | 0 |

Each bit of each library is encoded as an identifier including a symbol position. The absence of an identifier for a symbol position indicates a 0 and the presence of an identifier for a symbol position indicates a 1. In this example, the identifiers in the libraries are double stranded.

To perform an OR operation on the two libraries L1 and L2, the two library pools are combined. The identifiers for both libraries may be left in their double-stranded state for the OR operation. Because an OR operation indicates whether there is a 1 in either L1 or L2, the combination of the two pools is the fully determined OR operation output (as shown above in the OR column). At most, there will be twice as many identifier copies (as compared to the original libraries) for the same symbol position, which will still indicate the presence of a 1 at that symbol position (i.e., at symbol position b5). In some implementations, the double-stranded identifiers may be denatured to generate two single strands (i.e., one sense, or "positive", strand and one anti-sense, or "negative", strand for each double stranded identifier). We refer to the resulting two complementary single strands as "positive" and "negative" strands. In some implementations, a subsection of the libraries may be selected, an OR operation may be performed, and the result of the OR operation may replace the existing bit values in one or both of the existing libraries.

To perform an AND operation on the two libraries L1 and L2, double-stranded identifiers are first denatured to generate two single strands (i.e., one sense strand and one anti-sense strand for each double stranded identifier). Again, we refer to the resulting two complementary single strands as "positive" and "negative" strands. The positive and negative strands are separated into separate pools. In practice, this may be achieved by using an affinity tagged probe for either the positive or the negative strand (see Chemical Methods Section F on nucleic acid capture). The identifiers may be designed to contain common probe targets for this purpose. The positive strand of the double stranded identifier (e.g., the sense strand) from the first library and the negative strand of the double-stranded identifier (e.g., the anti-sense strand) from the second library are then pooled together, allowing the complementary single strands to hybridize. Assuming there are existing identifiers in both libraries (e.g., in L1 and L2 shown in the table above), the resulting combined pool will have a combination of single-strands of DNA and double-strands of DNA after hybridization is allowed to occur. A fully double-stranded identifier indicates that the identifier was present in both the first library L1 and the second library L2. The fully double-stranded identifiers may be selected from the pool to create the AND operation output. For instance, single-stranded identifiers may be selectively removed using a single-strand specific nuclease, such as S1 nuclease or Mung Bean nuclease, to cleave the single-stranded identifiers (and partially single-stranded) into small units. The fully double-stranded identifiers, being protected from cleavage, may then be isolated using techniques such as the nucleic acid capture techniques described in Chemical Methods Section F or size selection techniques described in Chemical Methods Section E. For example, the nucleic acid pool could be run on a chromatography gel such that only the fully complemented double stranded DNA would run at a certain length. The combined pool outputs are shown by the AND column in the table above. Details and additional examples of the steps necessary to perform these AND and OR operations are described below.

The random access methods described herein may be used to extract a portion of the library. For example, a subsection of a library may be extracted via random access. A logical operation (e.g., OR or AND) may be applied to the subsection. In some implementations, the resulting set of identifiers may replace the original values of the subsection within the library.

The operation single(X) takes a pool of identifiers (double stranded and/or single stranded) and returns only the single stranded nucleic acid identifiers (removing all double stranded identifiers). The operation double(X) takes a pool of identifiers (double stranded and/or single stranded) and returns only the double stranded identifiers (removing all single stranded identifiers). The operations make-single(X) and make-single*(X) converts all double stranded nucleic acid identifiers into their single stranded forms. (The starred version returns the negative strand while the non-starred version returns the positive strand.) The operation get(X, q) returns a pool of all identifiers matching query q. When q="all", the query matches and operates on all identifiers. The operation delete(X, q) deletes all identifiers (double stranded or single stranded) that satisfy query q. Queries may be implemented via random access as described previously. The operation combine(P, Q) returns a pool containing all identifiers in P or Q. We define the operation assign(X, Y) which assigns the result of Y to the variable name X. For brevity, we also denote this operation in the following form: X=Y. We assume that assignment operations execute under ideal conditions allowing variables to be reused without any "contamination" issues.

In the sequel, we assume that bitstreams a and b both of length l have been written into double stranded identifier libraries dsA and dsB, respectively, and that we are interested in computing on some sub-bitstreams $s = a_i \ldots a_j$ and $t = b_i \ldots b_j$, with the result of the computation to be stored in the sub-bitstream s. That is, we assume the following operations have been executed in the specified order initially, denoted by the initialize(dsA, dsB, s, t) operation:

| 1 | A = make-single(dsA) |
| 2 | A* = make-single*(dsA) |
| 3 | B = make-single(dsB) |
| 4 | B* = make-single*(dsB) |
| 5 | P = get(A, "s") |
| 6 | Q = get(B*, "t") |
| 7 | A = delete(A, "s") |
| 8 | B* = delete(B*, "t") |

Figure 32:
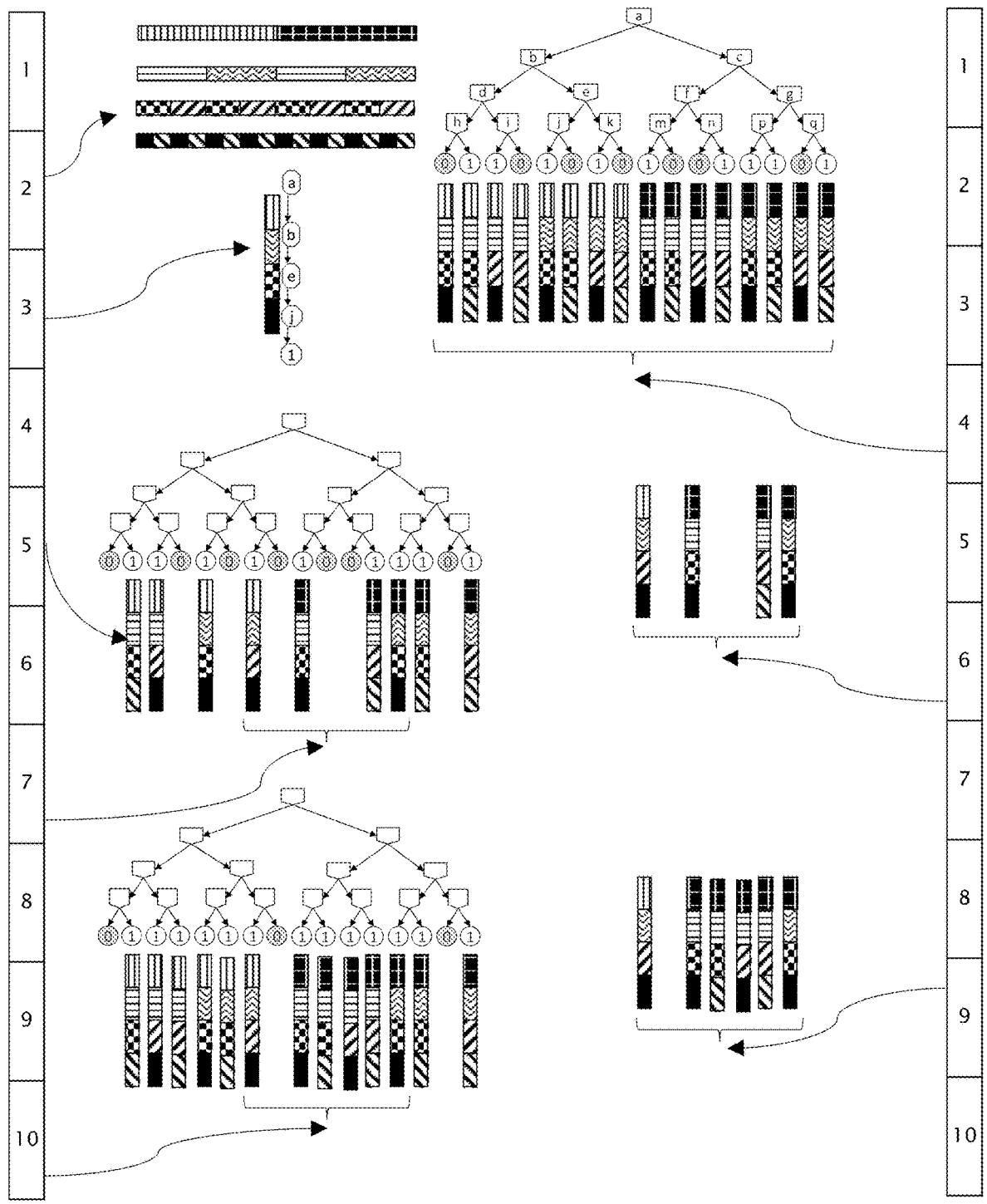
FIG. 32 shows an example of two source bitstreams and a universal identifier library prepared for computation using operations defined on identifier pools.

FIG. 32 illustrates an example setup for computing with identifier libraries. The figure illustrates an example combinatorial space of identifiers drawn as an abstract tree data structure (labeled 4). In this example, each level of the tree chooses between two components (shown by label 2). Each path from the root of the tree corresponds to a unique identifier (as illustrated by the example in label 3), and determines its order (or rank). Label 4 shows the single stranded universal identifier library. Label 5 shows a single stranded identifier library that encodes a specific bitstream, called "a" for example. Label 7 shows a sub-bitstream of "a" called "s" comprising seven bits. Similarly, label 10 shows a sub-bitstream "t" of bitstream "b" of the same length. As described in the initialization procedure for computing initialize(dsA, dsB, s, t), the sub-bitstreams to be computed on are available in pools P and Q (labeled 6 and 9 respectively) and ready for computation.

The operation and(s, t), defined as the bitwise logical conjunction of the bits in bitstreams s and t, may be implemented using the sequence of operations below.

| 1 | R = combine(P, Q*) |
| 2 | S = double(R) |
| 3 | T = make-single(S) |
| 4 | T* = make-single*(S) |
| 5 | A = combine(A, T) |
| 6 | A = combine(A, T*) |

The operation not(s), defined as the bitwise logical negation of the bits in bitstream s, may be implemented using the sequence of operations below:

| 1 | R = get(U*, "s") |
| 2 | S = combine(P, R) |
| 3 | T = single(S) |
| 4 | V = make-single(T) |
| 5 | A = combine(A, V) |
| 6 | A* = combine(A*, T) |

The operation or(s, t), defined as the bitwise logical disjunction of bits in bitstreams s and t, may be implemented using the sequence of operations below:

| 1 | R = get(B, "t") |
| 2 | A = combine(A, R) |
| 3 | A* = combine(A*, Q*) |

In some implementations, the or(s,t) operation may include combining dsA and dsB in a pool to resulting in a combination of identifiers that may be referred to as O (the output of the or(s,t) operation.

The operation nand(s, t), defined as the bitwise logical negation of the conjunction of the bits in bitstreams s and t, may be implemented using the sequence of operations below.

| 1 | R = combine(P, Q*) |
| 2 | S = single(R) |
| 3 | T = make-single(S) |
| 4 | T* = make-single*(S) |
| 5 | A = combine(A, T) |
| 6 | A* = combine(A, T*) |

In one embodiment, the operation single(X) may involve first combining X with either $U_s$ or $U_s^*$ so that the single stranded identifiers from X hybridize to the universal identifiers. Moreover, because the universal identifiers in $U_s$ and $U_s^*$ have a special search region, these molecules that hybridize to the universal identifiers may be accessed in a targeted manner.

In one embodiment, the operation double(X) may involve treating the identifiers in X with a single-stranded specific nuclease, such as S1 nuclease, and then running the resulting pool of DNA on a gel to isolate only identifiers that were not cleaved (and hence fully double-stranded).

Figure 33:
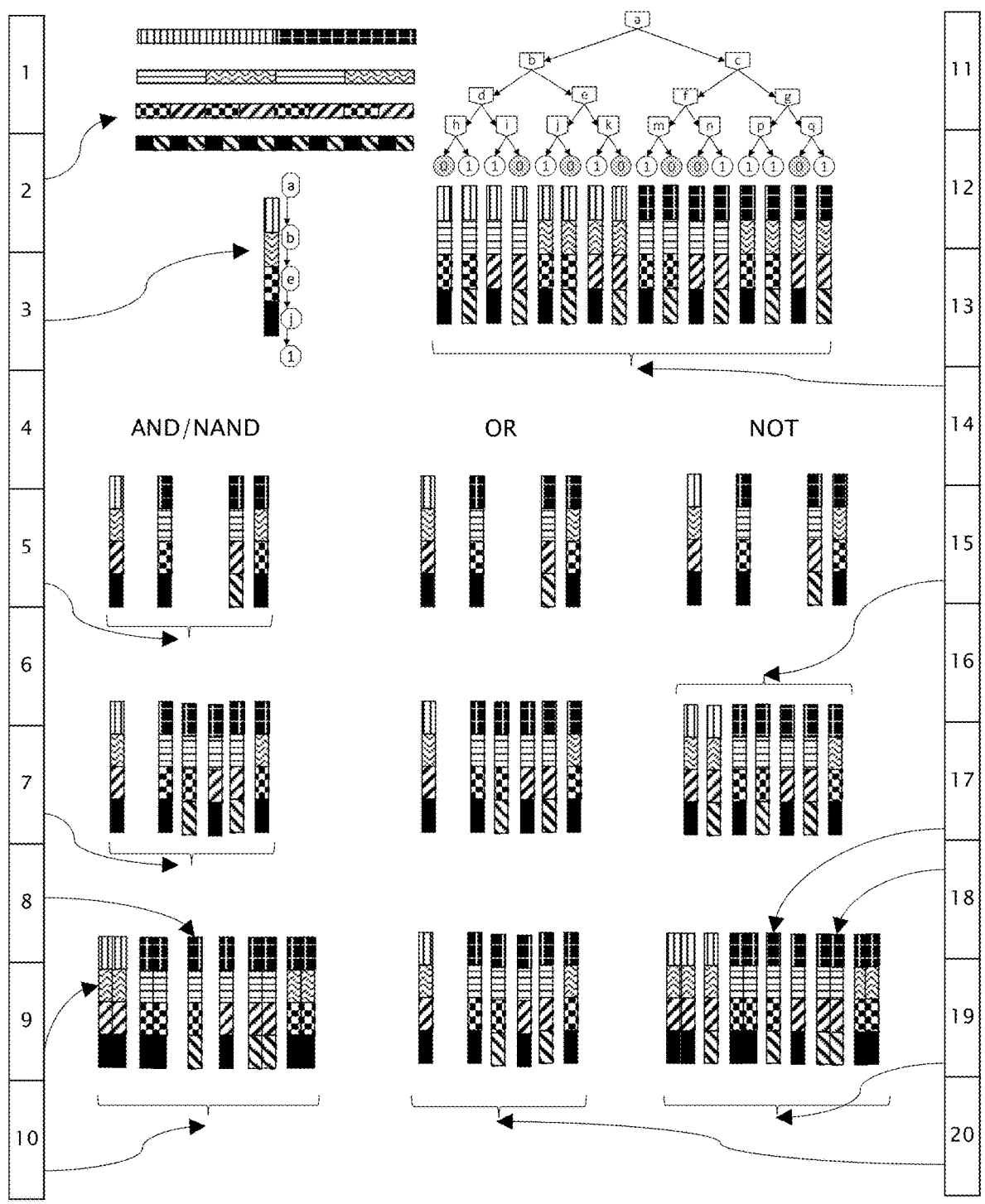
FIG. 33 shows the inputs to and results of three examples of logical operations performed on a pool of identifiers illustrating how identifier libraries may be used as a platform for in vitro computation.

FIG. 33 illustrates an example of how logical operations may be performed on bitstreams "s" and "t" encoded by identifier libraries. In this figure, we use a universal library (labeled 14) such that it is complementary to the pool being computed with. The column labeled AND/NAND shows how one may compute the conjunction of bitstreams "s" and "t" (labeled 5 and 7 respectively). We assume that the pools are reformatted using the correct universal library (U or U*). When the two pools are combined, complementary single stranded identifiers hybridize forming double identifiers, as shown (label 9, for example). The collection of double stranded identifiers in the resulting pool (labeled 10) encodes the result of the AND computation: separating out the double stranded products gives an identifier library representation of and(s, t). Alternatively, separating out the single stranded products gives the identifier library representation of nand(s, t). The column labeled OR shows how one may compute the disjunction of bitstreams "s" and "t". When the pools containing the identifiers representing "s" and "t" are combined, the resulting library contains the representation of or(s, t). The column labeled NOT shows how one may compute the negation of the bitstream "s". Here, the single stranded identifier library representing the bitstream "s" is combined with the complementary universal identifier library (labeled 15). As a result (labeled 19), all the double stranded products formed (labeled 18, for example) represent the "1" bits in "s" and may be discarded. The remaining single stranded products (for example, labeled 17) represent the "0" bits in "s" and thus correspond to the "1" bits in not(s). These single stranded products give the identifier library representation of not(s) and may be used for further computation.

Methods of Encoding and Reading Image Data

While an identifier library is agnostic to the contents of a bitstream encoded in it, it may be particularly useful in archiving image data due to its large size and natural long term social value. Therefore, it may be useful to encode image data with encoding schemes and formats specifically designed for such data. "Image data" refers to data that is presented, implicitly or explicitly, as a collection of vectors of some dimension, and has locality properties: the vectors presented have a notion of distance among them, and vectors close together are queried, operated on, or interpreted together. For example, in a photographic image, each pixel is a vector describing the location of the pixel and its color values, and nearby pixels typically form a region of one or more objects in the photograph and are therefore likely to be interpreted and operated on as a unit.

In one implementation, an image is mapped to an identifier library with an image encoding scheme where vectors from the original multidimensional image are ordered into a linear ordering defined by a mathematical function such as a space-filling curve. The possible values along some or all dimensions of the presented vectors may be mapped to specific components in the component library and some or all dimensions of the vectors may be mapped to layers within a product scheme for identifier construction. We refer to this as a native image encoding. For example, a grayscale image x pixels in width and y pixels in height, may be mapped to a product scheme for constructing identifiers in which the components in the first layer represent the x-coordinate of a pixel, the components in the second layer represent the y-coordinate of a pixel, and the components in the third layer represent, the grayscale intensity of the pixel. For example, an RGB-color image may be represented similarly with three orthogonal identifier libraries, one for each of the red, blue, and green color channels. In another embodiment, other alternative color models such as hue-saturation-value may be represented similarly. In another embodiment, the coordinates specifying the location of a pixel may be represented as described above, except where the components of the third layer, instead of each specifying an intensity value, each represents a bit position in a bit-string that specifies the intensity value and where the presence or absence of an identifier with each component specifies a value of '1' or '0' respectively. For example, in the former embodiment the third layer may comprise 256 components where each component at a particular pixel specifies 1 of 256 possible intensity values, and in the latter embodiment the third layer may comprise 8 components where each subset of these components at a particular pixel specifies 1 of 256 possible intensity values.

In some implementations, some or all components are associated with a range of values. For example, a component in the color value layer (the third layer) may be defined to represent an interval of color values in that color channel. For example, each component in the third layer of a red channel identifier may be mapped to a red color value range of ±10 points instead of a specific red color value.

In some implementations, if an image is encoded as defined above, then any cartesian section (neighborhood of pixels) in the image may be queried for color values using the random access schemes described previously, such as PCR or hybridization capture. Moreover, if the encoding scheme is such that each component in the third layer specifies an intensity value, then any color value may be queried for associated pixel coordinates using the random access schemes.

In some implementations, an image encoded with a native image encoding may be decoded at a plurality of resolutions. For example, an image that is x pixels wide and y pixels tall encoded with an RCM color model using approximately 3xy identifiers may be decoded at half the original resolution by sampling a uniformly random subset of half the identifiers. The contents of the original image may be reconstructed at a lower resolution from the sampled identifiers using image processing and interpolation techniques. Because a smaller sample is used in decoding the image, the cost and time of decoding is reduced.

In some implementations, low resolution decoding of multiple images and image processing may be used to identify images or sections of images of interest in an archive. This may be followed by high resolution decoding of these images or sections of images. This set of features may be useful, for example, in analyzing a large archive of surveillance images in which a specific visual feature is being sought. In another application, a video archive may be treated as a large archive of static image frames. In this application, random access and low resolution decoding may identify frames of interest. Then, surrounding frames may be decoded at a higher resolution to reconstruct video segments of interest. In this way, a large image or video archive may be stored at a high density, for many centuries, and still queried in parallel at low cost.

The following describes an example of image data storage and multi-resolution reading. An uncompressed image file may be encoded into identifiers such that each identifier or each contiguous group of identifiers represents a pixel of the image. For example, if the image is stored as a bitmap where each bit is a pixel that can have one of two colors (for example white or black), then each bit in the bitmap may be represented by an identifier, and the presence or absence of that identifier may represent one color or the other, respectively. To read the image back, the identifier library may be randomly sampled (as we would expect with standard next generation sequencing technologies). The read-back resolution of the image may be specified by defining the sample size of the read-out. So lower resolution versions of an image may be read back at a cheaper price than higher resolution versions. This may be useful when the objective for reading back an image does not require fine image details. Alternatively, low resolution versions of an image or several images may be inspected to determine a location to query (access) at a higher resolution.

Figure 34A:
FIG. 34A-34G show an example of storing an image file and reading it at multiple resolutions.
Figure 34B:
Figure 34C:
Figure 34D:
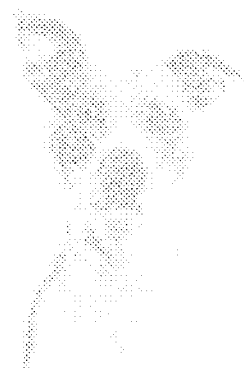
Figure 34E:
Figure 34F:
Figure 34G:

To further demonstrate this principle of multi-resolution control read-back, we consider an example image (FIG. 34) of a dog stored as a bitmap. The original image in FIG. 34A is 1476800 pixels (1300×1136 pixels), each stored as a bit (white or black). We simulate what would happen if each bit were an identifier and the image were encoded by building identifiers only for the black pixels. This requires 131820 identifiers. FIG. 34B demonstrates the resulting image from simulated sampling of 10× the total number of identifiers (1318200 sample size). It has similar details as the original image. FIG. 34C demonstrates the resulting image from simulated sampling of an equivalent number to the total number of identifiers (131820 sample size). FIG. 34D demonstrates the resulting image from simulated sampling of 10× less identifiers than the total number of identifiers (13182 sample size). Because the black pixels are so sparse, it is difficult to visualize the image. We may amplify the size of each dark pixel to help re-create the original. FIG. 34E shows the same image except with each black pixel amplified to 25 pixels. At this resolution some detail of the original image may be lost, for example, the strokes of fur. But more coarse details are still visible, for example, the eyes and nose. FIG. 34F demonstrates the resulting image from simulated sampling of 100× less identifiers than the total number of identifiers (1318 sample size). Because the black pixels are so sparse, it is difficult to visualize the image. Again, we may amplify the size of each dark pixel to help re-create the original. FIG. 34G shows the same image except with each black pixel amplified to 25 pixels. Although many details of the original image may have been lost, the image still shows the shape of the dog as well as some details about its color pattern.

An equivalent multi-resolution read-back may be performed even if each pixel of an image has more than two possible colors. For example, if each pixel has 256 possible colors instead of two, then each pixel may be represented by a subset of 8 identifiers. If each pixel has three color channels, for example RGB, each of 256 possible intensities, then the image may be stored with three orthogonal identifier libraries corresponding to each channel.

Methods of Data Randomization, Cryptography, and Authentication with DNA

The ability to generate and store random bitstreams using DNA may have applications in computations in cryptography and combinatorial algorithms. Many encryption algorithms, for example Data Encryption Standard (DES), require the use of random bits to guarantee security. Other encryption algorithms, for example Advanced Encryption Standard (AES), require the use of cryptographic keys. Typically, these random bits and keys are generated using a secure source of randomness, because any systematic patterns or biases in the random bits or the keys may be exploited to attack and break encrypted messages. Furthermore, the keys used to encrypt are typically required to be archived for decryption. The strength of the security of encryption methods is dependent on the length of the key used in the algorithm: generally the longer the key, the stronger the encryption. Methods like one-time-pads are one of the most secure encryption methods, but find limited application due to their lengthy key requirement.

The methods described in this document may be used to generate and archive extremely large collections of random keys that may be tens, hundreds, thousands, tens of thousands, or more bits in length. In one embodiment, a nucleic acid library may be generated in which each nucleic acid molecule satisfies the following design: it has a length of n bases with a variable region of k<n bases. The bases in the variable region are allowed to be chosen at random during the construction of the library. For example, n may be 100 and k may be 80; thus, a library of size $10^{50}$ different molecules may potentially be generated. A random sample of such a library, of size 1000 molecules for example, may be sequenced to obtain up to 1000-bit random keys which may be used for encryption.

In another embodiment, nucleic acid keys (nucleic acid molecules representing keys) described above may be attached to identifiers yielding an ordered collection of key sets. The ordered key sets may be used to synchronize the order in which keys are used by various parties in an encryption context. For example, an identifier library may be constructed combinatorially using a product scheme to obtain $10^{12}$ unique identifiers. Using microfluidic methods, each identifier may be collocated with a nucleic acid key, and assembled to form a nucleic acid sample comprising a unique identifier and a random key. Because the identifiers in the identifier library are ordered, keys may now be ordered and accessed and sequenced in any specified order.

In some implementations, keys attached to identifiers may be used to instantiate a random function that maps an input identifier to a string of random bits. Such random functions may be useful in applications that require functions that are easy to compute the value of but difficult to invert from a given value, such as hashing. In such an application, a library of keys, each assembled with a unique identifier, is used as the random function. When a value is to be hashed, it is mapped to an identifier. Next, the identifier is accessed from the key library using random access methods, such as hybridization capture or PCR. The identifier is attached to a key comprising sequences of random bases. This key is sequenced and translated into a string of bits and is used as the output of the random function.

Because nucleic acid molecular libraries may be cheaply and quickly copied, and because they may be covertly transported in small volumes, nucleic acid key sets generated as described above may be useful in contexts where a large number of encryption keys must be periodically distributed in a secure and covert way among multiple parties that are not geographically collocated. In addition, the keys may be reliably archived for extremely long periods of time enabling the secure storage of encrypted archived data.

FIGS. 35-38 illustrate embodiments of methods for creating, storing, accessing, and using random or encrypted data stored in DNA. DNA is depicted as strings comprising grey and black bars and symbols. Each depicted DNA represents a distinct species. A "species" is defined as one or more DNA molecule(s) of the same sequence. If "species" is used in a plural sense, then it may be assumed that every species in the plurality of species has a distinct sequence, though sometimes this is made explicit by writing "distinct species instead of "species".

Figure 35:
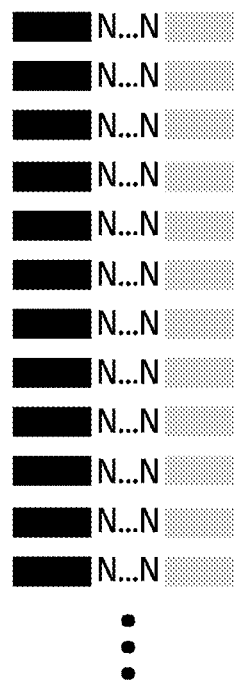
FIG. 35 shows an example method for generating entropy that may be used to create random bit strings.

FIG. 35 depicts an example of an entropy (or random data) generator using a large combinatorial space of DNA and a sequencer. The method begins with a random pool of DNA species, referred to as a seed. The seed should ideally contain a uniform distribution of every species of a defined combinatorial set of DNA, for example, all DNA species with 50 bases (with $4^{50}$ members). However, the full combinatorial space may be too large for every member to be represented in the seed, and so it is permissible that the seed contain a random subset of the combinatorial space instead of the entire combinatorial space. The seed species may be designed to have common sequences on the edges (the black and light grey bars) and then distinct sequences in the middle (N . . . N). Degenerate oligonucleotide synthesis strategies may be used to manufacture this starting seed in a rapid and inexpensive manner. The common edge sequences may enable amplification of the seed with PCR or compatibility with certain read-out (or sequencing) methods. As an alternative to degenerate oligonucleotide synthesis, combinatorial DNA assembly (multiplexed in one reaction) may also be used to rapidly and inexpensively generate a seed. The sequencer randomly samples species from the seed, and it does so in a random order. Because there is uncertainty in the species being read by the sequencer at any given time, the system may be classified as an entropy generator, and it may be used to generate random numbers or random streams of data, for example, as encryption keys.

Figure 36A:
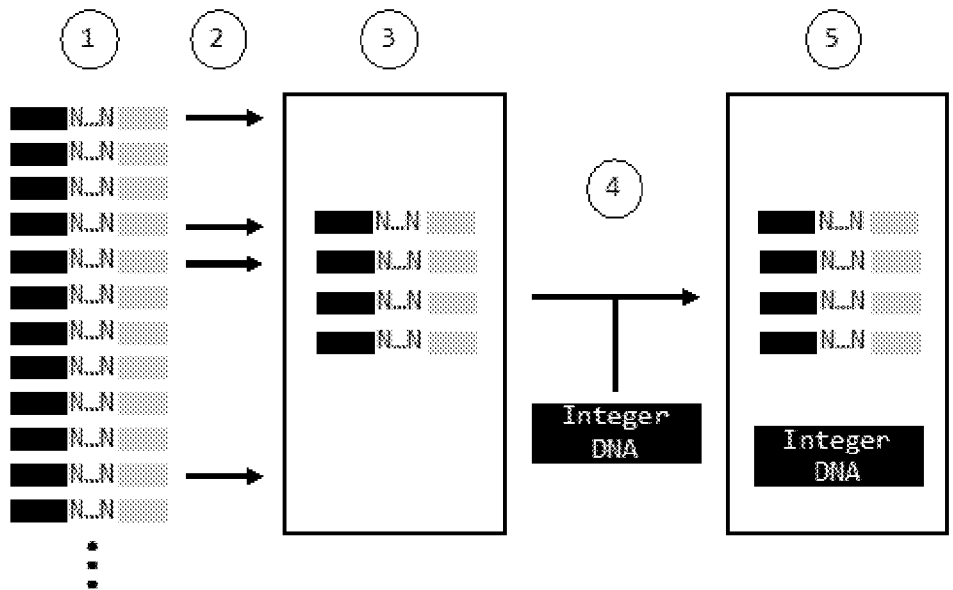
FIG. 36A-36C show an example method for generating and storing entropy (random bit strings)

FIG. 36A illustrates an example schematic of a method for storing randomly generated data in DNA. It begins with (1) a large random pool of DNA species, referred to as a seed. The seed should ideally contain a uniform distribution of every species of a defined combinatorial set of DNA, for example, all DNA species with 50 bases (with $4^{50}$ members). However, the full combinatorial space may be too large for every member to be represented in the seed, and so it is permissible that the seed contain a random subset of the combinatorial space. The seed may itself be generated from degenerate oligonucleotide synthesis or combinatorial DNA assembly. (2) Random data (or entropy) is generated by taking random subset of the species in the seed. For example, this may be accomplished by taking a proportional, fractional volume of the seed solution. For example, if the seed solution consists of an estimated 1 million species per microliter (uL), then a random subset of approximately 1 thousand species may be selected by taking a 1 nanoliter (nL) aliquot from the seed solution (assuming it is well-mixed). Alternatively, a subset may be selected by flowing an aliquot of the seed solution through a nanopore membrane and collecting the species only that pass the membrane. Counting the number of species that pass through the membrane may be achieved by measuring the voltage difference across the nanopores. This process may continue until a desirable number of signatures is detected (for example 100, 1000, 10000, or more species signatures). As another alternative method, single species may be isolated in small droplets (for example, with oil emulsions). The small droplets with single species may be detected by a fluorescent signature and sorted by a series of microfluidic channels into a collection chamber. (3) We may refer to each selected species as an identifier and, further, we may refer to the full subset of species selected as the "random identifier library" or RIL. To stabilize the information in the RIL and protect it from degradation, the RIL may be amplified with PCR primers that bind to common sequences on the ends of the species. To determine the identifiers in the RIL (and hence the data stored within), the RIL may be sequenced. True identifiers may be defined by the species in the sample with enrichment above a defined noise threshold. (4) Once the data contained in the RIL is determined, extra error checking and error correction species may be added to the RIL. For example, "integer DNA" that contains information on how many identifiers to expect (for example a checksum or a parity check) may be added to the RIL. The integer DNA may allow one to know how deeply to sequence the RIL in order to recover all of the information.

Figure 36B:
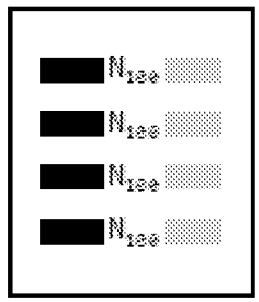
Figure 36C:
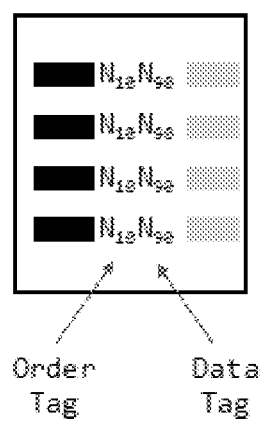

A RIL may be barcoded with a unique DNA tag. Several barcoded RILs may then be pooled together such that any given RIL may be individually accessed with a hybridization assay (or PCR) against its unique DNA tag. The unique DNA tags may be combinatorially assembled or synthesized and then assembled onto their corresponding RILs. FIG. 36B shows an example RIL comprising 4 species each containing one hundred random bases. The combinatorial space of possible species is $4^{100}$ and hence the RIL may contain $\log_2(4^{100}\text{ choose }4) \approx 725$ bits of information. FIG. 36C also shows an example RIL comprising 4 species each containing one hundred random bases. As an alternative to storing the information in the particular unordered combination of 4 species chosen out of a combinatorial space of $4^{100}$ (as in FIG. 36B), the final 90 random bases of each species may be reserved to store $\log_2(4^{90})=180$ bits of information, while the first 10 random bases may be reserved to establish a relative order between information stored in each of the 4 species. The relative order may be defined by a lexicographical ordering of the 10-base strings based on a defined ordering of the 4 bases (similar to the way in which words in the English language are ordered according to the order of letters in the alphabet). This method for assigning information to a RIF may be computationally faster to map to a binary string than the method described in FIG. 36B.

In the previous figure (FIG. 36), we discuss a strategy for barcoding multiple RILs and pooling them together. In doing so, an input-output mapping is created wherein the inputs correspond to barcode hybridization probes (for accessing the individual RILs) and outputs correspond to random data strings (encoded by the targeted RIL). Whereas in this method, pre-defined barcodes are assembled to random data for retrieval from a combined pool, FIG. 37A demonstrates a different method for creating input-output mappings between nucleic acid probes and random data strings where the barcodes (for accessing the data) are generated randomly along with the random data itself. For example, the barcode may be a pair of short sequences of DNA that may appear on both edges of one or multiple species. In this embodiment, the combinatorial space of the possible barcodes may be small compared to the total number all possible species in a pool such that each barcode is, by chance, associated with one or more species. For example, if a barcode is 3 bases on each edge of a random DNA sequence in a species (flanked by common sequences), then there are $4^6=4096$ possible barcodes and hence $4^6=4096$ primer pairs that may be built to access them (corresponding to 12-bit inputs). If a pool of DNA is selected such that it has approximately 400K species, then each barcode may be associated with approximately 100 species on average. In this embodiment, RILs are defined by the subset of species associated with each barcode. Following the preceding example, if each species comprises 25 random bases (or random sequences) aside from the bases (or sequences) used for barcoding, then a barcode associated with a RIL of 100 species may contain up to $\log_2 (4^{25}\text{choose}100) \approx 4475$ bits of information.

Figure 37A:
FIG. 37A-37B show an example method for organizing and accessing random bit strings using inputs.
Figure 37B:
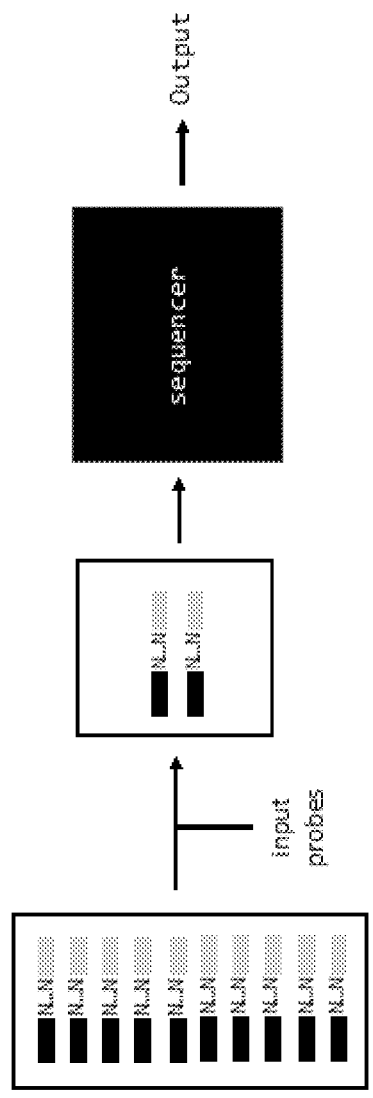

FIG. 37B demonstrates an implementation of a scheme for accessing and reading stored random data from a pool of barcoded RILs. The sequencer (or reader) may further comprise a function to manipulate the sequence data prior to returning the output. A hash function, for example, may make it difficult to use the output data string to perform a reverse chemical query and find its inputs. This functionality may be useful, for example, if the inputs are keys or credentials used for authentication.

The method of generating and storing query-able (or accessible) random strings of data may be particularly useful for generating and archiving encryption keys (generated from the random data strings). Each input may be used to access a different encryption key. For example, each input may correspond to a particular user, time range, and/or project in a private archival database. The encrypted data in the private archival database (potentially amounting to a very large amount of data) may be stored in conventional medium by an archival service provider while the encryption keys may be stored in DNA by the owner. Moreover, the potential latency and sophistication required to perform the chemical access protocol for a particular input may heighten the security barrier of the encryption method against hacking.

Figure 38:
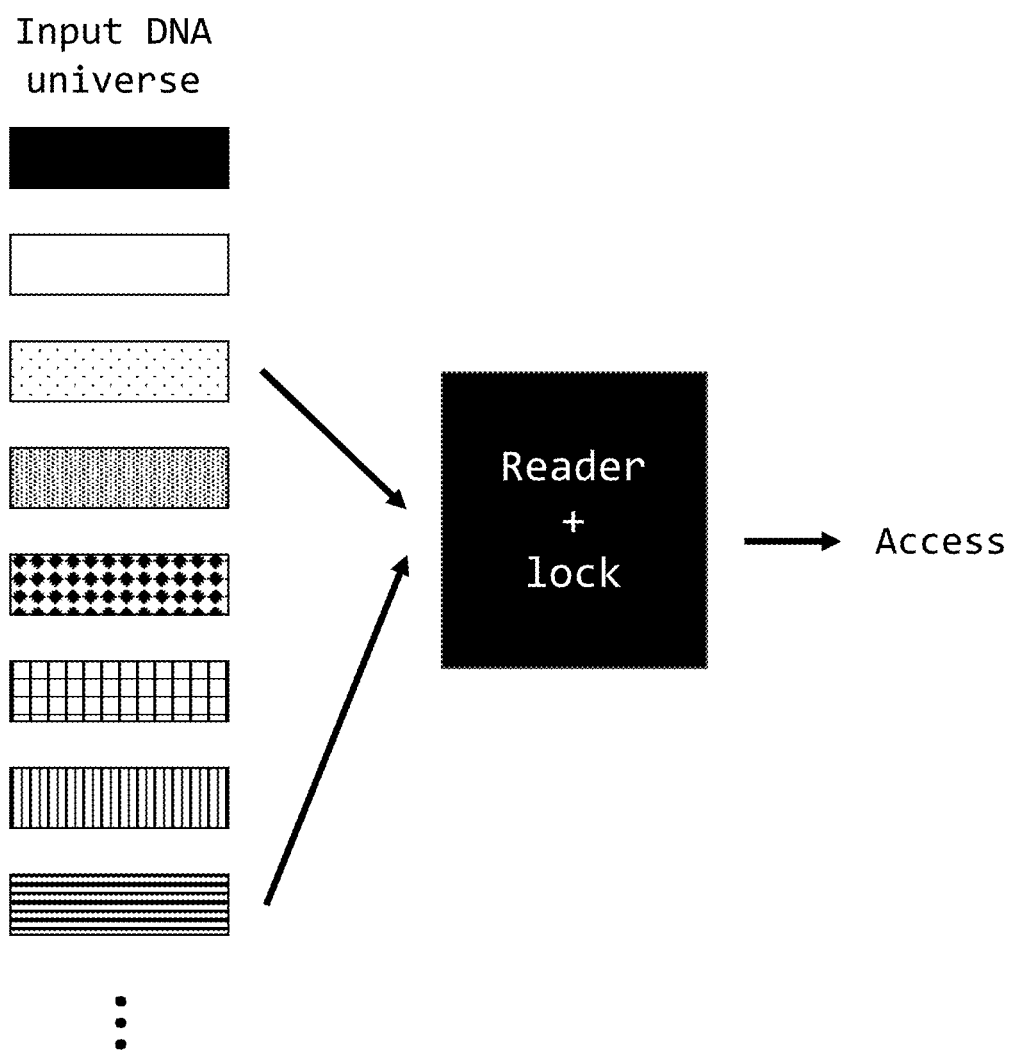
FIG. 38 shows an example method for securing and authenticating access to artifacts using physical DNA keys.

FIG. 38 illustrates an example system for securing and authenticating access to an artifact. The system requires a physical key comprising a particular combination of species of DNA taken from a large pool of possible species. A target combination of species, also referred to as an "identifier key", may for example be generated automatically by a combinatorial microfluidic-channel, electrowetting, or printing device, or manually by pipetting. A reader or sequencer with a built-in lock verifies a matching identifier key and enables access to an artifact. Alternatively, the reader may behave as a credential-token system where, instead of directly unlocking access to an artifact, it returns a token that may be used to access the artifact. The token may be generated, for example, by a built-in hashing function within the reader.

Methods of Tracking Entities and Tagging Objects with DNA

Identifier libraries dissolved in solvent may be sprayed, spread, dispensed, or injected into or on physical objects to tag them with information. For example, an unique identifier library may be used to tag distinct instances of a type of object. An identifier library tag on an object may act as a unique barcode, or it may contain more sophisticated information such as a product number, a manufacturing or shipping date, a location of origin, or any other information pertaining to the history of the object, for example a transaction list of previous owners. A primary advantage of using identifiers to tag objects is that the identifiers are undetectable, durable, and well suited to tag a vast number of object instances individually.

In another embodiment, one or more physical locations may each be tagged with unique identifiers from an identifier library. For example, physical sites A, B, and C may be ubiquitously tagged with an identifier library. An entity, for example, a vehicle, person, or any other object, that visits site A or comes in contact with site A may, intentionally or not, pick up a sample of the identifier library. Later upon accessing the entity, the sample may be gathered from the entity and chemically processed and decoded to identify which site was visited by the entity. An entity may visit more than one site and may pick up more than one sample. A similar process may be used to identify some or all the sites visited by the entity if the identifier libraries are disjoint. Such a scheme may have an application in covert tracking of entities. Some advantages of using this scheme are that identifiers are undetectable unless specifically sought, may be designed to be biologically inert, and may be used to uniquely tag a vast number of sites or entities.

In another embodiment, an identifier library may tag an entity. The entity may leave samples of the injected identifiers in sites that it visits. These samples may be gathered, processed and decoded to identify which entities may have visited a site.

Applications of Methods and Systems of Combinatorial DNA Assembly

The methods and systems described herein for combinatorial assembly of components into large defined sets of identifiers have been described thus far as they relate to information technology (for example, data storage, computing, and cryptography). However, these systems and methods may more generally be used for any application of high throughput combinatorial DNA assembly.

In one embodiment, we may create a library of combinatorial DNA that encodes for amino acid chains. Those amino acid chains may represent either peptides or proteins. The DNA fragments for assembly may comprise codon sequences. The junctions along which fragments assemble may be functionally or structurally inert codons that will be common to all members of the combinatorial library. Alternatively, the junctions along which fragments assemble may be introns that are eventually removed from messenger RNA which is later translated into the processed peptide chain. Certain fragments may not be codons, but rather barcode sequences that (in combination with other assembled barcodes) uniquely tag each combinatorial string of codons.

The assembled products (barcodes+string of codons) may be pooled together and encapsulated in droplets for in vitro expression assays, or pooled together and transformed into cells for in vivo expression assays. The assays may have a fluorescent output such that the droplets/cells may be sorted into bins by fluorescent strength and subsequently their DNA barcodes sequenced for the purpose of correlating each codon string with a particular output.

In another embodiment, we may create a library of combinatorial DNA that encodes for RNAs. For example, the assembled DNA may represent combinations of microDRNAs or CRISPR gRNAs. Either pooled in vitro or in vivo RNA expression assays may be performed as described above with either droplets or cells, and with barcodes to keep track of which droplets or cells contain which RNA sequence. However, some pooled assays may be done outside droplets or cells if the output itself is RNA sequencing data. Examples of such pooled assays include RNA aptamer screening and testing (for example, SELEX).

In another embodiment, we may create a library of combinatorial DNA that encodes for genes in a metabolic pathway. Each DNA fragment may contain a gene expression construct. The junctions along which fragments are assembled may represent inert DNA sequences in between genes. Either pooled in vitro or in vivo gene pathway expression assays may be performed as described above with either droplets or cells, and with barcodes to keep track of which droplets or cells contain which gene pathways.

In another embodiment, we may create a library of combinatorial DNA with different combinations of gene regulatory elements. Examples of gene regulatory elements include 5' untranslated regions (LTRs), ribosome binding sites (RBSs), introns, exons, promoters, terminators, and transcription factor (TF) binding sites. Either pooled in vitro or in vivo gene expression assays may be performed as described above with either droplets or cells, and with barcodes to keep track of which droplets or cells contain which genetic regulatory constructs.

In another embodiment, a library of combinatorial DNA aptamers may be created. Assays can be performed to test the ability of the DNA aptamers to bind ligands.

EXAMPLES

Example 1: Encoding Writing and Reading a Single Poem in DNA Molecules

Data to be encoded is a textfile containing a poem. The data is encoded manually with pipettes to mix together DNA components from two layers of 96 components to construct identifiers using the product scheme implemented with overlap extension PCR. The first layer, X, comprises 96 total DNA components. The second layer, Y, also comprises 96 total components. Prior to writing the DNA, the data is mapped to binary and then recoded to a uniform weight format where every contiguous (adjacent disjoint) string of 61 bits of the original data is translated to a 96 bit string with exactly 17 bit-values of 1. This uniform weight format may have natural error checking qualities. The data is then hashed into a 96 by 96 table to form a reference map.

Figure 18A:
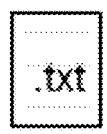
FIGS. 18A and 18B show examples of encoding, writing, and reading data encoded in nucleic acid molecules.
Figure 18A:
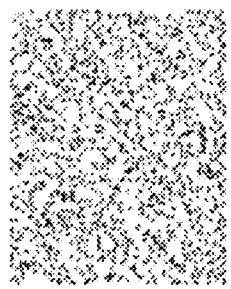
Figure 18A:
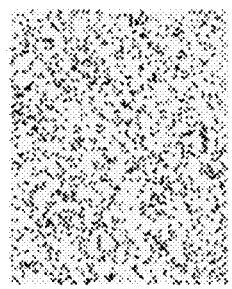

The middle panel of FIG. 18A shows the two-dimensional reference map of a 96 by 96 table encoding the poem into a plurality of identifiers. Dark points correspond to a '1' bit-value and white points corresponded to a '0' bit-value. The data is encoded into identifiers using two layers of 96 components. Each X value and Y value of the table is assigned a component and the X and Y components are assembled into an identifier using overlap extension PCR for each (X,Y) coordinate with a '1' value. The data was read back (e.g., decoded) by sequencing the identifier library to determine the presence or absence of each possible (X,Y) assembly.

The right panel of figure FIG. 18A shows a two-dimensional heat map of the abundances of sequences present in the identifier library as determined by sequencing. Each pixel represents a molecule comprising the corresponding X and Y components, and the greyscale intensity at that pixel represents the relative abundance of that molecule compared to other molecules. Identifiers are taken as the top 17 most abundant (X, Y) assemblies in each row (as the uniform weight encoding guarantees that each contiguous string of 96 bits may have exactly 17 '1' values, and hence 17 corresponding identifiers).

Example 2: Encoding a 62824 Bit Textile

Data to be encoded is a textfile of three poems totaling 62824 bits. The data is encoded using a Labcyte Echo® Liquid Handler to mix together DNA components from two layers of 384 components to construct identifiers using the product scheme implemented with overlap extension PCR. The first layer, X, comprises 384 total DNA components. The second layer, Y, also comprises 384 total components. Prior to writing the DNA, the data is mapped to binary and then receded to decrease the weight (number of bit-values of '1') and include checksums. The checksums are established so that there is an identifier that corresponds to a checksum for every contiguous string of 192 bits of data. The re-coded data has a weight of approximately 10,100, which corresponds to the number of identifiers to be constructed. The data may then be hashed into a 384 by 384 table to form a reference map.

Figure 18B:
Figure 18B:
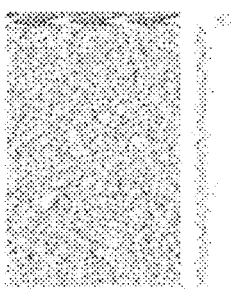
Figure 18B:
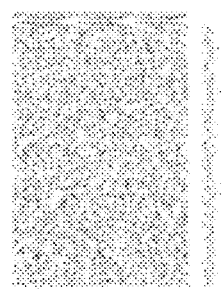

The middle panel of FIG. 18B shows a two-dimensional reference map of a 384 by 384 table encoding the textfile into a plurality of identifiers. Each coordinate (X,Y) corresponds to the bit of data at position X+(Y−1)*192. Black points correspond to a bit value of '1' and white points correspond to a bit value of '0'. The black points on the right side of the figure are the checksums and the pattern of black points on the top of the figure is the codebook (e.g., dictionary for de-coding the data). Each X value and Y value of the table may be assigned a component and the X and Y components are assembled into an identifier using overlap extension PCR for each (X, Y) coordinate with a '1' value. The data was read back (e.g., decoded) by sequencing the identifier library to determine the presence or absence of each possible (X, Y) assembly.

The right panel of FIG. 18B shows a two-dimensional heat map of the abundances of sequences present in the identifier library as determined by sequencing. Each pixel represents a molecule comprising the corresponding X and Y components, and the greyscale intensity at that pixel represents the relative abundance of that molecule compared to other molecules. Identifiers are taken as the top S most abundant (X, Y) assemblies in each row, where S for each row may be the checksum value.

In general, aspects of the subject matter and the functional operations described in this specification can be implemented in digital electronic circuitry, or in computer software, firmware, or hardware, including the structures disclosed in this specification and their structural equivalents, or in combinations of one or more of them. Aspects of the subject matter described in this specification can be implemented as one or more computer program products, i.e., one or more modules of computer program instructions encoded on a computer readable medium for execution by, or to control the operation of, data processing apparatus. The computer readable medium can be a machine-readable storage device, a machine-readable storage substrate, a memory device, a composition of matter affecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program may correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby. All references cited herein are incorporated by reference in their entirety and made part of this application.

What is claimed is:

1. A method for storing digital information into nucleic acid molecules, the method comprising:
   (a) receiving the digital information as a string of symbols, wherein each symbol in the string of symbols has a symbol value and a symbol position within the string of symbols;
   (b) forming a first identifier nucleic acid molecule by:
      (1) selecting, from a set of distinct component nucleic acid molecules that are separated into M different layers, one component nucleic acid molecule from each of the M layers;
      (2) depositing the M selected component nucleic acid molecules into a compartment;
      (3) physically assembling the M selected component nucleic acid molecules in (2) to form the first identifier nucleic acid molecule having first and second end molecules and a third molecule positioned between the first and second end molecules, such that the component nucleic acid molecules from first and second layers correspond to the first and second end molecules of the identifier nucleic acid molecule, and the component nucleic acid molecule in a third layer corresponds to the third molecule of the identifier nucleic acid molecule, to define a physical order of the M layers in the first identifier nucleic acid molecule, wherein the first layer has a highest priority, the second layer has a second highest priority, and the remaining M−2 layers have corresponding component nucleic acid molecules between the first and second end molecules;
   (c) forming a plurality of additional identifier nucleic acid molecules, each (1) having first and second end molecules and a third molecule positioned between the first and second end molecules, and (2) corresponding to a respective symbol position, wherein at least one of the first end molecule, second end molecule, and third molecule of at least one additional identifier nucleic acid molecule is identical to a target molecule of the first identifier nucleic acid molecule in (b), so as to enable a probe to select at least two identifier nucleic acid molecules corresponding to respective symbols having contiguous symbol positions within the string of symbols, and
   (d) collecting the identifier nucleic acid molecules in (b) and (c) in a pool having powder, liquid, or solid form.

2. The method of claim 1, wherein at least one of the first and second end molecules of the at least one additional identifier nucleic acid molecule is identical to a target molecule of the first identifier nucleic acid molecule in (b).

3. The method of claim 1 wherein physically assembling the M selected component nucleic acid molecules comprises ligation of the component nucleic acid molecules.

4. The method of claim 1, wherein the component nucleic acid molecules from each layer comprise at least one sticky end which is complementary to at least one sticky end of component nucleic acid molecules from another layer, so as to enable sticky end ligation for formation of the identifier nucleic acid molecules in (b) and (c).

5. The method of claim 1, wherein the first molecule of the at least one additional identifier nucleic acid molecule in (c) is identical to the first end molecule of the identifier nucleic acid molecule in (b), and the second end molecule of the at least one additional identifier nucleic acid molecule in (c) is identical to the second end molecule of the identifier nucleic acid molecule in (b).

6. The method of claim 1, further comprising using the probe to hybridize to the target molecule of at least some identifier nucleic acid molecules in the first identifier nucleic acid molecule and the plurality of additional identifier nucleic acid molecules to select identifier nucleic acid molecules corresponding to respective symbols having contiguous symbol positions.

7. The method of claim 1, further comprising applying a single PCR reaction to amplify at least two identifier nucleic acid molecules corresponding to respective symbols having contiguous symbol positions.

8. The method of claim 7, wherein the at least two identifier nucleic acid molecules corresponding to respective symbols having contiguous symbol positions are able to be further amplified by another PCR reaction that targets a specific component nucleic acid molecule in the third molecule of the identifier nucleic acid molecule.

9. The method of claim 1, wherein the component nucleic acid molecules in each layer are structured with first and second end regions, and the first end region of each component nucleic acid molecule from one of the M layers is structured to bind to the second end region of any component nucleic acid molecule from another of the M layers.

10. The method of claim 1, wherein M is greater than or equal to three.

11. The method of claim 1, wherein each symbol position within the string of symbols has a corresponding different identifier nucleic acid molecule.

12. The method of claim 1, wherein the identifier nucleic acid molecules in (b) and (c) are representative of a subset of a combinatorial space of possible identifier nucleic acid molecules, each including one component nucleic acid molecule from each of the M layers.

13. The method of claim 12, wherein a presence or absence of an identifier nucleic acid molecule in the pool in (d) is representative of the symbol value of the corresponding respective symbol position within the string of symbols.

14. The method of claim 1, wherein the symbols having contiguous symbol position encode similar digital information.

15. The method of claim 1, wherein a distribution of numbers of component nucleic acid molecules in each of the M layers is non-uniform.

16. The method of claim 15, wherein when the third layer includes more component nucleic acid molecules than either of the first layer or the second layer, a PCR query used to access the pool in (d) results in a larger pool of accessed identifier nucleic acid molecules than if the third layer included fewer component nucleic acid molecules than either of the first layer or the second layer.

17. The method of claim 16, wherein when the third layer includes fewer component nucleic acid molecules than either of the first layer or the second layer, a PCR query used to access the pool in (d) results in a smaller pool of accessed identifier nucleic acid molecules than if the third layer included more component nucleic acid molecules than either of the first layer or the second layer, wherein the smaller pool of accessed identifier nucleic acid molecules corresponds to a higher resolution of access to the symbols in the string of symbols.

18. The method of claim 1, wherein the pool in (d) is able to be used to access all identifier nucleic acid molecules in the pool that have particular component nucleic acid molecules at the first and second end molecules, in one PCR reaction.

19. The method of claim 1, wherein physically assembling the M selected component nucleic acid molecules uses click chemistry.

20. The method of claim 1, further comprising deleting at least some data collected in the pool.

21. The method of claim 20, further comprising using sequence-specific probes to pull-down select identifier nucleic acid molecules from the pool in (d) to selectively delete data.

22. The method of claim 21, wherein the select identifier nucleic acid molecules are selectively deleted using CRISPR-based methods.

23. The method of claim 20 further comprising obfuscating the identifier nucleic acid molecules in the pool in (d) to non-selectively delete data.

24. The method of claim 20, further comprising using sonication, autoclaving, treatment with bleach, bases, acids, ethidium bromide or other DNA modification agents, irradiation, combustion, and non-specific nuclease digestion to degrade the identifier nucleic acid molecules from the pool in (d) to non-selectively delete data.

25. The method of claim 1, further comprising:
dividing the string of symbols into one or more blocks of size no greater than a fixed length.

26. The method of claim 25, further comprising determining the size of each block based on the string of symbols, processing requirements, or an intended application of the digital information.

27. The method of claim 25, further comprising computing a hash of each block.

28. The method of claim 25, further comprising mapping the one or more blocks to a set of codewords that optimizes chemical conditions during encoding or decoding.

29. The method of claim 28, wherein the set of codewords have a fixed weight such that a fixed number of identifier nucleic acid molecules are assembled in each reaction compartment in a writer system, and in approximately equal concentration within each reaction compartment and across reaction compartments.

* * * * *

UNITED STATES PATENT AND TRADEMARK OFFICE
CERTIFICATE OF CORRECTION

| | |
|---|---|
| PATENT NO. | : 11,227,219 B2 |
| APPLICATION NO. | : 17/206803 |
| DATED | : January 18, 2022 |
| INVENTOR(S) | : Nathaniel Roquet et al. |

It is certified that error appears in the above-identified patent and that said Letters Patent is hereby corrected as shown below:

On the Title Page

Item (57) ABSTRACT: At Line 3, delete "sting" and replace with --string--

Signed and Sealed this
Eighteenth Day of October, 2022

Katherine Kelly Vidal
*Director of the United States Patent and Trademark Office*